US007868135B2

(12) United States Patent
Cameron et al.

(10) Patent No.: US 7,868,135 B2
(45) Date of Patent: Jan. 11, 2011

(54) COMPOSITIONS OF LIPOPEPTIDE ANTIBIOTIC DERIVATIVES AND METHODS OF USE THEREOF

(75) Inventors: Dale R. Cameron, Richmond (CA); Vincent A. Boyd, Vancouver (CA); Richard A. Leese, Suffern, NY (US); William V. Curran, Pearl River, NY (US); Donald B. Borders, Suffern, NY (US); Paulo W. M. Sgarbi, Richmond (CA); Shirley A. Wacowich-Sgarbi, Richmond (CA); Matthew Nodwell, Vancouver (CA); Yuchen Chen, Vancouver (CA); Qi Jia, Burnaby (CA); Dominique Dugourd, Vancouver (CA)

(73) Assignee: Biowest Therapeutics Inc., Vancouver, B.C. (CA)

( * ) Notice: Subject to any disclaimer, the term of this patent is extended or adjusted under 35 U.S.C. 154(b) by 289 days.

(21) Appl. No.: 10/880,442

(22) Filed: Jun. 28, 2004

(65) Prior Publication Data
US 2005/0153876 A1 Jul. 14, 2005

Related U.S. Application Data

(60) Provisional application No. 60/488,331, filed on Jul. 17, 2003, provisional application No. 60/564,912, filed on Apr. 23, 2004.

(51) Int. Cl.
*A61K 38/12* (2006.01)
(52) U.S. Cl. ..................................... 530/317
(58) Field of Classification Search ....................... None
See application file for complete search history.

(56) References Cited

U.S. PATENT DOCUMENTS

| 3,057,779 | A | | 10/1962 | Shay et al. | |
|---|---|---|---|---|---|
| 3,160,561 | A | | 12/1964 | Shibata et al. | |
| 3,639,582 | A | | 2/1972 | Umezawa et al. | |
| 3,781,420 | A | | 12/1973 | Nishimura et al. | |
| 3,817,973 | A | | 6/1974 | Bouchaudon et al. | |
| 4,524,135 | A | | 6/1985 | Abbott et al. | |
| 4,977,083 | A | | 12/1990 | Boeck | |
| 4,994,270 | A | | 2/1991 | Boeck et al. | |
| 5,028,590 | A | | 7/1991 | Fukuda et al. | |
| 5,039,789 | A | | 8/1991 | Fukuda et al. | |
| 5,629,288 | A | * | 5/1997 | Lattrell et al. | 514/9 |
| 5,912,226 | A | | 6/1999 | Baker et al. | |
| 6,146,872 | A | | 11/2000 | Ueda et al. | |
| 6,194,383 | B1 | | 2/2001 | Hammann et al. | |
| 6,716,962 | B2 | | 4/2004 | Borders et al. | |
| 7,125,844 | B2 | * | 10/2006 | Fardis et al. | 514/9 |
| 2002/0028771 | A1 | | 3/2002 | Curran et al. | |
| 2004/0138107 | A1 | | 7/2004 | Fardis et al. | |

FOREIGN PATENT DOCUMENTS

| AU | B-672691 | 10/1996 |
|---|---|---|
| EP | 629636 B1 | 12/1998 |
| WO | WO 99/43700 | 9/1999 |
| WO | WO 02/05837 | 1/2002 |
| WO | WO-02/05837 A1 | 1/2002 |
| WO | WO 03/057724 | 7/2003 |

OTHER PUBLICATIONS

Bodanszky, M. et al., "Structure of the Peptide Antibiotic Amphomycin," *Journal of the American Chemical Society* 95(7): 2352-2357, Apr. 4, 1973.
Boeck, L.D. et al., "Deacylation of A21978C, an Acidic Lipopeptide Antibiotic Complex, by *Actinoplanes utahensis*," *The Journal of Antibiotics* 41(8): 1085-1092, Aug. 1988.
Debono, M. et al., "Enzymatic and Chemical Modifications of Lipopeptide Antibiotic A21978C: The Synthesis and Evaluation of Daptomycin (LY146032)," *The Journal of Antibiotics* 41(8): 1093-1105, Aug. 1988.
Fujino, M., "On Glumamycin, a New Antibiotic. VI. An Approach to the Amino Acid Sequence," *Bulletin of the Chemical Society of Japan* 38(4): 517-522, 1965.
Hausmann, W.K. et al., "Structure Determination of Fatty Acids from the Antibiotic Aspartocin," in *Antimicrobial Agents and Chemotherapy—1963*, Proceeding of the Third Interscience Conference on Antimicrobial Agents and Chemotherapy, Sylvester, J.C. (ed.), American Society for Microbiology, 1963, pgs. 352-359.
Hausmann, W.K. et al., "α, β-Diaminobutyric Acid Obtained from Aspartocin," *The Journal of Antibiotics* 22(5): 207-210, May 1969.
Heinemann, B. et al., "Amphomycin, A New Antibiotic," *Antibiotics and Chemotherapy* 3: 1239-1242, 1953.
Hinuma, Y., "Zaomycin, A New Antibiotic from a *Streptomyces* sp.," *The Journal of Antibiotics, Ser. A* 7(4): 134-136, Aug. 1954.
Huber, F.M. et al., "The formation of daptomycin by supplying decanoic acid to *Strptomyces roseosporus* cultures producing the antibiotice complex A21978C," *Journal of Biotechnology* 7(4): 283-292, 1988.
Martin and Hausmann, "Isolation and Identification of D-$_a$-Pepecolic Acid, α[L], β-Methylaspartic Acid and α,β-Diaminobutyric Acid from the Polypeptide Antibiotic Aspartocin," *Journal of the American Chemical Society* 82: 2079, Apr. 20, 1960.
Naganawa, H. et al., "A Novel Fatty Acid from Laspartomycin," *The Journal of Antibiotics* 23(8): 423-424, Aug. 1970.
Naganawa, H. et al, "Laspartomycin, A New Anti-Staphylococcal Peptide," *The Journal of Antibiotics* 21(1): 55-62, Jan. 1968.
Shay, A.J. et al., "Aspartocin. I. Production, Isolation, and Characteristics," *Antibiotics Annual* 1959-1960, pp. 194-198.
Shoji, J-I et al., "Studies on Tsushimycin. I. Isolation and Characterization of an acidic acylpeptide containing a new fatty acid," *The Journal of Antibiotics* 21(7): 439-443, Jul. 1968.
Vértesy, L. et al., "Friulimicins: Novel Lipopeptide Antibiotics with Peptidoglycan Synthesis Inhibiting Activity from *Actinoplanes friuliensis* sp. nov. II. Isolation and Structural Characterization," *The Journal of Antibiotics* 53(8): 816-827, Aug. 2000.

* cited by examiner

*Primary Examiner*—Cecilia Tsang
*Assistant Examiner*—Thomas S Heard
(74) *Attorney, Agent, or Firm*—Frommer Lawrence & Haug LLP; Bruce E. Black

(57) ABSTRACT

The present invention provides derivatives of lipopeptide antibiotics that display antimicrobial activity against microorganisms, methods and compounds for synthesizing such antimicrobial derivatives and analogues, and methods of using the compounds in a variety of contexts, including in the treatment and prevention of microbial infections.

49 Claims, 23 Drawing Sheets

COMPOSITIONS OF LIPOPEPTIDE ANTIBIOTIC DERIVATIVES AND METHODS OF USE THEREOF

CROSS-REFERENCE TO RELATED APPLICATION

This application claims the benefit of U.S. Provisional Patent Application No. 60/488,331 filed Jul. 17, 2003; and U.S. Provisional Patent Application No. 60/564,912, filed Apr. 23, 2004, where these provisional applications are incorporated herein by reference in their entireties.

FIELD OF THE INVENTION

The present invention relates generally to the treatment of infectious disease, and more specifically, to methods and compounds for preparation of lipopeptide antibiotic derivative compositions comprising derivatives of lipopeptide antibiotics, and therapeutic uses thereof.

BACKGROUND OF THE INVENTION

Aside from a healthy host immune response, therapeutic regimens employing antibiotics now represent the primary course of treatment for most infectious diseases in developed countries. An important class of antibiotics effective against Gram-positive bacteria is lipopeptide antibiotics. Generally, lipopeptide antibiotics have either a cyclic peptide core or a cyclic depsipeptide core acylated with a lipophilic fragment. The lipophilic fragment (e.g., an unsaturated fatty acid) may vary in length and this length may affect the activity of a particular lipopeptide.

However, due to the widespread use of antibiotics, drug-resistance to these and other antibiotics is becoming an increasingly common problem all over the world for controlling several previously treatable infectious diseases. For example, infections due to Gram-positive, drug-resistant organisms, such as those due to vancomycin-resistant *Enterococci* (VRE) and methicillin-resistant *Staphylococcus aureus* (MRSA), are on the rise. Moreover, the leading cause of nosocomial infections (i.e., those arising in hospitals) is now due to Gram-positive cocci, and bacteria having resistance to multiple antibiotics is increasingly common.

Given the rampant rise of strains of microorganisms that are resistant to current antibiotic therapies, there is a continuing need for the development of novel antibiotics and antibiotics with novel mechanisms of action. The present invention meets such needs, and further provides other related advantages.

BRIEF SUMMARY

Briefly, the present invention provides lipopeptide derivatives, in particular amphomycin or aspartocin derivatives, and compositions of such lipopeptides for use in treating or preventing, for example, primary infection sites, secondary infections arising from a primary disease state, or infections associated with foreign bodies.

In one aspect, the present invention provides amphomycin-based or aspartocin-based lipopeptide antibiotics, wherein the antibiotic comprises a cyclic peptide "core" and a lipophilic substituent. The cyclic peptide core includes one or more amino acids having a side chain with an amine group, and derivatives thereof, which is typically at the 9-position of the core macrocyclic peptide. In one embodiment, the amino acid at the 9-position of the core macrocyclic peptide is a Dab$^9$. The macrocyclic peptide core also includes an at least one amino terminal exocyclic amino acid, which is typically Asp or Asn. In another embodiment, the amino terminal exocyclic amino acid is located between the cyclic portion of a core peptide and a lipophilic substituent.

In another aspect, the invention provides an antimicrobial compound and pharmaceutically acceptable salts thereof characterized by structure (IIa) $R^2$-L-R—$R^3$, wherein R is an amphomycin or aspartocin core cyclic peptide; $R^1$ is OH or $NH_2$ at amino acid position 1 of the R core cyclic peptide; L is selected from at least one amino acid, at least one substituted amino acid, —R'C(=O)—, —R'OC(=O)(NR')—, and —O-PhC(=O)—; $R^2$ is selected from —C(=O)$R^5$, —C(=O)O$R^5$, —C(=O)NH$R^4$, —C(=O)N$R^4R^4$, —C(=S)NH$R^4$, —C(=S)N$R^4R^4$, —C(=N$R^4$)NH$R^4$, and —C(=N$R^4$)N$R^4R^4$; $R^3$ is selected from —O$R^5$, —S$R^5$, N$R^5R^5$, —CN, —NO$_2$, —N$_3$, —C(=O)$R^5$, —C(=O)O$R^5$, —C(=O)N$R^5R^5$, —C(=S)N$R^5R^5$, —C(=N$R^5$)N$R^5R^5$, —C(=O)H, —$R^5$C(=O), —SO$_2R^5$, —S(=O)$R^5$, —P(=O)(O$R^5$)$_2$, —P(=O)(O$R^5$), —CO$_2$H, —SO$_3$H, —PO$_3$H, halogen, trihalomethyl, ($C_1$-$C_{25}$)alkyl, substituted ($C_1$-$C_{25}$)alkyl, ($C_1$-$C_{25}$)heteroalkyl, substituted ($C_1$-$C_{25}$)heteroalkyl, ($C_5$-$C_{10}$)aryl, substituted ($C_5$-$C_{10}$)aryl, ($C_5$-$C_{15}$)arylaryl, substituted ($C_5$-$C_{15}$)arylaryl, ($C_5$-$C_{15}$)biaryl, substituted ($C_5$-$C_{15}$)biaryl, 5 to 10 membered heteroaryl, substituted 5 to 10 membered heteroaryl, ($C_6$-$C_{26}$)arylalkyl, substituted ($C_6$-$C_{26}$)arylalkyl, 6 to 26 membered heteroarylalkyl, substituted 6 to 26 membered heteroarylalkyl, at least one amino acid, and at least one substituted amino acid; $R^4$ is independently selected from ($C_7$-$C_{10}$)alkyl, ($C_{17}$-$C_{26}$)arylalkyl and 17 to 26 membered heteroarylalkyl, a branched or straight-chained, saturated or singly or multiply unsaturated aliphatic or hydroxy aliphatic moiety having a chain length of from 7 to 25 carbon atoms, a primary or secondary amine, at least one amino acid, and at least one substituted amino acid; $R^5$ is independently selected from hydrogen, ($C_1$-$C_{10}$)alkyl, ($C_5$-$C_{10}$)aryl, 5 to 10 membered heteroaryl, ($C_6$-$C_{26}$)arylalkyl and 6 to 26 membered heteroarylalkyl, a branched or straight chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof, and; R' is independently one or more of the same or different substituents as defined for $R^3$ or $R^5$.

In certain embodiments, the instant disclosure provides any of the aforementioned compounds wherein $R^1$ is OH or $R^1$ is $NH_2$. In further embodiments, any of the aforementioned compounds has $R^2$ that is —C(=O)O$R^5$ or —C(=O)$R^5$, or that is —C(=O)NH$R^4$, —C(=S)NH$R^4$, or —C(=N$R^4$)NH$R^4$. In other embodiments, any of the aforementioned compounds are provided wherein $R^3$ is at least one amino acid selected from glycine, β-alanine, sarcosine, lysine, or any combination thereof, or is at least one amino acid selected from Gly, β-alanine, GABA, 5-aminopentanoic acid, 6-aminohexanoic acid, Lys, gDab, Sar, Orn, Dap, hLys, or any combination thereof. In related embodiments, the $R^3$ amino acid includes two amino acids selected from glycine-lysine or sarcosine-lysine. In certain embodiments, any of the aforementioned compounds are provided wherein $R^3$ further comprises at least one protecting group. In some embodiments, any of the aforementioned compounds wherein L is at least one amino acid or at least one substituted amino acid selected from p-aminophenylacetyl, (p-aminophenylpropanoyl)$_n$ wherein n is 1 or 2, m-aminophenylacetyl, (m-aminophenylpropanoyl)$_n$ wherein n is 1 or 2, o-aminophenylacetyl, (o-aminophenylpropanoyl)$_n$ wherein n is 1 or 2, GABA, p-aminobenzoic acid (PABA), m-aminobenzoic acid, o-aminobenzoic acid, p-hydrazinobenzoic acid, m-hydrazinobenzoic acid, o-hydrazinobenzoic acid, p-amino-trans-cinnamyl, o-amino-trans-cinnamyl, m-amino-trans-cinnamyl, L-BBTA, or any combination thereof. In certain embodiments, $R^2$ and $R^3$ are optionally substituted with a straight chain saturated aliphatic or hydroxy aliphatic moiety having a chain length of from 10 to 15 carbon atoms. In some embodiments, provided herein are certain compounds, such as compound 91 of Table 6D, compound 331 or 332 of Table 16, compound 86 of Table 6D, compound 87 or 280 of Table 7, or compound 89 of Table 8.

In a further aspect, the invention provides an antimicrobial compound and pharmaceutically acceptable salts thereof characterized by structure (IIa) $R^2$-L-R—$R^3$, wherein R is an amphomycin or aspartocin core cyclic peptide; $R^1$ is OH or $NH_2$ at amino acid position 1 of the R core cyclic peptide; L is selected from at least one amino acid, at least one substituted amino acid, —R'C(=O)—, and —R'OC(=O)(NR')—; $R^2$ is selected from —$OR^5$, —$SR^5$, $NR^5R^5$, —C(=O)$OR^5$, —C(=O)$R^5$, —C(=O)$NHR^4$, —C(=O)$NR^4R^4$, —C(=S)$NHR^4$, —C(=S)$NR^4R^4$, —C(=$NR^4$)$NHR^4$, —C(=$NR^4$)$NR^4R^4$, —$R^5$C(=O), —$SO_2R^5$, —S(=O)$R^5$, —P(=O)($OR^5$)$_2$, —P(=O)($OR^5$), —$CO_2H$, —$SO_3H$, —$PO_3H$, halogen, and trihalomethyl; $R^3$ is hydrogen; $R^4$ is independently selected from ($C_7$-$C_{10}$)alkyl, ($C_{17}$-$C_{26}$)arylalkyl and 17 to 26 membered heteroarylalkyl, a branched or straight-chained, saturated or singly or multiply unsaturated aliphatic or hydroxy aliphatic moiety having a chain length of from 7 to 25 carbon atoms, a primary or secondary amine, at least one amino acid, and at least one substituted amino acid; $R^5$ is independently selected from hydrogen, ($C_1$-$C_{10}$)alkyl, ($C_5$-$C_{10}$)aryl, 5 to 10 membered heteroaryl, ($C_6$-$C_{26}$)arylalkyl and 6 to 26 membered heteroarylalkyl, a branched or straight-chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof, and; R' is independently one or more of the same or different substituents as defined for $R^2$ or $R^5$.

In certain embodiments, the instant disclosure provides any of the aforementioned compounds wherein $R^1$ is OH or $R^1$ is $NH_2$. In further embodiments, any of the aforementioned compounds has $R^2$ that is —C(=O)$R^5$, —C(=O)$NHR^4$, —C(=S)$NHR^4$, or —C(=$NR^4$)$NHR^4$. In other embodiments, any of the aforementioned compounds are provided wherein $R^5$ is a 10 to 20 membered heteroarylalkyl, or a straight chain saturated aliphatic or hydroxy aliphatic moiety having a chain length of from 5 to 17 carbon atoms, or $R^4$ is a straight chain saturated aliphatic or hydroxy aliphatic moiety having a chain length of from 8 to 16 carbon atoms. In some embodiments, L is at least one amino acid or at least one substituted amino acid, such as glycine, sarcosine, phenylglycine, phenylalanine, O-methyl-aspartic acid, O-t-butyl-aspartic acid, p-aminobenzoic acid (PABA), m-aminobenzoic acid, p-hydrazino-benzoic acid, p-aminophenylpropanoic acid, (p-amino-phenylpropanoic acid)$_n$ wherein n is 1 or 2, L-BBTA, m-amino-phenylacetic acid, p-amino-phenylacetic acid (Apa), p-amino-trans-cinnamic acid, o-aminobenzoic acid, o,o-diamino benzoic acid, o,m-diamino benzoic acid, o,p-diaminobenzoic acid, m,p-diaminobenzoic acid, m,m-diaminobenzoic acid, o-amino-phenylacetic acid, m-amino-phenylacetic acid, p-amino-phenylacetic acid (Apa), aminothiazole acetic acid, or any combination thereof. In still other embodiments, any of the aforementioned compounds are provided wherein $R^3$ is at least one amino acid selected from Gly, β-alanine, GABA, 5-aminopentanoic acid, 6-aminohexanoic acid, Lys, gDab, Sar, Orn, Dap, or hLys. In still other embodiments, $R^3$ further comprises at least one protecting group. In still other embodiments, any of the aforementioned compounds include compound 103, 105, 106, 107, 112, 115, 116, 118, 311, 313, 314, 315 316, 317, 344, 345, 346, 358, 359, or 360 of Table 3; compound 104, 108, 109, 110, 111, 113, 122, 119, 281, 293, 294, 296, 297, 300, 301, 303, 310, 312 or 361 of Table 6D; compound 117 of Table 6C; compound 21, 85, 282, 283, 284, 285 or 123 of Table 7; compound 120 of Table 8; compound 305, 320, 319, 337, 374, 337, 305, 320 or 319 of Table 14; compound 286, 321, 304, 254, 307, 295 or 291 of Table 4; or compound 288, 306, 290, 362, 289, 292, 287 or 302 of Table 6A.

In yet another aspect, the invention provides an antimicrobial compound and pharmaceutically acceptable salts thereof characterized by structure (IVa) $R^2$-L-R-L-$R^3$ wherein R is an amphomycin or aspartocin core cyclic peptide; $R^1$ is OH or $NH_2$ at amino acid position 1 of the R core cyclic peptide; L is independently selected from at least one amino acid, at least one substituted amino acid, —C(=O)—, —R'C(=O)—, —$SO_2$—, —C(=S)—, —P(=O)—, —OP(=O)—, —OC(=O)—, —R'OC(=O)(NR')—, —NHC(=O)—, —O-PhC(=O)—, and —NR'C(=O)—, with the proviso that L at $Dab^9$ is —C(=O)—; $R^2$ is selected from —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)($OR^4$)$_2$, —P(=O)($OR^4$), —$CO_2H$, —$SO_3H$, —$PO_3H$, halogen, trihalomethyl, ($C_1$-$C_{25}$)alkyl, substituted ($C_1$-$C_{25}$)alkyl, ($C_1$-$C_{25}$)heteroalkyl, substituted ($C_1$-$C_{25}$)heteroalkyl, ($C_5$-$C_{10}$)aryl, substituted ($C_5$-$C_{10}$)aryl, ($C_5$-$C_{15}$)arylaryl, substituted ($C_5$-$C_{15}$)arylaryl, ($C_5$-$C_{15}$)biaryl, substituted ($C_5$-$C_{15}$)biaryl, 5-10 membered heteroaryl, substituted 5 to 10 membered heteroaryl, ($C_6$-$C_{26}$)arylalkyl, substituted ($C_6$-$C_{26}$)arylalkyl, 6 to 26 membered heteroarylalkyl, substituted 6 to 26 membered heteroarylalkyl, at least one amino acid, and at least one substituted amino acid; $R^3$ is selected from —C(=O)$OR^4$, —C(=O)$NR^4R^4$, —C(=S)$NR^4R^4$, —C(=$NR^4$)$NR^4R^4$, —C(=O)H, —$R^4$C(=O), —$CO_2H$, substituted ($C_1$-$C_{25}$)alkyl, substituted ($C_1$-$C_{25}$)heteroalkyl, substituted ($C_5$-$C_{10}$)aryl, substituted ($C_5$-$C_{15}$)arylaryl, substituted ($C_5$-$C_{15}$)biaryl, substituted 5 to 10 membered heteroaryl, substituted ($C_6$-$C_{26}$)arylalkyl, substituted 6 to 26 membered heteroarylalkyl, at least one amino acid, and at least one substituted amino acid, with the proviso that $R^3$ contain at least one of —C(=O)—, —C(=S)— or —C(=$NR^4$)—; $R^4$ is independently selected from hydrogen, ($C_1$-$C_{10}$)alkyl, ($C_5$-$C_{10}$)aryl, 5 to 10 membered heteroaryl, ($C_6$-$C_{26}$)arylalkyl and 6 to 26 membered heteroarylalkyl, a branched or straight-chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof and; R' is independently one or more of the same or different substituents as defined for $R^2$, $R^3$ or $R^4$.

In certain embodiments, the instant disclosure provides any of the aforementioned compounds wherein $R^1$ is OH or $R^1$ is $NH_2$. In further embodiments, any of the aforementioned compounds has $R^3$ that is —C(=O)— or —C(=S)—. In other embodiments, any of the aforementioned compounds include compound 210, 373, 223, 237, 235, or 81 of Table 12. In certain embodiments, $R^3$ is at least one amino acid or substituted amino acid selected from Gly, β-alanine, GABA, 5-aminopentanoic acid, 6-aminohexanoic acid, Lys, gDab, Sar, Orn, Dap, and hLys. In still other embodiments, $R^3$ further comprises at least one protecting group.

In yet another aspect, the invention provides an antimicrobial compound and pharmaceutically acceptable salts thereof, such as compound 3 of Table 1; compound 4 of Table 10; compound 60 of Table 13; compound 128 of Table 16; compound 147 of Table 1; compound 199 of Table 10; compound 253 of Table 4; or compound 278 of Table 4.

In another aspect, any of the aforementioned compounds may be structurally pure, or they may be in the form of a composition comprising a mixture of one or more structurally different compounds. In certain embodiments, the compounds of the invention may be in the form of a free acid or base, or in the form of a salt, such as a pharmaceutically acceptable salt. In still other embodiments, the core cyclic peptide is a β-isomer, anhydro isomer, or a dianhydro isomer.

In a further aspect, the present invention provides pharmaceutical compositions comprising any of the aforementioned compounds. In some embodiments, the compositions comprise one or more compounds of the invention and a pharmaceutically or physiologically acceptable carrier, excipient or diluent. The exact nature of the carrier, excipient, or diluent will depend upon the desired use for the composition, and may range from being suitable or acceptable for environmental or industrial uses, to being suitable or acceptable for veterinary uses, to being suitable or acceptable for human use (i.e., pharmaceutically acceptable).

In still another aspect, the present invention provides methods of synthesizing the compounds of the invention. In one embodiment, the compounds of the invention may be prepared from a parent amphomycin-based or aspartocin-based lipopeptide antibiotic isolated from culture by reacting the parent antibiotic with an appropriately protected reagent, such as an appropriately protected amino acid, under conditions suitable for attaching the reagent to the amino terminal amino group of an exocyclic amino acid or a β-nitrogen of a macrocyclic $Dab^9$ residue. In certain embodiments, protecting groups may be removed to yield compounds of the invention having a specific amino terminal subsituent with or without a linker, a specific $Dab^9$ subsituent with or without a linker, and any combination thereof. In some embodiments, such parent antibiotics are mixtures of compounds that differ from one another with respect to the structures of their macrocyclic peptide cores or lipophilic subsituents. In certain embodiments, the resultant amino terminal or $Dab^9$ derivative of the invention is obtained as a mixture of compounds, the structures and relative quantities of which are dictated by the structures and relative quantities of the compounds comprising the parent antibiotic mixture. In certain other embodiments, the component compounds comprising the parent antibiotic mixture are separated and isolated from one another before derivatization of an amino terminal amino acid or of a macrocyclic $Dab^9$ residue. Alternatively, the separation and isolation may be carried out on the resultant product of the amino terminal amino acid or $Dab^9$ derivatization reaction, either before or after removal of any protecting groups, to yield structurally pure amino terminal amino acid or $Dab^9$ derivatives of the invention, and any combination thereof.

In another related aspect, the structure of a fatty acid moiety at the amino terminus of a parent antibiotic is unknown. In certain embodiments, the lipophilic fatty acid moiety is removed and replaced with a lipophilic substiuent, amino acid substiuent, and combinations thereof, optionally attached via a linker group L, having a specified structure to provide amino terminal amino acid or $Dab^9$ derivative of the invention having precisely defined substituents with or without linkers. In one embodiment, the parent antibiotic mixture is protected at the β-amino group of the macrocyclic $Dab^9$ residue and delipidated to yield a delipidated intermediate, and this delipidated intermediate is then reacted with a desired lipophilic substiuent under acylating conditions to yield a synthetic antibiotic having a precisely defined lipophilic moiety. In another embodiment, this synthetic antibiotic may be derivatized according to the methods described above to yield $Dab^9$ derivatives of the invention.

The above-described synthetic pathways yield protected intermediate compounds and these intermediates constitute another aspect of the instant invention (as described above and herein, containing a protecting group).

In other aspects, the present invention provides methods of inhibiting the growth of microbes, such as Gram-positive bacteria. The method generally involves contacting a microbe with one or more compounds of the invention (or an acceptable salt thereof) in an amount effective to inhibit the growth of the microbe. The method may be practiced to achieve a microbistatic effect where the growth of the microbe is inhibited, or to achieve a microbicidal effect, where the microbe is killed.

In a related aspect, the present invention provides methods for treating or preventing microbial infections, such as infections caused by Gram-positive bacteria, in a subject such as human, plant or animal. In certain embodiments, the methods involve administering to a subject one or more compounds or compositions of the invention in an amount effective to treat or prevent the infection. The compounds or compositions may be administered systemically or applied topically, depending on the nature of the infection. In certain embodiments, compounds and compositions of the invention are used to treat or prevent skin and skin structure infections (including complicated infections), or pneumonia.

DETAILED DESCRIPTION OF THE INVENTION

Figure 1:
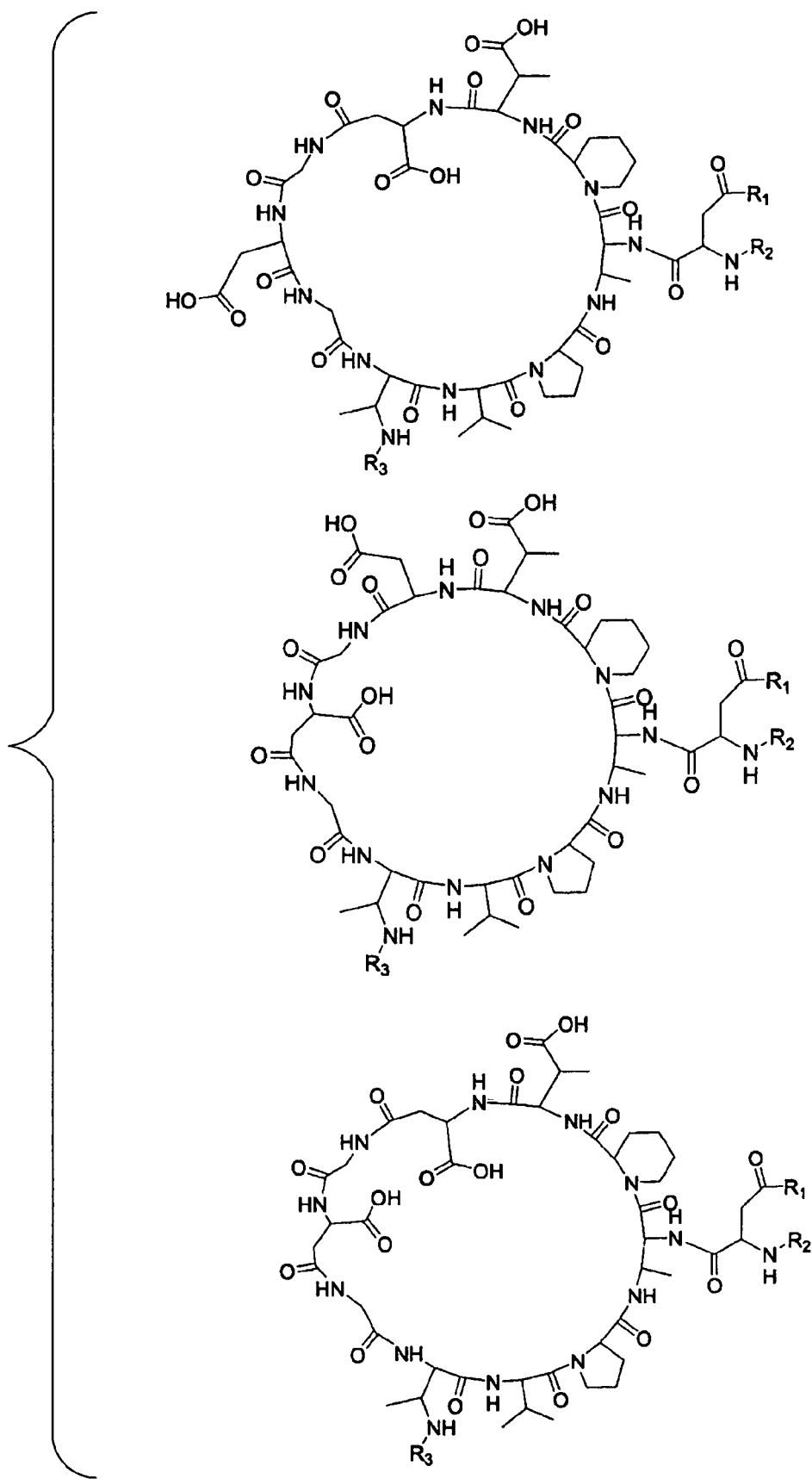
FIG. 1 is an illustration of exemplary β-isomers of the derivative lipopeptide antibiotic compounds of the invention.

As set forth above, the present invention provides compositions and methods for using and making antimicrobial lipopeptide derivatives to treat or prevent infectious diseases. The invention, therefore, relates generally to the surprising discovery that certain lipopeptide antibiotics may be chemically modified to maximize their in vivo and in vitro antimicrobial activity. In particular, these lipopeptide antibiotics are useful for treating or preventing infections involving Gram-positive bacteria, such as *Enterococci, Streptococci*, and *Staphylococci*, which may arise in a variety of settings (e.g., nosocomial infections, acne, and infections associated with intravascular penetration, such as in the use of hypodermic needles, catheters, and other medical devices). Discussed in more detail below are lipopeptide derivatives suitable for use within the present invention, as well as representative compositions and therapeutic uses.

Prior to setting forth the invention in more detail, it may be helpful to an understanding thereof to set forth definitions of certain terms to be used hereinafter.

As used herein, "amino acids" refer to a natural (those occurring in nature) amino acid, a substituted natural amino acid, a non-natural amino acid, a substituted non-natural amino acid, or any combination thereof. The designations for natural amino acids are herein set forth as either the standard one- or three-letter code. Natural polar amino acids include asparagine (Asp or N) and glutamine (Gln or Q); as well as basic amino acids such as arginine (Arg or R), lysine (Lys or K), histidine (His or H), and derivatives thereof; and acidic amino acids such as aspartic acid (Asp or D) and glutamic acid (Glu or E), and derivatives thereof. Natural hydrophobic amino acids include tryptophan (Trp or W), phenylalanine (Phe or F), isoleucine (Ile or I), leucine (Leu or L), methionine (Met or M), valine (Val or V), and derivatives thereof; as well as other non-polar amino acids such as glycine (Gly or G), alanine (Ala or A), proline (Pro or P), and derivatives thereof. Natural amino acids of intermediate polarity include serine (Ser or S), threonine (Thr or T), tyrosine (Tyr or Y), cysteine (Cys or C), and derivatives thereof. Unless specified otherwise, any amino acid described herein may be in either the D- or L-configuration. A capital letter indicates an L-enantiomer amino acid; a small letter indicates a D-enantiomer amino acid.

Other exemplary amino acids include cinnamic acids (such as aminocinnamic acids, amino-trans-cinnamic acids, amino-cis-cinnamic acids, o-amino-cinnamic acids, m-amino-cinnamic acids, p-amino-cinnamic acids, o-amino-trans-cinnamic acid, m-amino-trans-cinnamic acid, p-amino-trans-cinnamic acid, o-amino-cis-cinnamic acid, m-amino-cis-cinnamic acid, p-amino-cis-cinnamic acid), phenylglycine (Phg), 2,3-diaminobutyric acid (Dab), 2,4-diaminobutyric acid (gDab), 2,3-diaminopropionic acid (Dap), β-methylaspartate (MeAsp), cyclohexylalanine (β-Cha), norleucine (Nle), norvaline (Nvl), isonipecotic acid (Ina), pipecolic acid (homoproline) (Pip or hPro), phenylacetic acids (such as aminophenylacetic acids, diaminophenylacetic acids, triaminophenylacetic acids, o-amino-phenylacetic acid, m-amino-phenylacetic acid, p-amino-phenylacetic acid (Apa), o,o-diamino-phenylacetic acid, o,m-diamino-phenylacetic acid, o,p-diamino-phenylacetic acid, m,m-diamino-phenylacetic acid, m,p-diamino-phenylacetic acid, o,o,m-triamino-phenylacetic acid, o,o,p-triamino-phenylacetic acid, o,m,p-triamino-phenylacetic acid, m,m,p-triamino-phenylacetic acid, o,m,m-triamino-phenylacetic acid, o,o,m-triamino-phenylacetic acid), phenylpropanoic acids (such as aminophenylpropanoic acids, diaminophenylpropanoic acids, triaminophenylpropanoic acids, o-amino-phenylpropanoic acid, m-amino-phenylpropanoic acid, p-amino-phenylpropanoic acid, o,o-diamino-phenylpropanoic acid, o,m-diamino-phenylpropanoic acid, o,p-diamino-phenylpropanoic acid, m,m-diamino-phenylpropanoic acid, m,p-diamino-phenylpropanoic acid, o,o,m-triamino-phenylpropanoic acid, o,o,p-triamino-phenylpropanoic acid, o,m,p-triamino-phenylpropanoic acid, m,m,p-triamino-phenylpropanoic acid, o,m,m-triamino-phenylpropanoic acid, o,o,m-triamino-phenylpropanoic acid), 2-aminobutyric acid (Abu), sarcosine (Sar or N-methyl glycine), 6-aminohexanoic acid (Ahx), para-fluoro-Phenylalanine (p-F-Phe), γ-amino-butyric acid (GABA), benzoic acids (such as aminobenzoic acids, diaminobenzoic acids, triaminobenzoic acids, o-amino-benzoic acid, m-amino-benzoic acid, p-aminobenzoic acid (PABA), o,o-diamino-benzoic acid, o,m-diamino-benzoic acid, o,p-diamino-benzoic acid, m,m-diamino-benzoic acid, m,p-diamino-benzoic acid, o,o,m-triamino-benzoic acid, o,o,p-triamino-benzoic acid, o,m,p-triamino-benzoic acid, m,m,p-triamino-benzoic acid, o,m,m-triamino-benzoic acid, o,o,m-triamino-benzoic acid), hydrazinobenzoic acids (such as dihydrazinobenzoic acids, trihydrazinobenzoic acids, o-hydrazino-benzoic acid, m-hydrazino-benzoic acid, p-hydrazino-benzoic acid, o,o-dihydrazino-benzoic acid, o,m-dihydrazino-benzoic acid, o,p-dihydrazino-benzoic acid, m,m-dihydrazino-benzoic acid, m,p-dihydrazino-benzoic acid, o,o,m-trihydrazino-benzoic acid, o,o,p-trihydrazino-benzoic acid, o,m,p-trihydrazino-benzoic acid, m,m,p-trihydrazino-benzoic acid, o,m,m-trihydrazino-benzoic acid, o,o,m-trihydrazino-benzoic acid), homophenylalanine (homophe or hPhe), β-cyanoAlanine (β-cyano-Ala), methyl or ethyl aryl ethers of tyrosine (Tyr(Me) or Tyr(Et), respectively), aminoisobutyric acid (Aib, which is also known as α,α-dimethylglycine), S-methylcysteine (MeCys), N,N'-dimethyl-arginine ((Me)$_2$Arg), hydroxyProline (Hyp), citruline (Cit), N,N,N-trimethyllysine or N,N,N, —(CH$_3$)$_3$-lysine or γ,γ,γ-trimethyllysine ((Me)$_3$Lys), homolysine (homoLys or hLys), 5-aminopentanoic acid or aminovaleric acid (5-Ava), (S)-3-Benzo[b]thiophen-3-yl-aminopropanoic acid (L-BBTA), pyroglutamic acid (pGlu), aminothiazole acetic acids, 2-amino-thiazol-4-yl acetic acid, aminoheptanoic acids, aminooctanoic acids, aminononanoic acids, aminodecanoic acids, aminoundecanoic acids, aminododecanoic acids, 7-aminoheptanoic acid, 8-aminooctanoic acid, 9-aminononanoic acid, 10-aminodecanoic acid, 11-aminoundecanoic acid, 12-aminododecanoic acid, 3- or 4-mercaptoproline derivatives, N$^5$-acetyl-N$^5$-hydroxy-L-ornithine, α-N-hydroxyamino acids, and the like. An antimicrobial lipopeptide analog or derivative thereof may include any one or a combination of the above-noted amino acids or any one or a combination of the above-noted amino acids optionally substituted.

As used herein, "ATCC" refers to the American Type Culture Collection, Manassas, Va. 20108 (see also www.atcc.org), and "NRRL" refers to the Agriculture Research Service Culture Collection, Microbial Genomics and Bioprocessing Research Unit, National Center for Agriculture Utilization Research, Peoria, Ill. 61604 (see also nrrl.ncaur.usda.gov).

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" or "consisting essentially of" mean±15%. The use of the alternative (e.g., "or") should be understood to mean either one, both or any combination thereof of the alternatives. In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present invention.

As used herein, the term "alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include straight- or branched-hydrocarbons having from 1 to 25 carbon atoms, more preferably 5 to 20, and most preferably 10 to 18. The alkyls may have any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups comprising from 1 to 8 carbon atoms. The alkyl group may be substituted or unsubstituted.

"Alkanyl" refers to a saturated branched, straight-chain or cyclic alkyl group. Typical alkanyl groups include methanyl; ethanyl; propanyls such as propan-1-yl, propan-2-yl(isopropyl), cyclopropan-1-yl, etc.; butyanyls such as butan-1-yl, butan-2-yl (sec-butyl), 2-methyl-propan-1-yl(isobutyl), 2-methyl-propan-2-yl(t-butyl), cyclobutan-1-yl, etc.; and the like.

"Alkenyl" refers to an unsaturated branched, straight-chain, cyclic alkyl group, or combinations thereof having at least one carbon-carbon double bond derived by the removal of one hydrogen atom from a single carbon atom of a parent alkene. The group may be in either the cis or trans conformation about the double bond(s). Typical alkenyl groups include ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. The alkenyl group may be substituted or unsubstituted.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkydiyl groups include methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl, cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl or alkynyldiyl is used. In preferred embodiments, the alkyldiyl group is $(C_1$-$C_4)$alkyldiyl. Also preferred are saturated acyclic alkanyldiyl groups in which the radical centers are at the terminal carbons, e.g., methandiyl(methano); ethan-1,2-diyl (ethano); propan-1,3-diyl(propano); butan-1,4-diyl(butano); and the like (also referred to as alkylenos, defined infra).

"Alkyleno" refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno or alkyno is used. In preferred embodiments, the alkyleno group is $(C_1$-$C_6)$ or $(C_1$-$C_4)$ alkyleno. Also preferred are straight-chain saturated alkano groups, e.g., methano, ethano, propano, butano, and the like.

"Heteroalkyl, Heteroalkanyl, Heteroalkenyl, Heteroalkanyl, Heteroalkydiyl and Heteroalkyleno" refer to alkyl, alkanyl, alkenyl, alkynyl, alkydiyl and alkyleno groups, respectively, in which one or more of the carbon atoms (and any associated hydrogen atoms) are each independently replaced with the same or different heteroatoms or heteroatomic groups. Typical heteroatoms or heteroatomic groups that can be included in these groups include —O—, —S—, —Se—, —O—O—, —S—S—, —O—S—, —O—S—O—, —O—NR'—, —NR'—, —NR'—NR'—, =N—N=, —N=N—, —N=N—NR'—, —PH—, —P(=O)$_2$—, —O—P(=O)$_2$—, —SH$_2$—, —S(=O)$_2$—, —SnH$_2$— and the like, and combinations thereof, including —NR'—S (=O)$_2$—, where each R' is independently selected from hydrogen, alkyl, alkanyl, alkenyl, alkynyl, aryl, arylalkyl, heteroaryl and heteroarylalkyl, as defined herein.

"Aryl" refers to a monovalent aromatic hydrocarbon group derived by the removal of one hydrogen atom from a single carbon atom of a parent aromatic ring system. Typical aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is $(C_5$-$C_{14})$aryl, with $(C_5$-$C_{10})$ being even more preferred. Particularly preferred aryls are cyclopentadienyl, phenyl and naphthyl. The aryl group may be substituted or unsubstituted.

"Arylalkyl" refers to an acyclic alkyl group in which one of the hydrogen atoms bonded to a carbon atom, typically a terminal or sp$^3$ carbon atom is replaced with an aryl group. Typical arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl or arylalkynyl is used. In preferred embodiments, the arylalkyl group is ($C_6$-$C_{20}$)arylalkyl, e.g., the alkanyl, alkenyl or alkynyl moiety of the arylalkyl group is ($C_1$-$C_6$) and the aryl moiety is ($C_5$-$C_{14}$). In particularly preferred embodiments the arylalkyl group is ($C_6$-$C_{13}$), e.g., the alkanyl, alkenyl or alkynyl moiety of the arylalkyl group is ($C_1$-$C_3$) and the aryl moiety is ($C_5$-$C_{10}$).

"Heteroaryl" refers to a monovalent heteroaromatic group derived by the removal of one hydrogen atom from a single atom of a parent heteroaromatic ring system, which may be monocyclic or fused ring (i.e., rings that share an adjacent pair of atoms). Typical heteroaryl groups include groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-14 membered heteroaryl, with 5-10 membered heteroaryl being particularly preferred. The most preferred heteroaryl groups are those derived from thiophene, pyrrole, benzothiophene, benzofuran, indole, pyridine, quinoline, imidazole, oxazole and pyrazine. The heteroaryl group may be substituted or unsubstituted.

"Heteroarylalkyl" refers to an acyclic alkyl group in which one of the hydrogen atoms bonded to a carbon atom, typically a terminal or $sp^3$ carbon atom is replaced with a heteroaryl group. Where specific alkyl moieties are intended, the nomenclature heteroarylalkanyl, heteroarylalkenyl or heterorylalkynyl is used. In preferred embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In particularly preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

"Acyl" group refers to the C(=O)—R" group, where R" is selected preferably from hydrogen, hydroxy, alkyl, haloalkyl, cycloalkyl, aryl optionally substituted with one or more alkyl, haloalkyl, alkoxy, halo and substituted amino groups, heteroaryl (bonded through a ring carbon) optionally substituted with one or more alkyl, haloalkyl, alkoxy, halo and substituted amino groups and heteroalicyclic (bonded through a ring carbon) optionally substituted with one or more alkyl, haloalkyl, alkoxy, halo and substituted amino groups. Acyl groups include aldehydes, ketones, acids, acid halides, esters and amides. Preferred acyl groups are carboxy groups, e.g., acids and esters. Esters include amino acid ester derivatives. The acyl group may be attached to a compound's backbone at either end of the acyl group, i.e., via the C or the R". Where the acyl group is attached via the R", then C will bear another substituent, such as hydrogen, alkyl, and the like.

"Substituted" refers to a group in which one or more hydrogen atoms are each independently replaced with the same or different substituent(s). Typical substituents include —X, —$R^{13}$, —O—, =O, —OR, —$SR^{13}$, —S—, =S, —$NR^{13}R^{13}$, =$NR^{13}$, $CX_3$, —$CF_3$, —CN, —OCN, —SCN, —NO, $NO_2$, =$N_2$, —$N_3$, —S(=O)$_2$O—, —S(=O)$_2$OH, —S(=O)$_2R^{13}$, —OS(=O)$_2$O—, —OS(=O)$_2$OH, —OS(=O)$_2R^{13}$, —P(=O)(O$^-$)$_2$, —P(=O)(OH)(O$^-$), —OP(=O)$_2$(O$^-$), —C(=O)$R^{13}$, —C(=S)$R^{13}$, —C(=O)$OR^{13}$, —C(=O)O$^-$, —C(=S)$OR^{13}$, —$NR^{13}$—C(=O)—N($R^{13}$)$_2$, —$NR^{13}$—C(=S)—N($R^{13}$)$_2$, and —C(=$NR^{13}$)$NR^{13}R^{13}$, wherein each X is independently a halogen; each $R^{13}$ is independently hydrogen, halogen, alkyl, aryl, arylalkyl, arylaryl, arylheteroalkyl, heteroaryl, heteroarylalkyl $NR^{14}R^{14}$, —C(=O)$R^{14}$, and —S(=O)$_2R^{14}$; and each $R^{14}$ is independently hydrogen, alkyl, alkanyl, alkynyl, aryl, arylalkyl, arylheteralkyl, arylaryl, heteroaryl or heteroarylalkyl. Aryl containing substituents, whether or not having one or more sustitutions, may be attached in apara (p-), meta (m-) or ortho (o-) conformation, or any combination thereof.

"Pharmaceutically acceptable salt" refers to a salt of a compound of the invention that is pharmaceutically acceptable and that possesses the desired pharmacological activity of the parent compound. Such salts include the following: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, and the like.

In another aspect, any of the aforementioned compounds may have a core peptide that is derived from aspartocin. Naturally occurring aspartocin varies from naturally occurring amphomycin only in the acyl tail region. Generally, compounds of the instant invention may have the naturally occurring acyl tail, or a different (non-natural) acyl tail may be attached to the core peptide of amphomycin or aspartocin. Derivative lipopeptide compounds of the instant disclosure having a core peptide of aspartocin are made by similar or identical methods used to make derivative of amphomycin core peptide, and vary only in the source of the starting material, which is derived from a different *Streptomyces* species (e.g., *Streptomyces canus* produces amphomycin and *Streptomyces griseus* produces aspartocin). As used herein, any general description of the synthesis of lipopeptide derivatives of the invention, "amphomycin-based" should be understood to be interchangeably replaceable with "aspartocin-based" without altering the scope of the invention, unless otherwise indicated.

The following substituents are also designated herein by the following abbreviations, including cyclohexyl (cHex or cHexyl), picolinic acid (Pla), 2-pyrazine carboxylic acid (Pca), Acetyl (Ac), succinic Acid (Suc). In the naming of compounds listed in the examples, the substituent listed in front of "Amphomycin" (or "Aspartocin") indicates a substituent, such as an acyl tail or an amino acid, is attached at amino-terminus of the core peptide, while the substituent listed after "Amphomycin-9-" indicates a substituent attached at the Dab9 position of the peptide core. In addition, the short form $C_n$ (e.g., $C_{10}$, $C_{12}$, $C_{15}$) refers to a compound comprising a linear carbon chain, such as an acyl tail, with n carbon atoms. In the example of an acyl tail, the $C_n$ designation can equally describe an acyl tail by way of the following exemplary structural formula: $C_n$=CH$_3$—(CH$_2$)$_i$—C(=O)—, in which i=n−2. In a specific example, a $C_{15}$ designation for an acyl tail refers to the following structural formula: CH$_3$—(CH$_2$)$_{13}$—C(=O)—. As noted above, small italicized "o", "m" or "p" in the name of a compound refers to ortho, meta and para substitution positions, respectively. Ph, as used herein, refers to a phenyl ring, and -OSu refers to a succinimide activated compound, such as an amino acid (e.g., Ala-OSu), which can be produced with a reaction as described herein (see, for example, Example 1) or can be purchased commercially (such as from Bachem California Inc., Torrance, Calif.).

Lipopeptide Antibiotics and Derivatives Thereof

As noted above, the present invention provides lipopeptide antibiotic derivatives, pharmaceutically acceptable salts thereof, and uses thereof. The lipopeptide antibiotic derivatives of the present invention include a "core cyclic peptide" (also referred to as "core macrocyclic peptide" herein) and an amino-terminal lipophilic substituent. The "core cyclic peptide" refers to the cyclic peptide portion or cyclic depsipeptide of a lipophilic antibiotic that remains after the amino-terminal lipophilic substituent has been removed, which may include one or more exocyclic amino acids. The lipopeptide antibiotic derivatives of the present invention may have a lipophilic substituent attached to the core cyclic peptide (1) directly (e.g., as an amido or amino lipophilic substituent), (2) via one or more intervening exocyclic amino acids, or (3) via a "linker" (L) either directly to the core cyclic peptide or via one or more intervening exocyclic amino acids, as described herein. In a preferred embodiment, a "core cyclic peptide" is derived from A1437, aspartocin or amphomycin, and more preferably from aspartocin or amphomycin.

Common amphomycin-type lipopeptide antibiotics include amphomycin (glumamycin) (Heinemann et al., 1953, *Antibiot. Chemother.* 3: 1239-1242; Fujino et al., 1965, *Bull. Chem. Soc. Jap.* 38: 515; Bodanszky et al., 1973, *J. Am. Chem. Soc.* 95: 2352; Shibata et al., U.S. Pat. No. 3,160,561); aspartocin (Shay et al., U.S. Pat. No. 3,057,779; Shay et al., 1960, *Antibiotics Ann.* 194; Hausman et al., 1964, *Antimicrob. Ag. Chemother.* 352; Hausman et al., 1969, *J. Antibiotics* 22: 207; Martin et al., 1960, *J. Am. Chem. Soc.* 2079); crystallomycin (Gauze et al., 1957, *Antibiotiki* 2: 9-14); antibiotic A1437 (Hammann et al., EP 0 629 636 B1; Hammann et al., U.S. Pat. No. 6,194,383; Lattrell et al., U.S. Pat. No. 5,629,288); friulimycin (Vertesy et al., 2000, *J. Antibiotics* 53: 816); tsushimycin (Shoji et al., 1968, *J. Antibiotics* 21: 439; Nishimura et al., U.S. Pat. No. 3,781,420); and zaomycin (Hinuma, 1954, *J. Antibiotics* 7(4): 134-136; Kuroya, 1960, *Antibiotics Ann.* 194; Kuroya, J P 8150). The amphomycin-type lipopeptide antibiotics display their antibiotic activity against Gram-positive bacteria, such as, for example, *Streptococci*, *Staphylococci* and *Enterococci* and consist of a macrocyclic peptide "core" acylated at its amino-terminus with a lipophilic fatty acid.

Examples of other lipopeptide antibiotics useful in combination with compounds of the invention, or useful to derivatize with the methods of the instant invention, include laspartomycin (Umezawa et al., U.S. Pat. No. 3,639,582; Naganawa et al., 1968, *J. Antibiot.*, 21, 55; Naganawa et al., 1970, *J. Antibiot.*, 23, 423), brevistin (Shoji et al., 1976, *J. Antibiotics*, 29, 380), cerexin A (Shoji et al., 1976, *J. Antibiotics*, 29, 1268), cerexin B (Shoji et al., 1976, *J. Antibiotics*, 29, 1275), daptomycin (Debono et. al., 1988, *J. Antibiotics*, 41, 1093), Antibiotic A-30912 (Hoehn et al., U.S. Pat. No. 5,039,789), Antibiotic A-54145 (Fukada et al., U.S. Pat. No. 5,039,789; Boeck et al., 1990, *J. Antibiotics*, 43, 587), and Antibiotic A-21978C (Debono et al., 1988, *J. Antibiotics*, 41, 1093).

As used herein, "amphomycin lipopeptide antibiotic" or "aspartocin lipopeptide antibiotic" refers to an antibiotic comprising a macrocyclic peptide core that includes an amino acid having a side chain with a primary amino group, such as a Dab residue, and a lipophilic substituent, such as a fatty acid moiety. An amphomycin or aspartocin core macrocyclic peptide includes at least one exocyclic amino acid, which is generally an Asn or an Asp. The exocyclic amino acid(s) can be sandwiched between the cyclic peptide and the lipophilic substituent, or between the cyclic peptide and a linker having an attached lipophilic substituent. In certain aspects of the invention, R refers to an amphomycin or aspartocin core cyclic peptide, which is illustrated as follows:

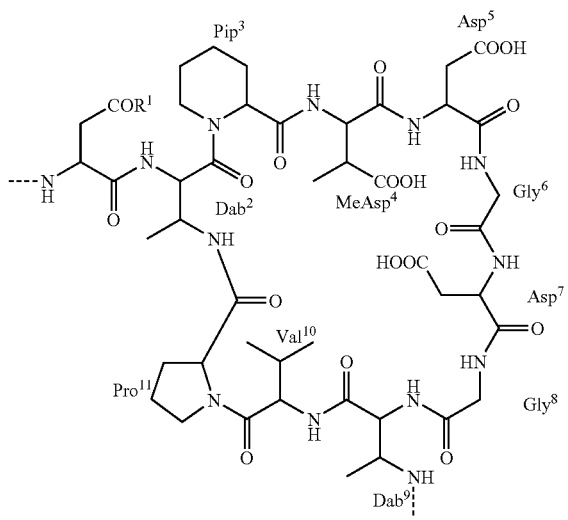

In the above core cyclic peptide moiety, the dashed line emanating from the exocyclic amino acid indicates the point of attachment of, for example, a linker L, one or more additional exocyclic amino acids, a lipophilic substituent, or any combination thereof. The dashed line emanating from residue Dab$^9$ indicates the point of attachment of, for example, a linker L, one or more additional exocyclic amino acids, a lipophilic substituent, or any combination thereof, as described herein. Alternatively, the above core cyclic peptide moiety is equivalently and interchangeably illustrated as follows (wherein the amino terminus of the core cyclic peptide is now on the right hand side of the illustration):

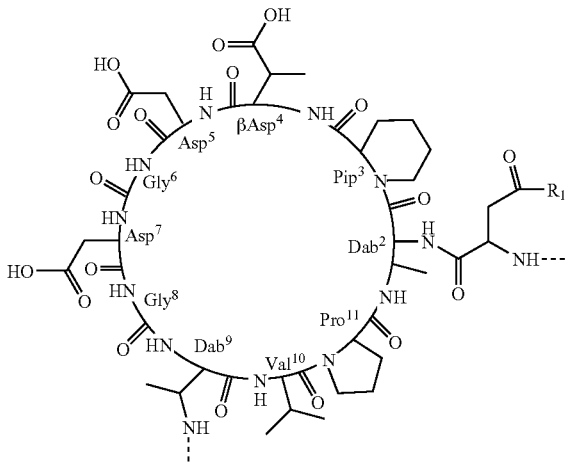

In certain embodiments, $R_1$ of the core cyclic peptide moiety will be —OH (i.e., the exocyclic amino acid is Asp), and such a compound can be referred to by its IUPAC name (CRC Handbook of Chemistry and Physics, CRC Press, Inc., Boca Raton, Fla., Weast, R. C, (ed.) and references therein) as follows: 3-Amino-N-[16-(1-amino-ethyl)-31-(1-carboxy-ethyl)-22,28-bis-(carboxymethyl)-13-isopropyl-4-methyl-2, 6,12,15,18,21,24,27,30,33-decaoxo-1,5,11,14,17,20,23,26, 29,32-decaaza-tricyclo[32.4.0.0$^{7,11}$]octatriacont-3-yl]-succinamic acid.

The tricyclic, macrocyclic core of this peptide is named "2,6,12,15,18,21,24,27,30,33-decaoxo-1,5,11,14,17,20,23, 26,29,32-decaaza-tricyclo[32.4.0.0$^{7,11}$]octatriacontane", in which Pro$^{11}$ represents one ring, Pip$^3$ represents another ring, and the cyclic lactam core of the cyclic peptide represents the third, 31 membered ring. The positions of each of the nitrogens of the tricyclic core are at positions 1, 5, 11, 14, 17, 20, 23, 26, 29, and 32. The positions of each of the carbonyls of the tricyclic core are at positions 2, 6, 12, 15, 18, 21, 24, 27, 30, and 33. The nitrogens and carbonyls, each taken together, represent the amide bonds of the cyclic peptide core. The carbons at positions 3, 7, 13, 16, 19, 22, 25, 28, 31 and 34 are the α-carbons of the amino acids making up the core cyclic peptide. The carbon atom at position 4 is the β-carbon of the sidechain of Dab$^2$, which forms the cyclic lactam by cyclizing with the carboxy terminus of the lipopeptide.

The β-methyl sidechain of Dab$^2$ is at position 4, and is referred to as "4-methyl". The α-nitrogen of Dab$^2$ is referred to as a "3-Amino" substituent at the 3-position. The "N-[" portion and the "]-succinamic acid" portion represent the Asp$^1$ amino acid (i.e., when $R_1$ is —OH), which can be the point of substitution of, for example, acyl tails (i.e., at Asp$^1$). The sidechain of β-Asp$^4$ is referred to as "1-carboxyethyl" at the 31 position of the tricyclic core. The sidechains of Asp$^5$ and Asp$^7$ are referred to as "bis-carboxymethyl" at the 28 and 22 positions of the tricyclic core, respectively. The sidechain of Val$^{10}$ is referred to as the "isopropyl" at the 13 position of the tricyclic core. Lastly, the Dab$^9$ sidechain is referred to as "1-aminoethyl" at the 16 position of the tricyclic core, which can be the point of substitution for Dab$^9$ substituents. It should be understood that the name would be identical for a core cyclic lipopeptide wherein $R_1$ is $NH_2$ (i.e., when the exocyclic amino acid is Asn), except that "succinamic acid" would be replaced by "succinamide".

By way of example, compound $C_{15}$-amphomycin-9-(β-Ala), would be named "3-(pentadecanoyl)amino-N-[16-[1-(3-amino-propionylamino)-ethyl]-31-(1-carboxy-ethyl)-22, 28-bis-(carboxymethyl)-13-isopropyl-4-methyl-2,6,12,15, 18,21,24,27,30,33-decaoxo-1,5,11,14,17,20,23,26,29,32-decaaza-tricyclo[32.4.0.0$^{7,11}$]octatriacont-3-yl]-succinamic acid", wherein two substituents, the acyl tail $C_{15}$ group (referred to as "pentadecanoyl") and the Dab$^9$ β-Ala group (referred to as ["1-(3-amino-propionylamino)-ethyl]"), are highlighted in bold for clarity.

In one embodiment, an amphomycin-based lipopeptide antibiotic is characterized by the following structure I:

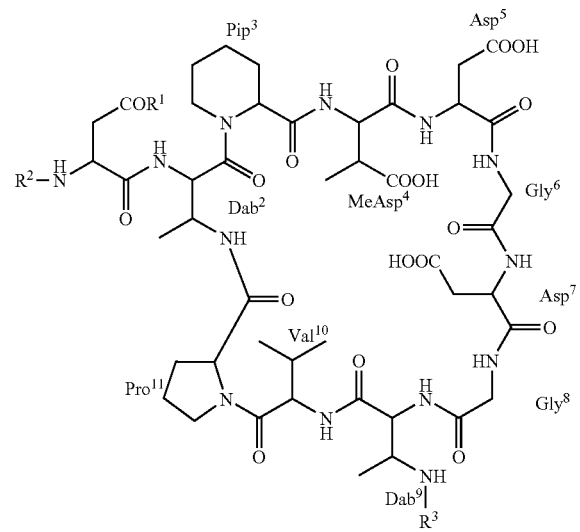

wherein:

$R^1$ is OH or $NH_2$; and
each of $R^2$ and $R^3$ are independently selected from hydrogen, —OR$^4$, —SR$^4$, NR$^4$R$^4$, —CN, —NO$_2$, —N$_3$, —C(=O)OR$^4$, —C(=O)R$^4$, —C(=O)NR$^4$R$^4$, —C(=S)NR$^4$R$^4$, —C(=NR$^4$)NR$^4$R$^4$, —C(=O)H, —R$^4$C(=O), —SO$_2$R$^4$, —S(=O)R$^4$, —P(=O)(OR$^4$)$_2$, —P(=O)(OR$^4$), —CO$_2$H, —SO$_3$H, —PO$_3$H, halogen, trihalomethyl, (C$_1$-C$_{25}$)alkyl, substituted (C$_1$-C$_{25}$)alkyl, (C$_1$-C$_{25}$)heteroalkyl, substituted (C$_1$-C$_{25}$) heteroalkyl, (C$_5$-C$_{10}$)aryl, substituted (C$_5$-C$_{10}$)aryl, (C$_5$-C$_{15}$)arylaryl, substituted (C$_5$-C$_{15}$)arylaryl, (C$_5$-C$_{15}$) biaryl, substituted (C$_5$-C$_{15}$)biaryl, 5-10 membered heteroaryl, substituted 5 to 10 membered heteroaryl, (C$_6$-C$_{26}$)arylalkyl, substituted (C$_6$-C$_{26}$)arylalkyl, 6 to 26 membered heteroarylalkyl, substituted 6 to 26 membered heteroarylalkyl, amino acid or substituted amino acid. Some exemplary and independently selected substitutions include —OR$^4$, —SR$^4$, NR$^4$R$^4$, —CN, —NO$_2$, —N$_3$, —C(=O)OR$^4$, —C(=O)R$^4$, —C(=O) NR$^4$R$^4$, —C(=S)NR$^4$R$^4$, —C(=NR$^4$)NR$^4$R$^4$, —C(=O)H, —R$^4$C(=O), —SO$_2$R$^4$, —S(=O)R$^4$, —P(=O)(OR$^4$)$_2$, —P(=O)(OR$^4$), —CO$_2$H, —SO$_3$H, —PO$_3$H, halogen, and trihalomethyl; wherein each R$^4$ is independently selected from hydrogen, (C$_1$-C$_{10}$)alkyl, (C$_5$-C$_{10}$)aryl, 5 to 10 membered heteroaryl, (C$_6$-C$_{16}$) arylalkyl and 6 to 16 membered heteroarylalkyl, a branched or straight-chained, saturated or singly or multiply unsaturated aliphatic or hydroxy aliphatic moiety having a chain length of from 6 to 25 carbon atoms, a primary or secondary amine, at least one amino acid, at least one substituted amino acid, and any combination thereof; with the proviso that R$^2$ and R$^3$ cannot both be hydrogen.

In certain embodiments, structure (I) intermediates are provided wherein R$^1$ is OH or NH$_2$; R$^2$ is hydrogen; and R$^3$ has a protecting group, such as protected amino acids Gly, Sar, β-Alanine, Gly-Lys or Sar-Lys.

In another embodiment, an amphomycin-based lipopeptide antibiotic is characterized by the following structure II:

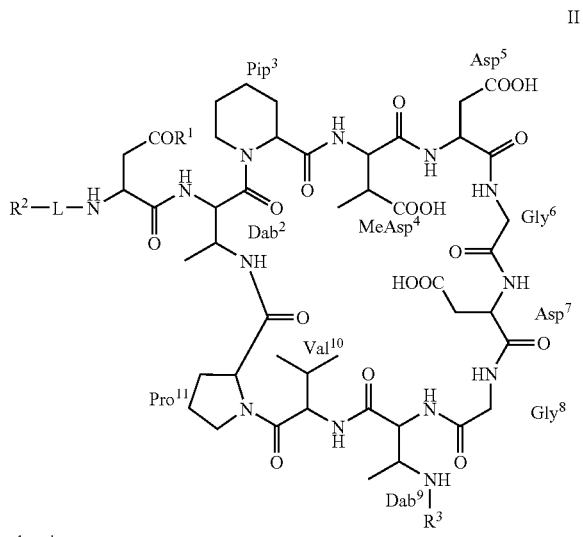

wherein:

$R^1$ is OH or $NH_2$;

L is selected from at least one amino acid or substituted amino acid, —C(=O)—, —R'C(=O)—, —$SO_2$, —C(=S)—, —P(=O)—, —OP(=O)—, —OC(=O)—, —R'OC(=O)(NR'R")—, —NHC(=O)—, —O-PhC(=O)—, or —NR'C(=O)—; and each of $R^2$ and $R^3$ are independently selected from hydrogen, —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)($OR^4$)$_2$, —P(=O)($OR^4$), —$CO_2$H, —$SO_3$H, —$PO_3$H, halogen, trihalomethyl, ($C_1$-$C_{25}$)alkyl, substituted ($C_1$-$C_{25}$)alkyl, ($C_1$-$C_{25}$)heteroalkyl, substituted ($C_1$-$C_{25}$) heteroalkyl, ($C_5$-$C_{10}$) aryl, substituted ($C_5$-$C_{10}$)aryl, ($C_5$-$C_{15}$)arylaryl, substituted ($C_5$-$C_{15}$)arylaryl, ($C_5$-$C_{15}$) biaryl, substituted ($C_5$-$C_{15}$)biaryl, 5-10 membered heteroaryl, substituted 5-10 membered heteroaryl, ($C_6$-$C_{26}$)arylalkyl, substituted ($C_6$-$C_{26}$)arylalkyl, 6 to 26 membered heteroarylalkyl, substituted 6 to 26 membered heteroarylalkyl, at least one amino acid, or at least one substituted amino acid. Some exemplary and independently selected substitutions include —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)($OR^4$)$_2$, —P(=O)($OR^4$), —$CO_2$H, —$SO_3$H, —$PO_3$H, halogen, and trihalomethyl; wherein each $R^4$ is independently selected from hydrogen, ($C_1$-$C_{10}$)alkyl, ($C_5$-$C_{10}$)aryl, 5 to 10 membered heteroaryl, ($C_6$-$C_{16}$)arylalkyl and 6 to 16 membered heteroarylalkyl, a branched or straight-chained, saturated or singly or multiply unsaturated aliphatic or hydroxy aliphatic moiety having a chain length of from 6 to 25 carbon atoms, a primary or secondary amine, at least one amino acid, and any combination thereof; and each of R' and R" are independently one or more of the same or different substituents defined for $R^2$, $R^3$, or $R^4$; with the proviso that $R^2$ and $R^3$ cannot both be hydrogen.

In a preferred embodiment, structure (II) is provided wherein:

$R^1$ is OH or $NH_2$;

L is selected from at least one amino acid, at least one substituted amino acid, —R'C(=O)—, —R'OC(=O)(NR')—, and —O-PhC(=O)—, wherein R' is independently one or more of the same or different substituents as defined for $R^3$ or $R^5$ as described herein;

$R^2$ is independently selected from —C(=O)$R^5$, —C(=O)$OR^5$, —C(=O)$NHR^4$, —C(=O)$NR^4R^4$, —C(=S)$NHR^4$, —C(=S)$NR^4R^4$, —C(=$NR^4$)$NHR^4$, and —C(=$NR^4$)$NR^4R^4$;

$R^3$ is independently selected from —$OR^5$, —$SR^5$, $NR^5R^5$, —CN, —$NO_2$, —$N_3$, —C(=O)$R^5$, —C(=O)$OR^5$, —C(=O)$NR^5R^5$, —C(=S)$NR^5R^5$, —C(=$NR^5$)$NR^5R^5$, —C(=O)H, —$R^5$C(=O), —$SO_2R^5$, —S(=O)$R^5$, —P(=O)($OR^5$)$_2$, —P(=O)($OR^5$), —$CO_2$H, —$SO_3$H, —$PO_3$H, halogen, trihalomethyl, ($C_1$-$C_{25}$)alkyl, substituted ($C_1$-$C_{25}$)alkyl, ($C_1$-$C_{25}$)heteroalkyl, substituted ($C_1$-$C_{25}$)heteroalkyl, ($C_5$-$C_{10}$)aryl, substituted ($C_5$-$C_{10}$)aryl, ($C_5$-$C_{15}$)arylaryl, substituted ($C_5$-$C_{15}$)arylaryl, ($C_5$-$C_{15}$)biaryl, substituted ($C_5$-$C_{15}$)biaryl, 5 to 10 membered heteroaryl, substituted 5 to 10 membered heteroaryl, ($C_6$-$C_{26}$)arylalkyl, substituted ($C_6$-$C_{26}$)arylalkyl, 6 to 26 membered heteroarylalkyl, substituted 6 to 26 membered heteroarylalkyl, at least one amino acid, and at least one substituted amino acid; and wherein each $R^4$ is independently selected from ($C_7$-$C_{10}$) alkyl, ($C_{17}$-$C_{26}$)arylalkyl and 17 to 26 membered heteroarylalkyl, a branched or straight-chained, saturated or singly or multiply unsaturated aliphatic or hydroxy aliphatic moiety having a chain length of from 7 to 25 carbon atoms, a primary or secondary amine, at least one amino acid, and at least one substituted amino acid; and wherein each $R^5$ is independently selected from hydrogen, ($C_1$-$C_{10}$)alkyl, ($C_5$-$C_{10}$)aryl, 5 to 10 membered heteroaryl, ($C_6$-$C_{26}$)arylalkyl and 6 to 26 membered heteroarylalkyl, a branched or straight chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof.

In certain embodiments, $R^2$ is —C(=O)$OR^5$ or —C(=O)$R^5$, or that is —C(=O)$NHR^4$, —C(=S)$NHR^4$, or —C(=$NR^4$)$NHR^4$. In still other embodiments, $R^3$ is at least one amino acid selected from glycine, β-alanine, sarcosine, lysine, or any combination thereof, or is at least one amino acid selected from Gly, β-alanine, GABA, 5-aminopentanoic acid, 6-aminohexanoic acid, Lys, gDab, Sar, Orn, Dap, hLys, or any combination thereof. In related embodiments, the $R^3$ amino acid includes two amino acids, such as glycine-lysine or sarcosine-lysine. Preferably, $R^3$ is amino acid glycine or β-alanine. In certain embodiments, $R^2$ and $R^3$ are optionally substituted with a straight chain saturated aliphatic or hydroxy aliphatic moiety having a chain length of from 10 to 15 carbon atoms. In particular embodiments wherein structure (II) intermediates are preferred, any of the aforementioned compounds are provided wherein $R^3$ further comprises at least one protecting group, as described herein.

In some embodiments, L of structure (II) is at least one amino acid or at least one substituted amino acid. For example, the amino acids or substituted amino acids may be p-aminophenylacetyl, (p-aminophenylpropanoyl)$_n$ wherein n is 1 or 2, m-aminophenylacetyl, (m-aminophenylpropanoyl)$_n$ wherein n is 1 or 2, o-aminophenylacetyl, (o-aminophenylpropanoyl)$_n$ wherein n is 1 or 2, GABA, p-aminobenzoic acid (PABA), m-aminobenzoic acid, o-aminobenzoic acid, p-hydrazinobenzoic acid, m-hydrazinobenzoic acid, o-hydrazinobenzoic acid, p-amino-trans-cinnamyl, m-amino-trans-cinnamyl, o-amino-trans-cinnamyl, L-BBTA, or any combination thereof. Preferably, L is p-aminophenylacetyl, PABA, m-aminobenzoic acid, o-aminobenzoic acid, p-amino-trans-cinnamyl, m-amino-trans-cinnamyl, o-amino-trans-cinnamyl, or any combination thereof. In certain preferred embodiments, the instant disclosure provides certain anitmicorbial lipopeptide compounds useful, for example, in treating or preventing microbial infections. Exemplary derivatives of structure (II) compounds include compounds 91, 331, 332, 86, 87, 280 or 89. In a preferred embodiment, the invention provides compound 280.

In still another embodiment, an amphomycin-based lipopeptide antibiotic is characterized by the following structure II:

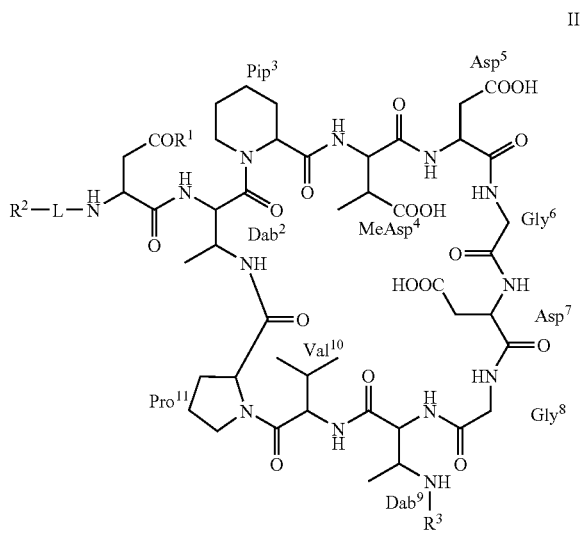

wherein:

$R^1$ is OH or $NH_2$;

L is selected from at least one amino acid, at least one substituted amino acid, —R'C(=O)—, and —R'OC(=O)(NR')—, wherein R' is independently one or more of the same or different substituents as defined for $R^2$ or $R^5$;

$R^2$ is selected from —$OR^5$, —$SR^5$, $NR^5R^5$, —C(=O)$OR^5$, —C(=O)$R^5$, —C(=O)$NHR^4$, —C(=O)$NR^4R^4$, —C(=S)$NHR^4$, —C(=S)$NR^4R^4$, —C(=$NR^4$)$NHR^4$, —C(=$NR^4$)$NR^4R^4$, —$R^5$C(=O), —$SO_2R^5$, —S(=O)$R^5$, —P(=O)($OR^5$)$_2$, —P(=O)($OR^5$), —$CO_2H$, —$SO_3H$, —$PO_3H$, halogen, and trihalomethyl;

$R^3$ is hydrogen;

wherein each $R^4$ is independently selected from ($C_7$-$C_{10}$)alkyl, ($C_{17}$-$C_{26}$)arylalkyl and 17 to 26 membered heteroarylalkyl, a branched or straight-chained, saturated or singly or multiply unsaturated aliphatic or hydroxy aliphatic moiety having a chain length of from 7 to 25 carbon atoms, a primary or secondary amine, at least one amino acid, and at least one substituted amino acid; and wherein each $R^5$ is independently selected from hydrogen, ($C_1$-$C_{10}$)alkyl, ($C_5$-$C_{10}$)aryl, 5 to 10 membered heteroaryl, ($C_6$-$C_{26}$)arylalkyl and 6 to 26 membered heteroarylalkyl, a branched or straight-chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof.

In certain embodiments, $R^2$ is —C(=O)$R^5$, —C(=O)$NHR^4$, —C(=S)$NHR^4$, or —C(=$NR^4$)$NHR^4$. In other embodiments, $R^5$ is a 10 to 20 membered heteroarylalkyl, or a straight chain saturated aliphatic or hydroxy aliphatic moiety having a chain length of from 5 to 17 carbon atoms. In yet other embodiments, $R^4$ is a straight chain saturated aliphatic or hydroxy aliphatic moiety having a chain length of from 8 to 16 carbon atoms. In some embodiments, L is at least one amino acid or substituted amino acid, such as glycine, sarcosine, phenylglycine, phenylalanine, O-methyl-aspartic acid, O-t-butyl-aspartic acid, p-aminobenzoic acid (PABA), m-aminobenzoic acid, p-hydrazino-benzoic acid, p-aminophenylpropanoic acid, (p-amino-phenylpropanoic acid)$_n$ wherein n is 1 or 2, L-BBTA, m-amino-phenylacetic acid, p-amino-phenylacetic acid (Apa), p-amino-trans-cinnamic acid, o-aminobenzoic acid, o,o-diamino benzoic acid, o,m-diamino benzoic acid, o,p-diaminobenzoic acid, m,p-diaminobenzoic acid, m,m-diaminobenzoic acid, o-amino-phenylacetic acid, m-amino-phenylacetic acid, p-amino-phenylacetic acid (Apa), aminothiazole acetic acid, or any combination thereof. Preferably L is m-aminobenzoic acid, o-aminobenzoic acid, m,m-diaminobenzoic acid, aminothiazole acetic acid, or PABA, most preferably L is PABA.

In still other embodiments, $R^3$ is at least one amino acid selected from Gly, β-alanine, GABA, 5-aminopentanoic acid, 6-aminohexanoic acid, Lys, gDab, Sar, Orn, Dap, or hLys. Alternatively, when providing intermediates of structure (II) derivatives, $R^3$ further comprises at least one protecting group.

In preferred embodiments, antimicrobial compounds of the disclosure are capable of treating or preventing a microbial infection, such as that caused by a Gram-positive bacterium. Exemplary compounds include 21, 85, 103, 104, 105, 106, 107, 108, 109, 110, 111, 112, 113, 115, 116, 117, 118, 119, 120, 122, 123, 254, 281, 282, 283, 284, 285, 286, 287, 288, 289, 290, 291, 292, 293, 294, 295, 296, 297, 300, 301, 302, 303, 304, 305, 306, 307, 310, 311, 312, 313, 314, 315, 316, 317, 319, 320, 321, 337, 344, 345, 346, 358, 359, 360, 361, 362, and 374. In certain preferred embodiments, lipopeptide derivatives of the instant invention include compound 85 or 108 or 119.

In another embodiment, an amphomycin-based lipopeptide antibiotic is characterized by the following structure III:

III

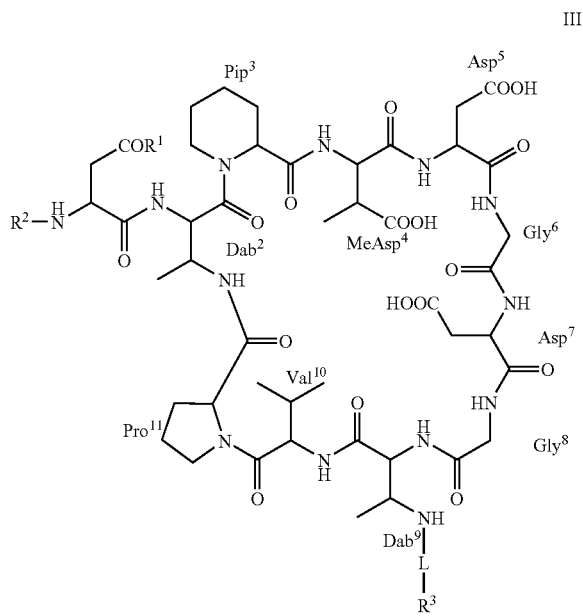

wherein:

$R^1$ is OH or $NH_2$;

L is selected from at least one amino acid or substituted amino acid, —C(=O)—, —R'C(=O)—, —$SO_2$, —C(=S)—, —P(=O)—, —OP(=O)—, —OC(=O)—, —R'OC(=O)(NR'R")—, —NHC(=O)—, —O-PhC(=O)—, or —NR'C(=O)—; and each of $R^2$ and $R^3$ are independently selected from hydrogen, —$OR^4$, —$SR^4$, $NR^4R^4$, —CN, —$NO_2$, —$N_3$, —C(=O)$OR^4$, —C(=O)$NR^4R^4$, —C(=S)$NR^4R^4$, —C(=$NR^4$)$NR^4R^4$, —C(=O)H, —$R^4$C(=O), —$SO_2R^4$, —$SOR^4$, —P(=O)$(OR^4)_2$, —P(=O)$(OR^4)$, —$CO_2H$, —$SO_3H$, —$PO_3H$, halogen, trihalomethyl, $(C_1-C_{25})$alkyl, substituted $(C_1-C_{25})$alkyl, $(C_1-C_{25})$heteroalkyl, substituted $(C_1-C_{25})$heteroalkyl, $(C_5-C_{10})$aryl, substituted $(C_5-C_{10})$aryl, $(C_5-C_{15})$arylaryl, substituted $(C_5-C_{15})$arylaryl, $(C_5-C_{15})$biaryl, substituted $(C_5-C_{15})$biaryl, 5 to 10 membered heteroaryl, substituted 5-10 membered heteroaryl, $(C_6-C_{26})$arylalkyl, substituted $(C_6-C_{26})$arylalkyl, 6 to 26 membered heteroarylalkyl, substituted 6 to 26 membered heteroarylalkyl, natural amino acids, non-natural amino acids, and substituted natural and non-natural amino acids. Some exemplary and independently selected substitutions include —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)$(OR^4)_2$, —P(=O)$(OR^4)$, —$CO_2H$, —$SO_3H$, —$PO_3H$, halogen, and trihalomethyl; wherein each $R^4$ is independently selected from hydrogen, $(C_1-C_{10})$alkyl, $(C_5-C_{10})$aryl, 5 to 10 membered heteroaryl, $(C_6-C_{16})$arylalkyl and 6 to 16 membered heteroarylalkyl, a branched or straight-chained, saturated or singly or multiply unsaturated aliphatic or hydroxy aliphatic moiety having a chain length of from 6 to 25 carbon atoms, a primary or secondary amine, at least one amino acid, at least one substituted amino acid, and any combination thereof; and each R' and R" are independently one or more of the same or different substituents defined for $R^2$, $R^3$, or $R^4$; with the proviso that $R^2$ and $R^3$ cannot both be hydrogen.

In certain embodiments, structure (III) intermediates are provided wherein $R^1$ is OH or $NH_2$; L is an amino acid selected from Gly and Sar; $R^2$ is hydrogen; and $R^3$ is an amino acid with a protecting group, such as Lys.

In another embodiment, an amphomycin-based lipopeptide antibiotic is characterized by the following structure IV:

IV

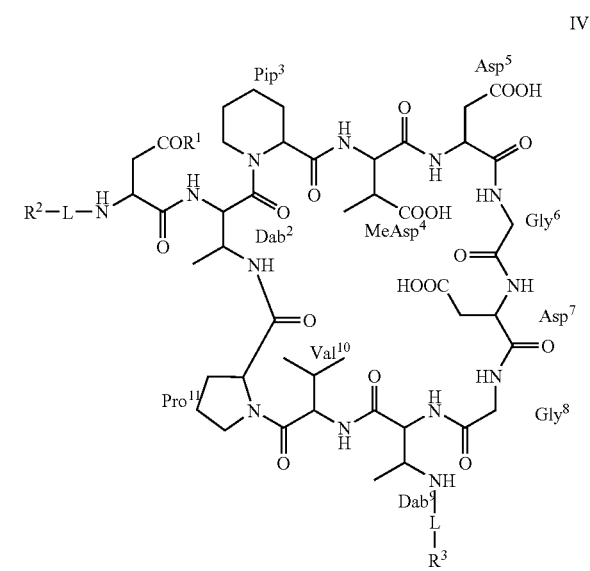

wherein:

$R^1$ is OH or $NH_2$;

L is selected from at least one amino acid or substituted amino acid, —C(=O)—, —R'C(=O)—, —OC(=O)—, —C(=O)R'—, —$SO_2$, —C(=S)—, —P(=O)—, —OP(=O)—, —R'OC(=O)(NR'R")—, —NHC(=O)—, —O-PhC(=O)—, or —NR'C(=O)—; and each of $R^2$ and $R^3$ are independently selected from hydrogen, —$OR^4$, —$SR^4$, $NR^4R^4$, —CN, —$NO_2$, —$N_3$, —C(=O)$OR^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)$(OR^4)_2$, —P(=O)$(OR^4)$, —$CO_2H$, —$SO_3H$, —$PO_3H$, halogen, trihalomethyl, $(C_1-C_{25})$alkyl, substituted $(C_1-C_{25})$alkyl, $(C_1-C_{25})$heteroalkyl, substituted $(C_1-C_{25})$heteroalkyl, $(C_5-C_{10})$aryl, substituted $(C_5-C_{10})$aryl, $(C_5-C_{15})$arylaryl, substituted $(C_5-C_{15})$arylaryl, $(C_5-C_{15})$biaryl, substituted $(C_5-C_{15})$biaryl, 5 to 10 membered heteroaryl, substituted 5-10 membered heteroaryl, $(C_6-C_{26})$arylalkyl, substituted $(C_6-C_{26})$arylalkyl, 6 to 26 membered heteroarylalkyl, substituted 6 to 26 membered heteroarylalkyl, at least one amino acid or substituted amino acid. Some exemplary and independently selected substitutions include —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)$(OR^4)_2$, —P(=O)$(OR^4)$, —$CO_2H$, —$SO_3H$, —$PO_3H$, halogen, and trihalomethyl; wherein each $R^4$ is independently selected from hydrogen, $(C_1-C_{10})$alkyl, $(C_5-C_{10})$aryl, 5 to 10 membered heteroaryl, $(C_6-C_{16})$arylalkyl and 6 to 16 membered heteroarylalkyl, a branched or straight-chained, saturated or singly or multiply unsaturated aliphatic or hydroxy aliphatic moiety having a chain length of from 6 to 25 carbon atoms, a primary or secondary amine, at least one amino acid or substituted amino acid, and any combination thereof; and each of R' are independently one or more of the same or different substituents defined for $R^2$, $R^3$, or $R^4$; with the proviso that $R^2$ and $R^3$ cannot both be hydrogen.

In a preferred embodiment, an amphomycin-based or aspartocin-based lipopeptide antibiotic of structure (IV) wherein $R^1$ is OH or $NH_2$;

L is independently selected from at least one amino acid, at least one substituted amino acid, —C(=O)—, —R'C(=O)—, —$SO_2$, —C(=S)—, —P(=O)—, —OP(=O)—, —OC(=O)—, —R'OC(=O)(NR')—, —NHC(=O)—, —O-PhC(=O)—, and —NR'C(=O)—, with the proviso that L at $Dab^9$ is —C(=O)—, wherein R' is independently one or more of the same or different substituents as defined for $R^2$, $R^3$ or $R^4$;

$R^2$ is selected from —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)($OR^4$)$_2$, —P(=O)($OR^4$), —$CO_2H$, —$SO_3H$, —$PO_3H$, halogen, trihalomethyl, ($C_1$-$C_{25}$)alkyl, substituted ($C_1$-$C_{25}$)alkyl, ($C_1$-$C_{25}$)heteroalkyl, substituted ($C_1$-$C_{25}$)heteroalkyl, ($C_5$-$C_{10}$)aryl, substituted ($C_5$-$C_{10}$)aryl, ($C_5$-$C_{15}$)arylaryl, substituted ($C_5$-$C_{15}$)arylaryl, ($C_5$-$C_{15}$)biaryl, substituted ($C_5$-$C_{15}$)biaryl, 5-10 membered heteroaryl, substituted 5 to 10 membered heteroaryl, ($C_6$-$C_{26}$)arylalkyl, substituted ($C_6$-$C_{26}$)arylalkyl, 6 to 26 membered heteroarylalkyl, substituted 6 to 26 membered heteroarylalkyl, at least one amino acid, and at least one substituted amino acid;

$R^3$ is selected from —C(=O)$OR^4$, —C(=O)$NR^4R^4$, —C(=S)$NR^4R^4$, —C(=$NR^4$)$NR^4R^4$, —C(=O)H, —$R^4$C(=O), —$CO_2H$, substituted ($C_1$-$C_{25}$)alkyl, substituted ($C_1$-$C_{25}$)heteroalkyl, substituted ($C_5$-$C_{10}$)aryl, substituted ($C_5$-$C_{15}$)arylaryl, substituted ($C_5$-$C_{15}$)biaryl, substituted 5 to 10 membered heteroaryl, substituted ($C_6$-$C_{26}$)arylalkyl, substituted 6 to 26 membered heteroarylalkyl, at least one amino acid, and at least one substituted amino acid, with the proviso that $R^3$ contain at least one of —C(=O)—, —C(=S)— or —C(=$NR^4$)—;

wherein each $R^4$ is independently selected from hydrogen, ($C_1$-$C_{10}$)alkyl, ($C_5$-$C_{10}$)aryl, 5 to 10 membered heteroaryl, ($C_6$-$C_{26}$)arylalkyl and 6 to 26 membered heteroarylalkyl, a branched or straight-chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof.

In certain embodiments, the instant disclosure provides lipopeptide derivative compounds of structure (IV) wherein $R^1$ is OH or $R^1$ is $NH_2$. In further embodiments, $R^3$ is —C(=O)— or —C(=S)—. In other preferred embodiments, there are provided compounds with antimicrobial activity. Exemplary compounds include 81, 210, 223, 235, 237, or 373. In certain embodiments, $R^3$ is at least one amino acid or substituted amino acid selected from Gly, β-alanine, GABA, 5-aminopentanoic acid, 6-aminohexanoic acid, Lys, gDab, Sar, Orn, Dap, and hLys. In particular embodiments wherein structure (IV) intermediates are preferred, any of the aforementioned compounds are provided wherein at least one of L or $R^3$ further comprises at least one protecting group, as described herein.

In other embodiments, provided are antimicrobial lipopeptide derivative compounds and pharmaceutically acceptable salts thereof, such as compound 3, 4, 60, 128, 147, 199, 253, or 278. Any of these derivatives or those described herein may be further formulated with a pharmaceutically acceptable carrier, excipient, or diluent.

In certain embodiments, the lipopeptide derivative compounds of the instant disclosure may be structurally pure, or they may be in the form of a composition comprising a mixture of one or more structurally different compounds. In certain embodiments, the compounds of the invention may be in the form of a free acid or base, or in the form of a salt, such as a pharmaceutically acceptable salt. In still other embodiments, the core cyclic peptide is a β-isomer, anhydro isomer, or a dianhydro isomer.

For convenience, derivatives of amphomycin core cyclic peptides can be abbreviated in the following ways:

| | |
|---|---|
| $R^2$—R—$R^3$ | (Ia); |
| $R^2$-L-R—$R^3$ | (IIa); |
| $R^2$—R-L-$R^3$ | (IIIa); and |
| $R^2$-L-R-L-$R^3$ | (IVa) | wherein R is an amphomycin core cyclic peptide (which includes exocyclic amino acid at position 1 where $R^1$ is attached), $R^2$ and $R^3$ may be any substituent described herein, including, for example, hydrogen, ($C_1$-$C_{25}$)alkyl, substituted ($C_1$-$C_{25}$)alkyl, ($C_1$-$C_{25}$)heteroalkyl, substituted ($C_1$-$C_{25}$)heteroalkyl, ($C_5$-$C_{10}$)aryl, substituted ($C_5$-$C_{10}$)aryl, ($C_5$-$C_{15}$)arylaryl, substituted ($C_5$-$C_{15}$)arylaryl, ($C_5$-$C_{15}$)biaryl, substituted ($C_5$-$C_{15}$)biaryl, 5 to 10 membered heteroaryl, substituted 5 to 10 membered heteroaryl, ($C_6$-$C_{26}$)arylalkyl, substituted ($C_6$-$C_{26}$)arylalkyl, 6 to 26 membered heteroarylalkyl, substituted 6 to 26 membered heteroarylalkyl, amino acids, and substituted amino acids, or the like, with the proviso that $R^2$ and $R^3$ are not both hydrogen. Optionally, $R^2$ and $R^3$ may be attached to the core cyclic peptide via a linker L moiety as described herein, including any kind of chemical functionality that can form a covalent bond with nitrogen known to those of ordinary skill in the art. Exemplary linkage groups L can include an amide, imide, sulfonamide, sulfonimide, amidine, carbonate, carbamate, thiourea, urea, and the like. In a certain embodiments, L is selected from one or more amino acid, one or more substituted amino acids, —C(=O)—, —$SO_2$, —C(=S)—, —P(=O)—, —OP(=O)—, —OC(=O)—, —R'OC(=O)(NR'R")—, —NHC(=O)—, —O-PhC(=O)—, and —NR'C(=O)—; and each R' is independently one or more of the same or different substituents defined herein for $R^2$, $R^3$, or $R^4$.

As is known in the art, lipopeptide antibiotics (e.g., amphomycin, aspartocin) isolated from cultures typically comprise mixtures of compounds that differ with respect to the structures of their macrocyclic cores (defined below) or their lipophilic substituents (e.g., fatty acid moieties). The various different compounds comprising the mixture may be separated from one another and isolated either as sub-mixtures or as structurally pure compounds, as described herein. As used herein, reference to a "lipopeptide antibiotic" is intended to include, inter alia, the mixtures naturally produced by the producing strain, as well as any sub-mixtures or structurally pure compounds isolated or derivatized therefrom.

Figure 2:
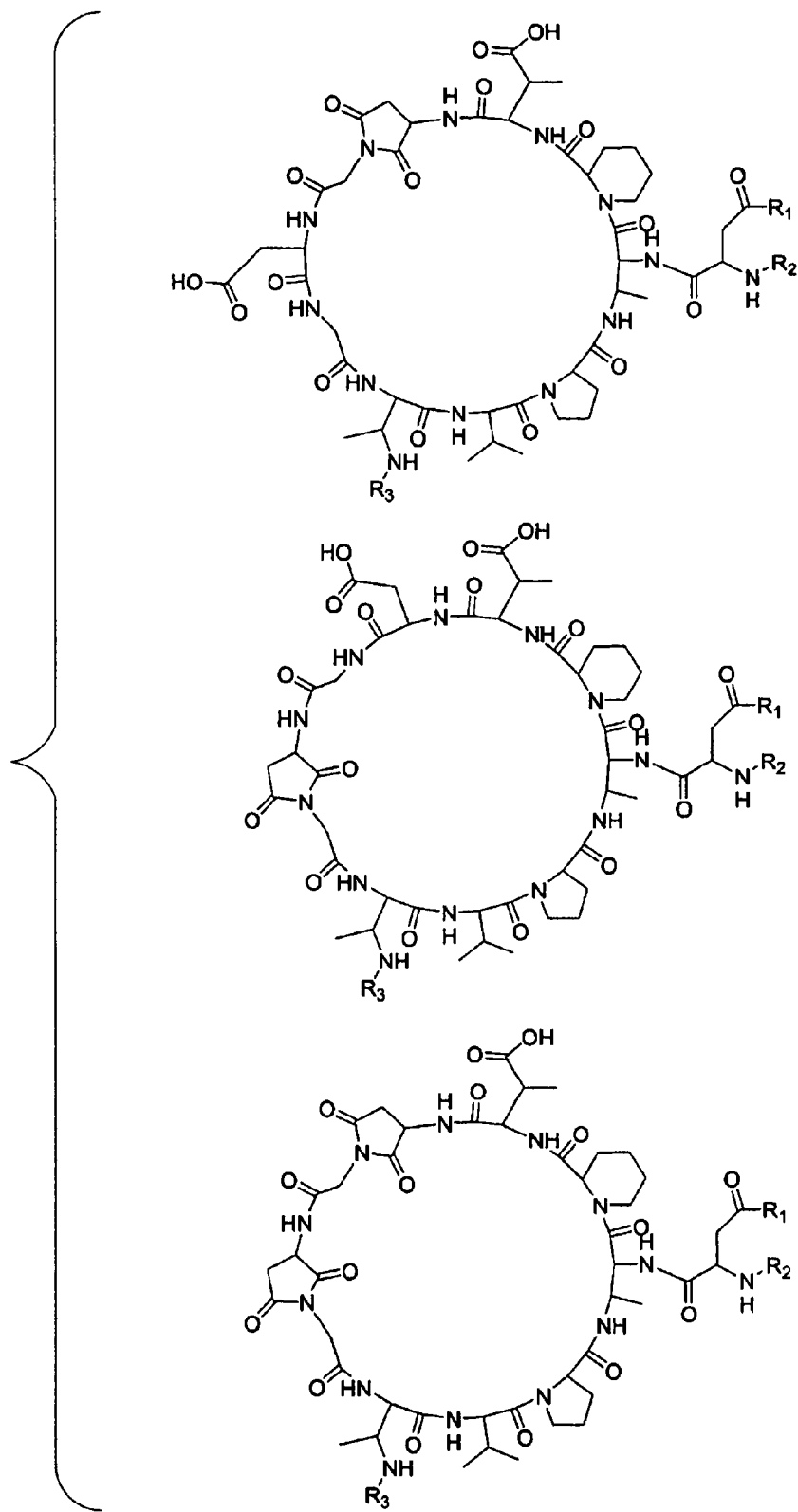
FIG. 2 is an illustration of exemplary anhydro and dianhydro isomers of the derivative lipopeptide antibiotic compounds of the invention.

Furthermore, the core cyclic peptides can be modified to include β-isomers, anhydro isomers, and dianhydro isomers. For example, the Asp-Gly pair (at positions 5,6 and 7,8, respectively) of an amphomycin or aspartocin core cyclic peptide can be modified from an α-linkage to a β-linkage. In the modification, the continuing peptide backbone changes from the α-acid to the β-acid of the aspartate residue. The resulting β-isomers can contain one or more of the following three possible structural modifications, without taking into account possible changes in stereochemistry: (a) 5,6-β with 7,8-α, (b) 5,6-α with 7,8-β, or (c) 5,6-β with 7,8-β. Each of these amphomycin or aspartocin core cyclic peptide β-isomers has the same molecular weight as an all α-amphomycin core cyclic peptide. Similarly, the Asp-Gly pair (at positions 5,6 and 7,8, respectively) of an amphomycin core cyclic peptide can be modified such that a molecule of water is lost to give an anhydro isomer or dianhydro isomer. Two possible mono-anhydro isomers can be formed by the loss of one molecule of water. If both positions are modified, a dianhydro isomer can be formed by the loss of two molecules of water. It should be understood that combinations of β-isomers and anhydro isomers are also possible, as are modifications to the stereochemistry of the individual aspartate residues. Hence, as used herein, reference to a "lipopeptide antibiotic" is intended to include any such modified structures, or combinations thereof, as well. Exemplary amphomycin core cyclic peptide β-isomers are illustrated in FIG. 1. Exemplary amphomycin core cyclic peptide anhydro and dianhydro isomers are illustrated in FIG. 2.

"Structurally pure" refers to a compound composition in which a substantial percentage, e.g., on the order of 95% to 100% and preferably ranging from about 95%, 96%, 97%, 98%, 99% or more, of the individual molecules comprising the composition each contain the same number and types of atoms attached to each other in the same order and with the same bonds. As used herein, "structurally pure" is not intended to distinguish different geometric isomers or different optical isomers from one another. For example, as used herein a mixture of cis- and trans-but-2,3-ene is considered structurally pure, as is a racemic mixture. When compositions are intended to include a substantial percentage of a single geometric isomer or optical isomer, the nomenclature "geometrically pure" and "optically or enantiomerically pure," respectively, are used.

The phrase "structurally pure" is also not intended to discriminate between different tautomeric forms or ionization states of a molecule, or other forms of a molecule that result as a consequence of equilibrium phenomena or other reversible interconversions. Thus, a composition of, for example, an organic acid is structurally pure even though some of the carboxyl groups may be in a protonated state (—COOH) and others may be in a deprotonated state (—COO⁻). Likewise, a composition comprising a mixture of keto and enol tautomers, unless specifically noted otherwise, is considered structurally pure.

In some embodiments, the compounds of the invention are lipopeptide derivatives of parent amphomycin-type lipopeptide antibiotics produced from cultures. Examples of such parent amphomycin-type lipopeptide antibiotics include amphomycin (glumamycin), aspartocin, crystallomycin, friulimycin, tsushimycin and zaomycin. Those of ordinary skill in the art will recognize that in these embodiments, the structures of the exocyclic amino acid(s) and the lipophilic substituent $R^2$ in formulae (I) to (IV) will be dictated in large part by the producing strain and culture conditions. Those of ordinary skill in the art will also recognize that in these embodiments, the parent amphomycin-type lipopeptide antibiotics may comprise mixtures of compounds that differ from one another with respect to the structure of the exocyclic amino acid or lipophilic substituent $R^2$. As will be discussed in more detail below in connection with the synthesis of the compounds of the invention, the desired compounds of the invention may be obtained by appropriate selection of the parent amphomycin-type lipopeptide antibiotic used as a starting material. For example, although preparations of aspartocin, amphomycin, zaomycin and tsushimycin isolated from cultures comprise mixtures of compounds, they are all believed to share the same amphomycin-type macrocyclic core: the amphomycin-type cyclic peptide core R in which $R^1$ is —OH. Likewise, in preparations of friulimycin, the components of the mixture are all believed to share the same amphomycin-type cyclic peptide core: the amphomycin-type cyclic peptide core R in which $R^1$ is —NH₂. Thus, it is believed that the compounds comprising these respective antibiotic mixtures differ from one another only with respect to the structures of their lipophilic substituent (i.e., fatty acid moieties). Alternatively, antibiotic A1437 comprises a mixture of compounds that are believed to differ from one another with respect to the structures of their amphomycin-type macrocyclic cores and fatty acid moieties (see, e.g., U.S. Pat. No. 6,194,383).

All of these various parent amphomycin-type lipopeptide antibiotics may be used as starting materials to produce the desired lipopeptide antibiotic (e.g., having a specific lipophilic substituent or $Dab^9$ substitution) of the invention. Structurally pure lipopeptide derivatives of the invention may be obtained by separating and isolating the component compounds of the parent amphomycin-based lipopeptide antibiotic starting material prior to derivatization of the core macrocyclic peptide, or, alternatively, separating the component compounds of the resultant mixture following derivatization, as will be described in more detail below.

In addition, in many instances, the exact structures of the fatty acid moieties of such parent amphomycin-type lipopeptide antibiotics are unknown. Compounds of the invention having a fatty acid moiety of a specified structure may be obtained by delipidating the parent amphomycin-type lipopeptide antibiotic starting material and reacting the delipidated intermediate with a fatty acid or other substituent (e.g., a lipophilic substituent) having a specified structure. The resultant product may optionally be derivatized, for example, at the $Dab^9$ residue, which would yield a $Dab^9$ derivative of the invention having a specified lipophilic substituent at the amino-terminus. Alternatively, a $Dab^9$ derivative of the invention, prepared by derivatizing a parent amphomycin-type lipopeptide antibiotic, may be delipidated and the $Dab^9$ derivatized delipidated intermediate reacted with a fatty acid or other substituent of specified structure.

Fatty acids suitable for use in producing an appropriate fatty acid moiety, or for attaching an appropriate fatty acid moiety to the core macrocyclic peptide, are well known in the art (see, e.g., Römpp Chemie Lexicon, Prof. Falbe and Prof. Regitz, $9^{th}$ Edition, Georg Thieme Verlag Stuttgart, New York; and Hawley, $3^{rd}$ Edition, Van Nostrand Reinhold Company, New York, each of which is incorporated herein by reference). In one embodiment, a fatty acid is selected that yields a compound of the invention having a fatty acid moiety that is identical to a fatty acid moiety of a known amphomycin-type lipopeptide antibiotic. Such fatty acids are well known to those of ordinary skill in the art. Illustrative examples are provided, e.g., in U.S. Pat. No. 6,194,383 (see especially Cols. 5-8), which is incorporated herein by reference.

However, the fatty acid need not correspond to a fatty acid of a known amphomycin-type lipopeptide antibiotic. Suitable fatty acids may include unbranched and saturated (e.g., caproic, enanthic, caprylic, pelargonic, capric, undecanoic, lauric, tridecanoic, myristic, pentadecanoic, palmitic, margaric, stearic, nonadecanoic, arachidic, behenic, lignoceric, pentacosenoic, and the like); branched and saturated (e.g., isobutyric, isovaleric, isopalmitic and the like, and corresponding acids in the ante-iso configuration and may contain methoxy or hydroxy substitutions); monoenoic (e.g., obtusilic, caproleic, lauroleic, linderic, myristoleic, physeteric, tsuzuic, palmitoleic, petroselinic, oleic, vaccenic, gadoleic, gondoic, cetoleic, erucic, nervonic, and the like); polyenoic (e.g., linoleic, γ-linoleic, arachidonic, stearidonic, and the like, and methylene interrupted polyenes, polymethylene interrupted polyenes, conjugated fatty acids, and halogenated fatty acids). See also U.S. Pat. No. 6,194,383, which is incorporated herein by reference.

In certain preferred embodiments, the fatty acid is a fatty acid moiety or a hydroxy fatty acid moiety with a chain length of from 6 to 25 carbon atoms and more preferably from 10-20 carbon atoms. The fatty acid or hydroxy fatty acid may be branched or linear, saturated or singly or multiply unsaturated, and combinations thereof. In one embodiment, the fatty acid is a saturated or singly unsaturated fatty acid comprising 10 or 18 carbon atoms, which is either linear or singly branched, preferably in the iso or ante-iso configuration. In another embodiment, the fatty acid is a saturated or singly unsaturated hydroxy fatty acid comprising 10 or 18 carbon atoms that is either linear or singly branched, preferably in the iso or ante-iso configuration. In a specific embodiment, the hydroxy fatty acid is hydroxylated at position 2, 3 or at the end of the chain.

In certain aspects, as shown for example in compounds having structures (I)-(III), $R^2$ (e.g., a lipophilic substituent) may be linked directly to the amino-terminal amino group of the Asp or Asn, and an $R^3$ substituent may be directly linked to the β-amino group of $Dab^9$, wherein $R^2$ and $R^3$ are independently selected from hydrogen, $(C_1-C_{25})$alkyl, substituted $(C_1-C_{25})$alkyl, $(C_1-C_{25})$heteroalkyl, substituted $(C_1-C_{25})$heteroalkyl, $(C_5-C_{10})$aryl, substituted $(C_5-C_{10})$aryl, $(C_5-C_{15})$arylaryl, substituted $(C_5-C_{15})$arylaryl, $(C_5-C_{15})$biaryl, substituted $(C_5-C_{15})$biaryl, 5-10 membered heteroaryl, substituted 5 to 10 membered heteroaryl, $(C_6-C_{26})$arylalkyl, substituted $(C_6-C_{26})$arylalkyl, 6 to 26 membered heteroarylalkyl, substituted 6 to 26 membered heteroarylalkyl, natural amino acids, non-natural amino acids, and substituted natural and non-natural amino acids; wherein $R^2$ and $R^3$ cannot both be hydrogen. Some exemplary and independently selected substitutions include —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)($OR^4$)$_2$, —P(=O)($OR^4$), —$CO_2H$, —$SO_3H$, —$PO_3H$, halogen, and trihalomethyl; wherein each $R^4$ is independently selected from hydrogen, $(C_1-C_{10})$alkyl, $(C_5-C_{10})$aryl, 5 to 10 membered heteroaryl, $(C_6-C_{16})$arylalkyl and 6 to 16 membered heteroarylalkyl, a branched or straight-chained, saturated or singly or multiply unsaturated aliphatic or hydroxy aliphatic moiety having a chain length of from 6 to 25 carbon atoms, a primary or secondary amine, at least one amino acid, at least one substituted amino acid, and any combination thereof.

In the compounds of structures (I) to (IV), $R^1$ may be —OH or —$NH_2$, which means the amino-terminal exocyclic amino acid is an Asp residue or an Asn residue, respectively. Whether the amino-terminal exocyclic amino acid is Asp or Asn will depend upon the choice of parent amphomycin-based lipopeptide antibiotic used as a starting material in the synthesis of the lipopeptide derivatives of the invention, or derivatives of the invention with specified lipophilic substituents and/or $Dab^9$ substituents, as will be apparent to those of ordinary skill in the art. For example, lipopeptide derivatives in which the amino-terminal exocyclic amino acid is Asp may be prepared from amphomycin, aspartocin, tsushimycin, or the Asp fraction of antibiotic A1437. Lipopeptide derivatives of the invention in which the amino-terminal exocyclic amino acid is Asn may be prepared from friulimycin or from the Asn fraction of antibiotic A1437. The Asp and Asn fractions of antibiotic A1437 may be isolated from a preparation of cultured antibiotic A1437 according to the methods described in, for example, U.S. Pat. No. 6,194,383, which are incorporated herein by reference.

In certain other aspects, the derivative antimicrobial compounds of structural formulae (I) to (IV) may have an $R^3$ substituent that includes hydrogen, —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)($OR^4$)$_2$, —P(=O)($OR^4$), —$CO_2H$, —$SO_3H$, —$PO_3H$, halogen, trihalomethyl, $(C_1-C_{25})$alkyl, substituted $(C_1-C_{25})$alkyl, $(C_1-C_{25})$heteroalkyl, substituted $(C_1-C_{25})$heteroalkyl, $(C_5-C_{10})$aryl, substituted $(C_5-C_{10})$aryl, $(C_5-C_{15})$arylaryl, substituted $(C_5-C_{15})$arylaryl, $(C_5-C_{15})$biaryl, substituted $(C_5-C_{15})$biaryl, 5-10 membered heteroaryl, substituted 5 to 10 membered heteroaryl, $(C_6-C_{26})$arylalkyl, substituted $(C_6-C_{26})$arylalkyl, 6 to 26 membered heteroarylalkyl, substituted 6 to 26 membered heteroarylalkyl, natural amino acids, non-natural amino acids, and substituted natural and non-natural amino acids. Some exemplary and independently selected substitutions include —$OR^4$, —$SR^4$, $NR^4R^4$, —CN, —$NO_2$, —$N_3$, —C(=O)$OR^4$, —C(=O)$R^4$, —C(=O)$NR^4R^4$, —C(=S)$NR^4R^4$, —C(=$NR^4$)$NR^4R^4$, —C(=O)H, —$R^4$C(=O), —$SO_2R^4$, —S(=O)$R^4$, —P(=O)($OR^4$)$_2$, —P(=O)($OR^4$), —$CO_2H$, —$SO_3H$, —$PO_3H$, halogen, and trihalomethyl; wherein each $R^4$ is independently selected from hydrogen, $(C_1-C_{10})$alkyl, $(C_5-C_{10})$aryl, 5 to 10 membered heteroaryl, $(C_6-C_{16})$arylalkyl and 6 to 16 membered heteroarylalkyl, a branched or straight-chained, saturated or singly or multiply unsaturated aliphatic or hydroxy aliphatic moiety having a chain length of from 6 to 25 carbon atoms, a primary or secondary amine, at least one amino acid, at least one substituted amino acid, and any combination thereof a primary amine group, a secondary amine group, one or more amino acids, and one or more substituted amino acids. In one preferred embodiment, the β-amino group of $Dab^9$ is directly attached to an $R^3$ substituent to form a primary or secondary amine having the formula —$NHR^3$, wherein $R^3$ is hydrogen, $(C_1-C_{25})$alkyl, substituted $(C_1-C_{25})$alkyl, $(C_1-C_{25})$heteroalkyl, substituted $(C_1-C_{25})$heteroalkyl, $(C_5-C_{10})$aryl, substituted $(C_5-C_{10})$aryl, $(C_5-C_{15})$arylaryl, substituted $(C_5-C_{15})$arylaryl, $(C_5-C_{15})$biaryl, substituted $(C_5-C_{15})$biaryl, 5-10 membered heteroaryl, substituted 5 to 10 membered heteroaryl, $(C_6-C_{26})$arylalkyl, substituted $(C_6-C_{26})$arylalkyl, 6 to 26 membered heteroarylalkyl, substituted 6 to 26 membered heteroarylalkyl, natural amino acids, non-natural amino acids, and substituted natural and non-natural amino acids, and any combination thereof. In another preferred embodiment, the primary or secondary amine group may be spaced away from the macrocyclic $Dab^9$ residue via an optional linking moiety, as described herein and shown, for example, in compound structures (III) and (IV). The present invention is based, in part, on the surprising discovery that amphomycin-based lipopeptide antibiotics derivatized at the amino terminal exocyclic amino acid, at the macrocyclic $Dab^9$ residue or at both positions, retain substantially the same antimicrobial properties of the parent amphomycin-type lipopeptide antibiotics from which they are derived, but can have altered solubility properties. For example, this may lead to amphomycin-based lipopeptide antibiotic derivatives having improved therapeutic properties or spectra as compared to parent amphomycin-type lipopeptide antibiotics from which they are derived.

Without wishing to be bound by theory, the optional linking moiety to attach either or both $R^2$ and $R^3$ to the core macrocyclic peptide may be preferred to introduce a sufficient number of atoms to separate the added substituent from the core cyclic peptide in the range of about 1 Å to about 10 Å. Typically, a linkage group is a moiety that, when taken together with the amino-terminal exocyclic amino acid amino nitrogen atom or the $Dab^9$ β-nitrogen atom to which the linkage group is bonded, yields a linkage that is stable to the physiologic conditions under which the compounds of the invention will be used. Examples of suitable linkages include amide, imide, sulfonamide, sulfonimide, amidine, carbonate, carbamate, thiourea, urea, and the like. Accordingly, examples of suitable linking groups include one or more amino acid, one or more substituted amino acid, a combination of one or more amino acid with one or more substituted amino acid, —C(=O)—, —S(=O)$_2$—, —C(=NH)—, —NHC(=O)—, —NHC(=S)—, —NHC(=O)NH—, —NHC(=S)NH— and —C(=O)O— groups.

A person of ordinary skill in the art will recognize that the exact number of atoms necessary to achieve a particularly desired spacing between the $R^2$ or $R^3$ substituents and the core cyclic peptide will depend upon, among other things, the types of atoms (e.g., N, O, S, C, etc.) and bonds (e.g., single, double, triple, etc.) comprising the linking moiety and, therefore, will be able to select additional substituents, if necessary, to yield an appropriate spacing. For example, the additional spacer substituents, which may be present or absent, may include virtually any combination of carbon or heteroatoms suitable for spacing. In certain embodiments, the linker L may further comprise a spacer moiety that is hydrophilic or hydrophobic, long or short, rigid, semirigid or flexible. For example, suitable groups that may comprise the spacer include —CH$_2$—, —CH=CH—, —C≡C—, —O—, —S—, —NH—, —NH—NH—, —N=N—, —C(=O)—, —S(=O)$_2$—, —S(=O)$_2$—O—, —C(=NH)—, and the like. Other spacers suitable for spacing, are known in the art, and include alkyl, heteroalkyl, acyclic heteroatomic bridges, aryl, arylaryl, arylalkyl, heteroaryl, heteroaryl-heteroaryl, substituted heteroaryl-heteroaryl, heteroarylalkyl, heteroaryl-heteroalkyl and the like. Thus, spacers may include single, double, triple or aromatic carbon-carbon bonds, nitrogen-nitrogen bonds, carbon-nitrogen, carbon-oxygen bonds or carbon-sulfur bonds, and may therefore include functionalities such as carbonyls, ethers, thioethers, carboxamides, sulfonamides, ureas, urethanes, hydrazines, and the like.

These and other groups, which will be apparent to those having ordinary skill in the art, may be used in a multitude of combinations to create suitable spacers or combined linker-spacers. In addition, the spacers may be optionally substituted with one or more of the same or different substituents as described herein. Choosing a suitable linker or spacer is within the capabilities of those having ordinary skill in the art. For example, where a rigid linker or spacer is desired, it may be a rigid polyunsaturated alkyl or an aryl, biaryl, heteroaryl, and the like. When a flexible linker or spacer is desired, it may be a flexible peptide, such as Gly-Gly-Gly, or a flexible saturated alkanyl or heteroalkanyl. Hydrophilic linkers or spacers may be, for example, polyalcohols or polyethers, such as polyalkyleneglycols. Hydrophobic linkers or spacers may be, for example, alkyls or aryls.

In certain preferred embodiments of derivatives of structural formulae (I)-(IV), substituent $R^2$ or $R^3$ may be one or more amino acid that is linked via its terminal carboxyl group to the amino-terminal amino group of the exocyclic amino acid or to the β-amino group of the macrocyclic $Dab^9$ residue, respectively, to form an amide linkage. Such amino acids may include α-, β- and γ-amino acids. The amino acids may optionally include side chain moieties, such as a side chain moiety of one of the twenty genetically encoded amino acids, or an analog thereof. In certain preferred embodiments, the substituent is an amino acid selected from glycine, proline, pipecolic acid, sarcosine, phenylalanine, phenylglycine, asparagine, tyrosine, tryptophan, leucine, alanine, isoleucine, valine, glutamine, threonine, β-alanine, 2,4-diaminobutyric acid, 2,3-diaminopropionic acid, β-methylaspartate, cyclohexylalanine, isonipecotic acid, ornithine, and 6-aminohexanoic acid. In other preferred embodiments, more than one amino acid substituent is added, such as glycine-leucine, glycine-lysine, lysine-glycine, glycine-leucine, proline-glycine, (β-alanine)-(6-aminohexanoic acid), (β-alanine)-ornithine, (β-alanine)-lysine, glycine-alanine, (6-aminohexanoic acid)-glycine, glycine-(6-aminohexanoic acid), glycine-glycine-glycine, glycine-lysine-glycine, glycine-glycine-lysine, glycine-lysine-lysine, lysine-lysine-lysine, lysine-lysine, glycine-valine, proline-lysine, glycine-ornithine, glycine-(2,3-diaminobutyric acid), glycine-(2,3-diaminopropionic acid), glycine-homolysine, sarcosine-(6-aminohexanoic acid), sarcosine-lysine. Any chiral centers in the amino acid may be in either the R- or S-configuration. Examples of suitable amino acids include the twenty genetically encoded amino acids; the various amino acids listed in Fasman, *CRC Practical Handbook at Biochemistry and Molecular Biology*, 1989, CRC Press, Inc., Boca Raton, Fla. at pages 4-60, and the α,β-unsaturated amino acids listed in Fasman, 1989, supra, at page 69. Other suitable amino acids will be apparent to those of ordinary skill in the art.

Methods of Synthesis

Figure 3:
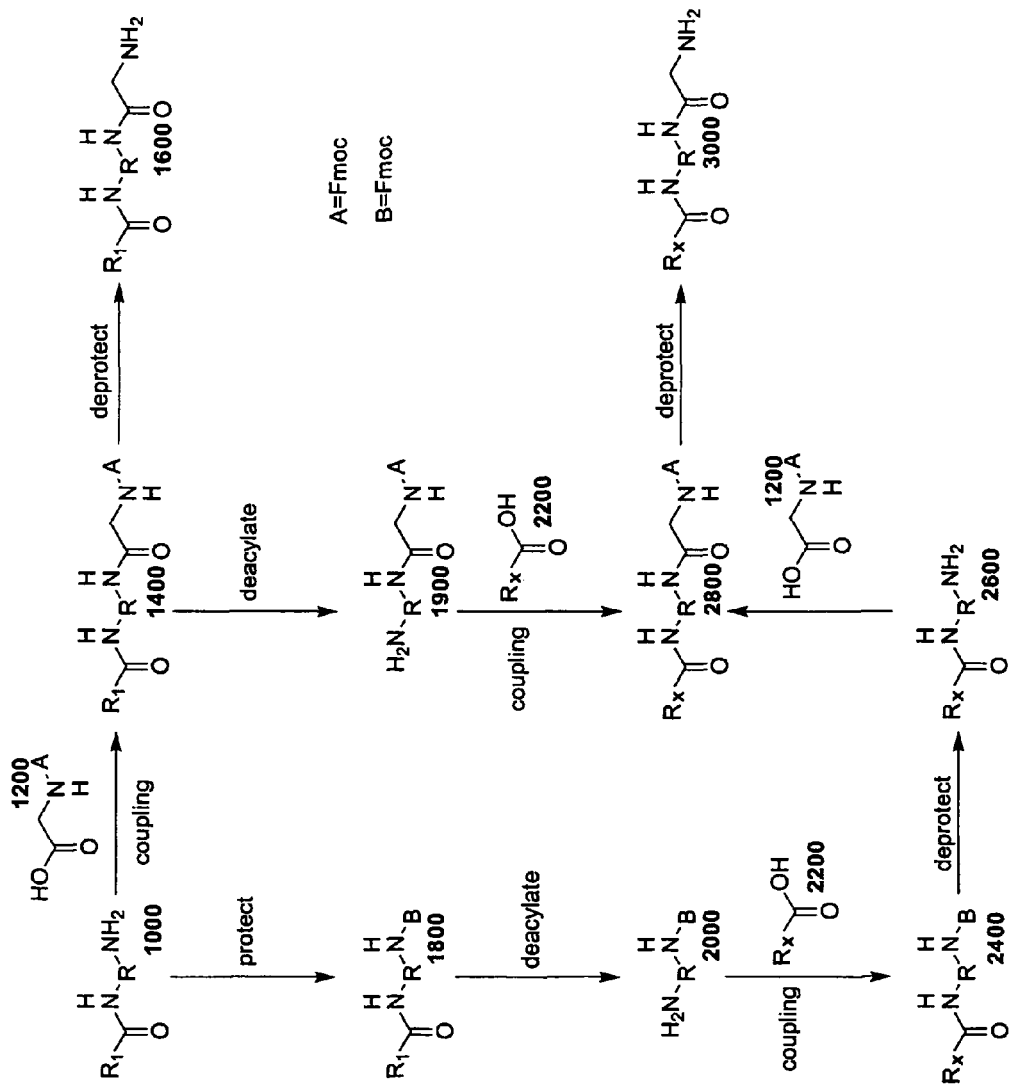
FIG. 3 is an illustration (Scheme I) of two general synthetic approaches for making derivative lipopeptide antibiotic compounds of the invention.

The compounds of the invention may be synthesized via several different synthetic routes using commercially available starting materials or starting materials prepared by conventional synthetic or biosynthetic methods. Two general synthetic approaches are illustrated in FIG. 3.

In Scheme (I), R and $R^1$ are as previously defined in structural formulae (I)-(IV). According to Scheme (I), a parent amphomycin-type lipopeptide antibiotic (or mixture of antibiotics) 10 is coupled with an appropriately protected reactant 12, which in the specific illustrated example is Fmoc-protected glycine, to yield $Dab^9$ protected intermediate (or mixture of intermediates) 14. The protected reactant may be any of the substituents described herein, including lipophilic substituents, other organic substituents, one or more amino acids (natural, non-natural, substituted, etc.), and the like. Reaction conditions for coupling primary amines, such as antibiotic (or mixture of antibiotics) 10, with carboxylic acids, such as reactant 12, to yield amide linkages are known to those of ordinary skill in the art and may be found in any compendium of standard synthetic methods or literature related to the synthesis of peptides and proteins. See e.g., March, J., *Advanced Organic Chemistry; Reactions, Mechanisms and Structure*, 4$^{th}$ ed., 1992; Larock, *Comprehensive Organic Transformations*, VCH, New York, 1999; Bodanzsky, *Principles of Peptide Synthesis*, Springer Verlag, 1984; Bodanzsky, *Practice of Peptide Synthesis*, Springer Verlag, 1984; Lloyd-Williams et al., *Chemical Approaches to the Synthesis of Peptides and Proteins*, CRC Press, 1997 (see especially pp. 105-114); and Atherton & Sheppard, *Solid Phase Peptide Synthesis: A Practical Approach*, IRL Press, 1989). Alternative reactive groups can be utilized, such as isocyanate (which would yield a urea) and others exemplified herein, in methods known in the art.

Protected intermediate 14 is then deprotected to yield Dab$^9$ derivative (or mixture of derivatives) 16. While the method is illustrated using an Fmoc protecting group, a person having ordinary skill in the art will recognize that other protecting groups may be employed. Moreover, in some instances, reactant 12 may include other or additional functionalities that may require protection. Groups suitable for protecting a wide variety of different functionalities, as well as conditions for their removal, are well known and will be apparent to those of ordinary skill in the art. Specific guidance for selectively protecting a wide variety of functionalities may be found, for example, in Greene & Wuts, *Protective Groups in Organic Synthesis*, 3$^{rd}$ edition, 1999 ("Greene & Wuts"). Preferred protecting groups are those that may be easily removed. Preferred groups for protecting primary amines are tert-butyloxycarbonyl ("t-Boc"), 9-fluorenylmethoxycarbonyl ("Fmoc") and benzyloxycarbonyl ("Z"). If the parent amphomycin-type lipopeptide antibiotic 10 is a mixture of individual components, it should be recognized by those with skill in the art that a mixture of derivatives 16 will result and can be individually, partially or completely isolated, or purified to yield a number of independent derivatives 16 with varied R$^1$ groups, as described herein. Representative derivatives 16 that were prepared by this method are shown in Table 16 and in Examples 367, 378, 369, 370, 371 and 372.

Parent amphomycin-type lipopeptide antibiotic 10 may be obtained by isolation from a culture of a microorganism known to produce the antibiotic. Microorganisms for producing amphomycin-type lipopeptide antibiotics are well known, as are conditions for isolating, and optionally further purifying, the resultant antibiotics. For example, strains for producing amphomycin (glumamycin) include *Streptomyces canus* (ATCC #12237; see also Heinemann et al., 1953, *Antibiot. Chemother.* 3: 1239-1242) and *Streptomyces zaomyceticus* (ATCC #13876; see also U.S. Pat. No. 3,160,561 to Shibata et al.). Strains for producing aspartocin include *Streptomyces griseus* subspecies *sprialis* (ATCC #13733; see also U.S. Pat. No. 3,057,779 to Shay et al.) and *Streptomyces violaceus* (Rossi-Doria) Waksman (ATCC #13734; see also U.S. Pat. No. 3,057,779). Strains for producing crystallomycin include *Streptomyces violaceoniger* var. *crystallomycini* (Gauze et al., 1957, Antibiotiki 2(6): 9-14). Strains for producing antibiotic A1437 include *Actinoplanes* sp. (DSM #7358; see also U.S. Pat. No. 6,194,383 to Hammann et al.). Strains for producing friulimycin include *Actinoplanes friuliensis* (HAG #010964). Strains for producing tsushimycin include *Streptomyces pseudogriseolus* Okami and Umezawa (ATCC pseudogriseolus #21139 and #21140; see also U.S. Pat. No. 3,781,420 to Nishimura et al.) and *Streptomyces pseudogriseolus* subspecies *glucofermentans* Nishimura and Otsuka (ATCC #21141; see also U.S. Pat. No. 3,781,420 to Nishimura et al.). Strains for producing zaomycin include *Streptomyces zaomyceticus* Hinuma (NRRL #B-2038). Conditions for culturing and isolating the various lipopeptide antibiotics are described herein and found in the above-cited patents and references, as well as the various references mentioned previously in connection with these various antibiotics.

The following description is an exemplary method for making amphomycin-based lipopeptide compounds using fermentation in a bioreactor. An amphomycin-based lipopeptide can be produced by fermentation in a 700-liter stainless steel bioreactor. Biochemical synthesis of amphomycin is performed by inoculating a medium composed of 1.0% dextrose, 0.5% molasses, 1.0% Bacto Peptone, and 0.1% CaCO$_3$ in 100 mL of tap water, with spore and mycelial scrapings from a slant of *Streptomyces griseus* ssp. *spiralis* (NRRL B-3290; BSP-M707). The inoculated medium is incubated at a temperature of about 28° C. on a rotary shaker at about 180 rotations per minute (RPM) for about 48 hours providing a substantial and uniform vegetative growth. This seed growth (10 ml) is transferred to 400 ml of the same medium in a 2-liter flask, which is incubated under the same conditions and then added to 9.6 liters of the same medium in a 16-liter fermentor to give the 3$^{rd}$ stage seed after 48 h, 200 rpm, 5 Lpm air flow. This final seed stage is used to inoculate 500 liters of medium containing 1 g/L CaCO$_3$, 10 g/L Grandma's Molasses (unsulfered), 10 g/L Difco Bacto Peptone, and 20 g/L Baker Dextrose adjusted to pH 7.1 prior to sterilization. Fermentation is conducted with agitation speed 200 rpm, air flow 125 Lpm, and 28° C. with addition of antifoam, Mazu DF204, as required. The fermentation broth is harvested after 114 hours.

After fermentation, the following exemplary process to obtain a crude preparation of the amphomycin-based lipopeptide can be used. The cells and other solids of the fermentation broth can be removed by centrifugation and the supernatant (470 L) is adjusted to pH 3.3 with HCl and allowed to stand at 14° C. for 2 hours. The precipitate that forms is removed by centrifugation and discarded. The decant is adjusted to pH 7.0 and ammonium sulfate is added to precipitate the crude antibiotic complex. The precipitate is sedimented by centrifugation, dissolved in water, adjusted to pH 7.0, and then freeze dried to obtain 2058 g of solid containing 5-7% of the amphomycin-based lipopeptide complex.

To further purify the amphomycin-based lipopeptide, an exemplary chelate procedure may be used as follows. The dark colored crude preparation, 68.3 grams, containing 5-7% of the amphomycin-based lipopeptide complex is dissolved in 500 ml distilled water and stirred as it is adjusted to pH 7.0 to maximize water solubility. Some insoluble material may form, which is separated by centrifugation, and then the remaining decant is adjusted to pH 3.5. The amphomycin-based lipopeptide complex is extracted by two sequential 1-butanol extractions (500 ml, 300 ml) and 600 ml of water is added to the combined butanol phases. The resulting two phase system is stirred and adjusted to pH 8.0 with 1 N NaOH to provide the amphomycin-based lipopeptide complex as a sodium salt in the aqueous phase. Calcium chloride (2.642 g) is added to the separated aqueous phase, and the amphomycin-based lipopeptide extracted into 1-butanol as a chelate by two sequential extractions (500 ml, 250 ml). To remove calcium, the 1-butanol phases is combined, mixed with 900 ml water, adjusted to pH 3.0, separated from the aqueous phase, and washed with 150 ml of water. The 1-butanol phase containing the amphomycin-based lipopeptide complex is combined with 500 ml water and adjusted to pH 7.0. To remove some residual pigments, the aqueous phase containing the antibiotic complex is adjusted to pH 3.0 and mixed with 500 ml of 1-butanol. The 1-butanol phase is separated, washed with 150 ml water (pH 2-3), combined with 500 ml water, and the mixture is then adjusted to pH 7.0. The aqueous phase containing the amphomycin-based lipopeptide complex as a partial sodium salt is evaporated under vacuum to remove residual 1-butanol and freeze-dried to obtain 3.6 g of a white powder. HPLC analysis of the purified complex is used to determine the purity of the amphomycin-based lipopeptide by 215 nm area % with peaks of the complex between 9.4 to 10.6 minutes (preferably being about 85% to about 95% pure, more preferably about 90% to about 95% pure). The HPLC system utilized can be a Prodigy® 5μ ODS(2) column eluted with an eight minute gradient of 10% to 75% acetonitrile at pH 7.2 with 0.05 M phosphate buffer.

As discussed previously, in most instances, amphomycin-type lipopeptide antibiotic or mixture of antibiotics 10, isolated from cultures are mixtures of compounds that differ with respect to the structures of $R^1$ and the cyclic peptide core R. For example, amphomycin is a mixture of compounds 10 in which $R^1$ is a mixture of iso and ante-iso $C_{12}$ and $C_{13}$ fatty acids. Aspartocin is a mixture of compounds 10 in which $R^1$ is a mixture of iso and ante-iso $C_{13}$ and $C_{14}$ fatty acids. Tsushimycin is a mixture of compounds 10 in which $R^1$ is a mixture of iso and ante-iso $C_{14}$ and $C_{15}$ fatty acids. In amphomycin, aspartocin and tsusimycin, the core cyclic peptide is connected to $R^1$ via an exocyclic aspartic acid amino acid. Friulimycin is a mixture of compounds 10 in which $R^1$ is a mixture of iso and ante-iso $C_{13}$ and $C_{15}$ fatty acids. In friulimycin, the core cyclic peptide is connected to $R^1$ via an exocyclic asparagine amino acid. Antibiotic A1437 is a complex mixture of 11 compounds, where $R^1$ is mixture of iso and ante-iso $C_{13}$, $C_{14}$ and $C_{15}$ fatty acids and the exocyclic amino acid can be either aspartic acid or asparagine. In many instances, culture conditions useful for producing one or more of the compounds of the mixtures in greater or lesser yields are known (see, e.g., *J. Biotechnology* 7: 283-292, 1988). Such methods may be used in conjunction with the invention to provide mixtures of $Dab^9$ derivatives having fatty acid moieties of defined molar ratios.

Amphomycin-type lipopeptide antibiotic (or mixture of antibiotics) 10 isolated from cultures may be used directly in Scheme (I) without prior separation and isolation of the various components of the mixtures, or they may be first separated, either with respect to the fatty acids or, in the case of antibiotic A1437, with respect to the exocyclic amino acid (e.g., aspartic acid or asparagine), into structurally pure compounds or sub-fractions or sub-mixtures. Methods for separating individual components or sub-mixtures of antibiotic preparations are well known in the art. Specific suitable methods are provided, for example, in U.S. Pat. No. 6,194,383 (see especially Cols. 10-12), and in the Examples section, infra.

In some instances, the structures of the fatty acid moieties of amphomycin-based lipopeptide antibiotic (or mixtures of antibiotics) 10 may be unknown. In certain instances, it may be desirable to have derivative compounds of the invention with specified substituents at the amino terminus, such as a fatty acid moiety, or macrocyclic $Dab^9$ position. In other instances, it may be desirable to have derivatives that are structurally pure, geometrically pure, or optically pure with respect to, for example, the lipophilic substituent. Accordingly, rather than isolating components of a cultured antibiotic preparation, it may be more convenient or desirable to replace the natural fatty acid moiety of the cultured antibiotic (or mixture of antibiotics) 10 with a specific substituent, which may be a particular fatty acid moiety or any other moiety that is capable of covalently binding to the N-terminus as described herein. As illustrated in Scheme (I), this may be achieved by several synthetic strategies.

According to a first strategy, amphomycin-type lipopeptide antibiotic (or mixture of antibiotics) 10 is first protected at the β-amino group of the macrocyclic $Dab^9$ residue to yield protected intermediate (or mixture of intermediates) 18. Again, while the illustrated protecting group is Fmoc, those of ordinary skill in the art will appreciate that other commonly known amine protecting groups may be used. Protected intermediate (or mixture of intermediates) 18 is then delipidated or deacylated to yield protected amphomycin-type macrocyclic core 20. Protected core 20 is then coupled with a reactive group 22, which is exemplified as a carboxylic acid, again using standard chemistries, to yield protected amphomycin-type lipopeptide antibiotic 24. It should be recognized by those skilled in the art that any reactive group that is capable of reacting with the N-terminus could be employed to yield other lipopeptide antibiotics 24, as described herein.

In the exemplified carboxylic acid 22, $R_x$ combined with its carbonyl —C(=O)— could represent either $R^2$ of structures (I) or (III), or $R^2$-L of structures (II) or (IV). Briefly, this carboxylic acid may be activated and purified by the following exemplary procedure (see Example 1 below). The carboxylic acid may be dissolved in dry dimethylformamide (DMF) under an inert atmosphere, hydroxysuccinimide added, and then cooled in an ice bath. Then, dicyclohexylcarbodiimide is added in two equal portions to the reaction mixture 10 minutes apart, after which, the mixture was stirred for while still on ice, allowed to warm to room temperature, and then stirred for at least 2 hours). The resulting crude product can then be concentrated in vacuo and purified by recrystallization using isopropanol and hexane, which provides a good yield and relatively clean activated ester.

The addition of the activated carboxylic acid to a protected core macrocyclic peptide may be accomplished by the following exemplary procedure (see, also, Examples). Protected amphomycin-based core peptide 20 (e.g., amphomycin-9-Fmoc) is dissolved in water and then diluted with dimethylformamide. A solution of sodium bicarbonate is slowly added and the mixture is then cooled in an ice bath. A predissolved solution of acyl activated ester 22 in DMF is added to the reaction mixture while still on ice, then the reaction mixture is allowed to stir for at least 6 hours at room temperature. Piperdine is added and the reaction mixture is stirred for an additional hour. The reaction is filtered, the insolubles washed with additional dimethylformamide, and the filtrate concentrated in vacuo until dry. Flash chromatography using a gradient system of methanol in chloroform (or methanol in ethyl acetate) provides a desired acyl tail-coupled amphomycin in good overall yield and purity.

Protected antibiotic 24 may then be deprotected to yield compound 26, reacted with reagent 12 to yield protected $Dab^9$ derivative 28, which, following deprotection, yields $Dab^9$ derivative 30. The addition of a substituent to the macrocyclic $Dab^9$ residue may be accomplished by the following exemplary procedure (see Examples below). The acyl-coupled amphomycin is suspended in dimethylformamide, charged with sodium bicarbonate, and then cooled in an ice bath. The succinimide activated carboxylic acid is predissolved in dimethylformamide, added to the reaction mixture while still on ice, and then the reaction is allowed to stir at least 6 hours at room temperature. The resulting crude product may be concentrated in vacuo and then subjected to standard deprotection conditions as required. Final purification by C18 Prepack B&J Solid Phase Column using a gradient system of acetonitrile in water provides clean product in good yield and purity.

When parent amphomycin-type lipopeptide antibiotic (or mixture of antibiotics) 10 is a mixture of compounds that all share the same amphomycin-type macrocyclic core, such as amphomycin, aspartocin, friulimycin, tsushimycin or zaomycin, this method may be used to synthesize $Dab^9$ derivatives of the invention that are structurally pure without having to isolate the various fatty acid fractions of the parent amphomycin-type lipopeptide antibiotic 10 from one another. Delipidation (or deacylation) yields a mixture comprising the various fatty acids and the same protected amphomycin-type macrocyclic core 19. The protected macrocyclic core 19 may be readily isolated in high purity from this mixture using any art-known technique, such as high performance liquid chromatography, counter current extraction, centrifugation, filtration, precipitation, ion exchange chromatography, gel electrophoresis, affinity chromatography, etc. Specific procedures that may be used directly or that may be routinely adapted to isolate a particular protected macrocyclic core are described in Debono et. al., 1988, *J. Antibiotics* 41: 1093 and U.S. Pat. No. 5,039,789 (see, e.g., Cols. 30-34), each of which is incorporated herein by reference. Additional chemistries and procedures that may be used directly to delipidate/deacylate and reacylate parent amphomycin-type lipopeptide antibiotic 10 are found in U.S. Pat. No. 5,629,288 to Lattrell et al., the disclosure of which is incorporated herein by reference.

In a preferred route, protected $Dab^9$ derivative 14 is delipidated/deacylated to yield protected amphomycin-type macrocyclic core 19 as a key intermediate. Intermediate 19 may have a variety of different $Dab^9$ substituents as described herein. Intermediate 19 can further be reacted with a reactive group 22, yielding protected $Dab^9$ derivative 28, which, following deprotection, yields $Dab^9$ derivative 30. This preferred route is advantageous in that it does not require separate protection of the macrocyclic $Dab^9$ β-amino group and it provides $Dab^9$ derivatives 30 in fewer overall steps.

Generally, the fatty acid moiety of protected amphomycin-type lipopeptide antibiotic (or mixture of antibiotics) 18 or protected $Dab^9$ derivative (or mixture of derivatives) 14 may be cleaved with an enzyme. The enzyme may be, for example, a degradative enzyme, such as a peptidase, esterase or thiolase, of which numerous examples exist in the art. Preferably, the enzyme is a deacylase.

In an exemplary embodiment, the cleavage step involves culturing a microorganism that produces a deacylase in an appropriate culture medium and contacting protected $Dab^9$ derivative (or mixture of derivatives) 14 or protected antibiotic (or mixture of antibiotics) 18 with the culture medium containing the deacylase. Microorganisms that produce deacylases are well known to those of ordinary skill in the art. In a preferred embodiment, the microorganism *Actinoplanes utahensis* (NRRL #12052) produces a suitable deacylase.

Growing inocula, inoculating media, culturing media and conditions for culturing such enzymes are also well known to those of ordinary skill in the art and exemplary methods for *Actinoplanes utahensis* (NRRL #12052) are described in Boeck et al., 1988, *J. Antibiot.* 41: 1085; Debono et al., 1988, *J. Antibiotics* 41: 1093; U.S. Pat. No. 4,524,135 (see, e.g., Cols. 22-23) and U.S. Pat. No. 5,039,789 (see, e.g., Col. 29, lines 9-63).

In one embodiment, compounds 14 or 18 are delipidated by contacting them with a culture medium comprising *Actinoplanes utahensis* (NRRL #12052) for about 4 to 16 hours at a temperature of about 29° C. The reaction may be monitored by chromatography or other routine techniques, thereby permitting shorter or longer incubations, as needed. Additional methods which may be used to delipidate compounds 14 or 18 are found in Debono et al, 1988, *J. Antibiotics* 41: 1093; U.S. Pat. No. 5,039,789 (see, e.g., Cols. 29-34) and U.S. Pat. No. 5,629,288.

While Scheme (I) illustrates certain $Dab^9$ derivatives of the invention in which substituent $R^6$ is attached to the macrocyclic $Dab^9$ residue via an amide linkage, those of ordinary skill in the art will recognize that $Dab^9$ derivatives including other linkages may be synthesized by routine modification of the illustrated schemes. Moreover, in some instances, substituent $R^3$ may include additional functionalities requiring protection. The identity of the protecting group will depend upon, among other things, the functionality being protected and other protecting groups present on the molecule, and will be apparent to those of ordinary skill in the art. Guidance may be found in Greene & Wuts, supra.

While Scheme (I) illustrates certain $Dab^9$ derivatives of the invention in which substituent $R^2$ or $R^2$-L is attached to the N-terminus via an amide linkage, those of ordinary skill in the art will recognize that derivatives including other linkages may be synthesized by routine modification of the illustrated schemes. Moreover, in some instances, substituent $R^2$ or $R^2$-L may include additional functionalities requiring protection. The identity of the protecting group will depend upon, among other things, the functionality being protected and other protecting groups present on the molecule, and will be apparent to those of ordinary skill in the art. Guidance may be found in Greene & Wuts, supra.

The derivative compounds of the invention may be isolated and purified using standard techniques, such as high performance liquid chromatography, counter current extraction, centrifugation, filtration, precipitation, ion exchange chromatography, gel electrophoresis, affinity chromatography, flash chromatography, etc. Specific methods of isolation are provided in the Examples section below. Any of the various parent antibiotics, core cyclic compounds, intermediate compounds, or derivative antibiotic compounds of the invention may also be isolated and purified using the extractive purification methods described in WO 02/055537, which is incorporated herein by reference. For example, HPLC purification can be performed on a BioCAD® Sprint™ Perfusion Chromatography® system using a Waters Symmetry-Prep C18 or C8 column (7 µm, 19×150 mm) for most of the methods used to prepare the derivative lipopeptide antibiotic compounds of the invention. In addition, purity analysis can be performed using a Spherisorb® S3 column (ODS2, 2.0×100 mm) on a Waters 2695 Separations system with a 996 Photodiode Detector (Waters, Milford, Mass.). For example, a linear gradient elution from 40% to 80% acetonitrile in Milli-Q® water can be used at 0.25 mL/min (each eluent containing 0.1% trifluoroacetic acid) over 15 minutes with a column temperature of 40° C., and data can be processed, for example, with the Millennium32™ Chromatography Manager V4 software (Waters, Milford, Mass.).

Those of ordinary skill in the art will appreciate that many of the derivative compounds of the invention, as well as the various compound species described herein, may exhibit the phenomena of tautomerism, conformational isomerism, geometric isomerism or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric or geometric isomeric forms of the compounds having one or more of the utilities described herein, as well as mixtures of these various different forms.

Moreover, although the exact optical configurations of the chiral centers of the various illustrated amphomycin-type macrocyclic cores are not specified, it is to be understood that the structural illustrations are intended to be a short-hand way of describing these cores, and are not intended to be limiting. It will be understood that the specific optical configurations are those possessed by the macrocyclic cores of the amphomycin-type lipopeptide antibiotics, whether they are known or unknown.

Also, while these structures of the peptide macrocycles comprising the various parent amphomycin-type lipopeptide antibiotics from which the lipopeptide derivatives of the invention are derived are believed to be correct, in some instances at a later date, errors may be revealed. Again, the structural illustrations are intended to be a short hand way of describing the various compounds and are not intended to be limiting. It should be understood that, in the derivative compounds of the disclosure, the structures of the peptide macrocycles are those possessed by the parent amphomycin-type lipopeptide antibiotics from which the specific derivatives are derived.

Characterization of Lipopeptide Derivatives

The lipopeptide derivatives of the invention generally exhibit antimicrobial activity against Gram-positive bacteria that is similar to that exhibited by conventional amphomycin-type lipopeptide antibiotics, as measured in in vitro and in vivo assays. Moreover, many of the lipopeptide derivatives of the disclosure display surprisingly improved therapeutic potential (such as reduced toxicity, an improved spectrum of activity, and enhanced pharmacokinetics/pharmacodynamic properties) as compared to conventional amphomycin-type lipopeptide antibiotics, making the amino terminal or $Dab^9$ derivatives of the invention particularly suited for therapeutic use (e.g., for systemic administration), or for favorable dosing regimens to combat infections caused by, for example, Gram-positive bacteria (e.g., *Staphylococcus* spp., *Streptococcus* spp., *Enterococcus* spp.).

Antimicrobial lipopeptide compounds of the disclosure may be identified as active by using, for example, in vitro screening assays known in the art, such as standard NCCLS bacterial inhibition assays or minimum inhibitory concentration (MIC) tests. See, e.g., National Committee on Clinical Laboratory Standards "Performance Standards for Antimicrobial Susceptibility Testing," NCCLS Document M100-S5 Vol. 14, No. 16, December 1994; "Methods for dilution antimicrobial susceptibility test for bacteria that grow aerobically-Third Edition," Approved Standard M7-A3, National Committee for Clinical Standards, Villanova, Pa. ("Approved Standard M7-A3"). Antimicrobial compounds are considered active when exhibiting an MIC of less than about 64 µg/mL. In certain preferred embodiments, the compounds have an MIC of less than about 64 µg/mL, less than about 32 µg/mL, less than about 16 µg/mL, or less than about 4 µg/mL against microorganisms, such as bacteria (particularly Gram positive bacteria). In certain embodiments, antimicrobial lipopeptide compounds that exhibit low toxicity or significant antimicrobial activity (e.g., less than 4 µg/mL or less than 16 µg/mL) may be preferred for use in treating or preventing systemic infections, including against antibiotic resistant microorganisms. In other embodiments, antimicrobial lipopeptide compounds of the disclosure may be preferred for use in treating or preventing topical infections (e.g., skin infections). Specific in vitro and in vivo assays suitable for demonstrating antimicrobial activity pertinent to a particular route of administration are provided in the Examples.

An exemplary pharmacokinetic parameter to aid in characterizing the properties of lipopeptide derivative compounds of the disclosure is post-antibiotic effect (PAE) of a lipopeptide derivative. For example, a bacterial culture with an initial count of $10^6$ to $10^7$ colony forming units per ml (CFU/ml) is treated with a certain concentration of lipopeptide derivative for a certain time and a parallel (control) culture is left untreated. After treatment, the lipopeptide derivative is removed from the culture (e.g., by dilution 1:1000 in fresh, lipopeptide derivative-free medium), and the untreated culture is manipulated in the same way. Then the cultures are further incubated and monitored for bacterial growth over time. Hence, a PAE can be defined as the time (which can be measured in minutes or hours) required for a lipopeptide derivative-treated culture to increase the number of CFU by 1 $log_{10}$ as compared to an untreated control. By way of background and not wishing to be bound by theory, a lipopeptide derivative having a measurable PAE activity will likely provide additional time for the host immune system to remove bacteria that might have survived antibiotic treatment and reproduced after the antibiotic is degraded, removed or filtered from the circulatory system. A longer PAE can influence the clinical outcome of antimicrobial therapy (i.e., a lower dose of a lipopeptide derivative may be used to treat an infection or the frequency of a dosing regimen can be reduced).

Another measure of the antimicrobial properties of the lipopeptide derivative compounds of this disclosure includes kill curve measurements. Kill curve experiments generally involve exposure of microorganisms to varying concentrations (e.g., multiples of a compound's MIC) of a test compound. The microorganisms may be in culture at log phase of growth or may be in a particular host tissue (e.g., lung) for up to 24 hours before exposure to a test compound. At selected time points, a sample of each culture or tissue can be analyzed for a titre of viable microorganisms, which is generally gauged against the time required for a compound to inhibit growth or kill bacteria. It is well established in the microbiological art that a compound is bactericidal if the compound kills 99.9% of bacterial cells within 24 hours (see, e.g., NCCLS guideline M26-A, Vol. 19 N#18).

A variety of in vivo models may be used to assess the antimicrobial properties of lipopeptide derivative compounds of this disclosure. For example, antimicrobial compounds of the instant disclosure may be tested for efficacy by measuring a compound's ability to protect a mouse against a microbial infection, such as an infection or disease caused by or related to Gram-positive bacteria, including *Staphylococcus aureus*, *Streptococcus pneumoniae*, and *Enterococcus faecalis*. Briefly, mice are individually infected (for example, intraperitoneally (i.p.)) with a bacterial inoculum of generally more than one $LD_{50}$ dose (50% lethal dose, e.g., 2-3 $LD_{50}$s). An $LD_{50}$ is the dose of bacteria required to kill 50% of an infected population, such as mice. A certain period after infection, mice are then individually treated, for example intravenously (i.v.), with a lipopeptide derivative of this disclosure. The mice are then monitored for a certain period of time (e.g., a few days up to one or more weeks) to observe whether the test lipopeptide derivatives were capable of protecting mice from a fatal systemic infection, or capable of protecting against the appearance of other symptoms of infection.

Other exemplary in vivo models of infection that may be used to assess, for example, the efficacy of an antimicrobial lipopeptide of the instant disclosure include the following: (A) a mouse (murine) model of lung infection (pneumonia) wherein the bacterial infection is administered intranasally (i.n.); (B) a murine thigh muscle model wherein the bacterial infection is administered intramuscularly (i.m.) in normal or neutropenic (immunocompromised) mice; and (C) a combination murine thigh muscle model (i.m. infection)/lung (i.n.) infection. Generally, an $ED_{50}$ (50% effective dose) for each lipopeptide derivative of the invention is measured. As used herein, an $ED_{50}$ can mean an effective dose to (a) protect 50% of animals infected (e.g., as in the i.p. and pneumonia models), or (b) produce 50% of maximum log reduction at 24 hours post-treatment (e.g., as in the thigh muscle and lung tissue models). In certain embodiments, $ED_{50}$ values can range from about 0.1 mg/kg to about 50 mg/kg, or from about 0.15 mg/kg to about 30 mg/kg, or from about 0.2 mg/kg to about 15 mg/kg, or from about 0.25 mg/kg to about 10 mg/kg.

Yet other exemplary in vivo models can be used to characterize the pharmacokinetics and pharmacodynamic parameters of antimicrobial compounds of this disclosure. Some parameters that can be measured include an in vivo half-life of a compound, elimination rate and clearance, volume of distribution, and bioavailability. For example, briefly, compounds can be administered as a single i.v. or oral (p.o.) dose in mice or rats. At various time points (ranging from 1 minute to 72 hours), blood from treated animals is collected and the concentration of lipopeptide derivative in the ex vivo plasma can be quantified by, for example, liquid chromatography with mass spectrometric detection (LC/MS). After quantification, pharmacokinetics parameters can be calculated using methods known in the art, such as a one compartment model with mono-exponential decay and linear regression analysis (see, e.g., Fantin et al., *Antimicrob. Agents Chemotherap.* 35: 1413. 1991).

Formulations and Compositions

Pharmaceutical compositions comprising the antimicrobial lipopeptide derivatives of the disclosure may be manufactured by means of conventional mixing, dissolving, granulating, dragee making, levigating, emulsifying, encapsulating, entrapping or lyophilizing processes. Pharmaceutical compositions may be formulated in conventional manner using one or more physiologically acceptable carriers, diluents, excipients or auxiliaries that facilitate formulating active antimicrobial lipopeptide derivatives into preparations that can be used pharmaceutically. A single antimicrobial lipopeptide derivative, a plurality of antimicrobial lipopeptide derivatives, or antimicrobial lipopeptide derivatives combined with one or more industrially or biologically active agents may be formulated with a pharmaceutically acceptable carrier, diluent or excipient to generate industrial and pharmaceutical compositions, respectively, of the instant disclosure.

Pharmaceutically acceptable carriers, diluents or excipients for therapeutic use are well known in the pharmaceutical art, and are described herein and, for example, in *Remington's Pharmaceutical Sciences*, Mack Publishing Co. (A. R. Gennaro, ed., 18$^{th}$ Edition, 1990) and in *CRC Handbook of Food, Drug, and Cosmetic Excipients*, CRC Press LLC (S. C. Smolinski, ed., 1992). In certain embodiments, antimicrobial lipopeptides derivatives may be formulated with a pharmaceutically or physiologically acceptable carrier, diluent or excipient is aqueous, such as water or a mannitol solution (e.g., about 1% to about 20%), hydrophobic (e.g., oil or lipid), or a combination thereof (e.g., oil and water emulsions). In certain embodiments, any of the pharmaceutical compositions described herein may be sterile.

The formulations of the present invention, having an amount of antimicrobial lipopeptide sufficient to treat or prevent an infection are, for example, particularly suitable for topical (e.g., creams, ointments, skin patches, eye drops, ear drops, shampoos) application or administration. Other routes of administration include, without limitation, oral, parenteral, sublingual, bladder wash-out, vaginal, rectal, enteric, suppository, nasal, or inhalation. The term parenteral, as used herein, includes subcutaneous, intravenous, intramuscular, intraarterial, intraabdominal, intraperitoneal, intraarticular, intraocular or retrobulbar, intraaural, intrathecal, intracavitary, intracelial, intraspinal, intrapulmonary or transpulmonary, intrasynovial, and intraurethral injection or infusion techniques. The pharmaceutical compositions of the present disclosure are formulated so as to allow the antimicrobial lipopeptide(s) contained therein to be bioavailable upon administration of the composition to a subject. The level of lipopeptide in serum and other tissues after administration can be monitored by various well-established techniques, such as bacterial, chromatographic or antibody (e.g., ELISA) based assays. In certain embodiments, antimicrobial lipopeptides derivatives, as described herein, are formulated for topical application to a target site on a subject in need thereof, such as an animal or a human. In other embodiments, antimicrobial lipopeptides derivatives are formulated for parenteral administration to a subject in need thereof (e.g., having Gram-positive bacterial infection), such as an animal or a human.

Proper formulation is dependent upon the route of administration chosen, as is known in the art. For example, in exemplary embodiments for topical administration, the antimicrobial lipopeptide derivatives of the disclosure may be formulated as solutions, gels, ointments, creams, suspensions, pastes, and the like. Systemic formulations are another embodiment, which includes those designed for administration by injection, e.g. subcutaneous, intravenous, intramuscular, intrathecal or intraperitoneal injection, as well as those designed for transdermal, transmucosal, oral, intranasal, or pulmonary administration. In one embodiment, the systemic formulation is sterile. In embodiments for injection, the antimicrobial lipopeptide derivatives of the instant disclosure may be formulated in aqueous solutions, preferably in physiologically compatible solutions or buffers such as Hanks's solution, Ringer's solution, mannitol solutions or physiological saline buffer. In certain embodiments, any of the compositions described herein may contain formulatory agents, such as suspending, stabilizing or dispersing agents. Alternatively, the antimicrobial lipopeptide derivatives may be in solid (e.g., powder) form for constitution with a suitable vehicle (e.g., sterile pyrogen-free water) before use. In embodiments for transmucosal administration, penetrants, solubilizers or emollients appropriate to the barrier to be permeated may be used in the formulation. For example, 1-dodecylhexahydro-2H-azepin-2-one (Azone®), oleic acid, propylene glycol, menthol, diethyleneglycol ethoxyglycol monoethyl ether (Transcutol®), polysorbate polyethylenesorbitan monolaurate (Tween®-20), and the drug 7-chloro-1-methyl-5-phenyl-3H-1,4-benzodiazepin-2-one (Diazepam), isopropyl myristate, and other such penetrants, solubilizers or emollients generally known in the art may be used in any of the compositions of the instant disclosure.

In other embodiments, the antimicrobial lipopeptide derivatives can be formulated with pharmaceutically acceptable carriers in the form of tablets, pills, dragees, capsules, liquids, gels, syrups, slurries, suspensions and the like, for oral ingestion by a subject or patient to be treated. In certain embodiments for oral solid formulations, such as powders, capsules or tablets, suitable excipients include fillers, such as sugars (e.g., lactose, sucrose, mannitol, sorbitol); cellulose preparations such as maize starch, wheat starch, rice starch, potato starch, gelatin, gum tragacanth, methyl cellulose, hydroxypropylmethyl-cellulose, sodium carboxymethylcellulose, or polyvinylpyrrolidone (PVP); granulating agents; or binding agents. Optionally, disintegrating agents may be added, such as cross-linked polyvinylpyrrolidone, agar, or alginic acid (or a salt thereof, such as sodium alginate). If desired, solid dosage forms may be sugar-coated or enteric-coated using standard techniques. In some embodiments for oral liquid preparations, such as suspensions, elixirs or solutions, suitable carriers, excipients or diluents include water, glycols, oils, alcohols, or combinations thereof. Additionally, flavoring agents, preservatives, viscosity-increasing agents, humectants, coloring agents, or the like, may be added. In embodiments for buccal administration, the compositions may take the form of, for example, tablets or lozenges, formulated as known in the art and described herein.

In embodiments for administration by inhalation, the compounds for use according to the present disclosure may be formulated for convenient delivery in the form of drops for intranasal administration, or in the form of an aerosol spray from pressurized packs or nebulizer having a suitable propellant (e.g., dichlorodifluoromethane, trichlorofluoromethane, dichlorotetrafluoroethane, carbon dioxide or other suitable gas). In certain embodiments, the drops or aerosol composition is sterile. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base, such as lactose or starch.

In other embodiments, the antimicrobial lipopeptide derivatives may be formulated into rectal or vaginal compositions such as suppositories or retention enemas, e.g., containing conventional suppository bases, such as cocoa butter or other glycerides.

In addition to the formulations described herein, the antimicrobial lipopeptide derivatives may also be formulated as a depot preparation. For example, antimicrobial lipopeptide derivatives of this disclosure can be in the form of the slow-release formulation such that they can provide activity over time. Such long-acting formulations may be administered by implantation (for example, subcutaneously or intramuscularly) or by intramuscular injection. In certain embodiments, the compounds may be formulated with suitable a polymer (including poly(lactides), poly(glycolides), poly(caprolactones), and blends thereof), a hydrophobic material, (including a physiologically acceptable oil, which can be in the form of an emulsion), an ion exchange resin, or as sparingly soluble derivatives (such as a sparingly soluble salt).

Alternatively, other pharmaceutical delivery systems may be employed. In certain embodiments, the compounds are formulated with liposomes or emulsions as delivery vehicles. Certain organic solvents, such as dimethylsulfoxide (DMSO), may also be employed. Additionally, the antimicrobial lipopeptide derivatives may be delivered using a sustained-release system, such as semipermeable matrices of solid or semi-solid polymers (e.g., thermopaste) containing the therapeutic agent. Sustained-release capsules may, depending on their chemical nature, release the compounds for a few days, for a few weeks, or for up to about 100 days.

As certain of the carboxyl groups of the antimicrobial lipopeptide derivatives of the invention are acidic, or the substituents $R^2$, $R^3$, $R^4$, and linkers L may include acidic or basic substituents, the antimicrobial lipopeptide derivatives may be included in any of the above-described formulations as a free acid, a free base, or as a pharmaceutically acceptable salt. Pharmaceutically acceptable salts are those salts that substantially retain the antimicrobial activity of the free acid or base, and which are prepared by reaction with a base or acid, respectively. Suitable acids and bases are well known to those of ordinary skill in the art. Pharmaceutical salts tend to be more soluble in aqueous and other protic solvents than is the corresponding free base or acid form.

The lipopeptide compositions may be administered to a subject as a single dosage unit (e.g., a tablet, capsule, injection or gel), or the compositions may be administered as a plurality of dosage units (e.g., in aerosol or injectable form). For example, the antimicrobial lipopeptide formulations may be sterilized and packaged in single-use, plastic laminated pouches or plastic tubes of dimensions selected to provide for routine, measured dispensing. In one example, the container may have dimensions anticipated to dispense 0.5 ml of the antimicrobial lipopeptide composition (e.g., a drop, gel or injection form) to a subject, or to a limited area of a target surface on or in a subject, to treat or prevent an infection. A target surface, for example, may be in the immediate vicinity of a skin infection (e.g., necrotizing fasciitis or other complicated skin infection), where the target surface area will depend on the extent of an infection.

The antimicrobial lipopeptide compositions may be provided in various forms, depending on the amount and number of different pharmaceutically acceptable excipients present. For example, the lipopeptide compositions may be in the form of a solid, a semi-solid, a liquid, a lotion, a cream, an ointment, a cement, a paste, a gel, or an aerosol. In a preferred embodiment, the lipopeptide formulation is in the form of a liquid or a gel. The pharmaceutically acceptable excipients suitable for use in the lipopeptide formulation compositions as described herein may optionally include, for example, a viscosity-increasing agent, a buffering agent, a solvent, a humectant, a preservative, a chelating agent (e.g., EDTA or EGTA), an oleaginous compound, an emollient, an antioxidant, an adjuvant, or the like. Exemplary buffering agents suitable for use with the antimicrobial lipopeptide derivatives or compositions thereof of the instant disclosure include monocarboxylate or dicarboxylate compounds (such as acetate, fumarate, lactate, malonate, succinate, or tartrate). Exemplary preservatives include benzoic acid, benzyl alcohol, phenoxyethanol, methylparaben, propylparaben, and the like. The function of each of these excipients is not mutually exclusive within the context of the present invention. For example, glycerin may be used as a solvent or as a humectant or as a viscosity-increasing agent.

Industrial and Therapeutic Uses

The antimicrobial lipopeptide derivatives of the invention can be used in a wide variety of applications to inhibit the growth of, or to kill, microorganisms (e.g., Gram-positive bacteria). For example, the antimicrobial lipopeptide derivatives may be used as disinfectants or as preservatives for a variety of materials, including foodstuffs, cosmetics, medicaments or other nutrient-containing materials. The antimicrobial lipopeptide derivatives can also be used to treat or prevent diseases related to, associated with, or caused by microbial infections in a subject, such as a human, plant or animal, and preferably a human (including immunocompromised or immunocompetent subjects). For example, the antimicrobial lipopeptide derivatives of this disclosure are useful for ameliorating, treating or preventing various clinical conditions, such as complicated skin or skin structure infections (e.g., necrotizing fasciitis), surgical wound infections, intra-abdominal infections, urinary tract infections or pyelonephritis, nosocomial infections, community-acquired infections (e.g., pneumonia), infective endocarditis, or the like.

In certain embodiments, the active antimicrobial compounds of the instant disclosure will be active against Gram-positive bacteria, such as *Streptococci* (including *S. pyogenes, S. pneumoniae, Viridans Streptococci*), *Staphylococci* (including *S. aureus, S. epidermidis,* coagulase-negative *Staphylococci*), and *Enterococci* (including *E. faecalis, E. faecium*), as well as antibiotic-resistant microorganisms, such as methicillin-resistant *Staphylococcus areus* (MRSA), methicillin-resistant *Staphylococcus epidermidis* (MRSE), vancomycin-resistant *Enterococci* (VRE), vancomycin-intermediate *S. areus* (VISA), penicillin-resistant *Streptococcus pneumoniae* (PRSP), penicillin-intermediate *S. pneumoniae* (PISP), or multidrug-resistant (MDR) microorganisms. Some other exemplary Gram-positive microorganisms against which antimicrobial compounds of the instant disclosure will be active include *Bacillus* spp., *Corynebacterium* spp., diphtheroids, *Listeria* spp., or the like.

For industrial use as a disinfectant or preservative, the antimicrobial lipopeptide derivatives can be added to a desired composition alone, as a mixture of the same or different antimicrobial lipopeptide derivatives, or in combination with other antimicrobial agents (e.g., antifungal, antiviral, antibacterial). The antimicrobial lipopeptide derivatives may be supplied as the compound per se, or may be combined, mixed or admixed with a variety of pharmaceutically acceptable carriers, diluents or excipients, as described herein.

When used therapeutically to treat or prevent microbial infections or diseases related thereto, antimicrobial lipopeptide derivatives of the instant disclosure can be administered or applied alone, as a plurality (e.g., two or more) of the same or different antimicrobial lipopeptide derivatives, in combination with other antimicrobial agents, or in combination with other pharmaceutically active agents. The antimicrobial lipopeptide derivatives can be administered or applied per se, or as a pharmaceutical composition. The specific pharmaceutical formulation will depend upon the desired mode of administration, as described herein, and will be apparent to those having ordinary skill in the art.

The therapeutic efficacy of an antimicrobial lipopeptide derivative or composition thereof according to the present disclosure is based on a successful clinical outcome and does not require 100% elimination of the microorganisms involved in or associated with the infection. Achieving a level of antimicrobial activity at, for example, the site of infection, which allows host survival, resolution of the infection or eradication of the causative agent, is sufficient. When host defenses are maximally effective, such as in an otherwise healthy individual, only a minimal antimicrobial effect may suffice. For example, reducing the organism load by even one log (a factor of 10) may permit the defenses of the host to control the infection. In certain embodiments, clinical therapeutic success may depend more on augmenting an early bactericidal effect rather than on a long-term effect because this allows time for activation of host defense mechanisms. This may be desirable in, for example, life-threatening acute infections (e.g., necrotizing fasciitis) or serious chronic infections (e.g., infective endocarditis).

The antimicrobial lipopeptide derivatives of the instant disclosure, or compositions thereof, can be used in an amount effective to achieve the intended purpose, which will depend on the particular application or indication. For example, for use as a disinfectant or preservative, an antimicrobially effective amount of an antimicrobial lipopeptide derivative or composition thereof is applied or added to the material to be disinfected or preserved. By "antimicrobial effective amount" is meant an amount of an antimicrobial lipopeptide derivative or composition of the invention that inhibits the growth of, or is lethal to, a target microbe. While the actual amount will depend on the particular target microbe and application, for use as a disinfectant or preservative, the antimicrobial lipopeptide derivatives, or compositions thereof, are usually added or applied to the material to be disinfected or preserved in relatively low amounts. Typically, the antimicrobial lipopeptide derivatives comprise less than about 5% by weight of the disinfectant solution or material to be preserved, preferably less than about 1% by weight and more preferably less than about 0.1% by weight. Those having ordinary skill in the art will be able to determine antimicrobially effective amounts of particular antimicrobial lipopeptide derivatives for particular applications or indications without undue experimentation using, for example, the in vitro or in vivo assays described herein.

As used herein, it should be understood that the terms "inhibit" and "kill" refer to the administration of a desired composition or compound, in an amount or for a time sufficient to reduce, inhibit, attenuate, prevent, eradicate, exterminate or alter at least one aspect or marker of microbial growth or survival in a statistically significant manner (i.e., is antimicrobially effective). Inhibition of bacterial growth or survival may be determined, for example, by measuring the number of bacterial colony forming units (CFUs) before exposure to antimicrobial lipopeptide derivative(s) as compared to the number of bacterial CFUs after exposure to antimicrobial lipopeptide derivative(s) (in vitro or in vivo).

For use in treating or preventing microbial infections, the antimicrobial lipopeptide derivatives of the invention and compositions thereof are administered or applied in a therapeutically effective amount. As used herein, "therapeutically effective amount" means an amount effective to ameliorate the symptoms of, or ameliorate, treat or prevent microbial infections. Determination of a therapeutically effective amount is well within the capabilities of those having ordinary skill in the art as described herein. As in the case of disinfectants and preservatives, a therapeutically effective dose for topical administration to treat or prevent microbial infections can be determined using, for example, the in vitro or in vivo assays discussed herein. The treatment may be applied while the infection is visible or when the infection is not visible. As used herein, it should be understood that the terms "treat", "prevent" and "ameliorate" refer to the therapeutic administration of a desired composition or compound, in an amount or for a time sufficient to treat, inhibit, attenuate, ameliorate, reduce, prevent or alter at least one aspect or marker of a disease in a statistically significant manner (i.e., is therapeutically effective).

The compositions and methods of the present invention would be therapeutically effective in treating or preventing complicated and uncomplicated skin or skin structure infections. Exemplary complicated and uncomplicated skin infections include impetigo, folliculitis, furunculosis (furuncle or skin boil), ecthyma, erysipelas, cellulitis, acute paronychia, felon, necrotizing fasciitis, Staphylococcal scalded skin infection, nodular lymphangitis, preseptal cellulitis, or periorbital cellulitis. The lipopeptide formulations as described herein may be applied topically as a cream, lotion, ointment or gel (or in any of these forms as part of or coated on a dressing) to the affected areas, or as an injectable solution, emulsion, suspension, etc. The lipopeptide formulations may be administered multiple times during the day, once a day, or in less frequent intervals (such as once a week or less), and the length of treatment may be for as long as the lesions are present or to prevent recurrent lesions. Alternatively, the lipopeptide composition may be formulated for oral or systemic administration to treat or prevent complicated skin or skin structure infections. In certain embodiments, antibiotic compounds and compositions thereof are provided for use in a method for treating or preventing a microbial infection, such as a complicated skin or skin structure infection, by administering to a subject in need thereof an antibiotic compound or composition thereof in an amount effective to treat or prevent the complicated skin infection.

The compositions and methods of the present invention would be therapeutically effective in treating or preventing complicated intra-abdominal infections. By way of background, complicated intra-abdominal infections are problems in clinical practice and consume substantial hospital resources, such as emergency department services, imaging services, operating room time, laboratory services, antibiotic therapy, and in-hospital care of variable intensity. Outcomes are heavily influenced by the rapidity of diagnosis and appropriate intervention and by the timeliness and efficacy of anti-infective therapy. Postoperative (nosocomial) infections are generally caused by more-resistant flora, which may include *Pseudomonas aeruginosa*, methicillin-resistant *Staphylococcus aureus, enterococci*, and *Candida* spp. For these infections, complex multidrug regimens are recommended because adequate empirical therapy appears to be important in reducing mortality. However, these infections remain an important area for clinical research. In certain embodiments, lipopeptide antibiotic compounds and compositions thereof of the instant disclosure are provided for use in a method for treating or preventing a microbial infection, including complicated intra-abdominal infections, such as those due to or associated with *S. aureus*.

The compositions and methods of the present invention would be therapeutically effective in treating or preventing complicated urinary tract infections or pyelonephritis. By way of background, complicated urinary tract infections (cUTI) is defined as a clinical syndrome in men or women characterized by the development of the systemic and local signs and symptoms of fever, chills, malaise, flank pain and back pain, occurring in the presence of a functional or anatomical abnormality of the urinary tract or in the presence of catheterization. Pyelonephritis is defined as a systemic, ascending urinary tract infection, clinically manifested by fever, chills, flank pain, nausea or vomiting, which is frequently associated with bacteremia due to the same pathogen as isolated in the urine. In the many cases, cUTI and pyelonephritis are caused by pathogens from the Enterobacteriaceae, and other etiologic agents include *Enterococci* spp. and *Pseudomonas* spp. In certain embodiments, lipopeptide antibiotic compounds and compositions thereof of the instant disclosure are provided for use in a method for treating or preventing a microbial infection, such as complicated urinary tract infections or pyelonephritis.

As used herein, an infection that is "complicated" refers to a disease condition upon which a morbid process or event has been superimposed, altering the symptoms and course of infection for the worse—the "complication" is not an essential part of the disease or infection, although the complication may arise from the disease or the infection, or from independent causes.

Another example of the therapeutic value of the compositions and methods of the present invention would be in the treatment of nosocomial infections. For example, infection by *S. aureus* may result in impetigenous lesions or infected wounds, and may be associated with increased infection rates following cardiac surgery, hemodialysis, orthopedic surgery and neutropenia, both disease-induced and iatrogenic. Nasal and extra-nasal carriage of *Staphylococci* spp. can result in hospital outbreaks of the same staphylococcal strain that is colonizing a patient's or a hospital worker's nasal passage or extra-nasal site. Much attention has been paid to the eradication of nasal colonization, but the results of treatment have been generally unsatisfactory. The use of topical antimicrobial substances, such as bacitracin, tetracycline, and chlorhexidine, results in the suppression of nasal colonization, as opposed to eradication. In certain embodiments, the antibiotic compounds and compositions thereof are provided for use in a method for treating or preventing nosocomial infections (such as nosocomial pneumonia), community-acquired pneumonia (i.e., caused by an organism found regularly outside a hospital setting, such as *Streptococcus pneumoniae, Hemophilus influenzae, Mycoplasma*), infections due to drug-resistant bacteria (such as VRE and MRSA), endocarditis (acute or subacute), and the like.

For systemic administration, a therapeutically effective dose can be estimated initially from in vitro or in vivo assays. For example, a dose can be formulated in animal models to achieve a circulating antimicrobial lipopeptide derivative concentration range that includes the MIC, as determined in cell culture. Initial dosages can also be estimated from in vivo data, e.g., animal models, using techniques that are well known in the art. One having ordinary skill in the art can readily optimize administration to humans based on animal data. Alternatively, initial dosages can be determined from the dosages administered of known amphomycin-type lipopeptide antibiotics (e.g., amphomycin, aspartocin, crystallomycin, antibiotic A1437, friulimycin, glumamycin, tsushimycin and zaomycin) by comparing the MIC of the specific antimicrobial lipopeptide derivative with that of the known antimicrobial agent, and adjusting the initial dosages accordingly. The optimal dosage may be obtained from these initial values by routine optimization.

Dosage amount and interval may be adjusted individually to provide plasma levels of one or more active antimicrobial lipopeptide derivatives that are sufficient to maintain a therapeutic effect. Generally, patient dosages for administration by injection range from about 0.1 to about 200 mg/kg/day, and preferably range from about 1.5 to about 15 mg/kg/day. In certain lipopeptide derivative embodiments, therapeutically effective serum levels may be achieved by administering a single dose daily, or by administering multiple doses each day over a specified time period. In other embodiments, therapeutically effective serum levels may also be achieved by administering at less frequent dosing schedules such as, for example, once every two days, twice a week, once a week or at longer intervals between dosing, or any combination thereof. For example, combination administration schedules may be utilized to reach therapeutically effective does, such as multiple does on one or more days followed by less frequent dosing such as, for example, once every two days, twice a week or once a week, or longer.

In cases of local administration or selective uptake, the effective local concentration of antimicrobial lipopeptide derivatives may not be related to plasma concentration. One having ordinary skill in the art will be able to optimize therapeutically effective local dosages without undue experimentation. The amount of antimicrobial lipopeptide derivative administered will be dependent upon, among other factors, the subject being treated, the subject's weight, the severity of the affliction, the manner of administration and the judgment of the prescribing physician.

The antimicrobial therapy may be repeated intermittently while infections are detectable, or even when they are not detectable. The therapy may be provided alone or in combination with other drugs, such as, for example, other antibiotics or antimicrobials, or other antimicrobial lipopeptide derivatives of this disclosure.

Preferably, a therapeutically effective dose of the antimicrobial lipopeptide derivatives described herein will provide therapeutic benefit without causing substantial toxicity. Toxicity of the antimicrobial lipopeptide derivatives can be determined using standard pharmaceutical procedures in cell cultures or experimental animals, e.g., by determining the $LD_{50}$ (the dose lethal to 50% of the population) or the $LD_{100}$ (the dose lethal to 100% of the population). Another measure of toxicity is the maximum tolerated dose (MTD), which is determined as a dose level that is not accompanied by mortality or life-threatening toxicity. The dose ratio between toxic and therapeutic effect is the therapeutic index. Antimicrobial lipopeptide derivatives that exhibit high therapeutic indices are preferred. The data obtained from these cell culture assays and animal studies can be used in formulating a dosage range that is not toxic for use in human subjects. The dosage of the antimicrobial lipopeptide derivatives described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition or need thereof (see, e.g., Fingl et al., 1975, In: *The Pharmacological Basis of Therapeutics*, Chapter 1).

For example, to examine acute toxicity, lipopeptide antibiotics of the invention can be tested in an animal model, such as Swiss CD1 mice, to determine the MTD. In certain embodiments, the animals used to test toxicity of a particular compound can be approximately 5-6 weeks old at the start of the experiment and weigh 22-26 g. The lipopeptides may be administered intravenously (i.v.) into, for example, the caudal tail vein at dose levels that range from about 50 to about 500 mg/kg, or from about 75 to about 250 mg/kg, or from about 100 to about 200 mg/kg, or at a dose range at or below 100 mg/kg. The animals are generally observed immediately after administration, 1-2 hours post administration, 5-8 hours post administration, and once daily thereafter. Observations include both the activity level of the mouse as well as any physical side effects from the administered dose. The animal weight is recorded on day 0 (immediately before dosing) and on day 7. The observed MTD for amphomycin and aspartocin was about 100 mg/kg. Thus, a lipopeptide derivative with an MTD greater than amphomycin and aspartocin (i.e., a subject can tolerate more of a compound before having detectable or even non-detectable side effects) should be considered as less toxic than amphomycin and aspartocin. In certain embodiments, the toxicity (MTD) of a lipopeptide compound of the instant disclosure is at or below 100 mg/kg, while in other embodiments the compounds have an MTD at or below 200 mg/kg. For example, certain exemplary lipopeptide antibiotic derivatives of the instant disclosure do not show acute toxicity (MTD) until in the range 200-400 mg/kg (i.v.) (e.g., compounds 4, 199, 278, and 280. In certain other embodiments, lipopeptide compounds of the instant disclosure display toxicity (MTD) in a range of about 50 mg/kg to about 200 mg/kg (i.v.) (e.g., compounds 3, 85, 108, and 119.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. The invention having been described, the following examples are intended to illustrate, and not limit, the invention.

EXAMPLES

The list of suppliers used to purchase the starting materials and reagents used in the methods described herein include Sigma Aldrich (and Fluka) (Oakville, Ontario), Advanced Chemtech (Louisville, Ky.), Bachem (Torrance, Calif.), Lancaster (Windham, N. H.), Chem-Impex International (Wooddale, Ill.), and Acros (Morris Plains, N.J.).

Example 1

Preparation of an Activated Acid

As is known in the art, any of a variety of carboxylic acids may be activated in the following or similar reaction. By way of example and not limitation, the preparation of an activated succinimide ester of pentadecanoic acid is described. Pentadecanoic acid (1.07 g, 4.4 mmol) was dissolved in 22 mL of dry dimethylformamide (DMF). Hydroxysuccinimide (0.52 g, 4.5 mmol) was added and the mixture cooled in an ice bath. Dicyclohexylcarbodiimide (1.07 g, 5.2 mmol) was added in two equal portions 10 minutes apart to the reaction mixture, after which the mixture was stirred for 20 minutes at about 4° C. The mixture was allowed to warm to room temperature and stirred for no less than 6 hours. The resulting crude product was concentrated in vacuo, purified by redissolving with isopropanol, and then the product was crystallized with hexane to afford relatively clean pentadecanoic acid succinimid-1-yl ester (1.32 g, 3.9 mmol). As noted above and described herein, a variety of carboxylic acids can be used to generate an activated succinimide ester, such as $C_{10}$-$C_{25}$ fatty acids.

Example 2

$C_{15}$-Amphomycin

Amphomycin-9-Fmoc (2.0 g, 1.5 mmol, 79% pure) was dissolved in 10 mL $H_2O$ and then diluted with 100 mL DMF. A 1M solution of sodium bicarbonate (7.5 mL) was slowly added to the mixture and then cooled in an ice bath. A predissolved solution of compound pentadecanoic acid succinimid-1-yl ester (1.32 g, 3.9 mmol) of Example 1 in 15 mL DMF was slowly added to the reaction mixture while still on ice, then the reaction was allowed to stir for at least 8 hours at room temperature. Piperidine (20 mL, 20% v/v) was added to the reaction and the mixture was stirred for an additional hour. All solids were filtered, the insolubles washed with additional DMF (approximately 15 mL), and then the filtrate was concentrated in vacuo until dry. Flash chromatography using a gradient system of methanol in ethyl acetate (40% methanol to neat, incremented by 20%) provided the title compound (1.34 g, 67% yield): 75% pure, MS (MALDI) calcd for $C_{60}H_{97}N_{13}O_{20}$ (M) 1320. found 1320. Purification by HPLC (gradient, 5% acetonitrile in water with 0.1% trifluoroacetic acid to 95% acetonitrile over 30 minutes) is also applicable.

Example 3

$C_{15}$-Amphomycin-9-Gly

Compound $C_{15}$-amphomycin (52 mg, 0.039 mmol) of Example 2 was suspended in 2.5 mL DMF and then charged with 197 μL 1M sodium bicarbonate (in water, 0.20 mmol). The reaction mixture was cooled using an ice bath. A predissolved solution of succinimide activated N-tert-butoxycarbonyl glycine (1.5 equiv, prepared as described for compound pentadecanoic acid succinimid-1-yl ester in Example 1) in 0.5 mL DMF was slowly added to the reaction mixture while still on ice, then the reaction was allowed to stir for at least 8 hours at room temperature. Upon concentrating in vacuo, the product was deprotected using 3 mL 4M HCl in dioxane for 30 minutes under standard conditions and then the solvent was evaporated in vacuo to provide the title compound. The title compound was purified by HPLC (gradient, 25% acetonitrile in water with 0.1% trifluoroacetic acid to 95% acetonitrile over 30 minutes) and lyophilized (34 mg, 63% yield): 89% pure, MS (MALDI) calcd for $C_{62}H_{100}N_{14}O_{21}$ (M) 1378. found 1377.

Example 4

$C_{15}$-Amphomycin-9-Gly-Lys

Compound $C_{15}$-amphomycin (30 mg, 0.023 mmol) of Example 2 was suspended in 2 mL DMF and then charged with 115 μL 1M sodium bicarbonate (in water, 0.12 mmol). The reaction mixture was cooled in an ice bath. A predissolved solution of succinimide activated N-(2-N-tert-butoxycarbonyl-6-(9H-fluoren-9-yl-methoxycarbonyl) lysinyl)glycine (1.5 equiv, prepared as described for compound pentadecanoic acid succinimid-1-yl ester in Example 1) in 0.5 mL DMF was slowly added to the reaction mixture while still on ice, then the reaction was allowed to stir approximately 12 hours at room temperature. Piperidine (0.4 mL, 20% v/v) was added and the reaction was stirred for 1 hour and then concentrated in vacuo. The crude product was mixed with 2 mL 4M HCl in dioxane for another hour and then concentrated in vacuo to provide the title compound, which was purified by HPLC (gradient, 25% acetonitrile in water with 0.1% trifluoroacetic acid to 95% acetonitrile over 30 minutes) and lyophilized (14 mg, 41% yield): 80% pure, MS (MALDI) calcd for $C_{68}H_{112}N_{16}O_{22}$ (M) 1506. found 1505.

Example 5

$C_{15}$-Amphomycin-9-Leu

Compound $C_{15}$-amphomycin (30 mg, 0.023 mmol) of Example 2 was suspended in 2 mL DMF and then charged with 114 μL 1M sodium bicarbonate (in water, 0.11 mmol). The reaction mixture was cooled in an ice bath. A predissolved solution of succinimide activated 2-N-(9H-fluoren-9-yl-methoxycarbonyl)leucine (1.5 equiv, prepared as described for compound pentadecanoic acid succinimid-1-yl ester in Example 1) in 0.5 mL DMF was slowly added to the reaction mixture while still on ice, then the reaction was allowed to stir approximately 8 hours at room temperature. Piperidine (400 mL, 20% v/v) was added, stirred an additional hour, and then the reaction mixture was evaporated in vacuo to provide the title compound. The title compound was purified by HPLC (gradient, 25% acetonitrile in water with 0.1% trifluoroacetic acid to 95% acetonitrile over 30 minutes) and lyophilized (5 mg, 15% yield): 74% pure, MS (MALDI) calcd for $C_{66}H_{108}N_{14}O_{21}$ (M) 1434. found 1433.

Example 6

$C_{10}$-Amphomycin

Amphomycin-9-Fmoc (20 mg, 0.015 mmol) and decanoic acid used in the method described in Example 2 provided the title compound, which was purified by HPLC and lyophilized (9 mg, 48% yield): 89% pure, MS (MALDI) calcd for $C_{55}H_{87}N_{13}O_{20}$ (M) 1250. found 1249.

Example 7

$C_{11}$-Amphomycin

Amphomycin-9-Fmoc (20 mg, 0.015 mmol) and undecanoic acid used in the method described in Example 2 provided the title compound, which was purified by HPLC and lyophilized (2 mg, 10% yield): 88% pure, MS (MALDI) calcd for $C_{56}H_{89}N_{13}O_{20}$ (M) 1264. found 1263.

Example 8

$C_{12}$-Amphomycin

Amphomycin-9-Fmoc (20 mg, 0.015 mmol) and dodecanoic acid used in the method described in Example 2 provided the title compound, which was purified by HPLC and lyophilized (3 mg, 15% yield): 87% pure, MS (MALDI) calcd for $C_{57}H_{91}N_{13}O_{20}$ (M) 1278. found 1277.

Example 9

$C_{13}$-Amphomycin

Amphomycin-9-Fmoc (20 mg, 0.015 mmol) and tridecanoic acid used in the method described in Example 2 provided the title compound, which was purified by HPLC and lyophilized (8 mg, 41% yield): 80% pure, MS (MALDI) calcd for $C_{58}H_{93}N_{13}O_{20}$ (M) 1292. found 1291.

Example 10

$C_{14}$-Amphomycin

Amphomycin-9-Fmoc (20 mg, 0.015 mmol) and tetradecanoic acid used in the method described in Example 2 provided the title compound, which was purified by HPLC and lyophilized (7 mg, 35% yield): 95% pure, MS (MALDI) calcd for $C_{59}H_{95}N_{13}O_{20}$ (M) 1306. found 1305.

Example 11

$C_{16}$-Amphomycin

Amphomycin-9-Fmoc (20 mg, 0.015 mmol) and hexadecanoic acid used in the method described in Example 2 provided the title compound, which was purified by HPLC and lyophilized (11 mg, 54% yield): 96% pure, MS (MALDI) calcd for $C_{61}H_{99}N_{13}O_{20}$ (M) 1335. found 1334.

Example 12

$C_{17}$-Amphomycin

Amphomycin-9-Fmoc (20 mg, 0.015 mmol) and heptadecanoic acid used in the method described in Example 2 provided the title compound, which was purified by HPLC and lyophilized (10 mg, 49% yield): 94% pure, MS (MALDI) calcd for $C_{62}H_{101}N_{13}O_{20}$ (M) 1349. found 1348.

Example 13

$C_{18}$-Amphomycin

Amphomycin-9-Fmoc (20 mg, 0.015 mmol) and octadecanoic acid used in the method described in Example 2 provided the title compound, which was purified by HPLC and lyophilized (5 mg, 24% yield): 92% pure, MS (MALDI) calcd for $C_{63}H_{103}N_{13}O_{20}$ (M) 1363. found 1362.

Example 14

Oleoyl-Amphomycin

Amphomycin-9-Fmoc (18.5 mg, 0.014 mmol) and octadec-9-enoic acid used in the method described in Example 2 provided the title compound, which was purified by HPLC and lyophilized (12 mg, 63% yield): 98% pure, MS (MALDI) calcd for $C_{63}H_{101}N_{13}O_{20}$ (M) 1361. found 1360.

Example 15

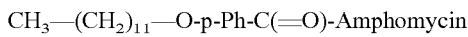
CH$_3$—(CH$_2$)$_{11}$—O-p-Ph-C(=O)-Amphomycin

Amphomycin-9-Fmoc (30 mg, 0.022 mmol) and 4-dodecyloxy-benzoic acid used in the method described in Example 2 provided the title compound, which was purified by HPLC and lyophilized (5 mg, 16% yield): 88% pure, MS (MALDI) calcd for $C_{64}H_{97}N_{13}O_{21}$ (M) 1385. found 1384.

Example 16

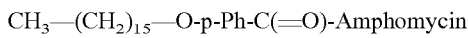
CH$_3$—(CH$_2$)$_{15}$—O-p-Ph-C(=O)-Amphomycin

Amphomycin-9-Fmoc (30 mg, 0.022 mmol) and para-hexadecanoxobenzoic acid used in the method described in Example 2 provided the title compound, which was purified by HPLC and lyophilized (4 mg, 12% yield): 70% pure, MS (MALDI) calcd for $C_{68}H_{105}N_{13}O_{21}$ (M) 1441. found 1440.

Example 17

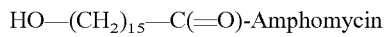
HO—(CH$_2$)$_{15}$—C(=O)-Amphomycin

Amphomycin-9-Fmoc (30 mg, 0.023 mmol) and 16-hydroxy-hexadecanoic acid used in the method described in Example 2 provided the title compound, which was purified by HPLC and lyophilized (8 mg, 26% yield): 85% pure, MS (MALDI) calcd for $C_{61}H_{99}N_{13}O_{21}$ (M) 1351. found 1351.

Example 18

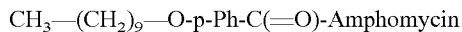
CH$_3$—(CH$_2$)$_9$—O-p-Ph-C(=O)-Amphomycin

Amphomycin-9-Fmoc (30 mg, 0.023 mmol) and para-decanoxobenzoic acid used in the method described in Example 2 provided the title compound, which was purified by HPLC and lyophilized (8 mg, 26% yield): 69% pure, MS (MALDI) calcd for $C_{62}H_{93}N_{13}O_{21}$ (M) 1356. found 1355.

Example 19

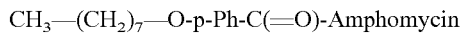
CH$_3$—(CH$_2$)$_7$—O-p-Ph-C(=O)-Amphomycin

Amphomycin-9-Fmoc (30 mg, 0.023 mmol) and para-octyloxybenzoic acid used in the method described in Example 2 provided the title compound, which was purified by HPLC and lyophilized (8 mg, 27% yield): 85% pure, MS (MALDI) calcd for $C_{60}H_{89}N_{13}O_{21}$ (M) 1328. found 1327.

Example 20

CH$_3$—(CH$_2$)$_{11}$—NH-Succinyl-Amphomycin

Amphomycin-9-Fmoc (30 mg, 0.023 mmol) and N-dodecyl-succinamic acid used in the method described in Example 2 provided the title compound, which was purified by HPLC and lyophilized (8 mg, 26% yield): 83% pure, MS (MALDI) calcd for $C_{61}H_{98}N_{14}O_{21}$ (M) 1364. found 1363.

Example 21

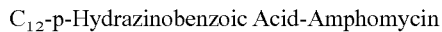
C$_{12}$-p-Hydrazinobenzoic Acid-Amphomycin

Amphomycin-9-Fmoc (30 mg, 0.023 mmol) and 4-(N'-tridecanoyl-hydrazino)-benzoic acid used in the method described in Example 2 provided the title compound, which was purified by HPLC and lyophilized (4 mg, 12% yield): 70% pure, MS (MALDI) calcd for $C_{65}H_{99}N_{15}O_{21}$ (M) 1427. found 1426.

Example 22

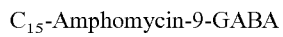
C$_{15}$-Amphomycin-9-GABA

Compound C$_{15}$-amphomycin (26 mg, 0.020 mmol) of Example 2 and (S)-2,4-bis-tert-butoxycarbonyl-aminobutyric acid used in the method described in Example 3 provided the title compound, which was purified by HPLC and lyophilized (11 mg, 40% yield): 85% pure, MS (MALDI) calcd for $C_{64}H_{104}N_{14}O_{21}$ (M) 1406. found 1405.

Example 23

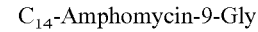
C$_{14}$-Amphomycin-9-Gly

Compound C$_{14}$-amphomycin (20 mg, 0.015 mmol) of Example 10 and N-tert-butoxycarbonyl glycine used in the method described in Example 3 provided the title compound, which was purified by HPLC and lyophilized (2 mg, 10% yield): 87% pure, MS (MALDI) calcd for $C_{61}H_{98}N_{14}O_{21}$ (M) 1364. found 1365.

Example 24

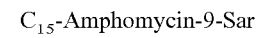
C$_{15}$-Amphomycin-9-Sar

Compound C$_{15}$-amphomycin (40 mg, 0.030 mmol) of Example 2 and N-tert-butoxycarbonyl-N-methylglycine used in the method described in Example 3 provided the title compound, which was purified by HPLC and lyophilized (24 mg, 57% yield): 100% pure, MS (MALDI) calcd for $C_{63}H_{102}N_{14}O_{21}$ (M) 1392. found 1391.

Example 25

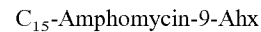
C$_{15}$-Amphomycin-9-Ahx

Compound C$_{15}$-amphomycin (40 mg, 0.030 mmol) of Example 2 and 6-tert-butoxycarbonylaminohexanoic acid used in the method described in Example 3 provided the title compound, which was purified by HPLC and lyophilized (25 mg, 58% yield): 92% pure, MS (MALDI) calcd for $C_{66}H_{108}N_{14}O_{21}$ (M) 1434. found 1433.

Example 26

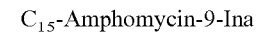
C$_{15}$-Amphomycin-9-Ina

Compound C$_{15}$-amphomycin (45 mg, 0.034 mmol) of Example 2 and N-tert-butoxycarbonyl isonipecotic acid used in the method described in Example 3 provided the title compound, which was purified by HPLC and lyophilized (11 mg, 23% yield): 89% pure, MS (MALDI) calcd for $C_{66}H_{106}N_{14}O_{21}$ (M) 1432. found 1431.

Example 27

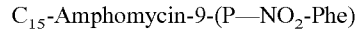
C$_{15}$-Amphomycin-9-(P—NO$_2$-Phe)

Compound C$_{15}$-amphomycin (30 mg, 0.023 mmol) of Example 2 and N-tert-butoxycarbonyl-para-nitro-phenylalanine used in the method described in Example 3 provided the title compound, which was purified by HPLC and lyophilized (9 mg, 26% yield): 99% pure, MS (MALDI) calcd for $C_{69}H_{105}N_{15}O_{23}$ (M) 1513. found 1512.

Example 28

$C_{15}$-Amphomycin-9-Gly-Phe

Compound $C_{15}$-amphomycin (30 mg, 0.023 mmol) of Example 2 and N—(N-tert-butoxycarbonyl phenylalaninyl) glycine used in the method described in Example 3 provided the title compound, which was purified by HPLC and lyophilized (9 mg, 26% yield): 77% pure, MS (MALDI) calcd for $C_{71}H_{109}N_{15}O_{22}$ (M) 1525. found 1524.

Example 29

$C_{15}$-Amphomycin-9-Glu

Compound $C_{15}$-amphomycin (30 mg, 0.023 mmol) of Example 2 and (S)-2-tert-butoxycarbonylamino-pentanedioic acid 5-tert-butyl ester used in the method described in Example 3 provided the title compound, which was purified by HPLC and lyophilized (10 mg, 30% yield): 92% pure, MS (MALDI) calcd for $C_{65}H_{104}N_{14}O_{23}$ (M) 1450. found 1449.

Example 30

$C_{15}$-Amphomycin-9-(P—F-Phe)

Compound $C_{15}$-amphomycin (30 mg, 0.023 mmol) of Example 2 and N-tert-butoxycarbonyl para-fluoro-phenylalanine used in the method described in Example 3 provided the title compound, which was purified by HPLC and lyophilized (9 mg, 27% yield): 99% pure, MS (MALDI) calcd for $C_{69}H_{105}FN_{14}O_{21}$ (M) 1486. found 1485.

Example 31

$C_{15}$-Amphomycin-9-(β-Cha)

Compound $C_{15}$-amphomycin (30 mg, 0.023 mmol) of Example 2 and N-tert-butoxycarbonyl-β-cyclohexylalanine used in the method described in Example 3 provided the title compound, which was purified by HPLC and lyophilized (4 mg, 12% yield): 83% pure, MS (MALDI) calcd for $C_{69}H_{112}N_{14}O_{21}$ (M) 1474. found 1473.

Example 32

$C_{15}$-Amphomycin-9-hPhe

Compound $C_{15}$-amphomycin (30 mg, 0.023 mmol) of Example 2 and (S)-2-tert-butoxycarbonylamino-4-phenylbutyric acid used in the method described in Example 3 provided the title compound, which was purified by HPLC and lyophilized (9 mg, 27% yield): 90% pure, MS (MALDI) calcd for $C_{70}H_{108}N_{14}O_{21}$ (M) 1482. found 1481.

Example 33

$C_{15}$-Amphomycin-9-Gly-Gly-Gly

Compound $C_{15}$-amphomycin (30 mg, 0.023 mmol) of Example 2 and (N-tert-butoxycarbonylglycinyl)glycinyl glycine used in the method described in Example 3 provided the title compound, which was purified by HPLC and lyophilized (13 mg, 38% yield): 89% pure, MS (MALDI) calcd for $C_{66}H_{106}N_{16}O_{23}$ (M) 1492. found 1491.

Example 34

$C_{15}$-Amphomycin-9-C(=O)—(CH$_2$)$_{10}$—NH$_2$

Compound $C_{15}$-amphomycin (30 mg, 0.023 mmol) of Example 2 and 11-tert-butoxycarbonylamino-undecanoic acid used in the method described in Example 3 provided the title compound, which was purified by HPLC and lyophilized (9 mg, 26% yield): 74% pure, MS (MALDI) calcd for $C_{71}H_{118}N_{14}O_{21}$ (M) 1504. found 1503.

Example 35

$C_{15}$-Amphomycin-9-(β-Cyano-Ala)

Compound $C_{15}$-amphomycin (30 mg, 0.023 mmol) of Example 2 and (S)-2-tert-butoxycarbonylamino-3-cyanopropionic acid used in the method described in Example 3 provided the title compound, which was purified by HPLC and lyophilized (7 mg, 22% yield): 99% pure, MS (MALDI) calcd for $C_{64}H_{101}N_{15}O_{21}$ (M) 1417. found 1416.

Example 36

$C_{15}$-Amphomycin-9-Ile

Compound $C_{15}$-amphomycin (40 mg, 0.030 mmol) of Example 2 and N-tert-butoxycarbonyl isoleucine used in the method described in Example 3 provided the title compound, which was purified by HPLC and lyophilized (13 mg, 30% yield): 77% pure, MS (MALDI) calcd for $C_{66}H_{108}N_{14}O_{21}$ (M) 1434. found 1433.

Example 37

$C_{15}$-Amphomycin-9-Gly-Val

Compound $C_{15}$-amphomycin (30 mg, 0.023 mmol) of Example 2 and (N-tert-butoxycarbonyl valinyl)glycine used in the method described in Example 3 provided the title compound, which was purified by HPLC and lyophilized (10 mg, 30% yield): 96% pure, MS (MALDI) calcd for $C_{67}H_{109}N_{15}O_{22}$ (M) 1477. found 1476.

Example 38

$C_{15}$-Amphomycin-9-Asn

Compound $C_{15}$-amphomycin (40 mg, 0.030 mmol) of Example 2 and N-tert-butoxycarbonyl asparagine used in the method described in Example 3 provided the title compound, which was purified by HPLC and lyophilized (18 mg, 41% yield): 100% pure, MS (MALDI) calcd for $C_{64}H_{103}N_{15}O_{22}$ (M) 1435. found 1434.

Example 39

$C_{15}$-Amphomycin-9-Tyr

Compound $C_{15}$-amphomycin (40 mg, 0.030 mmol) of Example 2 and N-tert-butoxycarbonyl tyrosine used in the method described in Example 3 provided the title compound, which was purified by HPLC and lyophilized (4 mg, 9% yield): 89% pure, MS (MALDI) calcd for $C_{69}H_{106}N_{14}O_{22}$ (M) 1484. found 1483.

Example 40

$C_{15}$-Amphomycin-9-Trp

Compound $C_{15}$-amphomycin (40 mg, 0.030 mmol) of Example 2 and N-tert-butoxycarbonyl tryptophan used in the method described in Example 3 provided the title compound, which was purified by HPLC and lyophilized (9 mg, 20% yield): 92% pure, MS (MALDI) calcd for $C_{71}H_{107}N_{15}O_{21}$ (M) 1507. found 1506.

Example 41

$C_{15}$-Amphomycin-9-Phg

Compound $C_{15}$-amphomycin (40 mg, 0.030 mmol) of Example 2 and (S)-tert-butoxycarbonylamino-phenylglycine used in the method described in Example 3 provided the title compound, which was purified by HPLC and lyophilized (10 mg, 23% yield): 97% pure, MS (MALDI) calcd for $C_{68}H_{104}N_{14}O_{21}$ (M) 1454. found 1453.

Example 42

$C_{15}$-Amphomycin-9-Gly-Gly

Compound $C_{15}$-amphomycin (30 mg, 0.023 mmol) of Example 2 and N-(tert-butoxycarbonylglycinyl)glycine used in the method described in Example 3 provided the title compound, which was purified by HPLC and lyophilized (9 mg, 28% yield): 98% pure, MS (MALDI) calcd for $C_{64}H_{103}N_{15}O_{21}$ (M) 1435. found 1434.

Example 43

$C_{15}$-Amphomycin-9-Gln

Compound $C_{15}$-amphomycin (38 mg, 0.029 mmol) of Example 2 and N-tert-butoxycarbonyl-glutamine used in the method described in Example 3 provided the title compound, which was purified by HPLC and lyophilized (7 mg, 17% yield): 88% pure, MS (MALDI) calcd for $C_{65}H_{105}N_{15}O_{22}$ (M) 1449. found 1448.

Example 44

$C_{15}$-Amphomycin-9-Thr

Compound $C_{15}$-amphomycin (41 mg, 0.031 mmol) of Example 2 and (2S,3S)-2-tert-butoxycarbonylamino-3-hydroxy-butyric acid used in the method described in Example 3 provided the title compound, which was purified by HPLC and lyophilized (7 mg, 16% yield): 74% pure, MS (MALDI) calcd for $C_{64}H_{104}N_{14}O_{22}$ (M) 1422. found 1421.

Example 45

$C_{15}$-Amphomycin-9-Pro-Gly

Compound $C_{15}$-amphomycin (27 mg, 0.020 mmol) of Example 2 and N—(N-tert-butoxycarbonylglycinyl) proline used in the method described in Example 3 provided the title compound, which was purified by HPLC and lyophilized (12 mg, 40% yield): 84% pure, MS (MALDI) calcd for $C_{67}H_{107}N_{15}O_{22}$ (M) 1475. found 1474.

Example 46

$C_{15}$-Amphomycin-9-Gly-Leu

Compound $C_{15}$-amphomycin (27 mg, 0.020 mmol) of Example 2 and N—(N-tert-butoxycarbonylleucinyl) glycine used in the method described in Example 3 provided the title compound, which was purified by HPLC and lyophilized (8 mg, 26% yield): 98% pure, MS (MALDI) calcd for $C_{68}H_{111}N_{15}O_{22}$ (M) 1491. found 1490.

Example 47

$C_{15}$-Amphomycin-9-Tyr(Et)

Compound $C_{15}$-amphomycin (30 mg, 0.023 mmol) of Example 2 and N-tert-butoxycarbonyl-O-ethyl tyrosine used in the method described in Example 3 provided the title compound, which was purified by HPLC and lyophilized (7 mg, 20% yield): 74% pure, MS (MALDI) calcd for $C_{71}H_{110}N_{14}O_{22}$ (M) 1512. found 1511.

Example 48

$C_{15}$-Amphomycin-9-Gly-Suc

In a first step, compound $C_{15}$-amphomycin (35 mg, 0.027 mmol) of Example 2 was subjected to N-tert-butoxycarbonyl glycine as described in the method of Example 3. After purification by HPLC, the intermediate was lyophilized. In a second step, this intermediate was mixed with N,N'-disuccinimidyl carbonate (10.4 mg, 0.041 mmol) in the presence of diisopropylethyl amine (DIEA, 1 mL) in DMF (3 mL) for one hour at room temperature, which was followed by evaporation in vacuo to provide a crude product of the title compound. The crude product was purified by HPLC (gradient, 25% acetonitrile in water with 0.1% trifluoroacetic acid to 95% acetonitrile over 30 minutes) and lyophilized (9 mg, 23% yield): 93% pure, MS (MALDI) calcd for $C_{66}H_{104}N_{14}O_{24}$ (M) 1478. found 1477.

Example 49

$C_{15}$-Amphomycin-9-Gly-Ac

In a first step, compound $C_{15}$-amphomycin (35 mg, 0.027 mmol) of Example 2 was coupled to N-tert-butoxycarbonyl glycine as described in the method of Example 3. After purification by HPLC, the intermediate was lyophilized. In a second step, this intermediate was mixed with acetic anhydride (25 µL) in the presence of DIEA (1 mL) in DMF (3 mL) for one hour at room temperature, which was followed by evaporation in vacuo to provide a crude product of the title compound. The crude product was purified by HPLC (gradient, 25% acetonitrile in water with 0.1% trifluoroacetic acid to 95% acetonitrile over 30 minutes) and lyophilized (4 mg, 11% yield): 89% pure, MS (MALDI) calcd for $C_{64}H_{102}N_{14}O_{22}$ (M) 1419. found 1420.

Example 50

$C_{13}$-Amphomycin-9-GABA

Compound $C_{13}$-amphomycin (25 mg, 0.019 mmol) of Example 9 and γ-N-tert-butoxycarbonyl-aminobutanoic acid used in the method described in Example 3 provided the title compound, which was purified by HPLC and lyophilized (10 mg, 38% yield): 100% pure, MS (MALDI) calcd for $C_{62}H_{100}N_{14}O_{21}$ (M) 1378. found 1377.

Example 51

$C_{14}$-Amphomycin-9-Gly-Lys

Compound $C_{14}$-amphomycin (25 mg, 0.019 mmol) of Example 10 and (N,N'-bis-tert-butoxycarbonyllysine)glycine used in the method described in Example 3 provided the title compound, which was purified by HPLC (gradient, 20-45% acetonitrile in water with 0.1% trifluoroacetic acid) and lyophilized (10 mg, 35% yield): 94% pure, MS (MALDI) calcd for $C_{67}H_{110}N_{16}O_{22}$ (M) 1492. found 1491.

Example 52

$C_{15}$-Amphomycin-9-Tyr(Me)

Compound $C_{15}$-amphomycin (30 mg, 0.023 mmol) of Example 2 and N-tert-butoxycarbonyl-O-methyl tyrosine used in the method described in Example 3 provided the title compound, which was purified by HPLC and lyophilized (3 mg, 9% yield): 67% pure, MS (MALDI) calcd for $C_{70}H_{108}N_{14}O_{22}$ (M) 1498. found 1497.

Example 53

$C_{13}$-Amphomycin-9-Gly

Compound $C_{13}$-amphomycin (20 mg, 0.015 mmol) of Example 9 and N-(tert-butoxycarbonyl)glycine used in the method described in Example 3 provided the title compound, which was purified by HPLC and lyophilized (12 mg, 59% yield): 99% pure, MS (MALDI) calcd for $C_{60}H_{96}N_{14}O_{21}$ (M) 1349. found 1348.

Example 54

$C_{13}$-Amphomycin-9-(β-Ala)

Compound $C_{13}$-amphomycin (20 mg, 0.015 mmol) of Example 9 and N-(tert-butoxycarbonyl)β-alanine used in the method described in Example 3 provided the title compound, which was purified by HPLC and lyophilized (12 mg, 58% yield): 93% pure, MS (MALDI) calcd for $C_{61}H_{98}N_{14}O_{21}$ (M) 1364. found 1363.

Example 55

$C_{13}$-Amphomycin-9-Sar

Compound $C_{13}$-amphomycin (20 mg, 0.015 mmol) of Example 9 and N-(tert-butoxycarbonyl)sarcosine used in the method described in Example 3 provided the title compound, which was purified by HPLC and lyophilized (12 mg, 58% yield): 95% pure, MS (MALDI) calcd for $C_{61}H_{98}N_{14}O_{21}$ (M) 1364. found 1363.

Example 56

$C_{13}$-Amphomycin-9-Ahx

Compound $C_{13}$-amphomycin (20 mg, 0.015 mmol) of Example 9 and 6-tert-butoxycarbonyl-aminohexanoic acid used in the method described in Example 3 provided the title compound, which was purified by HPLC and lyophilized (18 mg, 84% yield): 98% pure, MS (MALDI) calcd for $C_{64}H_{104}N_{14}O_{21}$ (M) 1406. found 1405.

Example 57

$C_{12}$-Amphomycin-9-GABA

Compound $C_{12}$-amphomycin (25 mg, 0.020 mmol) of Example 8 and γ-N-tert-butoxycarbonyl-aminobutanoic acid used in the method described in Example 3 provided the title compound, which was purified by HPLC and lyophilized (15 mg, 58% yield): 97% pure, MS (MALDI) calcd for $C_{61}H_{98}N_{14}O_{21}$ (M) 1364. found 1363.

Example 58

$C_{12}$-Amphomycin-9-Gly

Compound $C_{12}$-amphomycin (25 mg, 0.020 mmol) of Example 8 and N-(tert-butoxycarbonyl)glycine used in the method described in Example 3 provided the title compound, which was purified by HPLC and lyophilized (10 mg, 40% yield): 96% pure, MS (MALDI) calcd for $C_{59}H_{94}N_{14}O_{21}$ (M) 1335. found 1334.

Example 59

$C_{14}$-Amphomycin-9-(β-Ala)

Compound $C_{14}$-amphomycin (107 mg, 0.082 mmol) of Example 10 and N-(tert-butoxycarbonyl)β-alanine used in the method described in Example 3 provided the title compound, which was purified by HPLC and lyophilized (66 mg, 59% yield): 94% pure, MS (MALDI) calcd for $C_{62}H_{100}N_{14}O_{21}$ (M) 1378. found 1377.

Example 60

$C_{14}$-Amphomycin-9-Sar

Compound $C_{14}$-amphomycin (22 mg, 0.017 mmol) of Example 10 and N-(tert-butoxycarbonyl)sarcosine used in the method described in Example 3 provided the title compound, which was purified by HPLC and lyophilized (7 mg, 30% yield): 89% pure, MS (MALDI) calcd for $C_{62}H_{100}N_{14}O_{21}$ (M) 1378. found 1377.

Example 61

$C_{14}$-Amphomycin-9-Ahx

Compound $C_{14}$-amphomycin (22 mg, 0.017 mmol) of Example 10 and 6-(tert-butoxycarbonyl)-aminohexanoic acid used in the method described in Example 3 provided the title compound, which was purified by HPLC and lyophilized (9 mg, 38% yield): 87% pure, MS (MALDI) calcd for $C_{65}H_{106}N_{14}O_{21}$ (M) 1420. found 1419.

Example 62

$C_{14}$-Amphomycin-9-GABA

Compound $C_{14}$-amphomycin (22 mg, 0.017 mmol) of Example 10 and γ-N-tert-butoxycarbonyl-aminobutanoic acid used in the method described in Example 3 provided the title compound, which was purified by HPLC and lyophilized (4 mg, 17% yield): 88% pure, MS (MALDI) calcd for $C_{63}H_{102}N_{14}O_{21}$ (M) 1392. found 1391.

Example 63

$C_{13}$-Amphomycin-9-Ala

Compound $C_{13}$-amphomycin (22 mg, 0.017 mmol) of Example 9 and N-tert-butoxycarbonyl alanine used in the method described in Example 3 provided the title compound, which was purified by HPLC and lyophilized (9 mg, 40% yield): 84% pure, MS (MALDI) calcd for $C_{61}H_{98}N_{14}O_{21}$ (M) 1364. found 1363.

Example 64

$C_{13}$-Amphomycin-9-(D-Ala)

Compound $C_{13}$-amphomycin (22 mg, 0.017 mmol) of Example 9 and D-N-tert-butoxycarbonyl alanine used in the method described in Example 3 provided the title compound, which was purified by HPLC and lyophilized (13 mg, 57% yield): 89% pure, MS (MALDI) calcd for $C_{61}H_{98}N_{14}O_{21}$ (M) 1364. found 1363.

Example 65

$C_{13}$-Amphomycin-9-(D-Pro)

Compound $C_{13}$-amphomycin (22 mg, 0.017 mmol) of Example 9 and D-N-tert-butoxycarbonyl proline used in the method described in Example 3 provided the title compound, which was purified by HPLC and lyophilized (11 mg, 47% yield): 90% pure, MS (MALDI) calcd for $C_{63}H_{100}N_{14}O_{21}$ (M) 1390. found 1389.

Example 66

$C_{15}$-Amphomycin-9-(D-Ala)

Compound $C_{15}$-amphomycin (22 mg, 0.017 mmol) of Example 2 and D-N-tert-butoxycarbonyl alanine used in the method described in Example 3 provided the title compound, which was purified by HPLC and lyophilized (10 mg, 43% yield): 85% pure, MS (MALDI) calcd for $C_{63}H_{102}N_{14}O_{21}$ (M) 1392. found 1391.

Example 67

$C_{15}$-Amphomycin-9-(D-Pro)

Compound $C_{15}$-amphomycin (22 mg, 0.017 mmol) of Example 2 and D-N-tert-butoxycarbonyl proline used in the method described in Example 3 provided the title compound, which was purified by HPLC and lyophilized (11 mg, 47% yield): 77% pure, MS (MALDI) calcd for $C_{65}H_{104}N_{14}O_{21}$ (M) 1418. found 1417.

Example 68

$C_{15}$-Amphomycin-9-Gly-GABA

In a first step, compound $C_{15}$-amphomycin (38 mg, 0.029 mmol) of Example 2 was coupled to N-tert-butoxycarbonyl glycine as described in the method of Example 3. The intermediate was purified by HPLC and lyophilized. In a second step, this intermediate and γ-N-tert-butoxycarbonyl-aminobutanoic acid used in the method described in Example 3 provided the title compound, which was purified by HPLC and lyophilized (13 mg, 31% yield): 74% pure, MS (MALDI) calcd for $C_{65}H_{105}N_{15}O_{22}$ (M) 1449. found 1448.

Example 69

$C_{15}$-Amphomycin-9-Gly-(D-Ala)

In a first step, compound $C_{15}$-amphomycin (24 mg, 0.018 mmol) of Example 2 was initially coupled with N-tert-butoxycarbonyl glycinyl succinimide using the method described in Example 3. The resulting intermediate was purified by HPLC. In a second step, this purified intermediate and D-N-(tert-butoxycarbonyl)alanine used in the method described in Example 3 provided the title compound, which was purified by HPLC and lyophilized (9 mg, 37% yield): 75% pure, MS (MALDI) calcd for $C_{65}H_{105}N_{15}O_{22}$ (M) 1449. found 1448.

Example 70

$C_{15}$-Amphomycin-9-(β-Ala)-Ahx

In a first step, compound $C_{15}$-amphomycin (25 mg, 0.018 mmol) of Example 2 was initially coupled with N-tert-butoxycarbonyl β-alanine is described in the method of Example 3. The resulting intermediate was purified by HPLC. In a second step, this purified intermediate and 6-N-tert-butoxycarbonyl-aminohexanoic acid used as described in the method of Example 3 provided the title compound, which was purified by HPLC and lyophilized (21 mg, 74% yield): 84% pure, MS (MALDI) calcd for $C_{69}H_{113}N_{15}O_{22}$ (M) 1505. found 1504.

Example 71

$C_{15}$-Amphomycin-9-GABA-Val

In a first step, compound $C_{15}$-amphomycin (25 mg, 0.019 mmol) of Example 2 was coupled with γ-N-tert-butoxycarbonyl-aminobutanoic acid as described in the method of Example 3. The resulting intermediate was purified by HPLC and lyophilized. In a second step, this purified intermediate and N-tert-butoxycarbonyl valine used as described in the method of Example 3 provided the title compound, which was purified by HPLC and lyophilized (15.6 mg, 55% yield): 92% pure, MS (MALDI) calcd for $C_{69}H_{113}N_{15}O_{22}$ (M) 1505. found 1504.

Example 72

$C_{15}$-Amphomycin-9-GABA-Ahx

In a first step, compound $C_{15}$-amphomycin (25 mg, 0.019 mmol) of Example 2 was coupled with γ-N-tert-butoxycarbonyl-aminobutanoic acid as described in the method of Example 3. The resulting intermediate was purified by HPLC and lyophilized. In a second step, this purified intermediate and 6-tert-butoxycarbonylamine hexanoic acid used as described in the method of Example 3 provided the title compound, which was purified by HPLC and lyophilized

Example 73

C$_{12}$-Amphomycin-9-(β-Ala)

Compound C$_{12}$-amphomycin (30 mg, 0.023 mmol) of Example 8 and N-tert-butoxycarbonyl-β-alanine used in the method described in Example 3 provided the title compound, which was purified by HPLC and lyophilized (21.8 mg, 71% yield): 86% pure, MS (MALDI) calcd for C$_{60}$H$_{96}$N$_{14}$O$_{21}$ (M) 1349. found 1348.

Example 74

C$_{12}$-Amphomycin-9-Sar

Compound C$_{12}$-amphomycin (30 mg, 0.023 mmol) of Example 8 and N-tert-butoxycarbonyl-sarcosine used in the method described in Example 3 provided the title compound, which was purified by HPLC and lyophilized (19.7 mg, 64% yield): 78% pure, MS (MALDI) calcd for C$_{60}$H$_{96}$N$_{14}$O$_{21}$ (M) 1349. found 1348.

Example 75

C$_{16}$-Amphomycin-9-Sar

Compound C$_{16}$-amphomycin (30 mg, 0.022 mmol) of Example 11 and N-tert-butoxycarbonyl-sarcosine used in the method described in Example 3 provided the title compound, which was purified by HPLC and lyophilized (18.5 mg, 58% yield): 85% pure, MS (MALDI) calcd for C$_{64}$H$_{104}$N$_{14}$O$_{21}$ (M) 1406. found 1405.

Example 76

C$_{10}$-Amphomycin-9-(β-Ala)

Compound C$_{10}$-amphomycin (30 mg, 0.024 mmol) of Example 6 and N-tert-butoxycarbonyl-β-alanine used in the method described in Example 3 provided the title compound, which was purified by HPLC (gradient, 20-45% acetonitrile in water with 0.1% trifluoroacetic acid) and lyophilized (14.2 mg, 47% yield): 87% pure, MS (MALDI) calcd for C$_{58}$H$_{92}$N$_{14}$O$_{21}$ (M) 1321. found 1320.

Example 77

C$_{10}$-Amphomycin-9-Sar

Compound C$_{10}$-amphomycin (30 mg, 0.024 mmol) of Example 6 and N-tert-butoxycarbonyl-sarcosine used in the method described in Example 3 provided the title compound, which was purified by HPLC and lyophilized (18.4 mg, 61% yield): 78% pure, MS (MALDI) calcd for C$_{58}$H$_{92}$N$_{14}$O$_{21}$ (M) 1321. found 1320.

Example 78

C$_{17}$-Amphomycin-9-Sar

Compound C$_{17}$-amphomycin (30 mg, 0.022 mmol) of Example 12 and N-tert-butoxycarbonyl-sarcosine used in the method described in Example 3 provided the title compound, which was purified by HPLC and lyophilized (20 mg, 62% yield): 83% pure, MS (MALDI) calcd for C$_{65}$H$_{106}$N$_{14}$O$_{21}$ (M) 1420. found 1419.

Example 79

C$_{16}$-Amphomycin-9-(β-Ala)

Compound C$_{16}$-amphomycin (30 mg, 0.023 mmol) of Example 11 and N-tert-butoxycarbonyl-β-alanine used in the method described in Example 3 provided the title compound, which was purified by HPLC and lyophilized (17.8 mg, 56% yield): 93% pure, MS (MALDI) calcd for C$_{64}$H$_{104}$N$_{14}$O$_{21}$ (M) 1406. found 1405.

Example 80

C$_{17}$-Amphomycin-9-(β-Ala)

Compound C$_{17}$-amphomycin (30 mg, 0.022 mmol) of Example 12 and N-tert-butoxycarbonyl-β-alanine used in the method described in Example 3 provided the title compound, which was purified by HPLC and lyophilized (13.9 mg, 43% yield): 86% pure, MS (MALDI) calcd for C$_{65}$H$_{106}$N$_{14}$O$_{21}$ (M) 1420. found 1419.

Example 81

C$_{15}$-Amphomycin-9-Gly-C$_6$

Compound C$_{15}$-amphomycin-9-Gly (21 mg, 0.014 mmol) of Example 3 and hexanoic acid used in the method described in Example 3 provided the title compound, which was purified by HPLC and lyophilized (2 mg, 9% yield): 98% pure, MS (MALDI) calcd for C$_{68}$H$_{110}$N$_{14}$O$_{22}$ (M) 1476. found 1477.

Example 82

C$_{15}$-Amphomycin-9-Ala

Compound C$_{15}$-amphomycin (20 mg, 0.015 mmol) of Example 2 and N-tert-butoxycarbonyl-alanine used in the method described in Example 3 provided the title compound, which was purified by HPLC and lyophilized (6.3 mg, 30% yield): 78% pure, MS (MALDI) calcd for C$_{63}$H$_{102}$N$_{14}$O$_{21}$ (M) 1392. found 1391.

Example 83

CH$_3$—(CH$_2$)$_{15}$—NH—C(=O)-Amphomycin-9-Gly

Compound CH$_3$—(CH$_2$)$_{15}$—NH—C(=O)-amphomycin (20 mg, 0.0147 mmol) of Example 249 and N-tert-butoxycarbonyl-glycine used in the method described in Example 3 provided the title compound, which was purified by HPLC and lyophilized (2 mg, 9.5% yield): 66% pure, MS (MALDI) calcd for C$_{64}$H$_{105}$N$_{15}$O$_{21}$ (M) 1421. found 1420.

Example 84

CH$_3$—(CH$_2$)$_{15}$—SO$_2$-Amphomycin-9-Gly

Compound C$_{16}$—SO$_2$-Gly-amphomycin (30 mg, 0.022 mmol) of Example 99 and N-tert-butoxycarbonyl-glycine used in the method described in Example 3 provided the title compound, which was purified by HPLC and lyophilized (5 mg, 16% yield): 81% pure, MS (MALDI) calcd for $C_{65}H_{107}N_{15}O_{23}S$ (M) 1499. found 1498.

Example 85

$C_2$-PABA-Amphomycin

In a first step, amphomycin-9-Fmoc (30 mg, 0.022 mmol) was coupled with para-N-tert-butoxycarbonylaminobenzoic acid as described in the method of Example 3. In a second step, this intermediate from the first step was mixed with dodecanoyl chloride (7 μL, 0.033 mmol) in DMF (5 mL) in the presence of DIEA (20 μL, 0.11 mmol) for 3 hours under inert atmosphere to provide the title compound. The title compound was concentrated in vacuo, purified by HPLC (gradient, 25% acetonitrile in water with 0.1% trifluoroacetic acid to 95% acetonitrile over 30 minutes), and lyophilized (13.2 mg): 93% pure, MS (MALDI) calcd for $C_{64}H_{96}N_{14}O_{21}$ (M) 1398. found 1397.

Example 86

$C_{12}$-(p-Apa)-Amphomycin-9-Gly

Compound $C_{12}$-(p-aminophenylacetyl)-amphomycin (30 mg, 0.023 mmol) of Example 119 and N-tert-butoxycarbonyl glycine used in the method described in Example 3 provided the title compound, which was purified by HPLC and lyophilized (5 mg, 15% yield): 81% pure, MS (MALDI) calcd for $C_{67}H_{101}N_{15}O_{22}$ (M) 1469. found 1468.

Example 87

$C_{12}$-PABA-Amphomycin-9-Gly

Compound amphomycin-9-(N-Fmoc-Glycyl) (11.3 mg) of Example 271 was dissolved in 0.2 mL DMF, 0.02 mL water, and 0.03 mL 1M sodium bicarbonate. N-Dodecanoyl-para-aminobenzoic acid succinimid-1-yl ester (7 mg, as prepared in Example 274 and using a succinimidyl ester as prepared in Example 1) was added in two increments over 60 min with stirring at room temperature. After an additional 20 min of stirring, the reaction was diluted with 5 mL methanol containing about 300 mg ammonium acetate. The title compound was isolated on a Sephadex LH-20 column (2.5×42 cm) eluted with methanol at 2 mL/min and freeze-dried (9.5 mg): 88% pure, MS (FAB) calcd for $C_{66}H_{99}N_{15}O_{22}$ (M) 1455. found 1454.

Example 88

$CH_3-(CH_2)_{11}-O$-p-Ph-C(=O)-Amphomycin-9-Gly

Compound $CH_3-(CH_2)_{11}-O$-p-Ph-C(=O)-amphomycin (30 mg, 0.021 mmol) of Example 15 and N-tert-butoxycarbonyl glycine used in the method described in Example 3 provided the title compound, which was purified by HPLC and lyophilized (7 mg, 27% yield): 84% pure, MS (MALDI) calcd for $C_{66}H_{100}N_{14}O_{22}$ (M) 1442. found 1441.

Example 89

$C_{12}$-(p-Trans-Cinnamyl)-Amphomycin-9-Gly

Compound $C_{12}$-(p-amino-trans-cinnamyl)-amphomycin (30 mg, 0.021 mmol) of Example 120 and N-tert-butoxycarbonyl glycine used in the method described in Example 3 provided the title compound, which was purified by HPLC and lyophilized (7 mg, 23% yield): 85% pure, MS (MALDI) calcd for $C_{68}H_{101}N_{15}O_{22}$ (M) 1481. found 1480.

Example 90

$CH_3-(CH_2)_{11}-O$-p-Ph-C(=O)-Gly-Amphomycin-9-Gly

Compound $CH_3-(CH_2)_{11}-O$-p-Ph-C(=O)-Gly-amphomycin (30 mg, 0.021 mmol) of Example 121 and N-tert-butoxycarbonyl glycine used in the method described in Example 3 provided the title compound, which was purified by HPLC and lyophilized (6.5 mg, 19% yield): 88% pure, MS (MALDI) calcd for $C_{68}H_{103}N_{15}O_{23}$ (M) 1499. found 1498.

Example 91

$C_{14}$-PABA-Gly-Amphomycin-9-Gly

Compound amphomycin-9-(N-Fmoc-Glycyl) (11.3 mg) of Example 271 and N-Dodecanoyl-para-aminobenzoylglycine succinimid-1-yl ester (6.3 mg, as prepared in Example 276 and using a succinimidyl ester as prepared in Example 1) used in the method described in Example 3 provided the title compound (6.8 mg): 86% pure, MS (FAB) calcd for $C_{68}H_{102}N_{16}O_{23}$ (M) 1512. found 1512.

Example 92

$CH_3-(CH_2)_{11}-NH-C(=O)$-Amphomycin-9-Gly

Compound amphomycin-9-(N-Fmoc-Glycyl) (8.6 mg, 0.023 mmol) of Example 271 was dissolved in 0.2 mL DMF and 0.2 mL water, then 0.002 mL dodecylisocyanate was added. The mixture was stirred at 30° C. and monitored by HPLC. After 30 min, 0.01 mL piperidine was added and mixed at room temperature. After 40 min, the reaction was diluted with 5 mL methanol containing approximately 300 mg ammonium acetate. The title compound was isolated on a Sephadex LH-20 column (2.5×42 cm) eluted with methanol at 2 mL/min. The title compound-containing fractions were pooled, and the solvent stripped in vacuo. Upon redissolving the title compound in 2 mL distilled water, the sample was freeze-dried (5.5 mg): 77% pure, MS (FAB) calcd for $C_{60}H_{97}N_{15}O_{21}$ $(M+Na)^+$ 1386. found 1386.

Example 93

$C_{15}$-Amphomycin-9-Ahx-Gly

In a first step, compound $C_{15}$-amphomycin (38 mg, 0.029 mmol) of Example 2 was coupled with 6-tert-butoxycarbonyl-aminohexanoic acid as described in the method of Example 3. The resulting intermediate was purified by HPLC and lyophilized. In a second step, this purified intermediate and N-tert-butoxycarbonyl glycine used in the method described in Example 3 provided the title compound, which was purified by HPLC and lyophilized (12.7 mg, 30% yield): 99% pure, MS (MALDI) calcd for $C_{68}H_{111}N_{15}O_{22}$ (M) 1491. found 1490.

Example 94

$C_{15}$-Amphomycin-9-GABA-GABA

In a first step, compound $C_{15}$-amphomycin (25 mg, 0.019 mmol) of Example 2 was coupled with γ-N-tert-butoxycarbonyl-aminobutanoic acid as described in the method of Example 3. The resulting intermediate was purified by HPLC. In a second step, this purified intermediate and γ-N-tert-butoxycarbonyl-aminobutanoic acid used in the method described in Example 3 provided the title compound, which was purified by HPLC and lyophilized (3.7 mg, 9% yield): 99% pure, MS (MALDI) calcd for $C_{68}H_{111}N_{15}O_{22}$ (M) 1491. found 1490.

Example 95

$C_{15}$-Amphomycin-9-hPro

Compound $C_{15}$-amphomycin (23 mg, 0.017 mmol) of Example 2 and (S)—N-tert-butoxycarbonyl pipecolic acid used in the method described in Example 3 provided the title compound, which was purified by HPLC and lyophilized (3.2 mg, 13% yield): 70% pure, MS (MALDI) calcd for $C_{66}H_{106}N_{14}O_{21}$ (M) 1432. found 1431.

Example 96

$C_{15}$-Amphomycin-9-(D-Pip)

Compound $C_{15}$-amphomycin (175 mg, 0.133 mmol) of Example 2 and (R)—N-tert-butoxycarbonyl pipecolic acid used in the method described in Example 3 provided the title compound, which was purified by HPLC and lyophilized (60 mg, 32% yield): 77% pure, MS (MALDI) calcd for $C_{66}H_{106}N_{14}O_{21}$ (M) 1432. found 1431.

Example 97

$CH_3$—$(CH_2)_{11}$—NH—C(=O)-Amphomycin-9-(β-Ala)

Compound amphomycin-9-(N-Fmoc-β-Ala) (58 mg) of Example 273 and dodecylisocyanate used in the method described in Example 3 provided the title compound (20.7 mg): 91% pure, MS (FAB) calcd for $C_{61}H_{99}N_{15}O_{21}$ (M) 1379. found 1379.

Example 98

$CH_3$—$(CH_2)_{11}$—NH—C(=O)-Amphomycin-9-Sar

Compound amphomycin-9-(N-Fmoc-Sar) (62 mg) of Example 272 and dodecylisocyanate used in the method described in Example 3 provided the title compound (12.2 mg): 80% pure, MS (FAB) calcd for $C_{61}H_{99}N_{15}O_{21}$ (M) 1379. found 1380.

Example 99

$CH_3$—$(CH_2)_{15}$—$SO_2$-Gly-Amphomycin

In a first step, amphomycin-9-Fmoc (30 mg, 0.022 mmol) was coupled with N-tert-butoxycarbonyl glycine as described in the method of Example 3. The resulting intermediate was purified by HPLC and lyophilized. In a second step, this purified intermediate was dissolved in 10 mL DMF under an inert atmosphere. Pentadecanesulfonyl chloride (13.7 mg, 0.044 mmol) was added and the mixture was allowed to stir overnight to provide the title compound, which was purified by HPLC (gradient, 25% acetonitrile in water with 0.1% trifluoroacetic acid to 95% acetonitrile over 30 minutes) and lyophilized (5 mg): 89% pure, MS (MALDI) calcd for $C_{63}H_{104}N_{14}O_{22}S$ (M) 1442. found 1441.

Example 100

$CH_3$—$(CH_2)_9$—$SO_2$-Phe-Amphomycin

In a first step, amphomycin-9-Fmoc (30 mg, 0.022 mmol) was coupled with N-tert-butoxycarbonyl phenylalanine. The resulting intermediate was purified by HPLC and lyophilized. In a second step, this purified intermediate was coupled with decanesulfonyl chloride as described in the method of Example 99 to provide the title compound, which was purified by HPLC and lyophilized (7 mg, 21% yield): 91% pure, MS (MALDI) calcd for $C_{64}H_{98}N_{14}O_{22}S$ (M) 1448. found 1447.

Example 101

$CH_3$—$(CH_2)_9$—$SO_2$-Gly-Amphomycin-9-Lys

In a first step, amphomycin-9-Fmoc (30 mg, 0.022 mmol) was coupled with N-tert-butoxycarbonyl glycine and then in a second step with decanesulfonyl chloride as described in the method of Example 99 to provide a second intermediate, which was purified by HPLC and lyophilized. In a third step, the second intermediate was coupled with 2-N-tert-butoxycarbonyl-6-(9H-fluoren-9-yl-methoxycarbonyl)lysine as described in the method of Example 4 to provide the title compound, which was purified by HPLC and lyophilized (2 mg, 5.7% yield): 83% pure, MS (MALDI) calcd for $C_{65}H_{108}N_{16}O_{23}S$ (M) 1514. found 1513.

Example 102

$CH_3$—$(CH_2)_9$—$SO_2$-Gly-Amphomycin-9-Gly

In a first step, amphomycin-9-Fmoc (30 mg, 0.022 mmol) was coupled with N-tert-butoxycarbonyl glycine and then in a second step with decanesulfonyl chloride as described in the method of Example 99 to provide a second intermediate, which was purified by HPLC and lyophilized. In a third step, the second intermediate was coupled with N-tert-butoxycarbonyl glycine as described in the method of Example 3 to provide the title compound, which was purified by HPLC and lyophilized (6 mg, 18% yield): 78% pure, MS (MALDI) calcd for $C_{61}H_{99}N_{15}O_{23}S$ (M) 1443. found 1442.

Example 103

$C_{12}$-Gly-Amphomycin

Amphomycin-9-Fmoc (16.3 mg) was coupled with N-dodecanoyl glycine succinimid-1-yl ester (7.3 mg, as prepared in Example 274 and using a succinimidyl ester as prepared in Example 1) as described in the method of Example 3 to provide the title compound (10.5 mg): 90% pure, MS (FAB) calcd for $C_{59}H_{94}N_{14}O_{21}$ (M) 1335. found 1336.

Example 104

$C_8$-(p-Apa)-Amphomycin

Amphomycin-9-Fmoc (11.1 mg) and N-octanoyl-para-aminophenylacetic acid succinimid-1-yl ester (7.8 mg, as prepared in Example 274 and using a succinimidyl ester as prepared in Example 1) used in the method described in Example 3 provided the title compound (7.1 mg): 85% pure, MS (FAB) calcd for $C_{61}H_{90}N_{14}O_{21}$ (M) 1355. found 1355.

Example 105

$C_{14}$-Gly-Amphomycin

In a first step, amphomycin-9-Fmoc (26 mg, 0.020 mmol) was coupled with N-tert-butoxycarbonyl glycine as described in the method of Example 3. The resulting intermediate was purified by HPLC and lyophilized. In a second step, this purified intermediate and tetradecanoic acid used in the method described in Example 2 provided the title compound, which was purified by HPLC and lyophilized (6.4 mg, 24% yield): 92% pure, MS (MALDI) calcd for $C_{61}H_{98}N_{14}O_{21}$ (M) 1364. found 1363.

Example 106

$C_{16}$-Gly-Amphomycin

In a first step, amphomycin-9-Fmoc (26 mg, 0.020 mmol) was coupled with N-tert-butoxycarbonyl glycine as described in the method of Example 3. The resulting intermediate was purified by HPLC and lyophilized. In a second step, this purified intermediate and hexadecanoic acid used in the method described in Example 2 provided the title compound, which was purified by HPLC and lyophilized (9.7 mg, 35% yield): 96% pure, MS (MALDI) calcd for $C_{63}H_{102}N_{14}O_{21}$ (M) 1392. found 1391.

Example 107

$C_{18}$-Gly-Amphomycin

In a first step, amphomycin-9-Fmoc (26 mg, 0.020 mmol) was coupled with N-tert-butoxycarbonyl glycine as described in the method of Example 3. The resulting intermediate was purified by HPLC and lyophilized. In a second step, this purified intermediate and octadecanoic acid used in the method described in Example 2 provided the title compound, which was purified by HPLC and lyophilized (8.2 mg, 29% yield): 84% pure, MS (MALDI) calcd for $C_{65}H_{106}N_{14}O_{21}$ (M) 1420. found 1419.

Example 108

$C_{12}$-(p-Aminophenylpropanoyl)-Amphomycin

Amphomycin-9-Fmoc (10.6 mg) and N-dodecanoyl-para-aminophenyl propanoic acid succinimid-1-yl ester (6.1 mg, as prepared in Example 2744 and using a succinimidyl ester as prepared in Example 1) used in the method described in Example 3 provided the title compound (6.3 mg): 93% pure, MS (FAB) calcd for $C_{66}H_{100}N_{14}O_{21}$ (M) 1426. found 1426.

Example 109

$C_{12}$-(p-Aminophenylpropanoyl)$_2$-Amphomycin

In a first step, amphomycin-9-Fmoc (30 mg, 0.022 mmol) was coupled with 4-tert-butoxycarbonylaminophenyl propanoic acid as described in the method of Example 3. The resulting intermediate was purified by HPLC and lyophilized. In a second step, this purified intermediate was coupled with 4-tert-butoxycarbonylaminophenyl propanoic acid as described in the method of Example 3. The resulting second intermediate was purified by HPLC and lyophilized. In a third step, this purified second intermediate and dodecanoic acid used in the method described in Example 2 provided the title compound, which was purified by HPLC and lyophilized (1.5 mg, 4% yield): 86% pure, MS (MALDI) calcd for $C_{75}H_{109}N_{15}O_{22}$ (M) 1573. found 1572.

Example 110

$CH_3-(CH_2)_9-O$-p-Ph-C(=O)-Gly-Amphomycin

In a first step, amphomycin-9-Fmoc (30 mg, 0.022 mmol) was coupled with N-tert-butoxycarbonyl glycine as described in the method of Example 3. The resulting intermediate was purified by HPLC and lyophilized. In a second step, this purified intermediate and p-decanoxobenzoic acid used in the method described in Example 2 provided the title compound, which was purified by HPLC and lyophilized (8.9 mg, 28% yield): 88% pure, MS (MALDI) calcd for $C_{64}H_{96}N_{14}O_{22}$ (M) 1414. found 1413.

Example 111

$C_{12}$-(M-Apa)-Amphomycin

Amphomycin-9-Fmoc (11 mg) and N-dodecanoyl-meta-aminophenylacetic acid succinimid-1-yl ester (6.6 mg, as prepared in Example 274 and using a succinimidyl ester as prepared in Example 1) used in the method described in Example 3 provided the title compound (8.5 mg): 86% pure, MS (FAB) calcd for $C_{65}H_{98}N_{14}O_{21}$ (M) 1412. found 1412.

Example 112

$C_{15}$-[Asp-(OtBu)]-Amphomycin

Amphomycin-9-Fmoc (16.3 mg) was coupled with N-pentadecanoyl-O-t-butyl-aspartate succinimid-1-yl ester (7.2 mg, as prepared in Example 274 and using a succinimidyl ester as prepared in Example 1) as described in the method of Example 3 to provide the title compound (10.6 mg): 68% pure, MS (FAB) calcd for $C_{68}H_{110}N_{14}O_{23}$ (M) 1492. found 1492.

Example 113

$C_{10}$-(M-Apa)-Amphomycin

In a first step, amphomycin-9-Fmoc (30 mg, 0.022 mmol) was coupled with 3-tert-butoxycarbonylamino-phenylacetic acid as described in the method of Example 3. The resulting intermediate was purified by HPLC and lyophilized. In a second step, this purified intermediate and decanoic acid used in the method described in Example 2 provided the title compound, which was purified by HPLC and lyophilized

Example 114

(CH$_3$—(CH$_2$)$_7$)(CH$_3$—(CH$_2$)$_5$)CH—C(=O)-Gly-Amphomycin

Amphomycin-9-Fmoc (30 mg, 0.022 mmol) was coupled with N-(2-hexyl-decanoyl)glycine succinimid-1-yl ester (7.0 mg, as prepared in Example 274 and using a succinimidyl ester as prepared in Example 1) as described in the method of Example 3 to provide the title compound (14.4 mg): 84% pure, MS (FAB) calcd for C$_{61}$H$_{99}$N$_{13}$O$_{20}$ (M) 1335. found 1335.

Example 115

C$_{15}$-Phg-Amphomycin

Amphomycin-9-Fmoc (16.3 mg) was coupled with N-pentadecanoyl phenylalanine succinimid-1-yl ester (9.9 mg, as prepared in Example 274 and using a succinimidyl ester as prepared in Example 1) as described in the method of Example 3 to provide the title compound (6.3 mg): 75% pure, MS (FAB) calcd for C$_{68}$H$_{104}$N$_{14}$O$_{21}$ (M) 1454. found 1454.

Example 116

C$_{15}$-(D-Phe)-Amphomycin

In a first step, amphomycin-9-Fmoc (30 mg, 0.022 mmol) was coupled with D-N-tert-butoxycarbonyl phenylalanine as described in the method of Example 3. The resulting intermediate was purified by HPLC and lyophilized. In a second step, this purified intermediate and pentadecanoic acid used in the method described in Example 2 provided the title compound, which was purified by HPLC and lyophilized (11 mg, 33% yield): 60% pure, MS (MALDI) calcd for C$_{69}$H$_{106}$N$_{14}$O$_{21}$ (M) 1468. found 1467.

Example 117

Ph-O—(CH$_2$)$_{11}$-Gly-Amphomycin

Amphomycin-9-Fmoc (16.3 mg) was coupled with N-(11-phenoxyundecanoyl)glycine succinimid-1-yl ester (7.5 mg, as prepared in Example 276 and using a succinimidyl ester as prepared in Example 1) as described in the method of Example 3 to provide the title compound (12.4 mg): 87% pure, MS (FAB) calcd for C$_{64}$H$_{96}$N$_{14}$O$_{22}$ (M) 1414. found 1414.

Example 118

C$_{10}$-(L-BBTA)-Amphomycin

In a first step, amphomycin-9-Fmoc (30 mg, 0.022 mmol) was coupled with (S)-3-Benzo[b]thiophen-3-yl-2-tert-butoxycarbonylamino-propionic acid as described in the method of Example 3. The resulting intermediate was purified by HPLC and lyophilized. In a second step, this purified intermediate and decanoic acid used in the method described in Example 2 provided the title compound, which was purified by HPLC and lyophilized (4 mg, 12% yield): 84% pure, MS (MALDI) calcd for C$_{66}$H$_{96}$N$_{14}$O$_{21}$S (M) 1454. found 1453.

Example 119

C$_{12}$-(p-Apa)-Amphomycin

In a first step, amphomycin-9-Fmoc (30 mg, 0.022 mmol) was coupled with 4-tert-butoxycarbonyl-aminophenylacetic acid as described in the method of Example 3. The resulting intermediate was purified by HPLC and lyophilized. In a second step, this purified intermediate and dodecanoic acid used in the method described in Example 2 provided the title compound, which was purified by HPLC and lyophilized (10 mg, 31% yield): 75% pure, MS (MALDI) calcd for C$_{65}$H$_{98}$N$_{14}$O$_{21}$ (M) 1412. found 1411.

Example 120

C$_{12}$-(p-Amino-Trans-Cinnamyl)-Amphomycin

Amphomycin-9-Fmoc (11.1 mg) and N-Dodecanoyl-para-amino-trans-cinnamic acid succinimid-1-yl ester (7.8 mg, as prepared in Example 274 and using a succinimidyl ester as prepared in Example 1) used in the method described in Example 3 provided the title compound (7.4 mg): 84% pure, MS (FAB) calcd for C$_{66}$H$_{98}$N$_{14}$O$_{21}$ (M) 1424. found 1424.

Example 121

CH$_3$—(CH$_2$)$_{11}$—O-p-Ph-C(=O)-Gly-Amphomycin

In a first step, amphomycin-9-Fmoc (30 mg, 0.022 mmol) was coupled with N-tert-butoxycarbonyl glycine as described in the method of Example 3. The resulting intermediate was purified by HPLC and lyophilized. In a second step, this purified intermediate and para-dodecanoxobenzoic acid used in the method described in Example 2 provided the title compound, which was purified by HPLC and lyophilized (10 mg, 30% yield): 86% pure, MS (MALDI) calcd for C$_{66}$H$_{100}$N$_{14}$O$_{22}$ (M) 1442. found 1441.

Example 122

CH$_3$—(CH$_2$)$_9$-(p-Apa)-Amphomycin

In a first step, amphomycin-9-Fmoc (30 mg, 0.022 mmol) was coupled with 4-tert-butoxycarbonylaminophenylacetic acid as described in the method of Example 3. The resulting intermediate was purified by HPLC and lyophilized. In a second step, this purified intermediate and decanoyl acid used in the method described in Example 2 provided the title compound, which was purified by HPLC and lyophilized (3 mg, 7% yield): 62% pure, MS (MALDI) calcd for C$_{63}$H$_{94}$N$_{14}$O$_{21}$ (M) 1384. found 1383.

Example 123

C$_{12}$-PABA-Gly-Amphomycin

Amphomycin-9-Fmoc (15.8 mg) and N—(N-Dodecanoyl-para-aminobenzoyl) glycine succinimid-1-yl ester (6.3 mg, as prepared in Example 276 and using a succinimidyl ester as prepared in Example 1) used in the method described in Example 3 provided the title compound (7.6 mg): 82% pure, MS (FAB) calcd for $C_{66}H_{99}N_{15}O_{22}$ (M) 1455. found 1455.

Example 124

$C_{15}$-Amphomycin-9-(D-Orn)

Compound $C_{15}$-amphomycin (27 mg, 0.020 mmol) of Example 2 and (D)-5-tert-butoxycarbonylamino-2-(9H-fluoren-9-ylmethoxycarbonyl)-aminopentanoic acid used in the method described in Example 4 provided the title compound, which was purified by HPLC and lyophilized (13 mg, 44% yield): 85% pure, MS (MALDI) calcd for $C_{65}H_{107}N_{15}O_{21}$ (M) 1435. found 1434.

Example 125

$C_{14}$-Amphomycin-9-Gly-Lys

Compound $C_{14}$-amphomycin (100 mg, 0.077 mmol) of Example 10 and N-(2-N-tert-butoxycarbonyl-6-(9H-fluoren-9-yl-methoxycarbonyl)lysinyl)glycine used in the method described in Example 4 provided the title compound, which was purified by HPLC and lyophilized (60.5 mg, 54% yield): 85% pure, MS (MALDI) calcd for $C_{67}H_{110}N_{16}O_{22}$ (M) 1492. found 1491.

Example 126

$C_{14}$-Amphomycin-9-Lys

Compound $C_{14}$-amphomycin (22 mg, 0.017 mmol) of Example 10 and 2-N-tert-butoxycarbonyl-6-N-(9H-fluoren-9-yl-methoxycarbonyl)lysine used in the method described in Example 4 provided the title compound, which was purified by HPLC and lyophilized (9 mg, 38% yield): 77% pure, MS (MALDI) calcd for $C_{65}H_{107}N_{15}O_{21}$ (M) 1435. found 1434.

Example 127

$C_{14}$-Amphomycin-9-Orn

Compound $C_{14}$-amphomycin (22 mg, 0.017 mmol) of Example 10 and 6-N-tert-butoxycarbonyl-2-N-(9H-fluoren-9-yl-methoxycarbonyl)ornithine used in the method described in Example 4 provided the title compound, which was purified by HPLC and lyophilized (7 mg, 30% yield): 78% pure, MS (MALDI) calcd for $C_{64}H_{105}N_{15}O_{21}$ (M) 1421. found 1420.

Example 128

$C_{13}$-Amphomycin-9-Gly-Lys

Compound $C_{13}$-amphomycin (25 mg, 0.019 mmol) of Example 9 and N-(2-N-tert-butoxycarbonyl-6-N-(9H-Fluoren-9-yl-methoxycarbonyl)lysinyl)glycine used in the method described in Example 4 provided the title compound, which was purified by HPLC and lyophilized (13 mg, 46% yield): 93% pure, MS (MALDI) calcd for $C_{66}H_{108}N_{16}O_{22}$ (M) 1478. found 1477.

Example 129

$C_{15}$-Amphomycin-9-Lys

Compound $C_{15}$-amphomycin (27 mg, 0.020 mmol) of Example 2 and 2-N-tert-butoxycarbonyl-6-(9H-fluoren-9-yl-methoxycarbonyl)lysine used in the method described in Example 4 provided the title compound, which was purified by HPLC and lyophilized (9 mg, 30% yield): 99% pure, MS (MALDI) calcd for $C_{66}H_{109}N_{15}O_{21}$ (M) 1449. found 1448.

Example 130

$C_{15}$-Amphomycin-9-Orn

Compound $C_{15}$-amphomycin (27 mg, 0.020 mmol) of Example 2 and 6-N-tert-butoxycarbonyl-2-(9H-fluoren-9-yl-methoxycarbonyl)ornithine used in the method described in Example 4 provided the title compound, which was purified by HPLC and lyophilized (10 mg, 34% yield): 98% pure, MS (MALDI) calcd for $C_{65}H_{107}N_{15}O_{21}$ (M) 1435. found 1434.

Example 131

$C_{15}$-Amphomycin-9-gDab

Compound $C_{15}$-amphomycin (27 mg, 0.020 mmol) of Example 2 and (S)-2-tert-butoxycarbonylamino-4-(9H-fluoren-9-yl-methoxycarbonyl)-aminobutyric acid used in the method described in Example 4 provided the title compound, which was purified by HPLC and lyophilized (9 mg, 31% yield): 96% pure, MS (MALDI) calcd for $C_{64}H_{105}N_{15}O_{21}$ (M) 1421. found 1420.

Example 132

$C_{15}$-Amphomycin-9-Dap

Compound $C_{15}$-amphomycin (27 mg, 0.020 mmol) of Example 2 and (S)-2-tert-butoxycarbonylamino-3-(9H-fluoren-9-yl-methoxycarbonyl)-aminopropionic acid used in the method described in Example 4 provided the title compound, which was purified by HPLC and lyophilized (9 mg, 31% yield): 73% pure, MS (MALDI) calcd for $C_{63}H_{103}N_{15}O_{21}$ (M) 1407. found 1406.

Example 133

$C_{13}$-Amphomycin-9-Lys

Compound $C_{13}$-amphomycin (20 mg, 0.015 mmol) of Example 9 and 2-N-tert-butoxycarbonyl-6-(9H-fluoren-9-yl-methoxycarbonyl)lysine used in the method described in Example 4 provided the title compound, which was purified by HPLC and lyophilized (8 mg, 37% yield): 97% pure, MS (MALDI) calcd for $C_{64}H_{105}N_{15}O_{21}$ (M) 1421. found 1420.

Example 134

$C_{13}$-Amphomycin-9-Orn

Compound $C_{13}$-amphomycin (20 mg, 0.015 mmol) of Example 9 and 6-N-tert-butoxycarbonyl-2-(9H-fluoren-9-yl-methoxycarbonyl)ornithine used in the method described in Example 4 provided the title compound, which was purified by HPLC and lyophilized (9 mg, 42% yield): 86% pure, MS (MALDI) calcd for $C_{63}H_{103}N_{15}O_{21}$ (M) 1407. found 1406.

Example 135

$C_{13}$-Amphomycin-9-gDab

Compound $C_{13}$-amphomycin (20 mg, 0.015 mmol) of Example 9 and (S)-2-tert-butoxycarbonylamino-4-(9H-fluoren-9-yl-methoxycarbonyl)-aminobutyric acid used in the method described in Example 4 provided the title compound, which was purified by HPLC and lyophilized (12 mg, 57% yield): 92% pure, MS (MALDI) calcd for $C_{62}H_{101}N_{15}O_{21}$ (M) 1393. found 1392.

Example 136

$C_{13}$-Amphomycin-9-Dap

Compound $C_{13}$-amphomycin (20 mg, 0.015 mmol) of Example 9 and (S)-2-tert-butoxycarbonylamino-3-(9H-fluoren-9-yl-methoxycarbonyl)-aminopropionic acid used in the method described in Example 4 provided the title compound, which was purified by HPLC and lyophilized (9 mg, 43% yield): 93% pure, MS (MALDI) calcd for $C_{61}H_{99}N_{15}O_{21}$ (M) 1379. found 1378.

Example 137

$C_{12}$-Amphomycin-9-Lys

Compound $C_{12}$-amphomycin (25 mg, 0.020 mmol) of Example 8 and 2-N-tert-butoxycarbonyl-6-(9H-fluoren-9-yl-methoxycarbonyl)lysine used in the method described in Example 4 provided the title compound, which was purified by HPLC and lyophilized (14 mg, 53% yield): 100% pure, MS (MALDI) calcd for $C_{63}H_{103}N_{15}O_{21}$ (M) 1407. found 1407.

Example 138

$C_{12}$-Amphomycin-9-gDab

Compound $C_{12}$-amphomycin (25 mg, 0.020 mmol) of Example 8 and (S)-2-tert-butoxycarbonylamino-4-(9H-fluoren-9-yl-methoxycarbonyl)-aminobutyric acid used in the method described in Example 4 provided the title compound, which was purified by HPLC and lyophilized (6 mg, 23% yield): 100% pure, MS (MALDI) calcd for $C_{61}H_{99}N_{15}O_{21}$ (M) 1379. found 1378.

Example 139

$C_{14}$-Amphomycin-9-gDab

Compound $C_{14}$-amphomycin (22 mg, 0.017 mmol) of Example 10 and (S)-2-tert-butoxycarbonylamino-4-(9H-fluoren-9-yl-methoxycarbonyl)-aminobutyric acid used in the method described in Example 4 provided the title compound, which was purified by HPLC and lyophilized (6 mg, 26% yield): 84% pure, MS (MALDI) calcd for $C_{63}H_{103}N_{15}O_{21}$ (M) 1407. found 1406.

Example 140

$C_{14}$-Amphomycin-9-Dap

Compound $C_{14}$-amphomycin (22 mg, 0.017 mmol) of Example 10 and (S)-2-tert-butoxycarbonylamino-3-(9H-fluoren-9-yl-methoxycarbonyl)-aminopropionic acid used in the method described in Example 4 provided the title compound, which was purified by HPLC and lyophilized (6 mg, 26% yield): 70% pure, MS (MALDI) calcd for $C_{62}H_{101}N_{15}O_{21}$ (M) 1393. found 1392.

Example 141

$C_{16}$-Amphomycin-9-Gly-Lys

Compound $C_{16}$-amphomycin (30 mg, 0.022 mmol) of Example 11 and N-(2-N-tert-butoxycarbonyl-6-(9H-fluoren-9-yl-methoxycarbonyl)lysinyl)glycine used in the method described in Example 4 provided the title compound, which was purified by HPLC and lyophilized (4.5 mg, 13% yield): 79% pure, MS (MALDI) calcd for $C_{69}H_{114}N_{16}O_{22}$ (M) 1520. found 1519.

Example 142

$C_{17}$-Amphomycin-Gly-Lys

Compound $C_{17}$-amphomycin (30 mg, 0.022 mmol) of Example 12 and N-(2-N-tert-butoxycarbonyl-6-(9H-fluoren-9-yl-methoxycarbonyl)lysinyl)glycine used in the method described in Example 4 provided the title compound, which was purified by HPLC and lyophilized (5.2 mg, 15% yield): 82% pure, MS (MALDI) calcd for $C_{70}H_{116}N_{16}O_{22}$ (M) 1534. found 1533.

Example 143

$C_{12}$-Amphomycin-9-Gly-Lys

Compound $C_{12}$-amphomycin (30 mg, 0.023 mmol) of Example 8 and N-(2-N-tert-butoxycarbonyl-6-(9H-fluoren-9-yl-methoxycarbonyl)lysinyl)glycine used in the method described in Example 4 provided the title compound, which was purified by HPLC and lyophilized (3.4 mg, 10% yield): 80% pure, MS (MALDI) calcd for $C_{65}H_{106}N_{16}O_{22}$ (M) 1464. found 1463.

Example 144

$C_{15}$-Amphomycin-9-Sar-Orn

Compound $C_{15}$-amphomycin-9-Sar (27 mg, 0.020 mmol) of Example 24 and 6-N-tert-butoxycarbonyl-2-(9H-fluoren-9-yl-methoxycarbonyl)ornithine used in the method described in Example 4 provided the title compound, which was purified by HPLC and lyophilized (5 mg, 16% yield): 89% pure, MS (MALDI) calcd for $C_{68}H_{112}N_{16}O_{22}$ (M) 1506. found 1505.

Example 145

$C_{15}$-Amphomycin-9-Sar-gDab

Compound $C_{15}$-amphomycin-9-Sar (27 mg, 0.020 mmol) of Example 24 and (S)-2-tert-butoxycarbonylamino-4-(9H-fluoren-9-yl-methoxycarbonyl)-aminobutyric acid used in the method described in Example 4 provided the title compound, which was purified by HPLC and lyophilized (5.8 mg, 19% yield): 92% pure, MS (MALDI) calcd for $C_{67}H_{110}N_{16}O_{22}$ (M) 1492. found 1491.

Example 146

$C_{15}$-Amphomycin-9-Sar-Dap

Compound $C_{15}$-amphomycin-9-Sar (27 mg, 0.020 mmol) of Example 24 and (S)-2-tert-butoxycarbonylamino-3-(9H- fluoren-9-yl-methoxycarbonyl)-aminopropionic acid used in the method described in Example 4 provided the title compound, which was purified by HPLC and lyophilized (4.7 mg, 16% yield): 83% pure, MS (MALDI) calcd for $C_{66}H_{108}N_{16}O_{22}$ (M) 1478. found 1477.

Example 147

$C_{15}$-Amphomycin-9-(β-Ala)

Compound $C_{15}$-amphomycin (250 mg, 0.189 mmol) of Example 2 and N-tert-butoxycarbonyl-β-alanine used in the method described in Example 4 provided the title compound, which was purified by HPLC and lyophilized (26.1 mg, 10% yield): 91% pure, MS (MALDI) calcd for $C_{63}H_{102}N_{14}O_{21}$ (M) 1392. found 1391.

Example 148

$C_{15}$-Amphomycin-9-(β-Ala)-Orn

Compound $C_{15}$-amphomycin-9-(β-Ala) (35 mg, 0.025 mmol) of Example 147 and 6-N-tert-butoxycarbonyl-2-(9H-fluoren-9-yl-methoxycarbonyl)ornithine used in the method described in Example 4 provided the title compound, which was purified by HPLC and lyophilized (9.1 mg, 23% yield): 97% pure, MS (MALDI) calcd for $C_{68}H_{112}N_{16}O_{22}$ (M) 1506. found 1505.

Example 149

β-Isomer of $C_{15}$-Amphomycin-9-(β-Ala)

The title compound was obtained using the method described in Example 147, which compound is a secondary product (amphomycin core peptide β-isomer) of that reaction. The title compound was purified by HPLC and lyophilized (8.8 mg, 3% yield): 86% pure, MS (MALDI) calcd for $C_{63}H_{102}N_{14}O_{21}$ (M) 1392. found 1391.

Example 150

Anhydro Isomer of $C_{15}$-Amphomycin-9-(β-Ala)

The title compound was obtained using the method described in Example 147, which compound is a secondary product (amphomycin core peptide anhydro isomer) of that reaction. The title compound was purified by HPLC and lyophilized (18.4 mg, 7% yield): 80% pure, MS (MALDI) calcd for $C_{63}H_{100}N_{14}O_{20}$ (M) 1374. found 1373.

Example 151

$C_{15}$-Amphomycin-9-(D-Pro)-(D-Lys)

Compound $C_{15}$-amphomycin-9-(D-Pro) (60 mg, 0.042 mmol) of Example 67 and (D)-2-N-tert-butoxycarbonyl-6-(9H-fluoren-9-yl-methoxycarbonyl)lysine used in the method described in Example 4 provided the title compound, which was purified by HPLC and lyophilized (1.8 mg, 3% yield): 93% pure, MS (MALDI) calcd for $C_{71}H_{116}N_{16}O_{22}$ (M) 1546. found 1545.

Example 152

$C_{15}$-Amphomycin-9-Gly-(D-Lys)

In a first step, compound $C_{15}$-amphomycin (24 mg, 0.018 mmol) of Example 2 was coupled with N-tert-butoxycarbonyl glycine as described in the method of Example 3. The resulting intermediate was purified by HPLC and lyophilized. In a second step, this purified intermediate and (D)-6-N-(9H-fluoren-9-yl-methoxycarbonyl)-2-N-(tert-butoxycarbonyl) lysine used in the method described in Example 4 provided the title compound, which was purified by HPLC and lyophilized (16 mg, 58% yield): 82% pure, MS (MALDI) calcd for $C_{68}H_{112}N_{16}O_{22}$ (M) 1506. found 1505.

Example 153

$C_{15}$-Amphomycin-9-Gly-Orn

In a first step, compound $C_{15}$-amphomycin (24 mg, 0.018 mmol) of Example 2 was coupled with N-tert-butoxycarbonyl glycine as described in the method of Example 3. The resulting intermediate was purified by HPLC and lyophilized. In a second step, this purified intermediate and 2-N-tert-butoxycarbonyl-6-(9H-fluoren-9-yl-methoxycarbonyl) ornithine used in the method described in Example 4 provided the title compound, which was purified by HPLC and lyophilized (18 mg, 66% yield): 68% pure, MS (MALDI) calcd for $C_{67}H_{110}N_{16}O_{22}$ (M) 1492. found 1491.

Example 154

$C_{15}$-Amphomycin-9-Gly-gDab

In a first step, compound $C_{15}$-amphomycin (24 mg, 0.018 mmol) of Example 2 was coupled with N-tert-butoxycarbonyl glycine as described in the method of Example 3. The resulting intermediate was purified by HPLC and lyophilized. In a second step, this purified intermediate and (S)-2-tert-butoxycarbonylamino-4-(9H-fluoren-9-yl-methoxycarbonyl)-aminobutyric acid used in the method described in Example 4 provided the title compound, which was purified by HPLC and lyophilized (9.6 mg, 34% yield): 80% pure, MS (MALDI) calcd for $C_{66}H_{108}N_{16}O_{22}$ (M) 1478. found 1477.

Example 155

$C_{15}$-Amphomycin-9-(β-Ala)-Lys

In a first step, compound $C_{15}$-amphomycin (27 mg, 0.020 mmol) of Example 2 was coupled with N-tert-butoxycarbonyl-beta-alanine as described in the method of Example 3. The resulting intermediate was purified by HPLC and lyophilized. In a second step, this purified intermediate and 2-N-tert-butoxycarbonyl-6-(9H-fluoren-9-yl-methoxycarbonyl) lysine used in the method described in Example 4 provided the title compound, which was purified by HPLC and lyophilized (19 mg, 61% yield): 84% pure, MS (MALDI) calcd for $C_{69}H_{114}N_{16}O_{22}$ (M) 1520. found 1519.

Example 156

$C_{15}$-Amphomycin-9-GABA-Lys

In a first step, compound $C_{15}$-amphomycin (25 mg, 0.019 mmol) was coupled with γ-N-tert-butoxycarbonylamine butanoic acid as described in the method of Example 3. The resulting intermediate was purified by HPLC and lyophilized.

In a second step, this purified intermediate and 2-N-tert-butoxycarbonyl-6-(9H-fluoren-9-yl-methoxycarbonyl) lysine used in the method described in Example 4 provided the title compound, which was purified by HPLC and lyophilized (19.2 mg, 66% yield): 95% pure, MS (MALDI) calcd for $C_{70}H_{116}N_{16}O_{22}$ (M) 1534. found 1533.

Example 157

$C_{15}$-Amphomycin-9-Gly-Dap

In a first step, compound $C_{15}$-amphomycin (22 mg, 0.017 mmol) of Example 2 was coupled with N-tert-butoxycarbonyl glycine as described in the method of Example 3. The resulting intermediate was purified by HPLC and lyophilized. In a second step, this purified intermediate and (S)-2-tert-butoxycarbonylamino-3-(9H-fluoren-9-yl-methoxycarbonylamino)-propionic acid used in the method described in Example 4 provided the title compound, which was purified by HPLC and lyophilized (8.7 mg, 36% yield): 73% pure, MS (MALDI) calcd for $C_{65}H_{106}N_{16}O_{22}$ (M) 1464. found 1463.

Example 158

$C_{15}$-Amphomycin-9-Gly-hLys

In a first step, compound $C_{15}$-amphomycin (35 mg, 0.027 mmol) of Example 2 was coupled with N-tert-butoxycarbonyl glycine as described in the method of Example 3. The resulting intermediate was purified by HPLC and lyophilized. In a second step, this purified intermediate and (S)-2-tert-butoxycarbonylamino-7-(9H-fluoren-9-yl-methoxycarbonylamino)-heptanoic acid used in the method described in Example 4 provided the title compound, which was purified by HPLC and lyophilized (6.8 mg, 17% yield): 91% pure, MS (MALDI) calcd for $C_{69}H_{114}N_{16}O_{22}$ (M) 1520. found 1519.

Example 159

$C_{15}$-Amphomycin-9-GABA-gDab

In a first step, compound $C_{15}$-amphomycin (25 mg, 0.019 mmol) was coupled with γ-N-tert-butoxycarbonyl-aminobutanoic acid as described in the method of Example 3. The resulting intermediate was purified by HPLC and lyophilized. In a second step, this purified intermediate and (S)-2-tert-butoxycarbonylamino-4-(9H-fluoren-9-yl-methoxycarbonyl)-aminobutyric acid used in the method described in Example 4 provided the title compound, which was purified by HPLC and lyophilized (17.2 mg, 46% yield): 76% pure, MS (MALDI) calcd for $C_{68}H_{112}N_{16}O_{22}$ (M) 1506. found 1505.

Example 160

$C_{15}$-Amphomycin-9-Pro

Compound $C_{15}$-amphomycin (45 mg, 0.034 mmol) of Example 2 and N-(9H-fluoren-9-yl-methoxycarbonyl)-proline used in the method described in Example 5 provided the title compound, which was purified by HPLC and lyophilized (11 mg, 23% yield): 85% pure, MS (MALDI) calcd for $C_{65}H_{104}N_{14}O_{21}$ (M) 1418. found 1417.

Example 161

$C_{15}$-Amphomycin-9-Aib

Compound $C_{15}$-amphomycin (30 mg, 0.023 mmol) of Example 2 and 2-N-(9H-fluoren-9-yl-methoxycarbonyl)-2,2-dimethylglycine used in the method described in Example 5 provided the title compound, which was purified by HPLC and lyophilized (8 mg, 25% yield): 82% pure, MS (MALDI) calcd for $C_{64}H_{104}N_{14}O_{21}$ (M) 1406. found 1405.

Example 162

$C_{15}$-Amphomycin-9-MeCys

Compound $C_{15}$-amphomycin (40 mg, 0.030 mmol) of Example 2 and (S)-2-(9H-fluoren-9-yl-methoxycarbonyl)-amino-3-methylsulfanyl-propionic acid used in the method described in Example 5 provided the title compound, which was purified by HPLC and lyophilized (10 mg, 23% yield): 98% pure, MS (MALDI) calcd for $C_{64}H_{104}N_{14}O_{21}S$ (M) 1438. found 1437.

Example 163

$C_{15}$-Amphomycin-9-Nvl

Compound $C_{15}$-amphomycin (40 mg, 0.030 mmol) of Example 2 and (S)-2-(9H-fluoren-9-yl-methoxycarbonyl)-aminopentanoic acid used in the method described in Example 5 provided the title compound, which was purified by HPLC and lyophilized (9 mg, 21% yield): 97% pure, MS (MALDI) calcd for $C_{61}H_{106}N_{14}O_{21}$ (M) 1420. found 1419.

Example 164

$C_{15}$-Amphomycin-9-Abu

Compound $C_{15}$-amphomycin (40 mg, 0.030 mmol) of Example 2 and (S)-2-(9H-fluoren-9-yl-methoxycarbonyl)-aminobutanoic acid used in the method described in Example 5 provided the title compound, which was purified by HPLC and lyophilized (11 mg, 25% yield): 92% pure, MS (MALDI) calcd for $C_{64}H_{104}N_{14}O_{21}$ (M) 1406. found 1405.

Example 165

$C_{15}$-Amphomycin-9-Cit

Compound $C_{15}$-amphomycin (40 mg, 0.030 mmol) of Example 2 and (S)-2-(9H-fluoren-9-yl-methoxycarbonylamino)-5-ureido-pentanoic acid used in the method described in Example 5 provided the title compound, which was purified by HPLC and lyophilized (11 mg, 25% yield): 89% pure, MS (MALDI) calcd for $C_{66}H_{108}N_{16}O_{22}$ (M) 1478. found 1477.

Example 166

$C_{15}$-Amphomycin-9-(ME)$_2$Arg

Compound $C_{15}$-amphomycin (40 mg, 0.030 mmol) of Example 2 and (S)-2-(9H-fluoren-9-yl-methoxycarbonylamino)-N,N'-methylarginine used in the method described in Example 5 provided the title compound, which was purified by HPLC and lyophilized (2 mg, 4% yield): 87% pure, MS (MALDI) calcd for $C_{68}H_{113}N_{17}O_{21}$ (M) 1505. found 1504.

Example 167

$C_{15}$-Amphomycin-9-Hyp

Compound $C_{15}$-amphomycin (30 mg, 0.023 mmol) of Example 2 and (S)-4-hydroxy-pyrrolidine-1,2-dicarboxylic acid 1-(9H-fluoren-9-yl-methyl)ester used in the method described in Example 5 provided the title compound, which was purified by HPLC and lyophilized (12 mg, 37% yield): 71% pure, MS (MALDI) calcd for $C_{65}H_{104}N_{14}O_{22}$ (M) 1434. found 1433.

Example 168

$C_{15}$-Amphomycin-9-(p-Apa)

Compound $C_{15}$-amphomycin (35 mg, 0.027 mmol) of Example 2 and 4-N-(9H-fluoren-9-yl-methoxycarbonyl)aminophenylacetic acid used in the method described in Example 5 provided the title compound, which was purified by HPLC and lyophilized (4 mg, 10% yield): 90% pure, MS (MALDI) calcd for $C_{68}H_{104}N_{14}O_{21}$ (M) 1454. found 1453.

Example 169

$C_{15}$-Amphomycin-9-Val

Compound $C_{15}$-amphomycin (27 mg, 0.020 mmol) of Example 2 and N-(9H-fluoren-9-yl-methoxycarbonyl)valine used in the method described in Example 5 provided the title compound, which was purified by HPLC and lyophilized (6 mg, 21% yield): 64% pure, MS (MALDI) calcd for $C_{65}H_{106}N_{14}O_{21}$ (M) 1420. found 1419.

Example 170

$C_{15}$-Amphomycin-9-(ME)$_3$Lys

Compound $C_{15}$-amphomycin (31 mg, 0.023 mmol) of Example 2 and [(S)-5-Carboxy-5-(9H-fluoren-9-yl-methoxycarbonylamino)-pentyl]-trimethyl-ammonium used in the method described in Example 5 provided the title compound, which was purified by HPLC and lyophilized (8 mg, 23% yield): 87% pure, MS (MALDI) calcd for $C_{69}H_{116}N_{15}O_{21}$ (M) 1492. found 1491.

Example 171

$C_{15}$-Amphomycin-9-Nle

Compound $C_{15}$-amphomycin (27 mg, 0.020 mmol) of Example 2 and (S)-2-(9H-fluoren-9-yl-methoxycarbonylamino)-hexanoic acid used in the method described in Example 5 provided the title compound, which was purified by HPLC and lyophilized (10 mg, 34% yield): 95% pure, MS (MALDI) calcd for $C_{66}H_{108}N_{14}O_{21}$ (M) 1434. found 1433.

Example 172

$C_{15}$-Amphomycin-9-Lys

Compound $C_{15}$-amphomycin (26 mg, 0.019 mmol) of Example 2 and 6-formyl-N-2-(9H-fluoren-9-yl-methoxycarbonyl)lysine used in the method described in Example 5 provided the title compound, which was purified by HPLC and lyophilized (10 mg, 343% yield): 88% pure, MS (MALDI) calcd for $C_{67}H_{109}N_{15}O_{22}$ (M) 1477. found 1476.

Example 173

$C_{15}$-Amphomycin-9-(β-Ala)-(5-Ava)

Compound $C_{15}$-amphomycin-9-(β-Ala) (33 mg, 0.025 mmol) of Example 147 and 5-(9H-fluoren-9-yl-methoxycarbonylamino)-pentanoic acid used in the method described in Example 5 provided the title compound, which was purified by HPLC and lyophilized (8 mg, 21% yield): 83% pure, MS (MALDI) calcd for $C_{68}H_{111}N_{15}O_{22}$ (M) 1491. found 1490.

Example 174

$C_{15}$-Amphomycin-9-(β-Ala)-Val

In a first step, compound $C_{15}$-amphomycin (26 mg, 0.019 mmol) was coupled with N-tert-butoxycarbonyl β-alanine as described in the method of Example 3. The resulting intermediate was purified by HPLC and lyophilized. In a second step, this purified intermediate and N-(9H-fluoren-9-yl-methoxycarbonyl)valine used in the method described in Example 5 provided the title compound, which was purified by HPLC and lyophilized (10 mg, 35% yield): 76% pure, MS (MALDI) calcd for $C_{68}H_{111}N_{15}O_{22}$ (M) 1491. found 1490.

Example 175

β-Isomer of $C_{15}$-Amphomycin-9-(β-Ala)-Val

The title compound was obtained using the method described in Example 174, which compound is a secondary product (amphomycin core peptide β-isomer) of that reaction. The title compound was purified by HPLC and lyophilized (2.2 mg, 7% yield): 91% pure, MS (MALDI) calcd for $C_{68}H_{111}N_{15}O_{22}$ (M) 1491. found 1490.

Example 176

$C_{15}$-Amphomycin-9-(5-Ava)-(β-Ala)

In a first step, compound $C_{15}$-amphomycin (36 mg, 0.028 mmol) was coupled with 5-(9H-fluoren-9-yl-methoxycarbonylamino)-pentanoic acid as described in the method of Example 3. The resulting intermediate was purified by HPLC and lyophilized. In a second step, this purified intermediate and N-tert-butoxycarbonyl-β-alanine used in the method described in Example 5 provided the title compound, which was purified by HPLC and lyophilized (10.8 mg, 27% yield): 99% pure, MS (MALDI) calcd for $C_{68}H_{111}N_{15}O_{22}$ (M) 1491. found 1490.

Example 177

Preparation of Fmoc-Glycine Resin (GR)

A solution of N-(9H-fluoren-9-yl-methoxycarbonyl)-glycine (1.45 g, 4.8 mmol) and DIEA (2.83 mL, 16 mmol) in dichloromethane (DCM, 20 mL) was mixed with 2-chlorotrityl amine resin (2.11 g, 4 mmol). After stirring for 2 hours at room temperature, the resin was filtered, washed three times with a cocktail of DCM:methanol:DIEA (17:2:1), followed twice each by DCM, DMF, and finally DCM. The GR resin was allowed to dry (4.5 g, 4 mmol).

Example 178

Preparation of Fmoc-Lysine(Boc)-Resin (KR)

Use of 2-chlorotrityl amine resin (2.11 g, 4 mmol) and 2-N-tert-butoxycarbonyl-6-(9H-fluoren-9-yl-methoxycarbonyl)lysine as described in the method of Example 177 provided the title compound KR (4.5 g, 4 mmol).

Example 179

Preparation of Fmoc-Sarcosine Resin (SR)

Use of 2-chlorotrityl amine resin (2.11 g, 4 mmol) and N-(9H-fluoren-9-yl-methoxycarbonyl) sarcosine as described in the method of Example 177 provided the title compound SR (4.5 g, 4 mmol).

Example 180

Preparation of Fmoc-Glycine-Lysine(Boc)-OH (GK)

Resin KR (0.75 g, 0.67 mmol) of Example 178 was suspended in DMF (5 mL) and piperidine (1 mL, 20% v/v). After the mixture was stirred for 30 minutes, the resin was filtered and washed with DMF (twice, 5 mL each). The resin was suspended in 8 mL DMF. N-(9H-fluoren-9-yl-methoxycarbonyl)glycine (1.57 g, 3.35 mmol), O-benzotriazol-1-yl-N,N,N',N'-tetramethyluronium hexafluorophosphate (1.27 g, 3.35 mmol), 1-hydroxybenzotriazole (0.51 g, 3.35 mmol), and 0.74 mL N-methylmorpholine (6.7 mmol) were added and the mixture was stirred for 6 hours at room temperature. After filtering, the resin was washed with DMF (twice, 5 mL). Cleavage from the resin was accomplished using 5 mL of a mixture of acetic acid:tetrafluoroethane:DCM (2:2:6). After 2 hours, the cleaved resin was filtered, and the filtrate containing the product was concentrated in vacuo to provide a relatively clean title compound (GK) as a powder (240 mg).

Example 181

Preparation of Fmoc-D-Leucine-Glycine-OH (dLG)

Use of compound GR (0.75 g, 0.67 mmol) of Example 177 and N-(9H-fluoren-9-yl-methoxycarbonyl)leucine as described in the method of Example 180 provided the title compound dLG (154 mg).

Example 182

Preparation of 6-Fmoc-Aminohexanoyl-Glycine-OH (AG)

Use of compound GR (0.75 g, 0.67 mmol) of Example 177 and 6-(9H-fluoren-9-yl-methoxycarbonylamine)hexanoic acid as described in the method of Example 180 provided the title compound AG (163 mg).

Example 183

Preparation of 6-Fmoc-Aminohexanoyl-Sarcosine-OH (AS)

Use of compound SR (0.75 g, 0.67 mmol) of Example 179 and 6-(9H-fluoren-9-yl-methoxycarbonylamine)hexanoic acid as described in the method of Example 180 provided the title compound AS (161 mg).

Example 184

Preparation of Fmoc-Lysine(Boc)-Sarcosine-OH (KS)

Use of compound SR (0.75 g, 0.67 mmol) of Example 179 and 2-N-tert-butoxycarbonyl-6-(9H-fluoren-9-yl-methoxycarbonyl)lysine as described in the method of Example 180 provided the title compound KS (201 mg).

Example 185

Preparation of Fmoc-Lysine(Boc)-Glycine-Glycine-OH (KGG)

Resin GR (0.75 g, 0.67 mmol) of Example 177 was suspended in DMF (5 mL), and piperidine (1 mL, 20% v/v). After the mixture was stirred for 30 minutes, the resin was filtered and washed with DMF (twice, 5 mL each). The resin was suspended in 8 mL DMF. N-(9H-fluoren-9-yl-methoxycarbonyl)glycine (1.57 g, 3.35 mmol), O-benzotriazol-1-yl-N,N,N',N'-tetramethyluronium hexafluorophosphate (1.27 g, 3.35 mmol), 1-hydroxybenzotriazole (0.51 g, 3.35 mmol), and 0.74 mL N-methylmorpholine (6.7 mmol) was added and the mixture was stirred for 6 hours at room temperature. After filtering, the resin was washed with DMF (twice, 5 mL) and suspended in 5 mL DMF. 2-N-tert-butoxycarbonyl-6-(9H-fluoren-9-yl-methoxycarbonyl)lysine (1.57 g, 3.35 mmol), O-benzotriazol-1-yl-N,N,N',N'-tetramethyluronium hexafluorophosphate (1.27 g, 3.35 mmol), 1-hydroxybenzotriazole (0.51 g, 3.35 mmol), and 0.74 mL N-methylmorpholine (6.7 mmol) was added. The mixture was stirred for 6 hours at room temperature. After filtering, the resin was washed with DMF (twice, 5 mL). Cleavage from the resin was accomplished using 5 mL of a mixture of acetic acid:tetrafluoroethane:DCM (2:2:6). After 2 hours, the cleaved resin was filtered off and the filtrate containing the product was concentrated in vacuo providing a relatively clean title compound (KGG) as a powder (170 mg).

Example 186

Preparation of Fmoc-Glycine-Lysine(Boc)-Glycine-OH (GKG)

Resin KGR (0.67 mmol) was suspended in DMF (5 mL) and piperidine (1 mL, 20% v/v). After the mixture was stirred for 30 minutes, the resin was filtered and washed with DMF (twice, 5 mL each). The resin was resuspended in 8 mL DMF. N-(9H-fluoren-9-yl-methoxycarbonyl)glycine (1.0 g, 3.35 mmol), O-benzotriazol-1-yl-N,N,N',N'-tetramethyluronium hexafluorophosphate (1.27 g, 3.35 mmol), 1-hydroxybenzotriazole (0.51 g, 3.35 mmol), and 0.74 mL N-methylmorpholine (6.7 mmol) was added and the mixture was stirred for 6 hours at room temperature. After filtering, the resin was washed with DMF (twice, 5 mL). Cleavage from the resin was accomplished using 4 mL of a mixture of acetic acid:tetrafluoroethane:DCM (2:2:6). After 2 hours, the cleaved resin was filtered and the filtrate containing the product was concentrated in vacuo until a relatively clean title compound (GKG) was isolated as a powder (180 mg).

Example 187

Preparation of
Fmoc-Lysine(Boc)-Lysine(Boc)-Glycine-OH (KKG)

Resin KGR (0.67 mmol) was suspended in DMF (5 mL) and piperidine (1 mL, 20% v/v). After the mixture was stirred for 30 minutes, the resin was filtered and washed with DMF (twice, 5 mL each). The resin was resuspended in 8 mL DMF. 2-N-tert-butoxycarbonyl-6-(9H-fluoren-9-yl-methoxycarbonyl)lysine (1.5 g, 3.35 mmol), O-benzotriazol-1-yl-N,N,N',N'-tetramethyluronium hexafluorophosphate (1.27 g, 3.35 mmol), 1-hydroxybenzotriazole (0.51 g, 3.35 mmol), and 0.74 mL N-methylmorpholine (6.7 mmol) was added and the mixture was stirred for 6 hours at room temperature. After filtering, the resin was washed with DMF (twice, 5 mL). Cleavage from the resin was accomplished using 4 mL of a mixture of acetic acid:tetrafluoroethane:DCM (2:2:6). After 2 hours, the cleaved resin was filtered and the filtrate containing the product was concentrated in vacuo until a relatively clean title compound (KKG) was isolated as a powder (310 mg).

Example 188

Preparation of Fmoc-Lysine(Boc)-Lysine(Boc)-OH (KK)

Use of compound KR (0.75 g, 0.67 mmol) of Example 178 and 2-N-tert-butoxycarbonyl-6-(9H-fluoren-9-yl-methoxycarbonyl)lysine as described in the method of Example 187 provided the title compound KK (350 mg).

Example 189

Preparation of Fmoc-Lysine(Boc)-Lysine(Boc)-Lysine(Boc)-OH (KKK)

Using two couplings of 2-N-tert-butoxycarbonyl-6-(9H-fluoren-9-yl-methoxycarbonyl) lysine with KR (0.75 g, 0.67 mmol) of Example 178 as described in the method of Example 187 provided the title compound KKK (350 mg).

Example 190

$C_{15}$-Amphomycin-9-Gly-Lys-Gly

Compound $C_{15}$-amphomycin (25 mg, 0.019 mmol) of Example 2 and peptide GKG of Example 186 used in the method described in Example 4 provided the title compound, which was purified by HPLC and lyophilized (20 mg, 68% yield): 77% pure, MS (MALDI) calcd for $C_{70}H_{115}N_{17}O_{23}$ (M) 1563. found 1562.

Example 191

$C_{15}$-Amphomycin-9-Gly-Lys-Lys

Compound $C_{15}$-amphomycin (25 mg, 0.019 mmol) of Example 2 and peptide KKG of Example 187 used in the method described in Example 4 provided the title compound, which was purified by HPLC and lyophilized (16 mg, 52% yield): 74% pure, MS (MALDI) calcd for $C_{74}H_{124}N_{18}O_{23}$ (M) 1634. found 1633.

Example 192

$C_{15}$-Amphomycin-9-Gly-Gly-Lys

Compound $C_{15}$-amphomycin (25 mg, 0.019 mmol) of Example 2 and peptide KGG of Example 185 used in the method described in Example 4 provided the title compound, which was purified by HPLC and lyophilized (20 mg, 54% yield): 88% pure, MS (MALDI) calcd for $C_{70}H_{115}N_{17}O_{23}$ (M) 1563. found 1562.

Example 193

$C_{15}$-Amphomycin-9-Lys-Gly

Compound $C_{15}$-amphomycin (25 mg, 0.019 mmol) of Example 2 and peptide GK of Example 180 used in the method described in Example 4 provided the title compound, which was purified by HPLC and lyophilized (18 mg, 63% yield): 91% pure, MS (MALDI) calcd for $C_{68}H_{112}N_{16}O_{22}$ (M) 1506. found 1505.

Example 194

$C_{15}$-Amphomycin-9-Lys-Lys

Compound $C_{15}$-amphomycin (25 mg, 0.019 mmol) of Example 2 and peptide KK of Example 188 used in the method described in Example 4 provided the title compound, which was purified by HPLC and lyophilized (7 mg, 23% yield): 72% pure, MS (MALDI) calcd for $C_{72}H_{121}N_{17}O_{22}$ (M) 1577. found 1576.

Example 195

$C_{15}$-Amphomycin-9-Lys-Lys-Lys

Compound $C_{15}$-amphomycin (25 mg, 0.019 mmol) of Example 2 and peptide KKK of Example 189 used in the method described in Example 4 provided the title compound, which was purified by HPLC and lyophilized (18 mg, 56% yield): 91% pure, MS (MALDI) calcd for $C_{78}H_{133}N_{19}O_{23}$ (M) 1705. found 1704.

Example 196

$C_{15}$-Amphomycin-9-Gly-(D-Leu)

Compound $C_{15}$-amphomycin (25 mg, 0.019 mmol) of Example 2 and peptide dLG of Example 181 used in the method described in Example 4 provided the title compound, which was purified by HPLC and lyophilized (5.4 mg, 19% yield): 83% pure, MS (MALDI) calcd for $C_{68}H_{111}N_{15}O_{22}$ (M) 1491. found 1490.

Example 197

$C_{15}$-Amphomycin-9-Gly-Ahx

Compound $C_{15}$-amphomycin (25 mg, 0.019 mmol) of Example 2 and peptide AG of Example 182 used in the method described in Example 4 provided the title compound,

Example 198

$C_{15}$-Amphomycin-9-Sar-Ahx

Compound $C_{15}$-amphomycin (25 mg, 0.019 mmol) of Example 2 and peptide AS of Example 183 used in the method described in Example 4 provided the title compound, which was purified by HPLC and lyophilized (4.1 mg, 15% yield): 98% pure, MS (MALDI) calcd for $C_{68}H_{111}N_{15}O_{22}$ (M) 1491. found 1490.

Example 198

$C_{15}$-Amphomycin-9-Sar-Ahx

Compound $C_{15}$-amphomycin (25 mg, 0.019 mmol) of Example 2 and peptide AS of Example 183 used in the method described in Example 4 provided the title compound, which was purified by HPLC and lyophilized (3.5 mg, 12% yield): 98% pure, MS (MALDI) calcd for $C_{69}H_{113}N_{15}O_{22}$ (M) 1505. found 1504.

Example 199

$C_{15}$-Amphomycin-9-Sar-Lys

Compound $C_{15}$-amphomycin (25 mg, 0.019 mmol) of Example 2 and peptide KS of Example 184 used in the method described in Example 4 provided the title compound, which was purified by HPLC and lyophilized (2.5 mg, 9% yield): 84% pure, MS (MALDI) calcd for $C_{69}H_{114}N_{16}O_{22}$ (M) 1520. found 1519.

Example 200

$C_{15}$-Amphomycin-9-Dap-(β-N-(β-Ala))

Compound $C_{15}$-amphomycin (30 mg, 0.023 mmol) and (S)-3-[(9H-fluoren-9-yl-methoxycarbonyl)-β-alaninyl]amino-2-tert-butoxycarbonylamino propionic acid (the latter compound prepared using the method described in Example 180) used in the method described in Example 4 provided the title compound, which was purified by HPLC and lyophilized (2.8 mg, 7% yield): 85% pure, MS (MALDI) calcd for $C_{66}H_{108}N_{16}O_{22}$ (M) 1478. found 1477.

Example 201

$C_{15}$-Amphomycin-9-$C_6$

Compound $C_{15}$-amphomycin (27 mg, 0.020 mmol) of Example 2 was suspended in 1 mL DMF and then charged with 102 µL 1M sodium bicarbonate (in water, 0.10 mmol). The reaction mixture was cooled in an ice bath. A predissolved solution of succinimide activated hexanoic acid (1.5 equiv, prepared as described for compound pentadecanoic acid succinimid-1-yl ester of Example 1) in 0.5 mL DMF was slowly added to the reaction mixture while still on ice, then the reaction stirred for at least 8 hours at room temperature to provide a crude product of the title compound. This crude product was concentrated in vacuo, purified by HPLC (gradient, 25% acetonitrile in water with 0.1% trifluoroacetic acid to 95% acetonitrile over 30 minutes), and lyophilized (5 mg, 17% yield): 80% pure, MS (MALDI) calcd for $C_{66}H_{107}N_{13}O_{21}$ (M) 1419. found 1418.

Example 202

$C_{15}$-Amphomycin-9-Pla

Compound $C_{15}$-amphomycin (30 mg, 0.023 mmol) of Example 2 and picolinic acid used in the method described in Example 201 provided the title compound, which was purified by HPLC and lyophilized (10 mg, 31% yield): 100% pure, MS (MALDI) calcd for $C_{66}H_{100}N_{14}O_{21}$ (M) 1426. found 1425.

Example 203

$C_{15}$-Amphomycin-9-Pca

Compound $C_{15}$-amphomycin (30 mg, 0.023 mmol) of Example 2 and 2-pyrazinecarboxylic acid used in the method described in Example 201 provided the title compound, which was purified by HPLC and lyophilized (11 mg, 34% yield): 97% pure, MS (MALDI) calcd for $C_{65}H_{99}N_{15}O_{21}$ (M) 1427. found 1426.

Example 204

$C_{15}$-Amphomycin-9-(Carbamoyl-Leu)

Compound $C_{15}$-amphomycin (30 mg, 0.023 mmol) of Example 2 and N-carbamoyl leucine used in the method described in Example 201 provided the title compound, which was purified by HPLC and lyophilized (12 mg, 36% yield): 100% pure, MS (MALDI) calcd for $C_{67}H_{109}N_{15}O_{22}$ (M) 1477. found 1476.

Example 205

$C_{15}$-Amphomycin-9-$C_8$

Compound $C_{15}$-amphomycin (24 mg, 0.018 mmol) of Example 2 and octanoic acid used in the method described in Example 201 provided the title compound, which was purified by HPLC and lyophilized (4 mg, 15% yield): 85% pure, MS (MALDI) calcd for $C_{68}H_{111}N_{13}O_{21}$ (M) 1447. found 1446.

Example 206

$C_{15}$-Amphomycin-9-cHexyl

Compound $C_{15}$-amphomycin (27 mg, 0.020 mmol) of Example 2 and cyclohexanecarboxylic acid used in the method described in Example 201 provided the title compound, which was purified by HPLC and lyophilized (8 mg, 27% yield): 86% pure, MS (MALDI) calcd for $C_{67}H_{107}N_{13}O_{21}$ (M) 1431. found 1430.

Example 207

$C_{15}$-Amphomycin-9-$C_4$

Compound $C_{15}$-amphomycin (24 mg, 0.018 mmol) of Example 2 and butyric acid used in the method described in Example 201 provided the title compound, which was purified by HPLC and lyophilized (6 mg, 24% yield): 70% pure, MS (MALDI) calcd for $C_{64}H_{103}N_{13}O_{21}$ (M) 1391. found 1390.

Example 208

$C_{15}$-Amphomycin-9-(2-Norbornaneacetyl)

Compound $C_{15}$-amphomycin (27 mg, 0.020 mmol) of Example 2 and 2-norbornaneacetic acid used in the method described in Example 201 provided the title compound,

Example 209

$C_{15}$-Amphomycin-9-(N-Benzoyl-Tyr-PABA)

Compound $C_{15}$-amphomycin (27 mg, 0.020 mmol) of Example 2 and (S)-4-[2-benzoylamino-3-(4-hydroxy-phenyl)-propionylamino]-benzoic acid used in the method described in Example 201 provided the title compound, which was purified by HPLC and lyophilized (4 mg, 11% yield): 91% pure, MS (MALDI) calcd for $C_{83}H_{115}N_{15}O_{24}$ (M) 1707. found 1706.

Example 210

$C_{15}$-Amphomycin-9-((S)-(+)-5-Oxo-2-Tetrahydrofurancarbonyl)

Compound $C_{15}$-amphomycin (25 mg, 0.019 mmol) of Example 2 and (S)-(+)-5-oxo-2-tetrahydrofurancarboxylic acid used in the method described in Example 201 provided the title compound, which was purified by HPLC and lyophilized (6 mg, 22% yield): 80% pure, MS (MALDI) calcd for $C_{65}H_{101}N_{13}O_{23}$ (M) 1433. found 1433.

Example 211

$C_{15}$-Amphomycin-9-Phenylpropynyl

Compound $C_{15}$-amphomycin (27 mg, 0.020 mmol) of Example 2 and Phenylpropynoic acid used in the method described in Example 201 provided the title compound, which was purified by HPLC and lyophilized (3 mg, 10% yield): 70% pure, MS (MALDI) calcd for $C_{69}H_{101}N_{13}O_{21}$ (M) 1449. found 1448.

Example 212

$C_{15}$-Amphomycin-9-(Carbamoyl-β-Ala)

Compound $C_{15}$-amphomycin (30 mg, 0.023 mmol) of Example 2 and N-carbamoyl β-alanine used in the method described in Example 201 provided the title compound, which was purified by HPLC and lyophilized (14 mg, 43% yield): 99% pure, MS (MALDI) calcd for $C_{64}H_{103}N_{15}O_{22}$ (M) 1435. found 1434.

Example 213

$C_{15}$-Amphomycin-9-Acryl

Compound $C_{15}$-amphomycin (30 mg, 0.023 mmol) of Example 2 and acrylic acid used in the method described in Example 201 provided the title compound, which was purified by HPLC and lyophilized (3 mg, 10% yield): 95% pure, MS (MALDI) calcd for $C_{63}H_{99}N_{13}O_{21}$ (M) 1375. found 1374.

Example 214

$C_{15}$-Amphomycin-9-(1-Napthylacetyl)

Compound $C_{15}$-amphomycin (30 mg, 0.023 mmol) of Example 2 and 1-napthylacetic acid used in the method described in Example 201 provided the title compound, which was purified by HPLC and lyophilized (9 mg, 27% yield): 93% pure, MS (MALDI) calcd for $C_{72}H_{105}N_{13}O_{21}$ (M) 1489. found 1488.

Example 215

$C_{15}$-Amphomycin-9-(4-Phenoxybenzoyl)

Compound $C_{15}$-amphomycin (30 mg, 0.023 mmol) of Example 2 and 4-phenoxybenzoic acid used in the method described in Example 201 provided the title compound, which was purified by HPLC and lyophilized (5 mg, 15% yield): 87% pure, MS (MALDI) calcd for $C_{73}H_{105}N_{13}O_{22}$ (M) 1517. found 1516.

Example 216

$C_{15}$-Amphomycin-9-(2-Napthylacetyl)

Compound $C_{15}$-amphomycin (30 mg, 0.023 mmol) of Example 2 and 2-napthylacetic acid used in the method described in Example 201 provided the title compound, which was purified by HPLC and lyophilized (5 mg, 15% yield): 84% pure, MS (MALDI) calcd for $C_{72}H_{105}N_{13}O_{21}$ (M) 1489. found 1488.

Example 217

$C_{15}$-Amphomycin-9-(2-Furyl)

Compound $C_{15}$-amphomycin (30 mg, 0.023 mmol) of Example 2 and furan-2-carboxylic acid used in the method described in Example 201 provided the title compound, which was purified by HPLC and lyophilized (10 mg, 31% yield): 80% pure, MS (MALDI) calcd for $C_{65}H_{99}N_{13}O_{22}$ (M) 1415. found 1414.

Example 218

$C_{15}$-Amphomycin-9-Crotonyl

Compound $C_{15}$-amphomycin (30 mg, 0.023 mmol) of Example 2 and but-2-enoic acid used in the method described in Example 201 provided the title compound, which was purified by HPLC and lyophilized (7 mg, 22% yield): 91% pure, MS (MALDI) calcd for $C_{64}H_{101}N_{13}O_{21}$ (M) 1389. found 1388.

Example 219

$C_{15}$-Amphomycin-9-(3,4-(Methylenedioxy)Phenylacetyl)

Compound $C_{15}$-amphomycin (30 mg, 0.023 mmol) of Example 2 and 3,4-(methylenedioxy)phenyl acetic acid used in the method described in Example 201 provided the title compound, which was purified by HPLC and lyophilized (11 mg, 33% yield): 90% pure, MS (MALDI) calcd for $C_{69}H_{103}N_{13}O_{23}$ (M) 1483. found 1482.

Example 220

$C_{15}$-Amphomycin-9-$C_{10}$

Compound $C_{15}$-amphomycin (24 mg, 0.018 mmol) of Example 2 and decanoic acid used in the method described in (continues: which was purified by HPLC and lyophilized (8 mg, 27% yield): 91% pure, MS (MALDI) calcd for $C_{69}H_{109}N_{13}O_{21}$ (M) 1457. found 1456.)

Example 201 provided the title compound, which was purified by HPLC and lyophilized (10 mg, 37% yield): 80% pure, MS (MALDI) calcd for $C_{70}H_{115}N_{13}O_{21}$ (M) 1475. found 1474.

Example 221

$C_{15}$-Amphomycin-9-(γ-Oxo-5-Acenapthenebutanyl)

Compound $C_{15}$-amphomycin (24 mg, 0.018 mmol) of Example 2 and γ-oxo-5-acenapthenebutanic acid used in the method described in Example 201 provided the title compound, which was purified by HPLC and lyophilized (7 mg, 25% yield): 77% pure, MS (MALDI) calcd for $C_{76}H_{109}N_{13}O_{22}$ (M) 1557. found 1556.

Example 222

$C_{15}$-Amphomycin-9-Hydrocinnamyl

Compound $C_{15}$-amphomycin (24 mg, 0.018 mmol) of Example 2 and hydrocinnamic acid used in the method described in Example 201 provided the title compound, which was purified by HPLC and lyophilized (6 mg, 23% yield): 76% pure, MS (MALDI) calcd for $C_{69}H_{105}N_{13}O_{21}$ (M) 1453. found 1452.

Example 223

$C_{15}$-Amphomycin-9-(α-Ketobutyl)

Compound $C_{15}$-amphomycin (23 mg, 0.018 mmol) of Example 2 and α-keto-butyric acid used in the method described in Example 201 provided the title compound, which was purified by HPLC and lyophilized (9 mg, 37% yield): 87% pure, MS (MALDI) calcd for $C_{64}H_{101}N_{13}O_{22}$ (M) 1405. found 1404.

Example 224

$C_{15}$-Amphomycin-9-Geranyl

Compound $C_{15}$-amphomycin (23 mg, 0.018 mmol) of Example 2 and 3,7-dimethyl-octa-2,6-dienoic acid used in the method described in Example 201 provided the title compound, which was purified by HPLC and lyophilized (3 mg, 12% yield): 88% pure, MS (MALDI) calcd for $C_{70}H_{111}N_{13}O_{21}$ (M) 1471. found 1470.

Example 225

$C_{15}$-Amphomycin-9-(O-Anisyl)

Compound $C_{15}$-amphomycin (24 mg, 0.018 mmol) of Example 2 and 2-methoxybenzoic acid used in the method described in Example 201 provided the title compound, which was purified by HPLC and lyophilized (9 mg, 34% yield): 85% pure, MS (MALDI) calcd for $C_{68}H_{103}N_{13}O_{22}$ (M) 1455. found 1454.

Example 226

$C_{15}$-Amphomycin-9-Phenylacetyl

Compound $C_{15}$-amphomycin (25 mg, 0.019 mmol) of Example 2 and phenylacetic acid used in the method described in Example 201 provided the title compound, which was purified by HPLC and lyophilized (6 mg, 22% yield): 94% pure, MS (MALDI) calcd for $C_{68}H_{103}N_{13}O_{21}$ (M) 1439. found 1438.

Example 227

$C_{15}$-Amphomycin-9-(2-Butynyl)

Compound $C_{15}$-amphomycin (23 mg, 0.018 mmol) of Example 2 and but-2-ynoic acid used in the method described in Example 201 provided the title compound, which was purified by HPLC and lyophilized (7 mg, 29% yield): 84% pure, MS (MALDI) calcd for $C_{64}H_{99}N_{13}O_{21}$ (M) 1387. found 1386.

Example 228

$C_{15}$-Amphomycin-9-(3,5-BIS(CF$_3$)Phenylacetyl)

Compound $C_{15}$-amphomycin (23 mg, 0.018 mmol) of Example 2 and 3,5-bis(trifluoromethyl)phenyl acetic acid used in the method described in Example 201 provided the title compound, which was purified by HPLC and lyophilized (8 mg, 26% yield): 85% pure, MS (MALDI) calcd for $C_{70}H_{101}F_6N_{13}O_{21}$ (M) 1575. found 1574.

Example 229

$C_{15}$-Amphomycin-9-(3,4-Methylenedioxy-Cinnamyl)

Compound $C_{15}$-amphomycin (23 mg, 0.018 mmol) of Example 2 and 3,4-methylenedioxy-cinnamic acid used in the method described in Example 201 provided the title compound, which was purified by HPLC and lyophilized (5 mg, 18% yield): 81% pure, MS (MALDI) calcd for $C_{70}H_{103}N_{13}O_{23}$ (M) 1495. found 1494.

Example 230

$C_{15}$-Amphomycin-9-(Trans-Cinnamyl)

Compound $C_{15}$-amphomycin (24 mg, 0.019 mmol) of Example 2 and trans-cinnamic acid used in the method described in Example 201 provided the title compound, which was purified by HPLC and lyophilized (6 mg, 23% yield): 84% pure, MS (MALDI) calcd for $C_{69}H_{103}N_{13}O_{21}$ (M) 1451. found 1450.

Example 231

$C_{15}$-Amphomycin-9-Acetoxyacetyl

Compound $C_{15}$-amphomycin (23 mg, 0.018 mmol) of Example 2 and acetoxyacetic acid used in the method described in Example 201 provided the title compound, which was purified by HPLC and lyophilized (1 mg, 4% yield): 85% pure, MS (MALDI) calcd for $C_{64}H_{101}N_{13}O_{23}$ (M) 1421. found 1420.

Example 232

$C_{15}$-Amphomycin-9-(1-Adamantanylcarbonyl)

Compound $C_{15}$-amphomycin (30 mg, 0.023 mmol) of Example 2 and 1-adamantanylcarboxylic acid used in the method described in Example 201 provided the title compound, which was purified by HPLC and lyophilized (5 mg, 15% yield): 93% pure, MS (MALDI) calcd for $C_{71}H_{111}N_{13}O_{21}$ (M) 1483. found 1482.

Example 233

$C_{15}$-Amphomycin-9-(4-Cotininecarbonyl)

Compound $C_{15}$-amphomycin (30 mg, 0.023 mmol) of Example 2 and 4-cotininecarboxylic acid used in the method described in Example 201 provided the title compound, which was purified by HPLC and lyophilized (18 mg, 52% yield): 94% pure, MS (MALDI) calcd for $C_{71}H_{107}N_{15}O_{22}$ (M) 1523. found 1522.

Example 234

$C_{15}$-Amphomycin-9-(4-Fluorobenzoyl)

Compound $C_{15}$-amphomycin (25 mg, 0.019 mmol) of Example 2 and 4-fluorobenzoic acid used in the method described in Example 201 provided the title compound, which was purified by HPLC and lyophilized (7 mg, 25% yield): 82% pure, MS (MALDI) calcd for $C_{68}H_{102}FN_{13}O_{21}$ (M) 1457. found 1456.

Example 235

$C_{15}$-Amphomycin-9-(S-Acetylthioglycolyl)

Compound $C_{15}$-amphomycin (25 mg, 0.019 mmol) of Example 2 and S-acetylthioglycolic acid used in the method described in Example 201 provided the title compound, which was purified by HPLC and lyophilized (2 mg, 7% yield): 95% pure, MS (MALDI) calcd for $C_{64}H_{101}N_{13}O_{22}S$ (M) 1437. found 1436.

Example 236

$C_{15}$-Amphomycin-9-(4-Butoxybenzoyl)

Compound $C_{15}$-amphomycin (27 mg, 0.020 mmol) of Example 2 and 4-butoxybenzoic acid used in the method described in Example 201 provided the title compound, which was purified by HPLC and lyophilized (4 mg, 13% yield): 78% pure, MS (MALDI) calcd for $C_{71}H_{109}N_{13}O_{22}$ (M) 1497. found 1496.

Example 237

$C_{15}$-Amphomycin-9-(6-Oxoheptanoyl)

Compound $C_{15}$-amphomycin (27 mg, 0.020 mmol) of Example 2 and 6-oxoheptanoic acid used in the method described in Example 201 provided the title compound, which was purified by HPLC and lyophilized (9 mg, 30% yield): 98% pure, MS (MALDI) calcd for $C_{67}H_{107}N_{13}O_{22}$ (M) 1447. found 1446.

Example 238

$C_{15}$-Amphomycin-9-Oleate

Compound $C_{15}$-amphomycin (27 mg, 0.020 mmol) of Example 2 and octadec-9-enoic acid used in the method described in Example 201 provided the title compound, which was purified by HPLC and lyophilized (12 mg, 37% yield): 94% pure, MS (MALDI) calcd for $C_{78}H_{129}N_{13}O_{21}$ (M) 1585. found 1584.

Example 239

$C_{15}$-Amphomycin-9-(4-Pentylbenzoyl)

Compound $C_{15}$-amphomycin (24 mg, 0.019 mmol) of Example 2 and 4-pentylbenzoic acid used in the method described in Example 201 provided the title compound, which was purified by HPLC and lyophilized (3 mg, 11% yield): 74% pure, MS (MALDI) calcd for $C_{72}H_{111}N_{13}O_{21}$ (M) 1495. found 1494.

Example 240

$C_{15}$-Amphomycin-9-(3-Phenoxybenzoyl)

Compound $C_{15}$-amphomycin (25 mg, 0.019 mmol) of Example 2 and 3-phenoxybenzoic acid used in the method described in Example 201 provided the title compound, which was purified by HPLC and lyophilized (5 mg, 17% yield): 87% pure, MS (MALDI) calcd for $C_{73}H_{105}N_{13}O_{22}$ (M) 1517. found 1516.

Example 241

$C_{15}$-Amphomycin-9-(C(=O)—(Ch$_2$)$_2$-Piperidine)

Compound $C_{15}$-amphomycin (25 mg, 0.019 mmol) of Example 2 and 3-piperidin-1-yl-propionic acid used in the method described in Example 201 provided the title compound, which was purified by HPLC and lyophilized (8.5 mg, 31% yield): 84% pure, MS (MALDI) calcd for $C_{68}H_{110}N_{14}O_{21}$ (M) 1460. found 1459.

Example 242

$C_{15}$-Amphomycin-9-(N,N'-Dimethyl-GABA)

Compound $C_{15}$-amphomycin (25 mg, 0.019 mmol) of Example 2 and N,N'-dimethyl-γ-aminobutanoic acid used in the method described in Example 201 provided the title compound, which was purified by HPLC and lyophilized (6.2 mg, 23% yield): 98% pure, MS (MALDI) calcd for $C_{66}H_{108}N_{14}O_{21}$ (M) 1434. found 1433.

Example 243

$C_{15}$-Amphomycin-9-(N-Ethyl-Gly)

Compound $C_{15}$-amphomycin (42 mg, 0.032 mmol) of Example 2 and N-ethyl glycine used in the method described in Example 201 provided the title compound, which was purified by HPLC and lyophilized (5.2 mg, 12% yield): 80% pure, MS (MALDI) calcd for $C_{64}H_{104}N_{14}O_{21}$ (M) 1406. found 1405.

Example 244

$C_{15}$-Amphomycin-9-Sar-(N,N-Dimethyl-Gly)

Compound $C_{15}$-amphomycin (30 mg, 0.023 mmol) of Example 2 and N,N-dimethyl glycine used in the method described in Example 201 provided the title compound, which was purified by HPLC and lyophilized (9 mg, 32% yield): 99% pure, MS (MALDI) calcd for $C_{67}H_{109}N_{15}O_{22}$ (M) 1477. found 1476.

Example 245

$C_{15}$-Amphomycin-9-(N-Benzyl-Gly)

Compound $C_{15}$-amphomycin (55 mg, 0.042 mmol) of Example 2 and N-benzylglycine used in the method described in Example 201 provided the title compound, which was purified by HPLC and lyophilized (5 mg, 8% yield): 78% pure, MS (MALDI) calcd for $C_{69}H_{106}N_{14}O_{21}$ (M) 1468. found 1467.

Example 246

$C_{15}$-Amphomycin-9-(N,N-Diethyl-β-Ala)

Compound $C_{15}$-amphomycin (26 mg, 0.020 mmol) of Example 2 and N,N-diethyl β-alanine used in the method described in Example 201 provided the title compound, which was purified by HPLC and lyophilized (19.2 mg, 67% yield): 91% pure, MS (MALDI) calcd for $C_{67}H_{110}N_{14}O_{21}$ (M) 1448. found 1447.

Example 247

$C_{10}$-Amphomycin-9-$C_{10}$

Compound $C_{10}$-amphomycin (30 mg, 0.024 mmol) of Example 6 and decanoic acid used in the method described in Example 201 provided the title compound, which was purified by HPLC and lyophilized (7 mg, 22% yield): 79% pure, MS (MALDI) calcd for $C_{65}H_{105}N_{13}O_{21}$ (M) 1405. found 1404.

Example 248

$C_{15}$-Amphomycin-9-(N-Methyl-GABA)

Compound $C_{15}$-amphomycin (23 mg, 0.017 mmol) of Example 2 and N-tert-butoxycarbonyl-4-methyl-γ-aminobutanoic acid used in the method described in Example 201 provided the title compound, which was purified by HPLC and lyophilized (5.2 mg, 21% yield): 88% pure, MS (MALDI) calcd for $C_{65}H_{106}N_{14}O_{21}$ (M) 1420. found 1420.

Example 249

$CH_3$—$(CH_2)_{15}$—NH—C(=O)-Amphomycin

Amphomycin-9-Fmoc (50 mg, 0.038 mmol, 79% pure) was dissolved in 5 mL DMF at room temperature under an inert atmosphere. 1-Isocyanato-pentadecane (8.8 mg, 0.06 mmol) and DIEA (26 μL, 0.15 mmol) were added to the reaction and the mixture was stirred overnight. Piperidine (1 mL, 20% v/v) was added to the reaction and the mixture was stirred for an additional 3 hours. All solids were filtered, the insolubles washed with additional DMF (approximately 2 mL), and then the filtrate was concentrated in vacuo until dry. Purification by HPLC (gradient, 25% acetonitrile in water with 0.1% trifluoroacetic acid to 95% acetonitrile over 30 minutes) and lyophilization provided the title compound (21 mg, 40% yield): 94% pure, MS (MALDI) calcd for $C_{62}H_{102}N_{14}O_{20}$ (M) 1364. found 1363.

Example 250

$C_{15}$-Amphomycin-9-pGlu

Compound $C_{15}$-amphomycin of Example 2 and pyroglutamic acid used in the method described in Example 201 provided the title compound, which was purified by HPLC and lyophilized (13.1 mg, 30% yield): 86% pure, MS (MALDI) calcd for $C_{65}H_{102}N_{14}O_{22}$ (M) 1432. found 1434.

Example 251

$CH_3$—$(CH_2)_{11}$—NH—C(=O)-Amphomycin

Amphomycin-9-Fmoc (30 mg, 0.022 mmol) and 1-isocyanato-hexadecane used in the method described in Example 249 provided the title compound, which was purified by HPLC and lyophilized (2 mg, 7% yield): 77% pure, MS (MALDI) calcd for $C_{58}H_{94}N_{14}O_{20}$ (M) 1307. found 1306.

Example 252

$CH_3$—$(CH_2)_7$—NH—C(=O)-Amphomycin

Amphomycin-9-Fmoc (50 mg, 0.011 mmol) and octanyl isocyanate used in the method described in Example 249 provided the title compound, which was purified by HPLC and lyophilized (8 mg, 17% yield): 85% pure, MS (MALDI) calcd for $C_{54}H_{86}N_{14}O_{20}$ (M) 1252. found 1251.

Example 253

$CH_3$—$(CH_2)_{13}$—NH—C(=O)-Amphomycin

Amphomycin-9-Fmoc (51 mg, 0.011 mmol) and tetradecane isocyanate used in the method described in Example 249 provided the title compound, which was purified by HPLC and lyophilized (23 mg, 45% yield): 77% pure, MS (MALDI) calcd for $C_{60}H_{98}N_{14}O_{20}$ (M) 1336. found 1336.

Example 254

$CH_3$—$(CH_2)_{11}$—NH—C(=O)-Gly-Amphomycin

Amphomycin-9-Fmoc (15.8 mg) and Dodecanamidylglycine succinimid-1-yl ester (12.8 mg, as prepared in Example 275 and using a succinimidyl ester as prepared in Example 1) used in the method described in Example 3 provided the title compound (13.2 mg): 93% pure, MS (FAB) calcd for $C_{60}H_{97}N_{15}O_{21}$ (M) 1365. found 1365.

Example 255

$C_{15}$-Amphomycin-C(=O)—NH—N-Butyl

Compound $C_{15}$-amphomycin (30 mg, 0.023 mmol) of Example 2 was suspended in 2 mL DMF under an inert atmosphere and then charged with about 4 μL 1-isocyanatobutane (0.035 mmol). The mixture was stirred overnight and then concentrated in vacuo to provide the title compound, which was purified by HPLC (gradient, 25% acetonitrile in water with 0.1% trifluoroacetic acid to 95% acetonitrile over 30 minutes) and lyophilized (2 mg, 6% yield): 87% pure, MS (MALDI) calcd for $C_{65}H_{106}N_{14}O_{21}$ (M) 1420. found 1419.

Example 256

$C_{15}$-Amphomycin-C(=O)—NH-Cyclohexyl

Compound $C_{15}$-amphomycin (30 mg, 0.023 mmol) of Example 2 and 1-isocyanato-cyclohexane used in the method described in Example 255 provided the title compound, which was purified by HPLC and lyophilized (3 mg, 9% yield): 70% pure, MS (MALDI) calcd for $C_{67}H_{108}N_{14}O_{21}$ (M) 1446. found 1445.

Example 257

$C_{15}$-Amphomycin-C(=O)—NH-Furfuryl

Compound $C_{15}$-amphomycin (30 mg, 0.023 mmol) of Example 2 and 2-isocyanatomethyl-furan used in the method described in Example 255 provided the title compound, which was purified by HPLC and lyophilized (3 mg, 9% yield): 73% pure, MS (MALDI) calcd for $C_{66}H_{102}N_{14}O_{22}$ (M) 1444. found 1443.

Example 258

$C_{15}$-Amphomycin-C(=O)—NH-2-Fluorobenzyl

Compound $C_{15}$-amphomycin (30 mg, 0.023 mmol) of Example 2 and 2-fluorobenzyl isocyanate used in the method described in Example 255 provided the title compound, which was purified by HPLC and lyophilized (2 mg, 6% yield): 93% pure, MS (MALDI) calcd for $C_{68}H_{103}FN_{14}O_{21}$ (M) 1472. found 1471.

Example 259

$C_{15}$-Amphomycin-C(=O)—NH-M-CF$_3$-Phenyl

Compound $C_{15}$-amphomycin (30 mg, 0.023 mmol) of Example 2 and meta-(trifluoromethyl)phenyl isocyanate used in the method described in Example 255 provided the title compound, which was purified by HPLC and lyophilized (5 mg, 15% yield): 95% pure, MS (MALDI) calcd for $C_{68}H_{101}F_3N_{14}O_{21}$ (M) 1508. found 1507.

Example 260

$C_{15}$-Amphomycin-C(=O)—NH—P—CF$_3$-Phenyl

Compound $C_{15}$-amphomycin (30 mg, 0.023 mmol) of Example 2 and para-(trifluoromethyl)phenyl isocyanate used in the method described in Example 255 provided the title compound, which was purified by HPLC and lyophilized (4 mg, 12% yield): 86% pure, MS (MALDI) calcd for $C_{68}H_{101}F_3N_{14}O_{21}$ (M) 1508. found 1507.

Example 261

$C_{15}$-Amphomycin-C(=O)—NH-3-Fluorophenyl

Compound $C_{15}$-amphomycin (30 mg, 0.023 mmol) of Example 2 and 3-fluorophenyl isocyanate used in the method described in Example 255 provided the title compound, which was purified by HPLC and lyophilized (4 mg, 12% yield): 86% pure, MS (MALDI) calcd for $C_{67}H_{101}FN_{14}O_{21}$ (M) 1458. found 1457.

Example 262

$C_{15}$-Amphomycin-(D-Ser)

Compound $C_{15}$-amphomycin (27 mg, 0.020 mmol) of Example 2 was suspended in 1 mL DMF and then charged with 300 μL 1M sodium bicarbonate (in water, 0.20 mmol). The reaction mixture was cooled in an ice bath. A predissolved solution of succinimide activated (D)-3-O-tert-butyl-2-(9H-fluoren-9-yl-methoxycarbonyl)serine (1.5 equiv, prepared as described for compound pentadecanoic acid succinimid-1-yl ester of Example 1) in 0.5 mL DMF was slowly added to the reaction mixture while still on ice. Then the reaction was stirred for approximately 12 hours at room temperature. Piperidine (0.5 mL, 20% v/v) was added, the reaction was stirred for 1 hour, and then concentrated in vacuo. The crude product was mixed with 2 mL of cocktail (46:46:2:2 trifluoroacetic acid:DCM:water:triisopropylsilane) for another hour, and then concentrated in vacuo to provide the title compound, which was purified by HPLC (gradient, 25% acetonitrile in water with 0.1% trifluoroacetic acid to 95% acetonitrile over 30 minutes) and lyophilized (8 mg, 28% yield): 81% pure, MS (MALDI) calcd for $C_{63}H_{102}N_{14}O_{22}$ (M) 1408. found 1407.

Example 263

$C_{15}$-Amphomycin-(D-Tyr)

Compound $C_{15}$-amphomycin (27 mg, 0.020 mmol) of Example 2 and (D)-O-tert-Butyl-N-(9H-fluoren-9-yl-methoxycarbonyl)tyrosine used in the method described in Example 262 provided the title compound, which was purified by HPLC and lyophilized (12 mg, 39% yield): 77% pure, MS (MALDI) calcd for $C_{69}H_{106}N_{14}O_{22}$ (M) 1484. found 1486.

Example 264

$C_{15}$-Amphomycin-(D-Trp)

Compound $C_{15}$-amphomycin (27 mg, 0.020 mmol) of Example 2 and (D)-3-[2-Carboxy-2-(9H-fluoren-9-yl-methoxycarbonylamino)-ethyl]-indole-1-carboxylic acid tert-butyl ester used in the method described in Example 262 provided the title compound, which was purified by HPLC and lyophilized (11 mg, 36% yield): 80% pure, MS (MALDI) calcd for $C_{71}H_{107}N_{15}O_{21}$ (M) 1507. found 1506.

Example 265

$C_{13}$-Amphomycin-9-Glu

Compound $C_{13}$-amphomycin (25 mg, 0.019 mmol) of Example 9 was suspended in 1 mL DMF and then charged with 300 μL 1M sodium bicarbonate (in water, 0.20 mmol). The reaction mixture was cooled in an ice bath. A predissolved solution of succinimide activated (L)-2-tert-butoxycarbonylamino-pentanedioic acid 5-tert-butyl ester (1.5 equiv, prepared as described for compound pentadecanoic acid succininiid-1-yl ester of Example 1) in 0.5 mL DMF was slowly added to the reaction mixture, and upon removal from the ice bath, the reaction was allowed to stir for approximately 12 hours at room temperature and then concentrated in vacuo.

The crude product was mixed with 2 mL of cocktail (46:46:2:2 trifluoroacetic acid:DCM:water:triisopropylsilane) for another hour and then concentrated in vacuo to provide the title compound. The title compound was purified by HPLC (gradient, 25% acetonitrile in water with 0.1% trifluoroacetic acid to 95% acetonitrile over 30 minutes) and lyophilized (8 mg, 30% yield): 86% pure, MS (MALDI) calcd for $C_{63}H_{100}N_{14}O_{23}$ (M) 1422. found 1421.

Example 266

$C_{15}$-Amphomycin-9-(4-Hydroxybenzyl)

Compound $C_{15}$-amphomycin (38 mg, 0.029 mmol) of Example 2 was suspended in 2.5 mL DMF and then charged with 70 μL glacial acetic acid (pH ~4-5). 4-hydroxybenzaldehyde (37 mg, 0.303 mmol), predissolved in 1 mL DMF, was added to the reaction and the mixture was stirred for approximately 24 hours. Two equal portions of sodium cyanoborohydride (40 mg total, 0.637 mmol) were added over an hour period and then followed by 5 hours more of additional stirring before the solvent was removed in vacuo to provide the title compound. The title compound was purified by HPLC (gradient, 25% acetonitrile in water with 0.1% trifluoroacetic acid to 95% acetonitrile over 30 minutes) and lyophilized (14 mg, 34% yield): 99% pure, MS (MALDI) calcd for $C_{67}H_{101}N_{13}O_{22}$ (M) 1441. found 1440.

Example 267

$C_{15}$-Amphomycin-9-N,N-di-(p-Hydroxybenzyl)

The title compound was obtained using the method described in Example 20, which compound is a secondary product (dialkyl) of that reaction. The title compound was purified by HPLC and lyophilized (4 mg, 9% yield): 93% pure, MS (MALDI) calcd for $C_{74}H_{109}N_{13}O_{22}$ (M) 1533. found 1533.

Example 268

$C_{15}$-Amphomycin-9-(N,N-Dimethylglycine)

Compound $C_{15}$-amphomycin-9-Sar (15 mg, 0.011 mmol) of Example 24 and formaldehyde used in the method described in Example 20 provided the title compound, which was purified by HPLC and lyophilized (9.5 mg, 59% yield): 98% pure, MS (MALDI) calcd for $C_{64}H_{104}N_{14}O_{21}$ (M) 1406. found 1405.

Example 269

$CH_3$—$(CH_2)_9$—$SO_2$-Gly-Amphomycin

In a first step, amphomycin-9-Fmoc (30 mg, 0.022 mmol) was coupled with N-tert-butoxycarbonyl glycine as described in the method of Example 3. The resulting intermediate was purified by HPLC and lyophilized. In a second step, this purified intermediate was dissolved in 10 mL DMF under an inert atmosphere. Decanesulfonyl chloride (13.7 mg, 0.044 mmol) was added and the mixture was allowed to stir overnight to provide the title compound, which was purified by HPLC (gradient, 25% acetonitrile in water with 0.1% trifluoroacetic acid to 95% acetonitrile over 30 minutes) and lyophilized (5 mg): 89% pure, MS (MALDI) calcd for $C_{57}H_{92}N_{14}O_{22}S$ (M) 1357. found 1357.

Example 270

$CH_3$—$(CH_2)_{15}$—$SO_2$-Phe-Amphomycin

In a first step, amphomycin-9-Fmoc (30 mg, 0.022 mmol) was coupled with N-tert-butoxycarbonyl phenylalanine. The resulting intermediate was purified by HPLC and lyophilized. In a second step, this purified intermediate was coupled with pentadecanesulfonyl chloride as described in the method of Example 99 to provide the title compound, which was purified by HPLC and lyophilized (7 mg, 21% yield): 91% pure, MS (MALDI) calcd for $C_{70}H_{110}N_{14}O_{22}S$ (M) 1532. found 1532.

Example 271

Preparation of Amphomycin-9-(N-Fmoc-Gly)

Amphomycin-9-(N-Fmoc-Glycyl) complex (1.25 g, prepared by fermentation as described above) was dissolved in ammonium phosphate buffer (0.2M, pH 7.2) and combined with 1250 mL of solubilized deacylase enzyme and placed in an incubator at 28° C. for nine days. The product was combined with 438 g ammonium sulphate, adjusted to pH 3.5 with 1N HCl, and then filtered to remove the precipitated product. The precipitate was combined with about 170 mL 1-butanol and 170 mL water, the aqueous phase discarded, and the 1-butanol phase rinsed with water. The 1-butanol phase was mixed then with water and adjusted to ph 5.0. The extraction of the 1-butanol phase was repeated, and the combined aqueous phases were evaporated in vacuo to remove residual butanol. The remaining aqueous layer was freeze-dried to obtain 500 mg of white powder, crude product. The crude amphomycin-9-(N-Fmoc-Glycine) (400 mg) was dissolved in 10 mL of a pH 6.6 sodium phosphate buffer and filtered through a 0.45 micron PVDF membrane. The filtrate was injected onto a Delta-Pak C18 radial pak column (2.5×21 cm, Waters Corp.). The product was eluted using acetonitrile-modified, sodium phosphate-buffered eluents (22-28% acetonitrile over 120 min at 5 mL/min at room temperature. Product-containing fractions (as determined by analytical HPLC) were pooled and then the acetonitrile was evaporated in vacuo. The evaporated sample was desalted by adsorption onto 1.0 g of EnviChrom-P resin (Supelco); the resin was rinsed with 8 mL of distilled water and the product was stripped from the resin using 20 mL 60% acetonitrile. Acetonitrile was evaporated in vacuo and the remaining product solution was freeze-dried to produce 107 mg of the title compound (95% purity by HPLC (UV area % at 215 nm).

Example 272

Preparation of Amphomycin-9-(N-Fmoc-Sar)

Amphomycin-9-(N-Fmoc-sarcosyl) complex (2 g) was converted after a three day incubation as described in Example 271 to provide the title compound (911 mg).

Example 273

Preparation of Amphomycin-9-(N-Fmoc-β-Ala)

Amphomycin-9-(N-Fmoc-β-alanine) complex (2 g) was converted after a three day incubation as described in Example 271 to provide the title compound (1267 mg).

Example 274

Preparation of p-(N-Dodecanoylamino)-Benzoic Acid

4-Aminobenzoic acid (0.94 g, 6.85 mmol) was dissolved in 5 mL of pyridine and dodecanoyl chloride (1.58 mL, 6.85 mmol) was added. The mixture was stirred for 4 h at room temperature. The product was precipitated by dilution with water (50 mL), filtered, and dried to provide 1.96 g of the title compound.

Example 275

Preparation of N-Dodecamidoglycine

Glycine (0.40 g, 5.25 mmol) and 0.91 mL of diisopropylethylamine (5.25 mmol) were dissolved in 4 mL DMF and 6 mL water. Dodecylisocyanate (0.72 mL, 3.0 mmol) in 7 mL tetrahydrofuran was added and the mixture was stirred for 1 h at room temperature. Water (40 mL) was added and the resulting mixture was washed with ethyl acetate twice. The aqueous layer was acidified with 6N HCl, the resulting precipitate was filtered, and then dried to provide 575 mg of the title compound.

Example 276

Preparation of p-Dodecyloxybenzoylglycine

To a solution of 4-dodecyloxybenzoic acid (0.47 g, 1.53 mmol) and 0.27 mL of diisopropylethylamine (1.55 mmol) in 4 mL tetrahydrofuran was added fluoro-N,N,N,N-tetramethylforamidinium hexafluorophosphate (0.41 g, 1.54 mmol) and the reaction was stirred for 15 min at room temperature. To this mixture was added a solution of glycine ethyl ester hydrochloride (0.45 g, 3.2 mmol) and DIEA (0.53 mL, 3.04 mmol) in 5 mL of tetrahydrofuran and 5 mL of methylene chloride. The mixture was stirred for several hours at room temperature then diluted with 50 mL 1N hydrochloric acid and extracted with ethyl acetate. The organic layer was washed with water, saturated sodium bicarbonate, brine, then dried over magnesium sulfate. Evaporation in vacuo followed by trituration with hexane afforded the product (0.44 g). The product was dissolved in 10 mL methanol and 5 mL tetrahydrofuran, treated with 3 mL 1N sodium hydroxide, and then stirred for 1 h at room temperature. After several minutes, a thick precipitate was formed. The mixture was diluted with water (20 mL) and then warmed to 40° C. to make homogenous. The mixture was acidified with 5 mL 1N HCl, and the precipitate was filtered and dried, yielding 0.34 g of the title compound.

Example 277

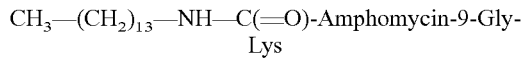
$CH_3$—$(CH_2)_{13}$—NH—C(=O)-Amphomycin-9-Gly-Lys

Compound $CH_3$—$(CH_2)_{13}$—NH—C(=O)-amphomycin (50 mg) of Example 253 and succinimide activated N-(2-N-tert-butoxycarbonyl-6-(9H-fluoren-9-yl-methoxycarbonyl) lysinyl)glycine (58 mg, prepared as described in Example 1) used in the method described in Example 3 provided the title compound (16 mg, 28% yield): 80% pure, MS (MALDI) calcd for $C_{68}H_{113}N_{17}O_{22}$ (M) 1521. found 1520.

Example 278

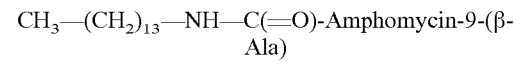
$CH_3$—$(CH_2)_{13}$—NH—C(=O)-Amphomycin-9-(β-Ala)

Compound $CH_3$—$(CH_2)_{13}$—NH—C(=O)-amphomycin (30 mg) of Example 253 and N-(tert-butoxycarbonyl)β-alanine used in the method described in Example 3 provided the title compound (8 mg, 25% yield): 70% pure, MS (MALDI) calcd for $C_{63}H_{103}N_{15}O_{21}$ (M) 1407. found 1406.

Example 279

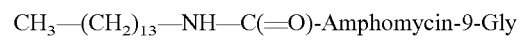
$CH_3$—$(CH_2)_{13}$—NH—C(=O)-Amphomycin-9-Gly

Compound $CH_3$—$(CH_2)_{13}$—NH—C(=O)-amphomycin (40 mg) of Example 253 and N-(tert-butoxycarbonyl)glycine used in the method described in Example 3 provided the title compound (8 mg, 31% yield): 74% pure, MS (MALDI) calcd for $C_{62}H_{101}N_{15}O_{21}$ (M) 1393. found 1392.

Example 280

$C_{12}$-PABA-Amphomycin-9-(β-Ala)

Compound $C_{12}$-p-aminobenzoyl-amphomycin (80 mg) of Example 85 and N-(tert-butoxycarbonyl)β-alanine used in the method described in Example 3 provided the title compound (4 mg, 4% yield): 73% pure, MS (MALDI) calcd for $C_{67}H_{101}N_{15}O_{22}$ (M) 1469. found 1468.

Example 281

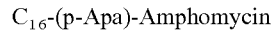
$C_{16}$-(p-Apa)-Amphomycin

In a first step, amphomycin-9-Fmoc (40 mg) was coupled with 4-tert-butoxycarbonyl-aminophenylacetic acid as described in the method of Example 3. The resulting intermediate was purified by HPLC and lyophilized. In a second step, this purified intermediate and hexadecanoic acid used in the method described in Example 2 provided the title compound, which was purified by HPLC and lyophilized (7.4 mg, 17% yield): 83% pure, MS (MALDI) calcd for $C_{69}H_{106}N_{14}O_{21}$ (M) 1468. found 1467.

Example 282

$C_8$-PABA-Amphomycin

In a first step, amphomycin-9-Fmoc (45 mg) was coupled with para-N-tert-butoxycarbonyl-aminobenzoic acid as described in the method of Example 3. In a second step, this intermediate from the first step was mixed with octanoyl chloride as described in the method of Example 3 to provide the title compound (13.3 mg, 28% yield): 70% pure, MS (MALDI) calcd for $C_{60}H_{88}N_{14}O_{21}$ (M) 1341. found 1340.

Example 283

$C_{10}$-PABA-Amphomycin

In a first step, amphomycin-9-Fmoc (45 mg) was coupled with para-N-tert-butoxycarbonyl-aminobenzoic acid as described in the method of Example 3. In a second step, this intermediate from the first step was mixed with decanoyl chloride as described in the method of Example 3 to provide the title compound (7.8 mg, 16% yield): 91.4% pure, MS (MALDI) calcd for $C_{62}H_{92}N_{14}O_{21}$ (M) 1369. found 1368.

Example 284

$C_{11}$-PABA-Amphomycin

In a first step, amphomycin-9-Fmoc (25 mg) was coupled with para-N-tert-butoxycarbonyl-aminobenzoic acid as described in the method of Example 3. In a second step, this intermediate from the first step was mixed with undecanoyl chloride as described in the method of Example 3 to provide the title compound (1.7 mg, 6% yield): 93% pure, MS (MALDI) calcd for $C_{63}H_{94}N_{14}O_{21}$ (M) 1384. found 1382.

Example 285

$C_{13}$-PABA-Amphomycin

In a first step, amphomycin-9-Fmoc (45 mg) was coupled with para-N-tert-butoxycarbonyl-aminobenzoic acid as described in the method of Example 3. In a second step, this intermediate from the first step was mixed with tridecanoyl chloride as described in the method of Example 3 to provide the title compound (2 mg, 4% yield): 75% pure, MS (MALDI) calcd for $C_{65}H_{98}N_{14}O_{21}$ (M) 1412. found 1411.

Example 286

$CH_3$—$(CH_2)_{10}$—NH—C(=O)-(β-Ala)-Amphomycin

In a first step, amphomycin-9-Fmoc (30 mg) was coupled with N-tert-butoxycarbonyl-β-alanine as described in the method of Example 3. In a second step, this intermediate from the first step was mixed with undecanyl isocyanate as described in the method of Example 3 to provide the title compound (7 mg, 23% yield): 91% pure, MS (MALDI) calcd for $C_{60}H_{97}N_{15}O_{21}$ (M) 1365. found 1364.

Example 287

$CH_3$—$(CH_2)_{15}$—NH—C(=O)-(p-Phenylacetyl)-Amphomycin

In a first step, amphomycin-9-Fmoc (47 mg) was coupled with para-N-tert-butoxycarbonyl-phenylacetic acid as described in the method of Example 3. In a second step, this intermediate from the first step was mixed with hexadecanyl isocyanate as described in the method of Example 3 to provide the title compound (6.3 mg, 12% yield): 90% pure, MS (MALDI) calcd for $C_{70}H_{109}N_{15}O_{21}$ (M) 1497. found 1495.

Example 288

$CH_3$—$(CH_2)_7$—NH—C(=O)-(p-Phenylacetyl)-Amphomycin

In a first step, amphomycin-9-Fmoc (47 mg) was coupled with para-N-tert-butoxycarbonyl-phenylacetic acid as described in the method of Example 3. In a second step, this intermediate from the first step was mixed with octanyl isocyanate as described in the method of Example 3 to provide the title compound (6.3 mg, 24% yield): 84% pure, MS (MALDI) calcd for $C_{62}H_{93}N_{15}O_{21}$ (M) 1384. found 1383.

Example 289

$CH_3$—$(CH_2)_{13}$—NH—C(=O)-(p-Phenylacetyl)-Amphomycin

In a first step, amphomycin-9-Fmoc (47 mg) was coupled with para-N-tert-butoxycarbonyl-phenylacetic acid as described in the method of Example 3. In a second step, this intermediate from the first step was mixed with tetradecanyl isocyanate as described in the method of Example 3 to provide the title compound (4.3 mg, 8% yield): 81% pure, MS (MALDI) calcd for $C_{68}H_{105}N_{15}O_{21}$ (M) 1469. found 1467.

Example 290

$CH_3$—$(CH_2)_{10}$—NH—C(=O)-(p-Phenylacetyl)-Amphomycin

In a first step, amphomycin-9-Fmoc (47 mg) was coupled with para-N-tert-butoxycarbonyl-phenylacetic acid as described in the method of Example 3. In a second step, this intermediate from the first step was mixed with undecanyl isocyanate as described in the method of Example 3 to provide the title compound (5.4 mg, 11% yield): 79% pure, MS (MALDI) calcd for $C_{65}H_{99}N_{15}O_{21}$ (M) 1427. found 1425.

Example 291

$CH_3$—$(CH_2)_{13}$—NH—C(=O)-(GABA)-Amphomycin

In a first step, amphomycin-9-Fmoc (40 mg) was coupled with N-tert-butoxycarbonyl-γ-aminobutyric acid as described in the method of Example 3. In a second step, this intermediate from the first step was mixed with tetradecanyl isocyanate as described in the method of Example 3 to provide the title compound (3 mg, 7.4% yield): 95% pure, MS (MALDI) calcd for $C_{64}H_{105}N_{15}O_{21}$ (M) 1421. found 1422.

Example 292

$CH_3$—$(CH_2)_{13}$—NH—C(=O)-(M-Phenylacetyl)-Amphomycin

In a first step, amphomycin-9-Fmoc (75 mg) was coupled with meta-N-tert-butoxycarbonyl-phenylacetic acid as described in the method of Example 3. In a second step, this intermediate from the first step was mixed with tetradecanyl isocyanate as described in the method of Example 3 to provide the title compound (3.8 mg, 5% yield): 90% pure, MS (MALDI) calcd for $C_{68}H_{105}N_{15}O_{21}$ (M) 1469. found 1469.

Example 293

C$_{10}$-(M-Aminobenzoyl)-Amphomycin

In a first step, amphomycin-9-Fmoc (47 mg) was coupled with meta-N-tert-butoxycarbonyl-aminobenzoic acid as described in the method of Example 3. In a second step, this intermediate from the first step was mixed with decanoyl chloride as described in the method of Example 3 to provide the title compound (8.6 mg, 19.2% yield): 86.8% pure, MS (MALDI) calcd for C$_{62}$H$_{92}$N$_{14}$O$_{21}$ (M) 1369. found 1370.

Example 294

C$_{11}$-(M-Aminobenzoyl)-Amphomycin

In a first step, amphomycin-9-Fmoc (47 mg) was coupled with meta-N-tert-butoxycarbonyl-aminobenzoic acid as described in the method of Example 3. In a second step, this intermediate from the first step was mixed with undecanoyl chloride as described in the method of Example 3 to provide the title compound (12.1 mg, 26.7% yield): 85.2% pure, MS (MALDI) calcd for C$_{63}$H$_{94}$N$_{14}$O$_{21}$ (M) 1384. found 1384.

Example 295

CH$_3$—(CH$_2$)$_{13}$—NH—C(=O)-(β-Ala)-Amphomycin

In a first step, amphomycin-9-Fmoc (40 mg) was coupled with N-tert-butoxycarbonyl-α-alanine as described in the method of Example 3. In a second step, this intermediate from the first step was mixed with tetradecanyl isocyanate as described in the method of Example 3 to provide the title compound (8 mg, 19.7% yield): 73.9% pure, MS (MALDI) calcd for C$_{63}$H$_{103}$N$_{15}$O$_{21}$ (M) 1407. found 1408.

Example 296

C$_{12}$-(M-Aminobenzoyl)-Amphomycin

In a first step, amphomycin-9-Fmoc (47 mg) was coupled with meta-N-tert-butoxycarbonyl-aminobenzoic acid as described in the method of Example 3. In a second step, this intermediate from the first step was mixed with dodecanoyl chloride as described in the method of Example 3 to provide the title compound (3.5 mg, 7.6% yield): 97% pure, MS (MALDI) calcd for C$_{64}$H$_{96}$N$_{14}$O$_{21}$ (M) 1398. found 1399.

Example 297

C$_{13}$-(M-Aminobenzoyl)-Amphomycin

In a first step, amphomycin-9-Fmoc (47 mg) was coupled with meta-N-tert-butoxycarbonyl-aminobenzoic acid as described in the method of Example 3. In a second step, this intermediate from the first step was mixed with tridecanoyl chloride as described in the method of Example 3 to provide the title compound (3.8 mg, 8.2% yield): 96% pure, MS (MALDI) calcd for C$_{65}$H$_{98}$N$_{14}$O$_{21}$ (M) 1412. found 1413.

Example 298

Boronate-Pinacol-Ester-Resin

Wang Resin (1.38 g, 0.94 meq/g, 1.30 mmol reactive sites) was swollen in DCM (DCM) for 1 hour. The solvent was drained and the beads were suspended in fresh DCM (5 mL). To this slurry there was added 4-carboxyphenylboronic acid pinacol ester (1 g), N,N-Dimethylaminopyridine (20 mg), and HOBt (90 mg). The solution was then stirred for 20 min, and DIPC (700 uL, 4.0 mmol) was added neat. The solution was then stirred at room temperature for 24 hours. The reaction mixture was drained, and the beads were washed with DMF, DMSO/H$_2$O, MeOH and DCM. Resin loading was assumed to be quantitative.

Example 299

4'-Octyl-Biphenyl-4-Carboxyl-Amphomycin

Part A: A sample of Resin-bound boronate pinacol ester from example PRE-1476 (112 mg, 0.94 mmol/g, 0.105 mmol) was swolled in DME for 30 min. The solvent was drained and replaced with 300 uL fresh DME. To this slurry there was added 4-N-octylbromobenzene (100 uL; huge excess), PdCl$_2$(dppf)-DCM (9 mg, 0.0105 mmol), and CsCO$_3$ (200 uL, 2M (aq), 0.42 mmol). The reaction vessel was sealed and heated to 80° C. for 3 hours. The solution was then drained and the beads were washed with H$_2$O, MeOH, DMF, DMSO and DCM. The beads were then suspended in 250 uL DCM/750 uL TFA for 1 hour. The solution from this step was collected and concentrated to give an oil. The lipidated biphenyl carboxylic acid was then crystallized from MeOH, filtered, washed with cold MeOH and dried under vacuum.

Part B: The lipidated biphenyl carboxylic acid (6.5 mg, 0.0209 mmol), HOBt (3.52 mg, 0.23 mmol) and DIPC (3.6 uL, 0.23 mmol) were combined in 200 uL DMF and stirred for 1.5 hours. To this solution there was added a slurry of amphomycin-9-Fmoc (22 mg, 0.0167) and DIEA (50 uL; large excess) in 200 uL DMSO and the reaction mixture was stirred at room temperature for 40 min. At this time, the solution was poured into Et$_2$O, and the resulting solid collected by centrifugation. The solid was redissolved in 1 mL 20% piperidine in DMF, and allowed to stand for one hour at room temperature before Et$_2$O was added and the resulting solid collected by centrifugation. The solid was washed with Et$_2$O and dried under vacuum. The crude solid was purified by RP-HPLC and the product was isolated by lyophilization to provide the title compound (0.56 mg, 2.4% yield): 67.3% pure, MS (MALDI) calcd for C$_{66}$H$_{93}$N$_{13}$O$_{20}$ (M) 1389. found 1389.

Example 300

C$_{13}$-(p-Apa)-Amphomycin

In a first step, amphomycin-9-Fmoc (30 mg) was coupled with 4-N-tert-butoxycarbonyl-aminophenyl acetic acid as described in the method of Example 3. The resulting intermediate was purified by HPLC and lyophilized. In a second step, this purified intermediate and tridecanoic acid used in the method described in Example 2 provided the title compound, which was purified by HPLC and lyophilized (2 mg, 6.8% yield): 95% pure, MS (MALDI) calcd for C$_{66}$H$_{100}$N$_{14}$O$_{21}$ (M) 1426. found 1427.

Example 301

C$_{14}$-(p-Apa)-Amphomycin

In a first step, amphomycin-9-Fmoc (30 mg) was coupled with 4-N-tert-butoxycarbonyl-aminophenylacetic acid as described in the method of Example 3. The resulting intermediate was purified by HPLC and lyophilized. In a second step, this purified intermediate and tetradecanoic acid used in the method described in Example 2 provided the title compound, which was purified by HPLC and lyophilized (1 mg, 3.4% yield): 93% pure, MS (MALDI) calcd for $C_{67}H_{102}N_{14}O_{21}$ (M) 1440. found 1441.

Example 302

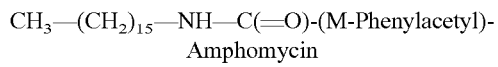
$CH_3$—$(CH_2)_{15}$—NH—C(=O)-(M-Phenylacetyl)-Amphomycin

In a first step, amphomycin-9-Fmoc (30 mg) was coupled with meta-N-tert-butoxycarbonyl-aminophenylacetic acid as described in the method of Example 3. In a second step, this intermediate from the first step was mixed with hexadecanyl isocyanate as described in the method of Example 3 to provide the title compound (2.4 mg, 7.8% yield): 72% pure, MS (MALDI) calcd for $C_{70}H_{109}N_{15}O_{21}$ (M) 1497. found 1497.

Example 303

$C_{14}$-(M-Apa)-Amphomycin

In a first step, amphomycin-9-Fmoc (30 mg) was coupled with meta-tert-butoxycarbonyl-aminophenylacetic acid as described in the method of Example 3. The resulting intermediate was purified by HPLC and lyophilized. In a second step, this purified intermediate and tetradecanoic acid used in the method described in Example 2 provided the title compound, which was purified by HPLC and lyophilized (6.5 mg, 21.8% yield): 74% pure, MS (MALDI) calcd for $C_{67}H_{102}N_{14}O_{21}$ (M) 1440. found 1441.

Example 304

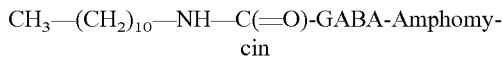
$CH_3$—$(CH_2)_{10}$—NH—C(=O)-GABA-Amphomycin

In a first step, amphomycin-9-Fmoc (40 mg) was coupled with N-tert-butoxycarbonyl-γ-aminobutyric acid as described in the method of Example 3. In a second step, this intermediate from the first step was mixed with undecanyl isocyanate as described in the method of Example 3 to provide the title compound (2 mg, 5.1% yield): 83.6% pure, MS (MALDI) calcd for $C_{61}H_{99}N_{15}O_{21}$ (M) 1379. found 1380.

Example 305

N,N'-di-$C_8$-(M,M-Diaminobenzoyl)-Amphomycin

In a first step, amphomycin-9-Fmoc (30 mg) was coupled with meta,meta-N,N'-di-tert-butoxycarbonyl-phenylacetic acid as described in the method of Example 3. In a second step, this intermediate from the first step was mixed with octanoyl chloride as described in the method of Example 85 to provide the title compound (3.7 mg, 11% yield): 99.5% pure, MS (MALDI) calcd for $C_{68}H_{103}N_{15}O_{22}$ (M) 1483. found 1484.

Example 306

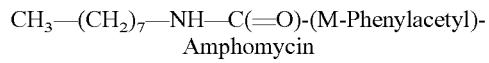
$CH_3$—$(CH_2)_7$—NH—C(=O)-(M-Phenylacetyl)-Amphomycin

In a first step, amphomycin-9-Fmoc (30 mg) was coupled with meta-N-tert-butoxycarbonyl-phenylacetic acid as described in the method of Example 3. In a second step, this intermediate from the first step was mixed with octanyl isocyanate as described in the method of Example 3 to provide the title compound (4.7 mg, 16.4% yield): 89% pure, MS (MALDI) calcd for $C_{62}H_{93}N_{15}O_{21}$ (M) 1384. found 1385.

Example 307

$CH_3$—$(CH_2)_{13}$—NH—C(=O)-Gly-Amphomycin

In a first step, amphomycin-9-Fmoc (35 mg) was coupled with N-tert-butoxycarbonyl-glycine as described in the method of Example 3. In a second step, this intermediate from the first step was mixed with tetradecanyl isocyanate as described in the method of Example 3 to provide the title compound (13 mg, 36.6% yield): 70.9% pure, MS (MALDI) calcd for $C_{62}H_{101}N_{15}O_{21}$ (M) 1393. found 1394.

Example 308

1-Dodecyl-1H-(1,2,3)-Triazole-4-Carboxylic Acid

A mixture of propiolic acid (46 μL, 0.7419 mmol) and 1-azido-dodecane (156.8 mg, 0.7419 mmol) was heated to 120° C. in a capped vial for 14 h, to yield the title triazole as white, crystalline solid (189.3 mg, 91% yield). The product was used without further purification.

Example 309

1-Dodecyl-1H-(1,2,3)-Triazole-4-Carboxyl-Amphomycin

In a first step, amphomycin-9-Fmoc (47 mg) was coupled with 1-dodecyl-1H-(1,2,3)-triazole-4-carboylic acid from Example 308 as described in the method of Example 3 to provide the title compound (1.3 mg, 2.9% yield): 83% pure, MS (MALDI) calcd for $C_{60}H_{94}N_{16}O_{20}$ (M) 1359. found 1361.

Example 310

$C_{15}$-(M-Apa)-Amphomycin

In a first step, amphomycin-9-Fmoc (30 mg) was coupled with meta-tert-butoxycarbonyl-aminophenyl acetic acid as described in the method of Example 3. The resulting intermediate was purified by HPLC and lyophilized. In a second step, this purified intermediate and tetradecanoic acid used in the method described in Example 2 provided the title compound, which was purified by HPLC and lyophilized (1.1 mg, 3% yield): 79% pure, MS (MALDI) calcd for $C_{68}H_{104}N_{14}O_{21}$ (M) 1454. found 1455.

Example 311

$C_{13}$-(Asp-(OMe))-Amphomycin

Amphomycin-9-Fmoc (30 mg) was coupled with N-tridecanoyl-O-methyl-aspartate succinimid-1-yl ester (39 mg) as described in the method of Example 112 to provide the title compound (3.7 mg, 12% yield): 93% pure, MS (MALDI) calcd for $C_{63}H_{100}N_{14}O_{23}$ (M) 1422. found 1421.

Example 312

$C_{15}$-(p-Apa)-Amphomycin

In a first step, amphomycin-9-Fmoc (30 mg) was coupled with 4-N-tert-butoxycarbonyl-aminophenylacetic acid as described in the method of Example 3. The resulting intermediate was purified by HPLC and lyophilized. In a second step, this purified intermediate and pentadecanoic acid used in the method described in Example 2 provided the title compound, which was purified by HPLC and lyophilized (1.7 mg): 73.9% pure, MS (MALDI) calcd for $C_{68}H_{104}N_{14}O_{21}$ (M) 1454. found 1457.

Example 313

$C_{15}$-(Asp-(OME))-Amphomycin

Amphomycin-9-Fmoc (66 mg) was coupled with N-pentadecanoyl-O-methyl-aspartate succinimid-1-yl ester as described in the method of Example 112 to provide the title compound (14.3 mg): 91% pure, MS (MALDI) calcd for $C_{65}H_{104}N_{14}O_{23}$ (M) 1450. found 1450.

Example 314

$C_{11}$-(Asp-(OtBu))-Amphomycin

Amphomycin-9-Fmoc (60 mg) was coupled with N-undecanoyl-O-t-butyl-aspartate succinimid-1-yl ester as described in the method of Example 112 to provide the title compound (16.6 mg): 85% pure, MS (MALDI) calcd for $C_{64}H_{102}N_{14}O_{23}$ (M) 1436. found 1437.

Example 315

$C_{13}$-(Asp-(OtBu))-Amphomycin

Amphomycin-9-Fmoc (58 mg) was coupled with N-tridecanoyl-O-t-butyl-aspartate succinimid-1-yl ester as described in the method of Example 112 to provide the title compound (20.5 mg): 93% pure, MS (MALDI) calcd for $C_{66}H_{106}N_{14}O_{23}$ (M) 1464. found 1465.

Example 316

$C_{11}$-(Asp-(OMe))-Amphomycin

Amphomycin-9-Fmoc (66 mg) was coupled with N-undecanoyl-O-methyl-aspartate succinimid-1-yl ester as described in the method of Example 112 to provide the title compound (10.1 mg): 92% pure, MS (MALDI) calcd for $C_{61}H_{96}N_{14}O_{23}$ (M) 1393. found 1394.

Example 317

$C_{15}$-(Asp-(Ome))-Amphomycin

Amphomycin-9-Fmoc (30 mg) was coupled with N-pentadecanoyl-O-methyl-aspartate succinimid-1-yl ester as described in the method of Example 112 to provide the title compound (15.3 mg, 45% yield): 93% pure, MS (ES+) calcd for $C_{65}H_{104}N_{14}O_{23}$ (M) 1450. found 1451.

Example 318

$C_{15}$-Amphomycin-9-C(=O)—NH—(O—$CF_3$-Phenyl)

Compound $C_{15}$-amphomycin (30 mg, 0.023 mmol) of Example 2 and ortho-(trifluoromethyl)phenyl isocyanate used in the method described in Example 255 provided the title compound, which was purified by HPLC and lyophilized (7 mg, 21.9% yield): 96% pure, MS (MALDI) calcd for $C_{68}H_{101}F_3N_{14}O_{21}$ (M) 1508. found 1510.

Example 319

N,N'-di-$C_6$-(M,M-Diaminobenzoyl)-Amphomycin

In a first step, N,N'-di-$C_6$-(meta,meta-diaminobenzoic acid) was prepared from meta,meta-diaminobenzoic acid and hexanoyl chloride as described in the method of Example 274. In a second step, amphomycin-9-Fmoc (30 mg) was coupled with N,N'-di-$C_6$-(meta,meta-diaminobenzoic acid) as described in the method of Example 299 (Part B) to provide the title compound (8.6 mg, 20% yield): 95% pure, MS (MALDI) calcd for $C_{64}H_{95}N_{15}O_{22}$ (M) 1427. found 1428.

Example 320

N,N'-di-$C_{12}$-(M,M-Diaminobenzoyl)-Amphomycin

In a first step, N,N'-di-$C_{12}$-(meta,meta-diaminobenzoic acid) was prepared from meta,meta-diaminobenzoic acid and dodecanoyl chloride as described in the method of Example 274. In a second step, amphomycin-9-Fmoc (30 mg) was coupled with N,N'-di-$C_{12}$-(meta,meta-diaminobenzoic acid) as described in the method of Example 299 (Part B) to provide the title compound (1.7 mg, 4% yield): 94% pure, MS (MALDI) calcd for $C_{76}H_{119}N_{15}O_{22}$ (M) 1595. found 1596.

Example 321

$CH_3$—$(CH_2)_7$—NH—C(=O)-(β-Ala)-Amphomycin

In a first step, amphomycin-9-Fmoc (30 mg) was coupled with N-tert-butoxycarbonyl-β-alanine as described in the method of Example 3. In a second step, this intermediate from the first step was mixed with octanyl isocyanate as described in the method of Example 3 to provide the title compound (5 mg, 18% yield): 89.5% pure, MS (MALDI) calcd for $C_{57}H_{91}N_{15}O_{21}$ (M) 1322. found 1323.

Example 322

(4-Phenylbenzoyl)-Amphomycin

Amphomycin-9-Fmoc (70 mg) was coupled with 4-phenylbenzoic acid as described in the method of Example 299 (Part B) to provide the title compound (8.8 mg, 13% yield): 97.6% pure, MS (MALDI) calcd for $C_{58}H_{77}N_{13}O_{20}$ (M) 1276. found 1277.

Example 323

(2-(Phenylmethyl)-Benzoyl)-Amphomycin

Amphomycin-9-Fmoc (70 mg) was coupled with 2-(phenylmethyl)benzoic acid as described in the method of Example 299 (Part B) to provide the title compound (15.3 mg, 22% yield): 95.7% pure, MS (MALDI) calcd for $C_{59}H_{79}N_{13}O_{20}$ (M) 1290. found 1291.

Example 324

N,N-Diethyl-PABA-Amphomycin

Amphomycin-9-Fmoc (70 mg) was coupled with para-N,N-diethylaminobenzoic acid (N,N-Diethyl-PABA) as described in the method of Example 299 (Part B) to provide the title compound (15.1 mg, 22% yield): 98.4% pure, MS (MALDI) calcd for $C_{56}H_{82}N_{14}O_{20}$ (M) 1271. found 1272.

Example 325

(3,4,5-Trimethoxybenzoyl)-Amphomycin

Amphomycin-9-Fmoc (70 mg) was coupled with 3,4,5-trimethoxybenzoic acid as described in the method of Example 299 (Part B) to provide the title compound (7.9 mg, 11.4% yield): 89.2% pure, MS (MALDI) calcd for $C_{57}H_{83}N_{13}O_{23}$ (M) 1318. found 1319.

Example 326

(4-Tbutylbenzoyl)-Amphomycin

Amphomycin-9-Fmoc (70 mg) was coupled with 4-tert-butylbenzoic acid as described in the method of Example 299 (Part B) to provide the title compound (9.2 mg, 13.4% yield): 91.5% pure, MS (MALDI) calcd for $C_{56}H_{81}N_{13}O_{20}$ (M) 1256. found 1257.

Example 327

(3-(Phenoxy)-Benzoyl)-Amphomycin

Amphomycin-9-Fmoc (70 mg) was coupled with 3-(phenoxy)benzoic acid as described in the method of Example 299 (Part B) to provide the title compound (5.9 mg, 8.7% yield): 92% pure, MS (MALDI) calcd for $C_{58}H_{77}N_{13}O_{21}$ (M) 1292. found 1293.

Example 328

$C_{15}$-Amphomycin-9-(D-Dap)

Compound $C_{15}$-amphomycin (27 mg, 0.020 mmol) of Example 2 and (R)-2-tert-butoxycarbonylamino-3-(9H-fluoren-9-yl-methoxycarbonyl)-aminopropionic acid used in the method described in Example 4 provided the title compound, which was purified by HPLC and lyophilized (7 mg, 12% yield): 88.5% pure, MS (MALDI) calcd for $C_{63}H_{103}N_{15}O_{21}$ (M) 1407. found 1407.

Example 329

β-Isomer of $CH_3$—$(CH_2)_{13}$—NH—C(=O)-Amphomycin

The title compound was obtained using the method described in Example 253, which compound is a secondary product of that reaction (i.e., 1-isomer refers to the amphomycin core peptide). MS and analytical HPLC analysis was used to identify the title compound, which was purified by HPLC and lyophilized (4 mg, 1.6% yield): 97.5% pure, MS (MALDI) calcd for $C_{60}H_{98}N_{14}O_{20}$ (M) 1336. found 1336.

Example 330

β-Isomer of $CH_3$—$(CH_2)_{10}$—NH—C(=O)-(GABA)-Amphomycin

The title compound was obtained using the method described in Example 304, which compound is a secondary product of that reaction (i.e., β-isomer refers to the amphomycin core peptide). MS and analytical HPLC analysis was used to identify the title compound, which was purified by HPLC and lyophilized (2 mg, 5% yield): 99.9% pure, MS (MALDI) calcd for $C_{61}H_{99}N_{15}O_{21}$ (M) 1379. found 1379.

Example 331

Lys-Gly-Amphomycin-9-$C_{15}$

In a first step, amphomycin-9-Fmoc (70 mg) was coupled with Boc-Lys(Boc)-Gly (ChemImpex) as described in the method of Example 299 (Part B) to provide Boc-Lys(Boc)-Gly-amphomycin. In a second step, pentadecanoic acid was coupled to the Boc-Lys(Boc)-Gly-amphomycin as described in the method of Example 299 (Part B) to provide Boc-Lys(Boc)-Gly-amphomycin-9-$C_{15}$. This product was deprotected under standard conditions (4N HCl/dioxane) to provide the title compound after workup as described in the method of Example 299 (Part B). (14 mg, 17.5% yield): 90% pure, MS (MALDI) calcd for $C_{68}H_{112}N_{16}O_{22}$ (M) 1506. found 1507.

Example 332

Lys-Gly-Amphomycin-9-$C_{13}$

In a first step, amphomycin-9-Fmoc (70 mg) was coupled to Boc-Lys(Boc)-Gly, followed by coupling with tridecanoic acid in a second step, and finally deprotected as described in the method of Example 331 to provide the title compound. (11 mg, 17.8% yield): 89% pure, MS (MALDI) calcd for $C_{66}H_{108}N_{16}O_{22}$ (M) 1478. found 1479.

Example 333

(11-(Phenoxy)Undecanoyl)-Amphomycin

Amphomycin-9-Fmoc (100 mg) was coupled with 11-(phenoxy)undecanoic acid as described in the method of Example 299 (Part B) to provide the title compound (37.7 mg, 36.8% yield): 94% pure, MS (MALDI) calcd for $C_{62}H_{93}N_{13}O_{21}$ (M) 1356. found 1357.

Example 334

N—$C_{12}$-((1S,4S)-4-Aminocyclohexylcarboxylic Acid)

In a first step, 4-aminocyclohexylcarboxylic acid (1.12 mL) was dissolved in DMF (5 mL), DIEA (0.824 mL) was added, and then the mixture cooled to 0° C. Dodecanoyl chloride (3.64 mL) was added and the mixture stirred for 1.5 hr. The mixture was extracted into EtOAc and washed three (3) times with HCl (1M (aq)) followed by four (4) washes with NaCl (sat.) and dried over $MgSO_4$. The resulting solid was triturated with hot hexanes, then filtered and washed with hexanes, which resulted in small white needle crystals that were further utilized without additional purification or characterization.

Example 335

C$_{12}$-((1S,4S)-4-Aminocyclohexylcarbonyl)-Amphomycin

In a first step, N—C$_{12}$-((1S,4S)-4-aminocyclohexylcarboxylic acid was prepared from dodecanoyl chloride and (1S,4S)-4-aminocyclohexylcarboxylic acid as described in the method of Example 334. In a second step, amphomycin-9-Fmoc (100 mg) was coupled with N—C$_{12}$-((1S,4S)-4-aminocyclohexylcarboxylic acid as described in the method of Example 299 (Part B) to provide the title compound (16 mg, 21.5% yield): 76.7% pure, MS (MALDI) calcd for C$_{64}$H$_{102}$N$_{14}$O$_{21}$ (M) 1404. found 1405.

Example 336

(2-Dodecanoylamino-Thiazol-4-yl)-Acetic Acid

In a first step, (2-amino-thiazol-4-yl)-acetic acid ethyl ester is coupled to dodecanoyl chloride as described in the method of Example 334 to provide (2-Dodecanoylamino-thiazol-4-yl)-acetic acid ethyl ester as a crude solid. In a second step, the crude solid of (2-Dodecanoylamino-thiazol-4-yl)-acetic acid ethyl ester was deprotected using LiOH (2-fold excess) in THF/H$_2$O to provide the title compound as a crude solid, which was used directly without further purification or characterization.

Example 337

(2-Dodecanoylamino-Thiazol-4-yl)Acetyl-Amphomycin

Amphomycin-9-Fmoc (100 mg) was coupled with (2-dodecanoylamino-thiazol-4-yl)-acetic acid (crude solid as prepared in Example 336) as described in the method of Example 299 (Part B) to provide the title compound (8.1 mg, 9.2% yield): 89% pure, MS (MALDI) calcd for C$_{64}$H$_{99}$N$_{15}$O$_{21}$S (M) 1447. found 1448.

Example 338

8-Dodecyloxy-Quinoline-2-Carboxylic Acid

In a first step, dodecyl bromide (767 µL, 3.2 mmol), NaI (478 mg, 3.2 mmol) and NaH (76 mg, 3.2 mmol) were added to a solution of 8-hydroxyl-quinoline-2-carboxylic acid methyl ester (2.11 mmol) stirring in DMF (dry, 10 mL), and the red reaction was allowed to stir overnight. The crude material resulting from removal of solvents by rotary evaporation was taken into DCM, washed with water, dried over Na$_2$SO$_4$, and filtered. The resulting solution was evaporated to dryness and the desired intermediate, 8-dodecyloxy-quinoline-2-carboxylic acid methyl ester, was obtained by HPLC (isocratic, 75% acetonitrile, 25% water) yielding 169 mg (about 14% yield). This intermediate was in turn deprotected using LiOH in THF/H$_2$O as described in the method of Example 336 to yield the title compound, which was utilized further without additional purification or characterization.

Example 339

(8-Dodecyloxy-Quinoline-2-Carbonyl)-Amphomycin

Amphomycin-9-Fmoc (30 mg) was coupled with 8-dodecyloxy-quinoline-2-carboxylic acid (as prepared in Example 338) as described in the method of Example 2 to provide the title compound (24.5 mg, 37% yield): 95% pure, MS (ES+) calcd for C$_{67}$H$_{98}$N$_{14}$O$_{21}$ (M) 1436. found 1437.

Example 340

β-Isomer of (8-Dodecyloxy-Quinoline-2-Carbonyl)-Amphomycin

The title compound was obtained using the method described in Example 339, which compound is a secondary product of that reaction (i.e., β-isomer refers to the amphomycin core peptide). MS and analytical HPLC analysis was used to identify the title compound, which was purified by HPLC and lyophilized (7.1 mg, 11% yield): 95% pure, MS (MALDI) calcd for C$_{67}$H$_{98}$N$_{14}$O$_{21}$ (M) 1436. found 1437.

Example 341

C$_{15}$-Amphomycin-9-Phe

Compound C$_{15}$-amphomycin (57 mg, 0.043 mmol) of Example 2 and succinimide activated N-tert-butoxycarbonyl phenylalanine used in the method described in Example 3 provided the title compound, which was purified by HPLC and lyophilized (57 mg, 5.5% yield): 85.5% pure, MS (MALDI) calcd for C$_{69}$H$_{106}$N$_{14}$O$_{21}$ (M) 1468. found 1470.

Example 342

C$_{15}$-Amphomycin-9-C$_{15}$

Compound C$_{15}$-amphomycin (57 mg, 0.0438 mmol) of Example 2 and pentadecanoic acid used in the method described in Example 201 provided the title compound, which was purified by HPLC and lyophilized (2 mg, 3.6% yield): 87.7% pure, MS (MALDI) calcd for C$_{75}$H$_{125}$N$_{13}$O$_{21}$ (M) 1545. found 1547.

Example 343

C$_{15}$-Amphomycin-9-([2-(2-Methoxy-Ethoxy)-Ethoxy]-Acetyl)

Compound C$_{15}$-amphomycin (40 mg, 0.031 mmol) of Example 2 and [2-(2-Methoxy-ethoxy)-ethoxy]-acetic acid used in the method described in Example 201 provided the title compound, which was purified by HPLC and lyophilized (3 mg, 7.9% yield): 87% pure, MS (MALDI) calcd for C$_{67}$H$_{109}$N$_{13}$O$_{24}$ (M) 1481. found 1484.

Example 344

C$_{10}$-Sar-Amphomycin

In a first step, N-decanoyl sarcosine succinimid-1-yl ester was prepared from decanoyl chloride and sarcosine as described by the method in Example 274, and converted into a succinimidyl ester as described in Example 1. In a second step, Amphomycin-9-Fmoc (25 mg) was coupled with N-decanoyl sarcosine succinimid-1-yl ester as described in the method of Example 3 to provide the title compound (11 mg, 42.3% yield): 99.1% pure, MS (MALDI) calcd for C$_{58}$H$_{92}$N$_{14}$O$_{21}$ (M) 1321. found 1323.

Example 345

C$_{14}$-Sar-Amphomycin

In a first step, N-tetradecanoyl sarcosine succinimid-1-yl ester was prepared from tetradecanoyl chloride and sarcosine as described by the method in Example 274, and converted into a succinimidyl ester as described in Example 1. In a second step, Amphomycin-9-Fmoc (40 mg) was coupled with N-tetradecanoyl sarcosine succinimid-1-yl ester as described in the method of Example 3 to provide the title compound (1 mg, 2.4% yield): 80.9% pure, MS (MALDI) calcd for $C_{62}H_{100}N_{14}O_{21}$ (M) 1378. found 1380.

Example 346

$C_8$-Sar-Amphomycin

In a first step, N-octanoyl sarcosine succinimid-1-yl ester was prepared from octanoyl chloride and sarcosine as described by the method in Example 274, and converted into a succinimidyl ester as described in Example 1. In a second step, Amphomycin-9-Fmoc (40 mg) was coupled with N-octanoyl sarcosine succinimid-1-yl ester as described in the method of Example 3 to provide the title compound (1.9 mg, 3.1% yield): 98.2% pure, MS (MALDI) calcd for $C_{56}H_{88}N_{14}O_{21}$ (M) 1293. found 1295.

Example 347

$C_{15}$-Amphomycin-9-$C_{12}$

Compound $C_{15}$-amphomycin (25 mg, 0.019 mmol) of Example 2 and dodecanoic acid used in the method described in Example 201 provided the title compound, which was purified by HPLC and lyophilized (7.3 mg, 27% yield): 87.8% pure, MS (MALDI) calcd for $C_{72}H_{119}N_{13}O_{21}$ (M) 1503. found 1505.

Example 348

$C_{15}$-Amphomycin-9-(11-Phenoxyundecanoyl)

Compound $C_{15}$-amphomycin (25 mg, 0.019 mmol) of Example 2 and 11-phenyoxyundecanoic acid used in the method described in Example 201 provided the title compound, which was purified by HPLC and lyophilized (7.9 mg, 27% yield): 75.2% pure, MS (MALDI) calcd for $C_{77}H_{121}N_{13}O_{22}$ (M) 1581. found 1583.

Example 349

$C_{15}$-Amphomycin-9-(3-Furan-2-yl-Acryloyl)

Compound $C_{15}$-amphomycin (25 mg, 0.019 mmol) of Example 2 and 3-Furan-2-yl-acrylic acid used in the method described in Example 201 provided the title compound, which was purified by HPLC and lyophilized (13 mg, 48.1% yield): 94% pure, MS (MALDI) calcd for $C_{67}H_{101}N_{13}O_{22}$ (M) 1441. found 1442.

Example 350

$C_{15}$-Amphomycin-9-(3-(Benzenesulfonyl)Propionoyl)

Compound $C_{15}$-amphomycin (26 mg, 0.020 mmol) of Example 2 and 3-(benzenesulfonyl)propionic acid used in the method described in Example 201 provided the title compound, which was purified by HPLC and lyophilized (7.3 mg, 27% yield): 92.6% pure, MS (MALDI) calcd for $C_{69}H_{105}N_{13}O_{23}S$ (M) 1517. found 1519.

Example 351

$C_{15}$-Amphomycin-9-(4-(Pyren-2-yl)Butyroyl)

Compound $C_{15}$-amphomycin (26 mg, 0.020 mmol) of Example 2 and 4-(pyren-2-yl)butyric acid used in the method described in Example 201 provided the title compound, which was purified by HPLC and lyophilized (9.3 mg, 12.2% yield): 90.4% pure, MS (MALDI) calcd for $C_{80}H_{111}N_{13}O_{21}$ (M) 1591. found 1591.

Example 352

$C_{15}$-Amphomycin-9-Suc

Compound $C_{15}$-amphomycin (38 mg) of Example 2 and succinic anhydride (30 mg) were dissolved in DMF, then DIPEA (1 eq.) was added and the mixture shaken overnight. Workup of this reaction afforded the title compound after HPLC and lyophilization (6 mg, 14.6% yield): 99.1% pure, MS(MALDI) calcd for $C_{64}H_{101}N_{13}O_{23}$ (M) 1421. found 1423.

Example 353

$C_{15}$-Amphomycin-9-Pro-Lys

Compound $C_{15}$-amphomycin (24 mg, 0.018 mmol) of Example 2 was coupled with succinimide activated (α-N-Fmoc-,ε-N'-tert-butoxycarbonyl Lysyl)Proline as described in the method of Example 3. The resulting intermediate was purified by HPLC and lyophilized and then deprotected with piperidine as described in Example 2 (using the deprotection and isolation/purification steps only) to provide the title compound, which was purified by HPLC and lyophilized (6.1 mg, 22.6% yield): 88.9% pure, MS (MALDI) calcd for $C_{71}H_{116}N_{16}O_{22}$ (M) 1546. found 1548.

Example 354

Boc-Amphomycin

Compound amphomycin-9-Fmoc (151.2 mg, 0.11 mmol) was dissolved in water (5 mL) and the pH adjusted to approximately 12 using NaOH (1M), while stirring at 0° C. (ice bath). Di-tert-butyl dicarbonate (185.6 mg) dissolved in acetonitrile was added with stirring at 0° C., and the resulting mixture was allowed to stir until the reaction was complete (overnight). Piperidine in DMF (20% v/v) was then added to remove the Fmoc group at the $Dab^9$ position, and the title compound was produced as described in the method of Example 2 (using the deprotection and isolation/purification steps only). The resulting product was used directly.

Example 355

Amphomycin-9-(β-Ala)

Boc-amphomycin (20 mg, as prepared in Example 354) was coupled with Boc-β-Ala-OSu (Bachem AG, Switzerland) as described in the method of Example 3 to provide the title compound (9.2 mg, 16.4% yield): 94.1% pure, MS (MALDI) calcd for $C_{48}H_{74}N_{14}O_{20}$ (M) 1167. found 1169.

Example 356

Amphomycin-9-Sar

Boc-amphomycin (20 mg, prepared in Example 354) was coupled with Boc-Sarcosine-OSu (Bachem AG, Switzerland) as described in the method of Example 3 to provide the title compound (11.3 mg, 57.9% yield): 81.5% pure, MS (MALDI) calcd for $C_{48}H_{74}N_{14}O_{20}$ (M) 1167. found 1169.

Example 357

Gly-Amphomycin-9-Fmoc

Amphomycin-9-Fmoc (176.5 mg, 0.134 mmol) was coupled with succinimide activated N-tert-butoxycarbonyl glycine as described in the method of Example 3 to provide the title compound (160.2 mg), which was used directly in further reactions without additional purification or characterization.

Example 358

$C_6$-Gly-Amphomycin

Gly-amphomycin-9-Fmoc (25 mg, 0.018 mmol), as prepared in Example 357, was coupled with succinimide activated n-hexanoic acid as described in the method of Example 2 to provide the title compound compound (7.9 mg, 31.7% yield): 83.9% pure, MS (MALDI) calcd for $C_{53}H_{82}N_{14}O_{21}$ (M) 1251. found 1253.

Example 359

$C_8$-Gly-Amphomycin

Gly-amphomycin-9-Fmoc (25 mg, 0.018 mmol), as prepared in Example 357, was coupled with succinimide activated n-octanoic acid as described in the method of Example 2 to provide the title compound compound (3.7 mg, 16.1% yield): 82% pure, MS (MALDI) calcd for $C_{55}H_{86}N_{14}O_{21}$ (M) 1279. found 1281.

Example 360

$C_{10}$-Gly-Amphomycin

Gly-amphomycin-9-Fmoc (25 mg, 0.018 mmol), as prepared in Example 357, was coupled with succinimide activated n-decanoic acid as described in the method of Example 2 to provide the title compound compound (8.7 mg, 37.8% yield): 91.7% pure, MS (MALDI) calcd for $C_{57}H_{90}N_{14}O_{21}$ (M) 1307. found 1309.

Example 361

$C_8$-(M-Apa)-Amphomycin

In a first step, amphomycin-9-Fmoc (30 mg) was coupled with meta-tert-butoxycarbonyl-aminophenyl acetic acid as described in the method of Example 3. The resulting intermediate was purified by HPLC and lyophilized. In a second step, this purified intermediate and octanoic acid used in the method described in Example 2 provided the title compound, which was purified by HPLC and lyophilized (6.9 mg, 18% yield): 72% pure, MS (MALDI) calcd for $C_{61}H_{90}N_{14}O_{21}$ (M) 1355. found 1357.

Example 362

$CH_3$—$(CH_2)_{10}$—NH—C(=O)-(M-Phenylacetyl)-Amphomycin

In a first step, amphomycin-9-Fmoc (30 mg) was coupled with meta-N-tert-butoxycarbonyl-phenylacetic acid as described in the method of Example 3. In a second step, this intermediate from the first step was mixed with undecanyl isocyanate as described in the method of Example 3 to provide the title compound (2.3 mg, 1.5% yield): 82% pure, MS (MALDI) calcd for $C_{65}H_{99}N_{15}O_{21}$ (M) 1427. found 1429.

Example 363

1-Adamantane-C(=O)-Amphomycin

Amphomycin-9-Fmoc was coupled with succinimide activated Adamantane-1-carboxylic acid as described in the method of Example 2 to provide the title compound (4.1 mg): 90% pure, MS (FAB) calcd for $C_{56}H_{83}N_{13}O_{20}$ (M) 1258. found 1259.

Example 364

(10-Methyl-Undec-2-Enoyl)-Amphomycin

Amphomycin complex was produced by fermentation of Streptomyces canus, and subsequently submitted to liquid chromatography (LC) and MS to identify the title compound. Once identified in the amphomycin complex, the title compound was purified by HPLC and used directly to make derivative lipopeptide antibiotics. (2.0 mg): 98% pure, MS (FAB) calcd for $C_{57}H_{89}N_{13}O_{20}$ (M) 1276. found 1277.

Example 365

(10-Methyl-Dodec-2-Enoyl)-Amphomycin

Amphomycin complex was produced and analyzed as described in Example 364. The title compound was purified by HPLC and used directly to make derivative lipopeptide antibiotics. (11.0 mg): 97% pure, MS (FAB) calcd for $C_{58}H_{91}N_{13}O_{20}$ (M) 1290. found 1291.

Example 366

(12-Methyl-Tetradec-2-Enoyl)-Aspartocin

Aspartocin complex was produced by fermentation of Streptomyces griseus and analyzed as described in Example 364. The title compound was purified by HPLC and used directly to make derivative lipopeptide antibiotics. (10.0 mg): 96% pure, MS (MALDI) calcd for $C_{60}H_{95}N_{13}O_{20}$ (M) 1319. found 1319.

Example 367

(10-Methyl-Dodec-2-ENOYL)-Amphomycin-9-Gly

Compound (10-methyl-dodec-2-enoyl)-amphomycin, as prepared in Example 365, was coupled with succinimide activated Fmoc-glycine as described in the method of Example 2 to provide the title compound (10.5 mg): 84% pure, MS (FAB) calcd for $C_{60}H_{94}N_{14}O_{21}$ (M) 1347. found 1348.

Example 368

(10-Methyl-Dodec-2-Enoyl)-Amphomycin-9-Sar

Compound (10-methyl-dodec-2-enoyl)-amphomycin, as prepared in Example 365, was coupled with succinimide activated Fmoc-sarcosine as described in the method of Example 2 to provide the title compound (10.6 mg): 89% pure, MS (FAB) calcd for $C_{61}H_{96}N_{14}O_{21}$ (M) 1362. found 1362.

Example 369

(10-Methyl-Dodec-2-Enoyl)-Amphomycin-9-(β-Ala)

Compound (10-methyl-dodec-2-enoyl)-amphomycin, as prepared in Example 365, was coupled with succinimide activated Fmoc-β-Alanine as described in the method of Example 2 to provide the title compound (10.9 mg): 86% pure, MS (FAB) calcd for $C_{61}H_{96}N_{14}O_{21}$ (M) 1362. found 1362.

Example 370

(12-Methyl-Tetradec-2-Enoyl)-Aspartocin-9-Gly

Compound (12-methyl-tetradec-2-enoyl)-aspartocin, as prepared in Example 366, was coupled with succinimide activated Fmoc-glycine as described in the method of Example 2 to provide the title compound (10.5 mg): 80% pure, MS (FAB) calcd for $C_{62}H_{98}N_{14}O_{21}$ (M) 1376. found 1376.

Example 371

(12-Methyl-Tetradec-2-Enoyl)-Aspartocin-9-Sar

Compound (12-methyl-tetradec-2-enoyl)-aspartocin, as prepared in Example 365, was coupled with succinimide activated Fmoc-sarcosine as described in the method of Example 2 to provide the title compound (11.6 mg): 91% pure, MS (FAB) calcd for $C_{63}H_{100}N_{14}O_{21}$ (M) 1390. found 1390.

Example 372

(12-Methyl-Tetradec-2-Enoyl)-Aspartocin-9-(β-Ala)

Compound (12-methyl-tetradec-2-enoyl)-aspartocin, as prepared in Example 365, was coupled with succinimide activated Fmoc-β-alanine as described in the method of Example 2 to provide the title compound (11.8 mg): 91% pure, MS (FAB) calcd for $C_{63}H_{100}N_{14}O_{21}$ (M) 1390. found 1390.

Example 373

(12-Acetylaminododecanoyl)-Amphomycin

Amphomycin-9-Fmoc was coupled with succinimide activated 12-acetylaminododecanoic acid as described in the method of Example 2 to provide the title compound (11 mg): 78% pure, MS (FAB) calcd for $C_{59}H_{94}N_{14}O_{21}$ (M) 1335. found 1336.

Example 374

(12-Aminododecoyl)-Amphomycin

Amphomycin-9-Fmoc was coupled with succinimide activated N-Fmoc-12-aminododecanoic acid as described in the method of Example 2 to provide the title compound (5 mg): 84% pure, MS (FAB) calcd for $C_{57}H_{92}N_{14}O_{20}$ (M) 1293. found 1293.

Example 375

Assay for Antimicrobal Activity

The antimicrobial lipopeptide derivatives described herein were tested for antimicrobial activity against Gram-positive bacteria as follows. The minimum inhibitory concentrations (MIC) of the antimicrobial lipopeptide derivatives of the invention were determined using NCCLS guidelines M7-A6 (2003) with a slight modification in that doubling serial dilutions were used to dilute the test compounds. The broth phase microdilution method was used. Isolated colonies of *Staphylococcus aureus* (MSSA) from an 18-24 hour blood agar plate cultures were used to inoculate cation adjusted Mueller-Hinton broth (CAMHB) supplemented with 0.625 mM calcium. In 96-well plates, a volume of 90 μL of a bacterial suspension having $10^5$ colony forming units (CFU)/mL of culture was added to 10 μL of increasing concentrations of each compound of the invention (doubling in concentration each adjacent well and ranging from about 0.125 μg/mL to about 64 μg/mL). A negative control containing media alone and a positive growth control containing bacteria with media alone were also included. MICs were determined after incubating the plates at about 37° C. for 24 hours. Activity of several antimicrobial lipopeptide derivatives of the invention are shown in Tables 1-16. The MIC was recorded as the lowest concentration of a test antimicrobial compound that completely inhibited bacterial growth. However, a range of MIC values shows a range of activity for compounds tested multiple times. The unit value for the all the MIC values is μg/mL, and the natural amphomycin complex has an MIC of approximately 1.4 μg/mL against MSSA cultured as described above. In Tables 1 to 16, R is the core cyclic peptide of amphomycin or aspartocin, which can be in the form of a β-isomer, an anhydro, a dianhydro, or any combination thereof. A person of skill in the art will appreciate that the amino group of exocyclic amino acid at position 1 and the amino group of $Dab^9$ shown in the structures above each of Tables 1 to 16 is to merely illustrate the attachment site of substituents to the core cyclic peptide and should not be interpreted as a hydrazino group (i.e., the displayed amino groups, although shown for convenience, are actually a part of structure R, as in). Furthermore, a person of skill in the art will appreciate that all the pounds, or groups of compounds, derived from the various combinations of and substituents shown in Tables 1 to 16, are disclosed by the present the same extent as if each compound or group of compounds was set forth individually.

TABLE 1

| Compound # | m | $R_1$ | MIC |
|---|---|---|---|
| 3 | 1 | —$NH_2$ | 0.25-2 |
| 147 | 2 | —$NH_2$ | 0.25-1 |
| 22 | 3 | —$NH_2$ | 1-2 |
| 25 | 5 | —$NH_2$ | 1 |
| 34 | 11 | —$NH_2$ | 32-64 |
| 207 | 2 | —$CH_3$ | 16 |
| 201 | 4 | —$CH_3$ | 32 |
| 205 | 6 | —$CH_3$ | 16 |
| 220 | 8 | —$CH_3$ | 2 |
| 347 | 10 | —$CH_3$ | >64 |
| 342 | 13 | —$CH_3$ | >64 |
| 348 | 9 | —O-Phenyl | >64 |

TABLE 2

| Compound # | m | i | n | j | r | X | MIC |
|---|---|---|---|---|---|---|---|
| 33 | 1 | 1 | 1 | 1 | 1 | —NH— | 0.5-1 |
| 42 | 1 | 1 | 1 | 0 | — | —NH— | 1 |
| 68 | 1 | 1 | 2 | 0 | — | —NH— | 2 |
| 70 | 2 | 1 | 5 | 0 | — | —NH— | 2 |
| 72 | 3 | 1 | 5 | 0 | — | —NH— | 8 |
| 197 | 1 | 1 | 5 | 0 | — | —NH— | 0.25-0.5 |
| 173 | 2 | 1 | 4 | 0 | — | —NH— | 1 |
| 176 | 4 | 1 | 2 | 0 | — | —NH— | 4 |
| 93 | 5 | 1 | 1 | 0 | — | —NH— | 4 |
| 94 | 3 | 1 | 3 | 0 | — | —NH— | 2 |
| 212 | 2 | 0 | — | 1 | 0 | —NH— | 1 |
| 81 | 1 | 0 | — | 1 | 4 | —$CH_2$— | 32 |
| 49 | 1 | 0 | — | 1 | 0 | —$CH_2$— | 4 |

TABLE 3

| Compound # | n | m | X (stereochemistry) | $R_1$ | MIC |
|---|---|---|---|---|---|
| 6 | 8 | 0 | — | —H | 32-64 |
| 7 | 9 | 0 | — | —H | 32-64 |
| 8 | 10 | 0 | — | —H | 4-8 |
| 9 | 11 | 0 | — | —H | 0.5-1 |
| 10 | 12 | 0 | — | —H | 1 |
| 2 | 13 | 0 | — | —H | 0.5-4 |
| 11 | 14 | 0 | — | —H | 0.5 |
| 12 | 15 | 0 | — | —H | 1-2 |
| 13 | 16 | 0 | — | —H | 2 |
| 358 | 4 | 1 | —H | —H | >64 |
| 359 | 6 | 1 | —H | —H | >64 |
| 360 | 8 | 1 | —H | —H | >64 |
| 103 | 10 | 1 | —H | —H | 8-16 |
| 105 | 12 | 1 | —H | —H | 0.5 |
| 106 | 14 | 1 | —H | —H | 0.5 |
| 107 | 16 | 1 | —H | —H | 2 |
| 346 | 6 | 1 | —H | —$CH_3$ | >64 |
| 344 | 8 | 1 | —H | —$CH_3$ | >64 |
| 345 | 12 | 1 | —H | —$CH_3$ | 64 |
| 115 | 13 | 1 | -Phenyl (L) | —H | 2 |
| 116 | 13 | 1 | -Benzyl (D) | —H | 1 |
| 118 | 8 | 1 | —$CH_2$-(3-Benzo[b]thiophene) (L) | —H | 2 |
| 316 | 9 | 1 | —$CH_2$—C(=O)—OMe (L) | —H | >64 |
| 311 | 11 | 1 | —$CH_2$—C(=O)—OMe (L) | —H | 8 |
| 313 | 13 | 1 | —$CH_2$—C(=O)—OMe (L) | —H | 0.5-1 |
| 317 | 13 | 1 | —$CH_2$—C(=O)—OMe (D) | —H | 1 |
| 314 | 9 | 1 | —$CH_2$—C(=O)—OtBu (L) | —H | 8 |
| 315 | 11 | 1 | —$CH_2$—C(=O)—OtBu (L) | —H | 1 |
| 112 | 13 | 1 | —$CH_2$—C(=O)—OtBu (L) | —H | 0.5 |

TABLE 4

[Structure: alkyl-(CH2)n-NH-C(=O)-[NH-CH2-(CH2)i-C(=O)]m-NH-R-NH-R3]

| Compound # | n | i | m | R3 | MIC |
|---|---|---|---|---|---|
| 252 | 7 | — | 0 | —H | 32 |
| 286 | 10 | 2 | 1 | —H | 2 |
| 321 | 7 | 2 | 1 | —H | >64 |
| 304 | 10 | 3 | 1 | —H | 4 |
| 330[†] | 10 | 3 | 1 | —H | >64[†] |
| 251 | 11 | — | 0 | —H | 2 |
| 254 | 11 | 1 | 1 | —H | 2-4 |
| 92 | 11 | — | 0 | -Gly | 0.25-0.5 |
| 97 | 11 | — | 0 | -β-Ala | 0.25 |
| 98 | 11 | — | 0 | -Sar | 0.5 |
| 253 | 13 | — | 0 | —H | 0.5-1 |
| 329[†] | 13 | — | 0 | —H | 4[†] |
| 277 | 13 | — | 0 | -Gly-Lys | 0.5-1 |
| 278 | 13 | — | 0 | -β-Ala | 0.5 |
| 279 | 13 | — | 0 | -Gly | 0.5 |
| 307 | 13 | 1 | 1 | —H | 0.5 |
| 295 | 13 | 2 | 1 | —H | 0.5 |
| 291 | 13 | 3 | 1 | —H | 2 |
| 249 | 15 | — | 0 | —H | 2-4 |
| 83 | 15 | — | 0 | -Gly | 2 |

[†]Indicates core is a β-isomer of core peptide

TABLE 5

[Structure: alkyl-(CH2)n-SO2-NH-CH(Rx)-C(=O)-NH-R-NH-R3]

| Compound # | n | R3 | Rx (Stereochemistry) | MIC |
|---|---|---|---|---|
| 269 | 9 | —H | —H | 4-8 |
| 100 | 9 | —H | -Benzyl (L) | 4 |
| 102 | 9 | -Gly | —H | 8 |
| 101 | 9 | -Lys | —H | 32 |
| 99 | 15 | —H | —H | 0.5-1 |
| 270 | 15 | —H | -Benzyl (L) | 16-32 |
| 84 | 15 | -Gly | —H | 2-4 |

TABLE 6A

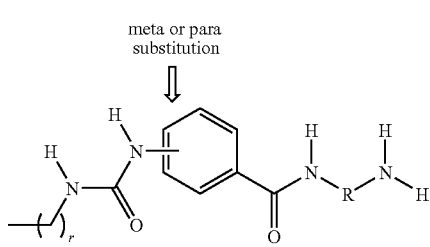

meta or para substitution

| Compound # | r | meta/para | MIC |
|---|---|---|---|
| 288 | 7 | p | 16 |
| 306 | 7 | m | 16 |
| 290 | 10 | p | 1 |
| 362 | 10 | m | 0.5 |

TABLE 6A-continued

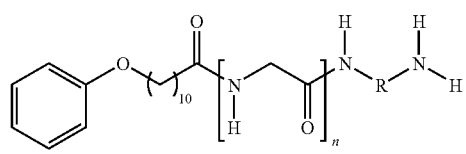

meta or para substitution

| Compound # | r | meta/para | MIC |
|---|---|---|---|
| 289 | 13 | p | 2 |
| 292 | 13 | m | 1 |
| 287 | 15 | p | 4 |
| 302 | 15 | m | 4 |

TABLE 6B

[Structure: alkyl-(CH2)r-[C6H4-C(=O)-NH-CH2-C(=O)]n-NH-R-NH-H with O linker]

| Compound # | r | n | MIC |
|---|---|---|---|
| 18 | 9 | 0 | 0.5-1 |
| 15 | 11 | 0 | 2-4 |
| 19 | 7 | 0 | 0.5 |
| 16 | 15 | 0 | 2-4 |
| 110 | 9 | 1 | 0.5 |

TABLE 6C

[Structure: phenoxy-(CH2)10-C(=O)-[NH-CH2-C(=O)]n-NH-R-NH-H]

| Compound # | n | MIC |
|---|---|---|
| 117 | 1 | 8 |
| 333 | 0 | 1 |

TABLE 6D

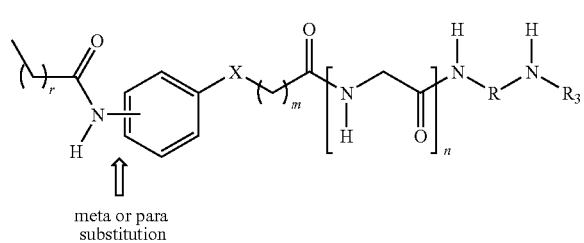

meta or para substitution

| Compound # | r | meta/para | X | m | n | R3 | MIC |
|---|---|---|---|---|---|---|---|
| 361 | 6 | m | — | 1 | 0 | —H | >64 |
| 113 | 8 | m | — | 1 | 0 | —H | 16 |
| 111 | 10 | m | — | 1 | 0 | —H | 0.5-1 |
| 303 | 12 | m | — | 1 | 0 | —H | 0.5 |
| 310 | 13 | m | — | 1 | 0 | —H | 1 |
| 312 | 13 | p | — | 1 | 0 | —H | 1 |
| 104 | 6 | p | — | 1 | 0 | —H | 2 |
| 122 | 8 | p | — | 1 | 0 | —H | 8 |
| 119 | 10 | p | — | 1 | 0 | —H | 0.25 |
| 300 | 11 | p | — | 1 | 0 | —H | 0.225 |
| 301 | 12 | p | — | 1 | 0 | —H | 2 |
| 281 | 14 | p | — | 1 | 0 | —H | 2 |
| 86 | 10 | p | — | 1 | 0 | -Gly | 0.25 |
| 91 | 10 | p | — | 0 | 1 | -Gly | 2 |
| 108 | 10 | p | — | 2 | 0 | —H | 0.5 |
| 109 | 10 | p | (a) | 2 | 0 | —H | 2 |
| 293 | 8 | m | — | 0 | 0 | —H | 2 |
| 294 | 9 | m | — | 0 | 0 | —H | 0.5 |
| 296 | 10 | m | — | 0 | 0 | —H | 0.25 |
| 297 | 11 | m | — | 0 | 0 | —H | 0.25 |

(a) =

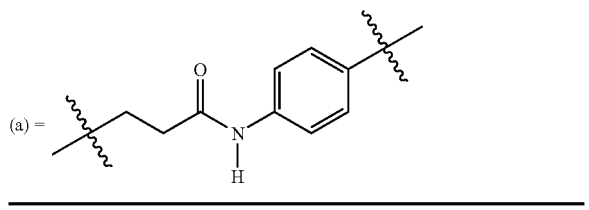

TABLE 7

| Compound # | n | X | m | R3 | MIC |
|---|---|---|---|---|---|
| 282 | 6 | — | 0 | —H | 32 |
| 283 | 8 | — | 0 | —H | 2 |
| 284 | 9 | — | 0 | —H | 16 |
| 85 | 10 | — | 0 | —H | 2-4 |
| 285 | 11 | — | 0 | —H | 0.25 |
| 21 | 10 | —NH— | 0 | —H | 1 |
| 87 | 10 | — | 0 | -Gly | 0.25-0.5 |
| 123 | 10 | — | 1 | —H | 1 |
| 91 | 10 | — | 1 | -Gly | 2 |
| 280 | 10 | — | 0 | -β-Ala | 1 |

TABLE 8

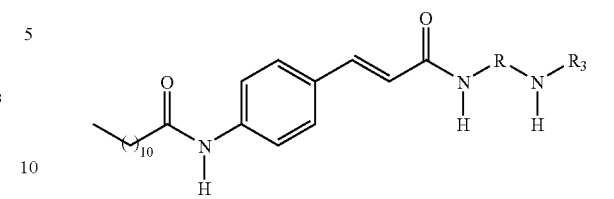

| Compound # | R3 | MIC |
|---|---|---|
| 120 | —H | 0.5 |
| 89 | -Gly | 0.5-1 |

TABLE 9

| Cmpd # | Amino Acid (AA) | MIC | Cmpd # | Amino Acid (AA) | MIC |
|---|---|---|---|---|---|
| 3 | -Gly | 0.25-2 | 166 | —N,N'-dimethyl-Arg | 32 |
| 22 | -GABA | 1-2 | 170 | —N,N,N-(Me)3-Lys | 2 |
| 161 | -Aib | 8 | 171 | -Nle | 8 |
| 160 | -Pro | 4 | 262 | -D-Ser | 4 |
| 26 | -Ina | 4 | 263 | -D-Tyr | 32 |
| 5 | -Leu | 16-32 | 264 | -D-Trp | 8 |
| 24 | -Sar | 0.5-1 | 124 | -D-Orn | 4 |
| 25 | -Ahx | 1 | 212 | -Carbamoyl-(β-Ala) | 1 |
| 27 | -p-nitro-Phe | 32-64 | 172 | -N-formyl-Leu | 16 |
| 341 | -Phe | >64 | 52 | -Tyr(Me) | 16 |
| 29 | -Glu | 1 | 130 | -Orn | 1 |
| 38 | -Asn | 2 | 132 | -Dap | 2 |
| 39 | -Tyr | 32-64 | 328 | -D-Dap | 2 |
| 40 | -Trp | 32-64 | 242 | —N,N-dimethyl-GABA | 1-2 |
| 167 | -Hyp | 4-8 | 245 | —N-benzyl-Gly | 1 |
| 168 | -Apa | 32-64 | 147 | -β-Ala | 0.25-1 |
| 43 | -Gln | 8-16 | 82 | -Ala | 2 |
| 44 | -Thr | 2-4 | 96 | -D-Pip | 1 |
| 30 | -p-F-Phe | 32-64 | 129 | -Lys | 1 |
| 31 | -β-Cha | 16 | 131 | -gDab | 1 |
| 32 | -hPhe | 8 | 66 | -D-Ala | 4 |
| 35 | -β-cyano-alanine | 8-16 | 67 | -D-Pro | 1-2 |
| 204 | -Carbamoyl-Leu | 16 | 243 | —N-ethyl-Gly | 0.5-1 |
| 36 | -Ile | 8-16 | 246 | —N,N-diethyl-β-Ala | 2 |
| 169 | -Val | 4 | 268 | —N,N-dimethyl-Gly | 1 |
| 41 | -Phg | 4 | 95 | -Pip | 2 |
| 162 | -MeCys | 8 | 48 | -Gly-Suc | 8 |
| 163 | -Nvl | 8 | 49 | -Gly-Ac | 4 |
| 164 | -Abu | 4 | 2 | -H (non-AA control) | 4 |
| 165 | -Cit | 4 | | | |

TABLE 10

| Cmpd # | A₁ | A₂ | A₃ | MIC | Cmpd # | A₁ | A₂ | A₃ | MIC |
|---|---|---|---|---|---|---|---|---|---|
| 28 | -Gly- | -Phe | — | 2 | 33 | -Gly- | -Gly- | -Gly | 0.5-1 |
| 4 | -Gly- | -Lys | — | 1-2 | 37 | -Gly- | -Val | — | 2-4 |
| 42 | -Gly- | -Gly | — | 1 | 45 | -Pro- | -Gly | — | 32 |
| 46 | -Gly- | -Leu | — | 1 | 191 | -Gly- | -Lys- | -Lys | 8 |
| 190 | -Gly- | -Lys- | -Gly | 1 | 193 | -Lys- | -Gly | — | 4-8 |
| 192 | -Gly- | -Gly- | -Lys | 0.5-1 | 195 | -Lys- | -Lys- | -Lys | 4 |
| 194 | -Lys- | -Lys | — | 2 | 152 | -Gly- | -(D-Lys) | — | 2 |
| 68 | -Gly- | -GABA | — | 2 | 153 | -Gly- | -Orn | — | 2 |
| 69 | -Gly- | -(D-Ala) | — | 1 | 154 | -Gly- | -gDab | — | 4 |
| 70 | -β-Ala- | -Ahx | — | 2 | 155 | -β-Ala- | -Lys | — | 8 |
| 174 | -β-Ala- | -Val | — | 2 | 72 | -GABA- | -Ahx | — | 8 |
| 71 | -GABA- | -Val | — | 4 | 157 | -Gly- | -gDab | — | 4-8 |
| 156 | -GABA- | -Lys | — | 1 | 197 | -Gly- | -Ahx | — | 0.25-0.5 |
| 198 | -Sar- | -Ahx | — | 4 | 199 | -Sar- | -Lys | — | 0.5-1 |
| 144 | -Sar- | -Orn | — | 4 | 145 | -Sar- | -gDab | — | 2 |
| 146 | -Sar- | -Dap | — | 2 | 200 | -Dap- | -β-N-(β-Ala) | — | 1 |
| 158 | -Gly- | -hLys | — | 1-2 | 148 | -β-Ala- | -Orn | — | 0.5-1 |
| 159 | -GABA- | -gDab | — | 0.5-1 | 173 | -Ahx- | -Gly | — | 1 |
| 176 | -5-Ava- | -(β-Ala) | — | 4 | 93 | -Ahx- | -Gly | — | 4 |
| 94 | -GABA- | -GABA | — | 2 | 353 | -Pro- | -Lys | — | >64 |
| 209 | -PABA- | -Benzyl Tyr | — | 8 | 151 | -(D-Pro)- | -(D-Lys) | — | 16 |

TABLE 11

| Compound # | Rₐ | R_b | MIC |
|---|---|---|---|
| 266 | -p-hydroxyphenyl | —H | 8-16 |
| 267 | -p-hydroxyphenyl | -p-hydroxyphenyl | 8 |

TABLE 12

| Cmpd # | R₃ | MIC | Cmpd # | R₃ | MIC |
|---|---|---|---|---|---|
| 206 | cyclohexyl | 8 | 208 | norbornyl | 4 |
| 210 | γ-butyrolactone | 2 | 213 | allyl | 2 |
| 373 | pyrrolidinone | >64 | 343 | -OCH₂CH₂OCH₂CH₂OCH₃ | 64 |

TABLE 12-continued
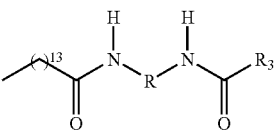
| Cmpd # | R₃ | MIC | Cmpd # | R₃ | MIC |
|---|---|---|---|---|---|
| 352 | 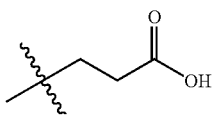 | >64 | 318 | 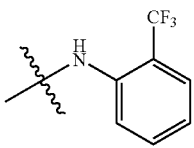 | 64 |
| 349 | 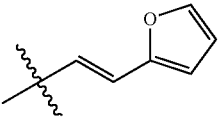 | 64 | 350 | 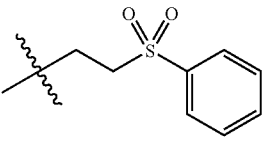 | 64 |
| 218 | 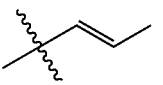 | 8 | 224 | 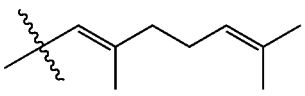 | 8 |
| 223 | 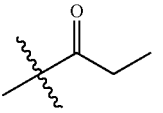 | 16 | 237 | 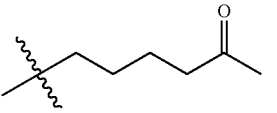 | 16 |
| 232 | 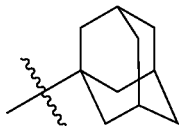 | 4 | 227 | 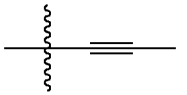 | 32 |
| 238 | 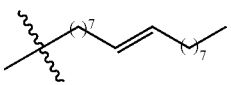 | 1-2 | 231 | 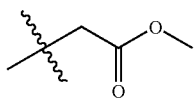 | 8 |
| 241 | 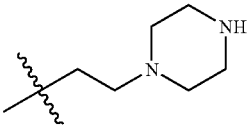 | 1-2 | 351 | 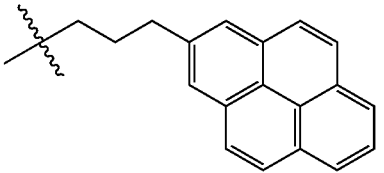 | >64 |
| 235 | 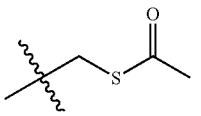 | 2 | 81 | 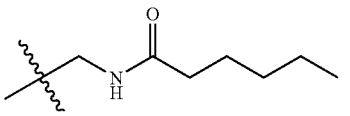 | 32 |

TABLE 13
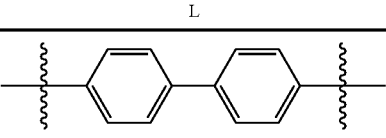
| | | -Gly | -β-Ala | -GABA | -Sar | -Orn | -(D-Orn) | -Dab | -gDab | -Gly-Lys | -Gly-(D-Lys) |
|---|---|---|---|---|---|---|---|---|---|---|---|
| n | 8 | — | 76/16 | — | 77/32 | — | — | — | — | — | — |
| | 10 | 58/4-8 | 73/2-4 | 57/16 | 74/4 | — | — | — | 138/32 | 143/2-4 | — |
| | 11 | 53/8 | 54/2-4 | 50/1 | 55/1 | 134/32 | — | 136/4 | 135/8 | 128/1 | — |
| | 12 | 23/8-16 | 59/0.5-1 | 62/0.5-1 | 60/0.5 | 127/4 | — | 140/32 | 139/4 | 125/1-2 | — |
| | 13 | 3/0.25-2 | 147/0.25-1 | 22/1-2 | 24/0.5-1 | 130/1 | 124/4 | 132/2 | 131/1 | 4/1-2 | 152/2 |
| | 14 | — | 79/1 | — | 75/1 | — | — | — | — | 141/2 | — |
| | 15 | 80/0.5-1 | — | 78/1 | — | — | — | — | 142/32 | — | — |
Compound #/MIC
Gly = Glycine, β-Ala = β-Alanine, GABA = γ-aminobutyric acid, Sar = Sarcosine, Orn = Ornithine, Dap = 2,3-Diaminopropanoic acid, gDab = 2,4-Diaminobutanoic acid, Gly-Lys = Glycine-Lysine.
TABLE 14
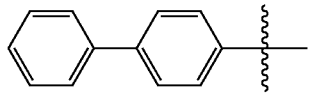
| Cmpd # | n | i | m | X | L | | MIC |
|---|---|---|---|---|---|---|---|
| 299 | 6 | 1 | — | —CH$_2$— | 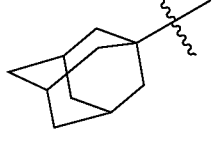 | | 0.25 |
| 322 | — | 0 | — | — | 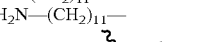 | | >64 |
| 374 | 0 | 1 | — | —C(=O)NH— | —(CH$_2$)$_{11}$— | | >64 |
| 375 | — | 0 | — | — | H$_2$N—(CH$_2$)$_{11}$— | | >64 |
| 336 | — | 0 | — | — | 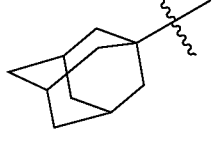 | | >64 |
| 327 | — | 0 | — | — | 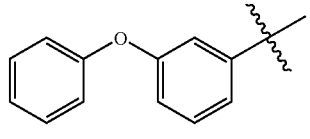 | | >64 |
| 326 | — | 0 | — | — | 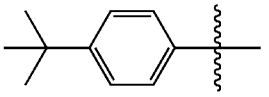 | | >64 |
| 325 | — | 0 | — | — | 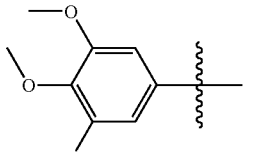 | | >64 |

TABLE 14-continued
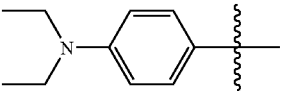
| Cmpd # | n | i | m | X | L | MIC |
|---|---|---|---|---|---|---|
| 324 | — | 0 | — | — | 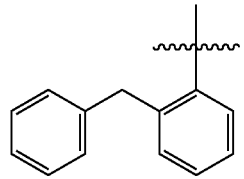 | >64 |
| 323 | — | 0 | — | — | 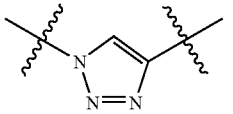 | >64 |
| 309 | 10 | 1 | — | —CH₂— | 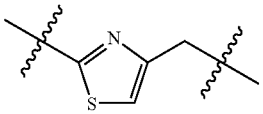 | 1 |
| 337 | 13 | 1 | — | —NH— | 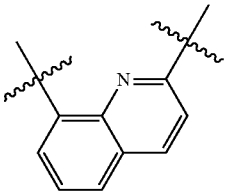 | 0.25-1 |
| 339 | 11 | 1 | — | —O— | 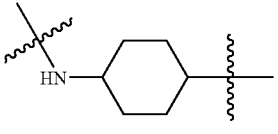 | 0.5 |
| 340† | 11 | 1 | — | —O— | | 4† |
| 335 | 10 | 1 | — | —CH₂— | 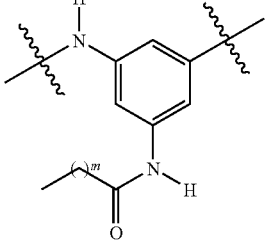 | 4 |
| 305 | 6 | 1 | 6 | —C(=O)— | | 1 |
| 320 | 10 | 1 | 10 | | | 2 |
| 319 | 4 | 1 | 4 | | | 64 |
†Indicates core is a β-isomer of core peptide

TABLE 15

Tail—NH—R—NH—AA (with H on N)

| Cmpd # | Tail | AA | MIC |
|---|---|---|---|
| 364 | (isopropyl-terminated chain with C=O, ~C11 branched unsaturated acyl) | —H | 4-8 |
| 365 | (longer branched unsaturated acyl) | —H | 0.5-1 |
| 367 | | -Gly | 1-2 |
| 368 | | -Sar | 1-2 |
| 369 | | -(β-Ala) | 1-2 |
| 366 | (longest branched unsaturated acyl) | —H | 0.125-0.25 |
| 370 | | -Gly | 0.25-0.5 |
| 371 | | -Sar | 0.5 |
| 372 | | -(β-Ala) | 0.25-0.5 |

TABLE 16

$A_2$—$A_1$—NH—R—NH—$R_3$

| Cmpd # | $A_2$ | $A_1$ | $R_3$ | MIC |
|---|---|---|---|---|
| 4 | — | $C_{15}$— | -Gly-Lys | 1-2 |
| 128 | — | $C_{13}$— | -Gly-Lys | 1 |
| 331 | Lys- | -Gly- | —$C_{15}$ | >64 |
| 332 | Lys- | -Gly- | —$C_{13}$ | >64 |
| 147 | — | $C_{15}$— | -(β-Ala) | 0.25-1 |
| 24 | — | $C_{15}$— | -Sar | 0.5-1 |
| 355 | — | — | -(β-Ala) | >64 |
| 356 | — | — | -Sar | >64 |

Example 376

Comparison of Compounds in MIC Assay

Antimicrobial lipopeptide derivatives of the instant invention were tested for antimicrobial activity against Gram-positive bacteria in a variety of media conditions. The mean inhibitory concentrations (MIC) of the antimicrobial lipopeptide derivatives were determined as described in Example 376. The various media used are described in Table 17. The MIC was recorded as the lowest concentration of antimicrobial that completely inhibited growth and are provided in Table 18.

Some lipopeptide antibiotic derivatives of the invention showed better broad-spectrum activity against Gram-positive bacteria than other compounds under a variety of assay conditions. In certain embodiments, compounds having specific lipophilic substituents attached to the amino-terminal amino acid by a urea linker had unexpectedly better activity when compared to compounds having lipophilic substituents directly attached as linear carbon tails (i.e., with no $Dab^9$ substitution). For example, see compound 253 as compared to either compound 2 or compound 11. In another embodiment, the addition of a dipeptide (Glycine-Lysine) at the $Dab^9$ position produced a compound with an unexpected increase in activity, especially against Staphylococcus aureus in media E or F (see, e.g., compound 199 as compared to compound 2). Another example of a $Dab^9$ substitution increasing both serum and broth MICs against Staphylococcus aureus is compound 80 as compared to compound 12. In addition, the relative differences in broth and serum MICs, depending on the $Dab^9$ substituent, highlights the unexpected and unique differences of known compounds as compared to compound derivatives of the instant invention (see, e.g., compound 15 as compared to compound 88, and compound 2 as compared to compound 147). Furthermore, unexpected variations in MIC profile were observed as a result of small variations in $Dab^9$ structure (e.g., D- vs L-amino acids). For example, see compound 160 as compared to compound 67, and compound 69 as compared to compound 4. Finally, the difference in calcium effect is unexpected and larger on broth MIC, as observed for some $Dab^9$ derivatives (see compound 251 as compared to compound 92, compound 98, and compound 97).

TABLE 17

Strains and Media used for the MIC testing of compounds

| | Species | Strain | Phenotype | Media used |
|---|---|---|---|---|
| A | Enterococcus faecium | EFM0101 | VRE, MDR | CAMHB supplemented with 0.625 mM calcium |

TABLE 17-continued

Strains and Media used for the MIC testing of compounds

| | Species | Strain | Phenotype | Media used |
|---|---|---|---|---|
| B | Enterococcus faecalis | EFS0004 | VSE | CAMHB |
| C | Enterococcus faecalis | EFS0004 | VSE | CAMHB supplemented with 0.625 mM calcium |
| D | Enterococcus faecalis | EFS0004 | VSE | CAMHB supplemented with 0.625 mM Calcium and 30% bovine serum |
| E | Staphylococcus aureus | SAU0017 | MSSA | CAMHB supplemented with 0.625 mM calcium |
| F | Staphylococcus aureus | SAU0017 | MSSA | CAMHB supplemented with 0.625 mM calcium and 30% bovine serum |
| G | Staphylococcus aureus | SAU0031 | VISA | CAMHB supplemented with 0.625 mM calcium |
| H | Staphylococcus aureus | SAU0065 | MRSA | CAMHB supplemented with 0.625 mM calcium |
| I | Staphylococcus epidermidis | SEP0375 | MRSE | CAMHB supplemented with 0.625 mM calcium |
| J | Streptococcus pneumoniae | SPN0002 | PISP | CAMHB supplemented with 0.625 mM calcium and 3% laked horse blood |
| K | Streptococcus pneumoniae | SPN0023 | PRSP | CAMHB supplemented with 0.625 mM calcium and 3% laked horse blood |
| L | Streptococcus pneumoniae | SPN0032 | PSSP | CAMHB supplemented with 0.625 mM calcium and 3% laked horse blood |
| M | Streptococcus pyogenes | SPY0001 | PenS | CAMHB supplemented with 0.625 mM calcium and 3% laked horse blood |

Abbreviations: CAMHB (cation adjusted Mueller-Hinton broth), VRE (vancomycin resistant Enterococci), MDR (multi-drug resistant), VSE (vancomycin sensitive Enterococci), MSSA (methicillin sensitive *S. aureus*), VISA (vancomycin intermediate *S. aureus*), MRSA (methicillin resistant *S. aureus*), MRSE (methicillin resistant *S. epidermidis*), PISP (penicillin intermediate *S. pneumoniae*), PRSP (penicillin resistant *S. pneumoniae*), PSSP (penicillin sensitive *S. pneumoniae*), and PenS (penicillin sensitive).

TABLE 18

Broad Spectrum Comparative Data

| Cmpd # | A | B | C | D | E | F | G | H | I | J | K | L | M |
|---|---|---|---|---|---|---|---|---|---|---|---|---|---|
| 251 | 4 | 8 | 4 | 32 | 2 | 8 | 4 | 2 | 2 | 0.5 | 1 | 1 | 2 |
| 15 | 2-4 | 2-4 | 1-4 | >64 | 2-4 | 32 | 4-8 | 2-8 | 2-4 | 0.125-1 | 0.125-0.5 | 0.25-1 | 0.5-2 |
| 2 | 4 | 2 | 1 | 64 | 4 | 8 | 8 | 4 | 4 | 0.125 | 0.125 | 0.5 | 1 |
| 160 | 8 | 16 | 8 | >64 | 4 | >64 | 16 | 4 | 4 | 0.5 | 0.25 | 2 | 2 |
| 4 | 1 | 1-4 | 1-2 | >64 | 0.5-1 | 4 | 8 | 1-4 | 1-2 | 0.25 | 0.25 | 0.25-0.5 | 0.25 |
| 11 | 0.5-1 | 0.5 | 0.5-1 | 64 | 0.5 | 8-16 | 2-4 | 2-4 | 1 | 0.25 | 0.125 | 0.25 | 0.25-0.5 |
| 12 | 0.5-1 | 0.5-1 | 1 | 64 | 1-2 | 32-64 | 4-8 | 1-2 | 2 | 0.25 | 0.125 | 0.25-0.5 | 0.5 |
| 67 | 2 | 2-4 | 2 | 64 | 1-2 | 8-16 | 8 | 2 | 2 | 0.5 | 0.5 | 0.5 | 0.5-1 |
| 69 | 4 | 8 | 4 | >64 | 1 | 32 | 8 | 2 | 4 | 1 | 1 | 2 | 1 |
| 199 | 0.5-1 | 1-2 | 1-2 | 64 | 0.25-1 | 4-8 | 4-8 | 1-2 | 0.5-1 | 0.25 | 0.25 | 0.25-0.5 | 0.25 |
| 80 | 0.5-1 | 0.5-1 | 0.5-1 | >64 | 0.5-1 | 16-32 | 8 | 2 | 1-2 | 0.125 | 0.125 | 0.25 | 0.25-0.5 |
| 88 | 0.25-0.5 | 0.5-1 | 0.25-0.5 | >64 | 0.5-1 | 32-64 | 2-4 | 0.5-1 | 0.5-1 | 0.25 | 0.125 | 0.25 | 0.25-0.5 |
| 147 | 0.5-1 | 2 | 0.5-1 | 32 | 0.25-0.5 | 2 | 2 | 1 | 0.5-1 | 0.125 | 0.125 | 0.125 | 0.125 |
| 92 | 1-2 | 6-16 | 2-4 | 64 | 0.25-0.5 | 8 | 4 | 1-2 | 0.5-1 | 0.25 | 0.125 | 0.25 | 0.25 |
| 253 | 0.5-1 | 1 | 0.5-1 | 16-32 | 0.5-1 | 2-4 | 2-4 | 1-2 | 1 | 0.125 | 0.125 | 0.125 | 0.25 |
| 97 | 2 | 64 | 4 | 64 | 0.25 | 16 | 4 | 1 | 1 | 0.125 | 0.25 | 0.125 | 0.5 |
| 98 | 2 | 32 | 4 | >64 | 0.5 | 16 | 4 | 1 | 1 | 0.125 | 0.25 | 0.5 | 0.5 |

A-M represent media conditions as defined in Table 17.

Example 377

Bactericidal Activity of Lipopeptide Derivatives

Kill curve experiments were performed with both *Staphylococcus aureus* (SAU0017) and *Enterococcus faecalis* (EFS0004) organisms grown to log phase, which were suspended in cation-adjusted Mueller-Hinton broth with additional 0.625 mM $Ca^{+2}$ to a concentration of $10^6$ CFU/mL. The cultures were then exposed to varying concentrations (i.e., multiples of the MIC) of a lipopeptide derivative and incubated at about 37° C. At selected time points from about 0 hours to about 24 hours, a sample of each culture was analyzed for a titre of viable organisms (CFU/ml), which was compared against the time required for each compound to kill bacteria. Based on NCCLS guideline M26-A (Vol. 19 N#18), a compound is considered bactericidal if it kills 99.9% of bacterial cells after 24 hours.

Figure 4A:
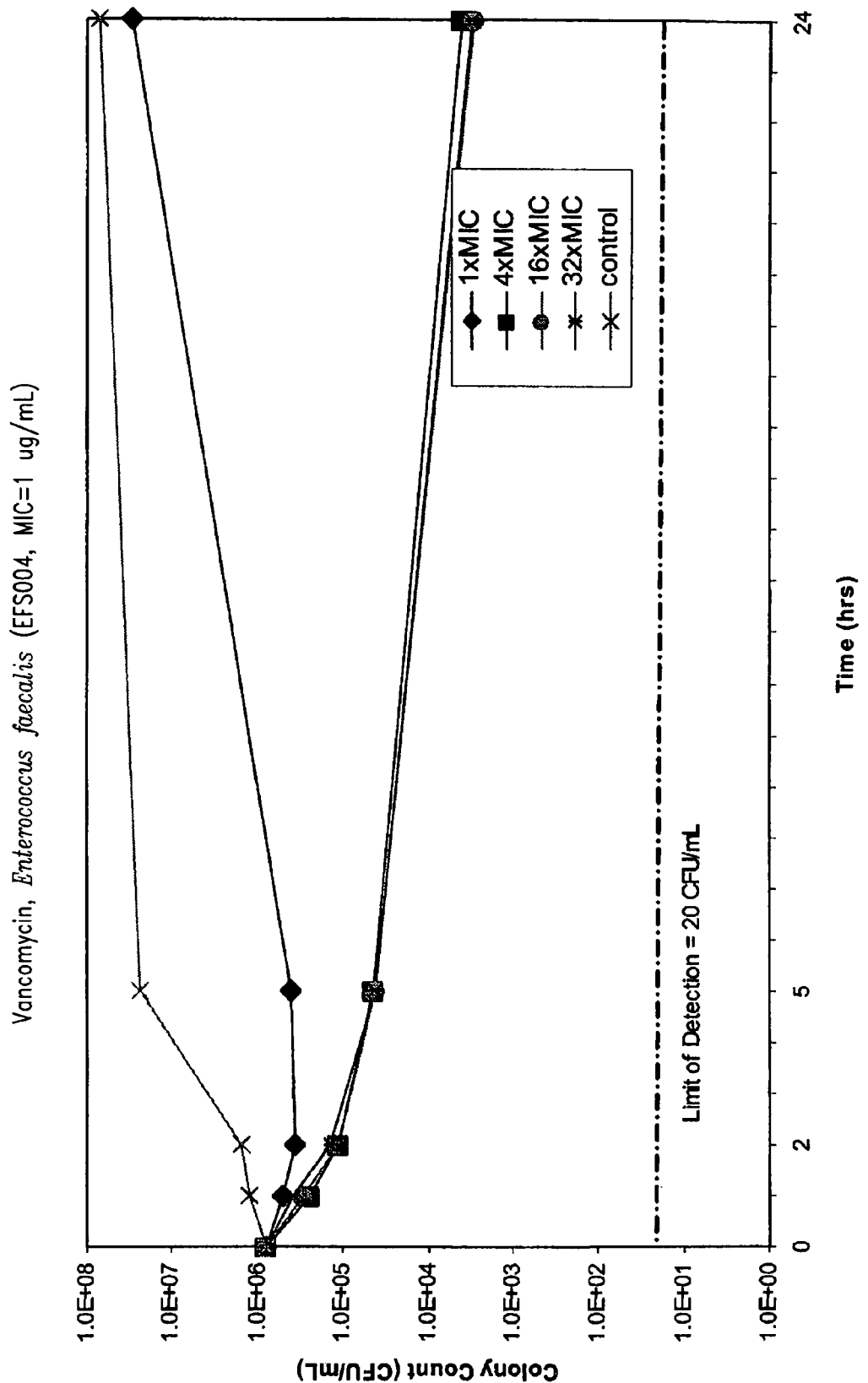
FIGS. 4A-4I show kill curves for various lipopeptide derivatives against *Enterococcus faecalis*.
Figure 4B:
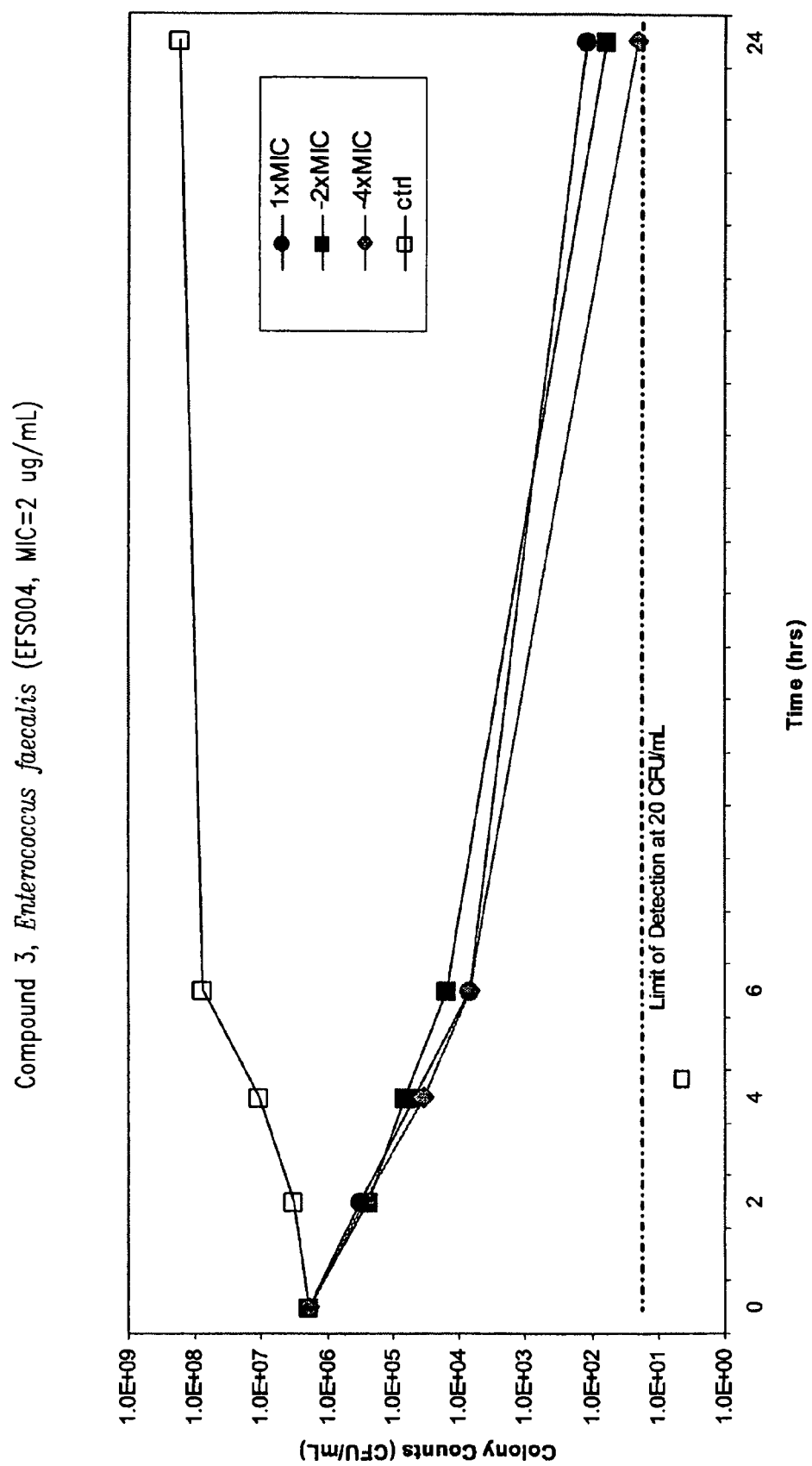
Figure 4C:
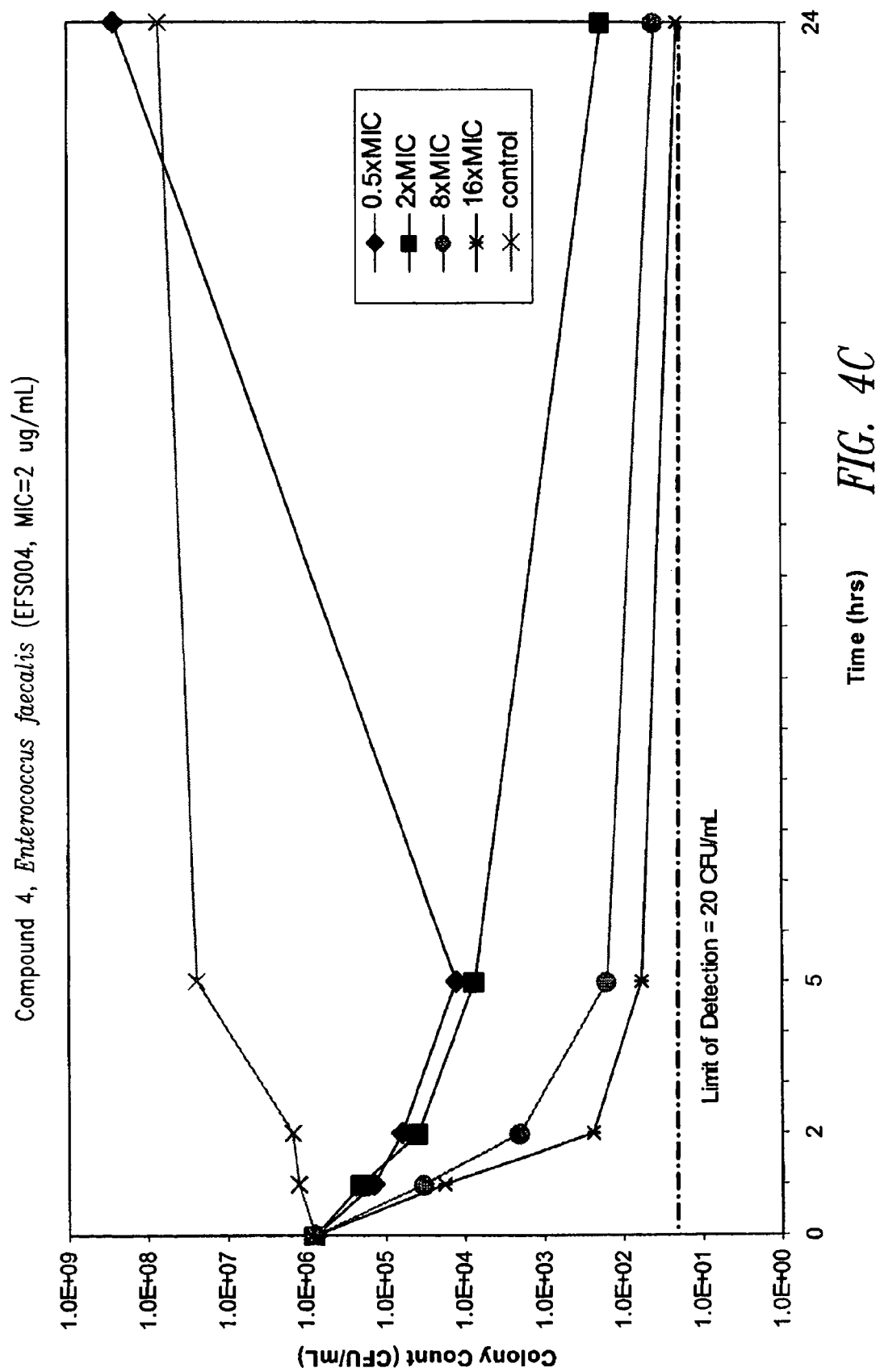
Figure 4D:
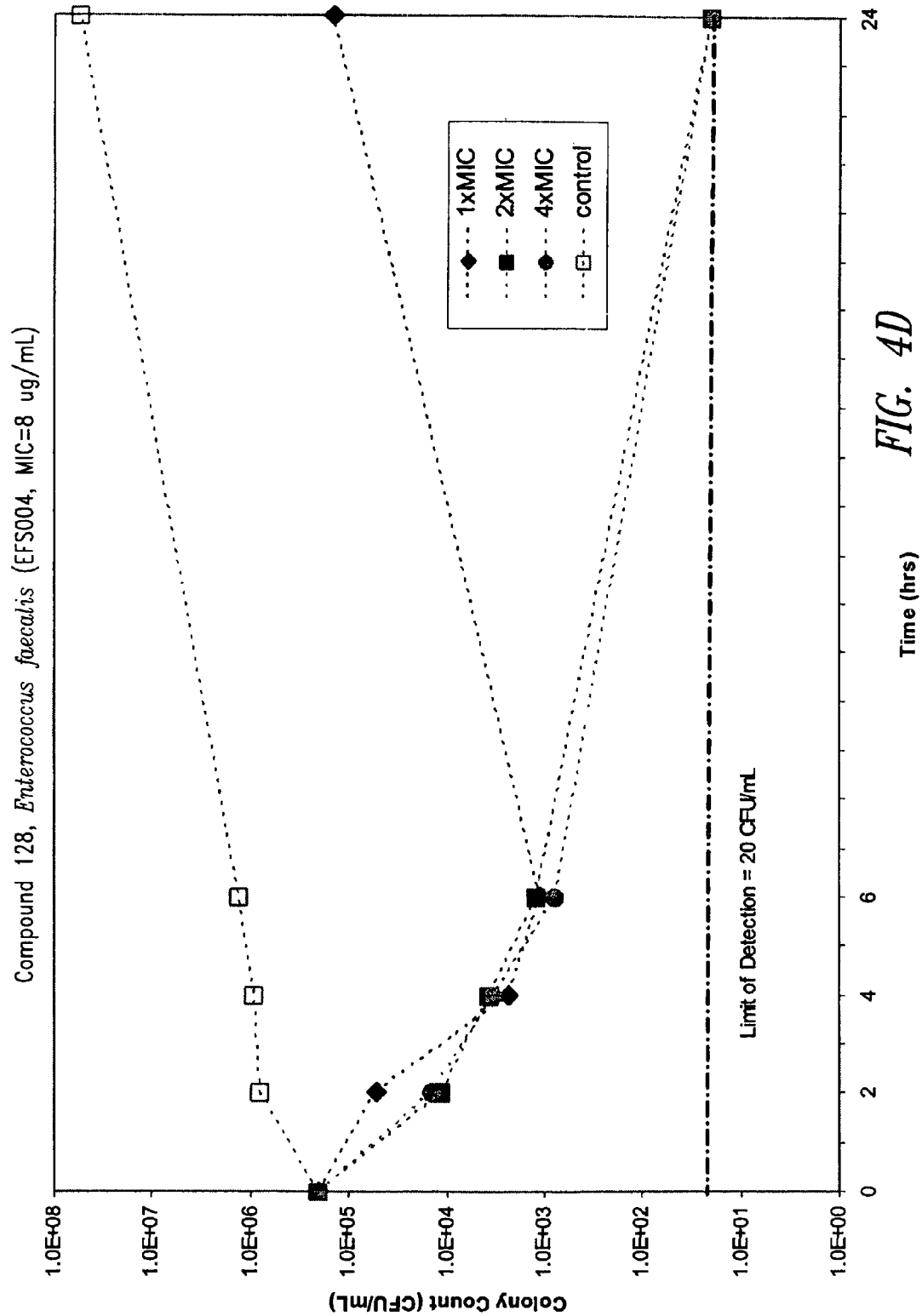
Figure 4E:
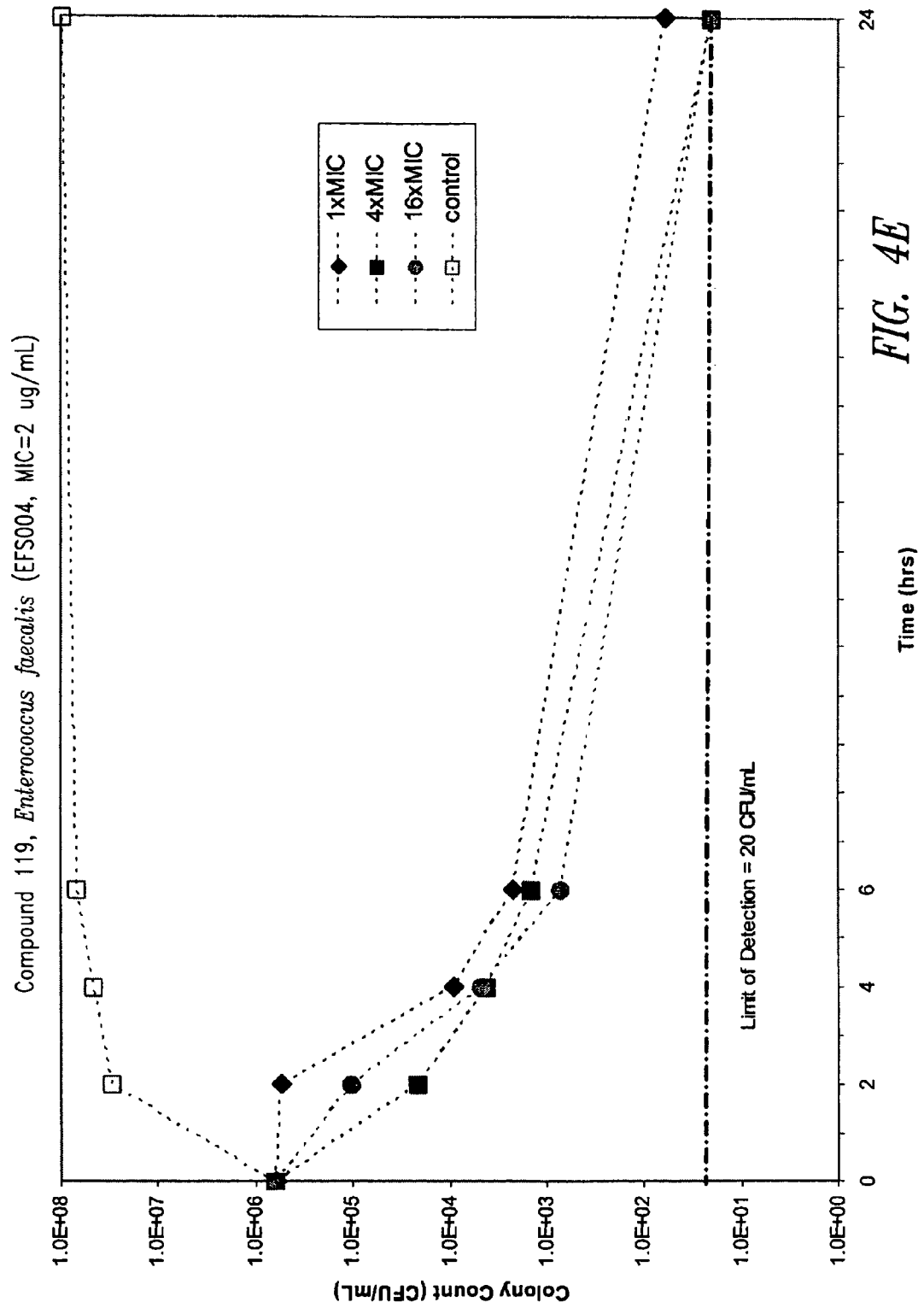
Figure 4F:
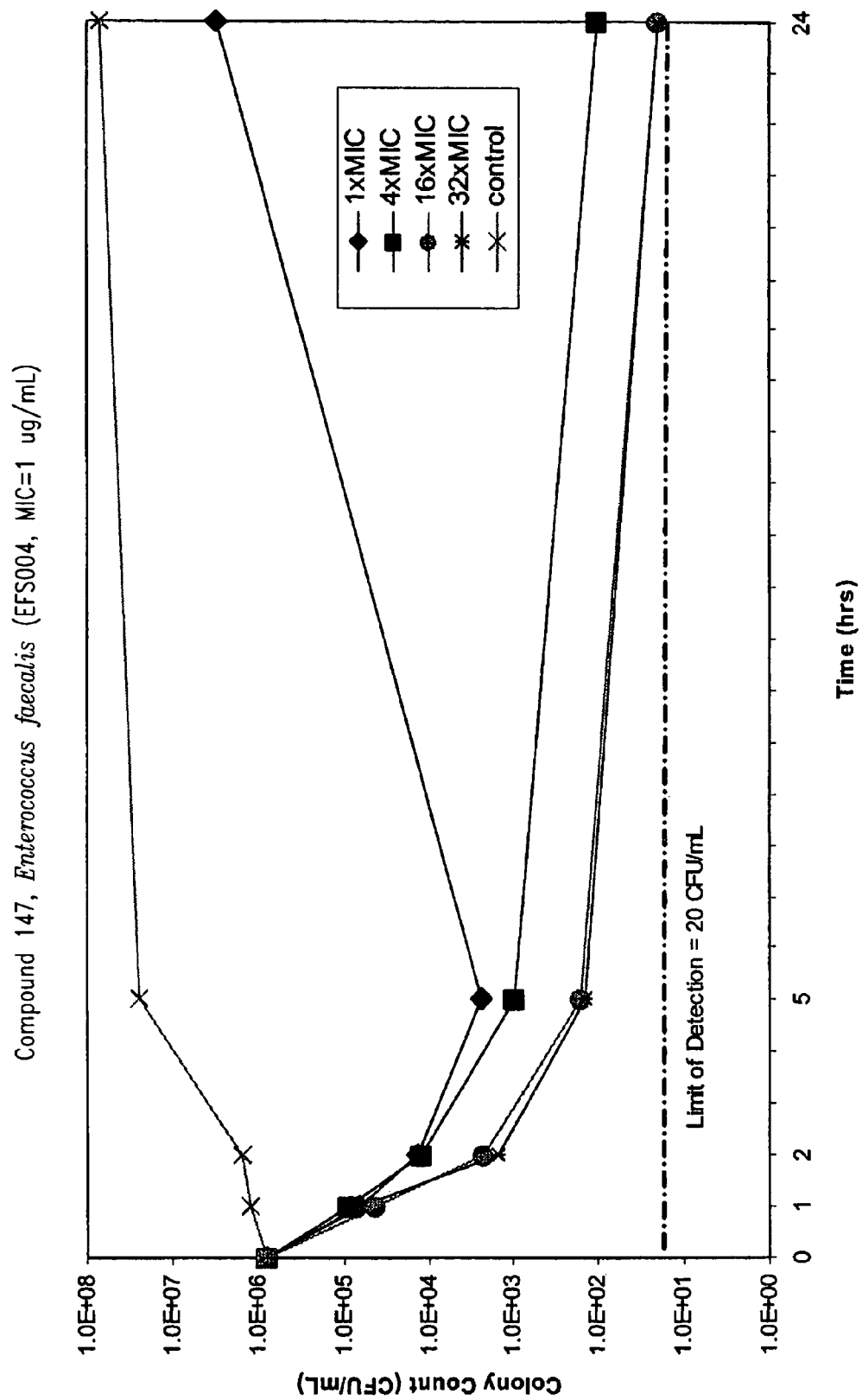
Figure 4G:
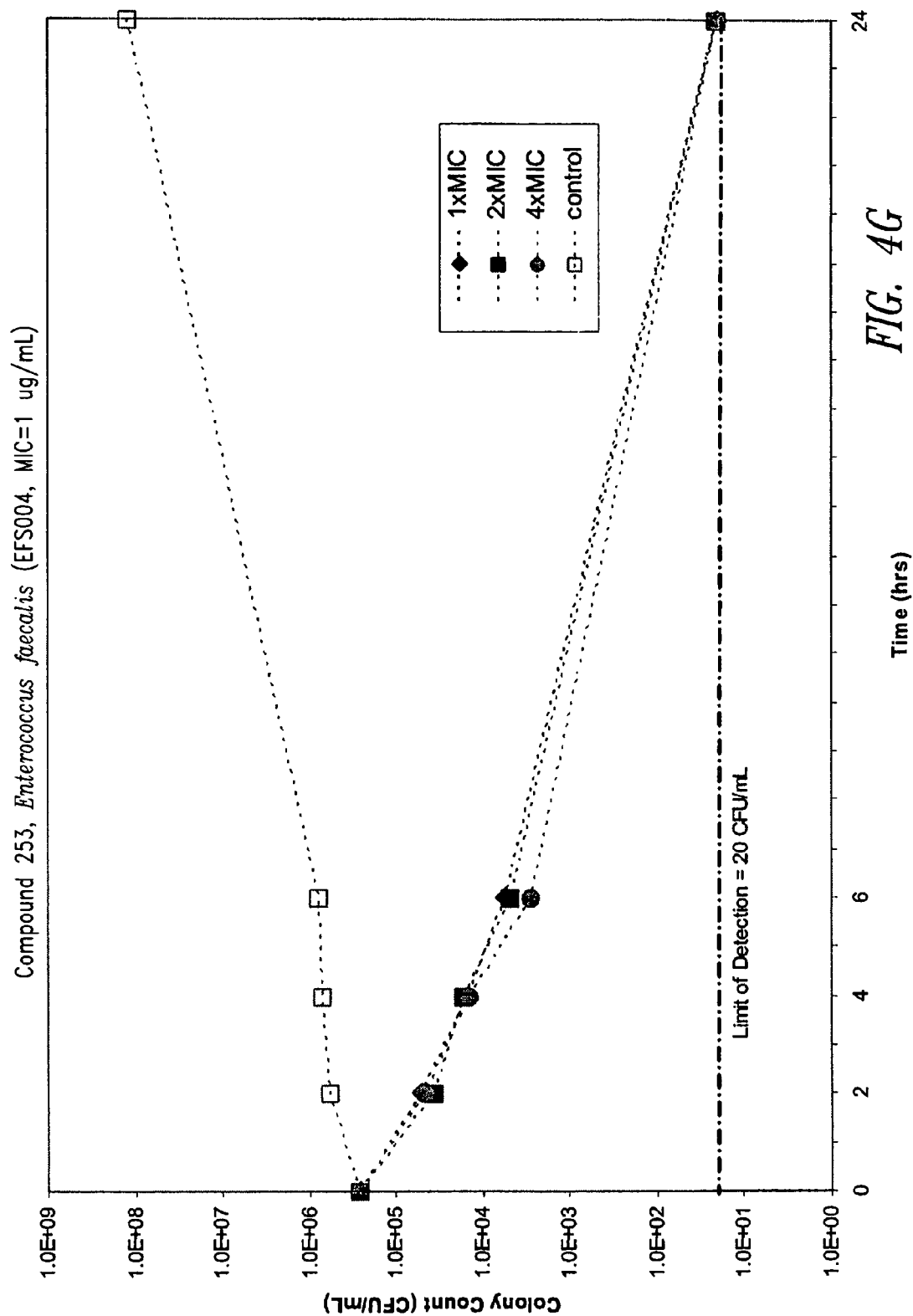
Figure 4H:
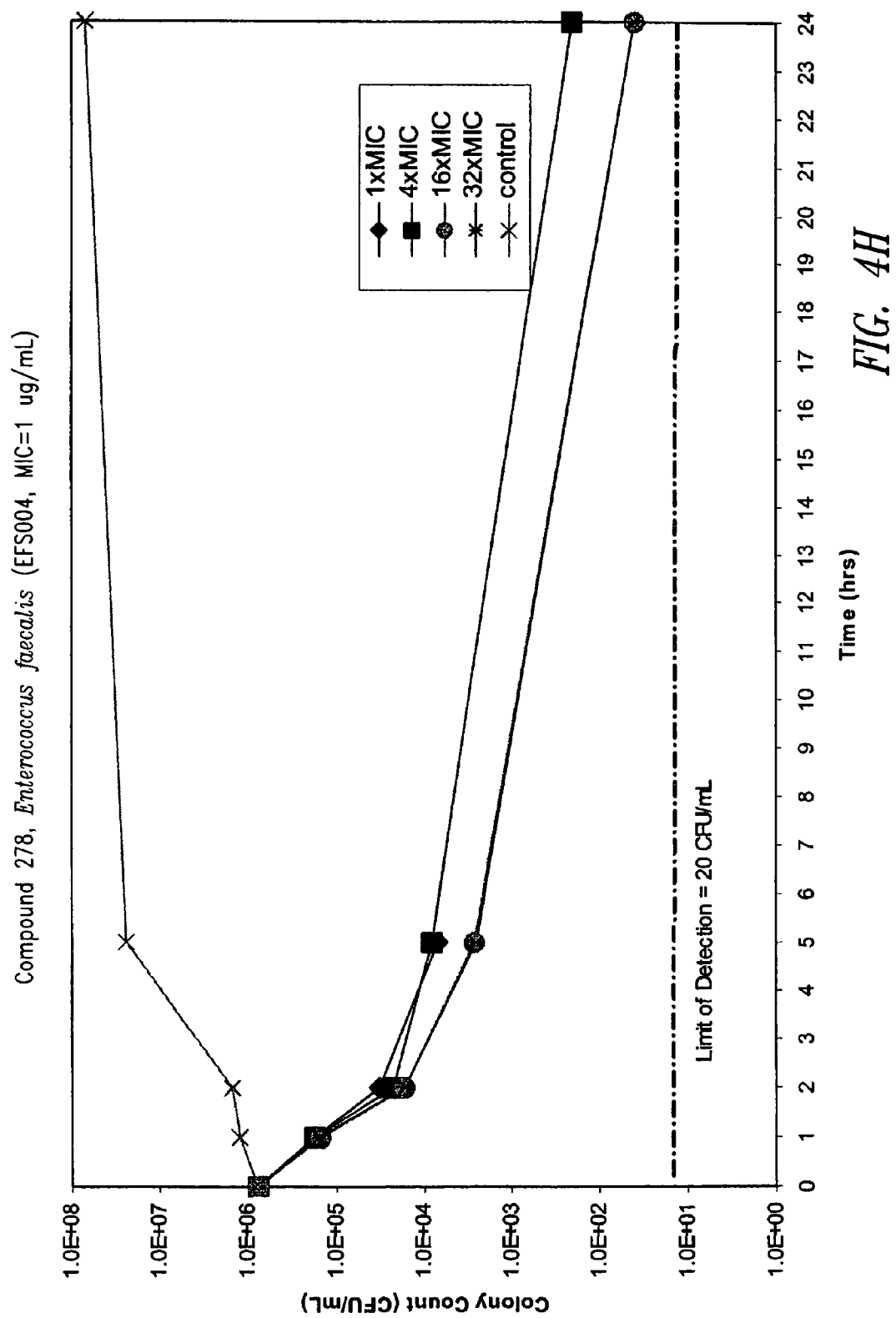
Figure 4I:
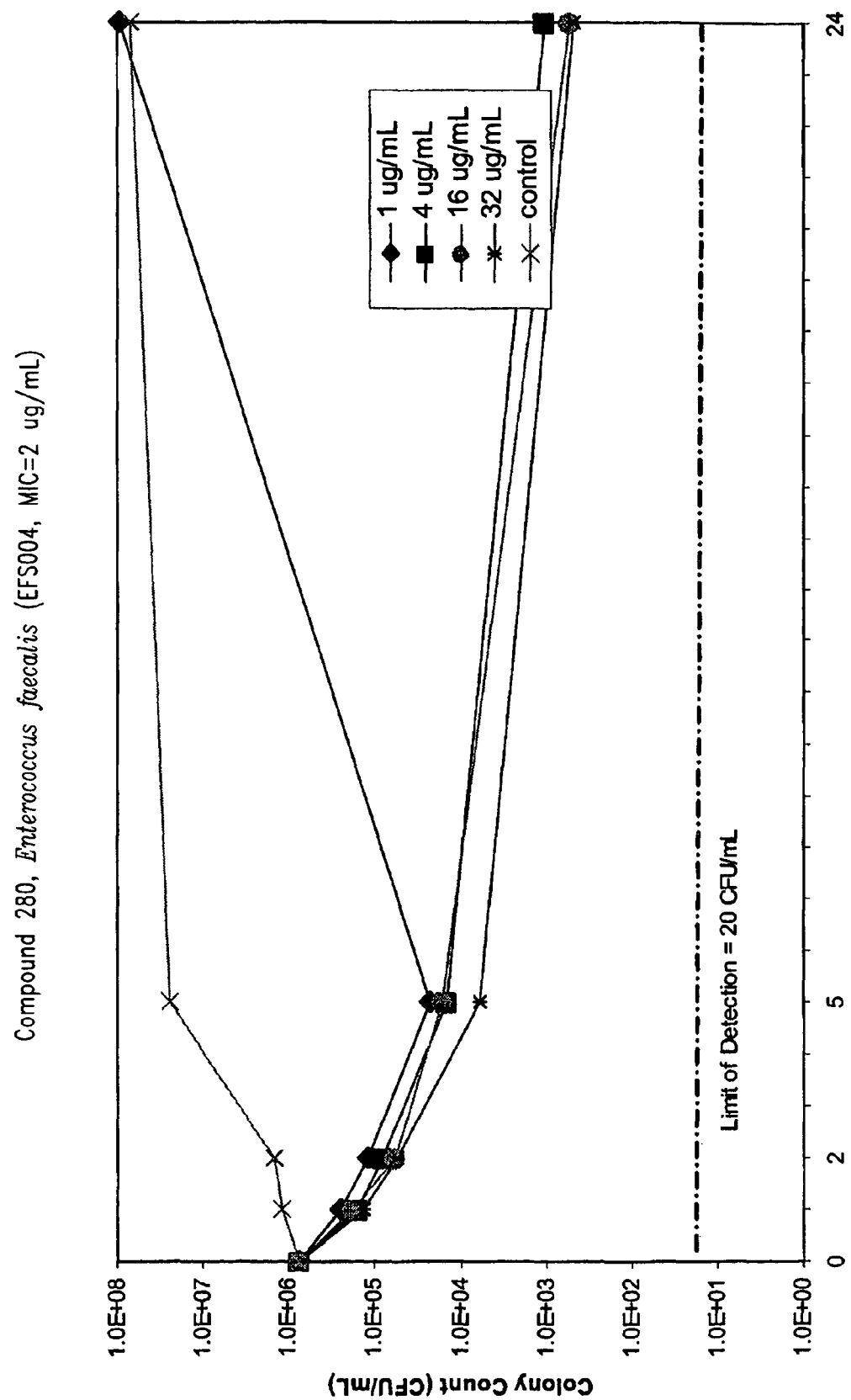
Figure 5A:
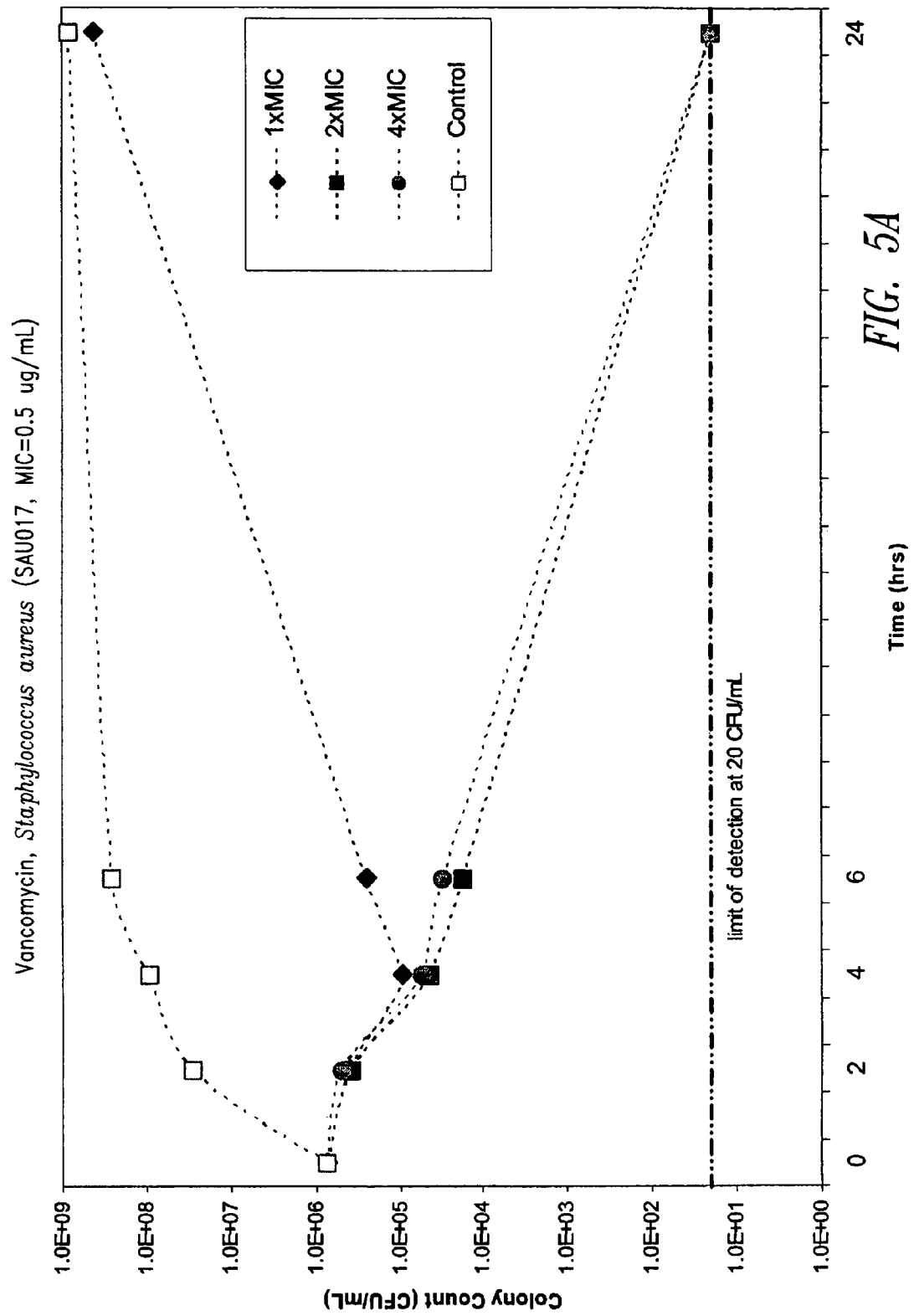
FIGS. 5A-5K show kill curves for various lipopeptide derivatives against *Staphylococcus aureus*.
Figure 5B:
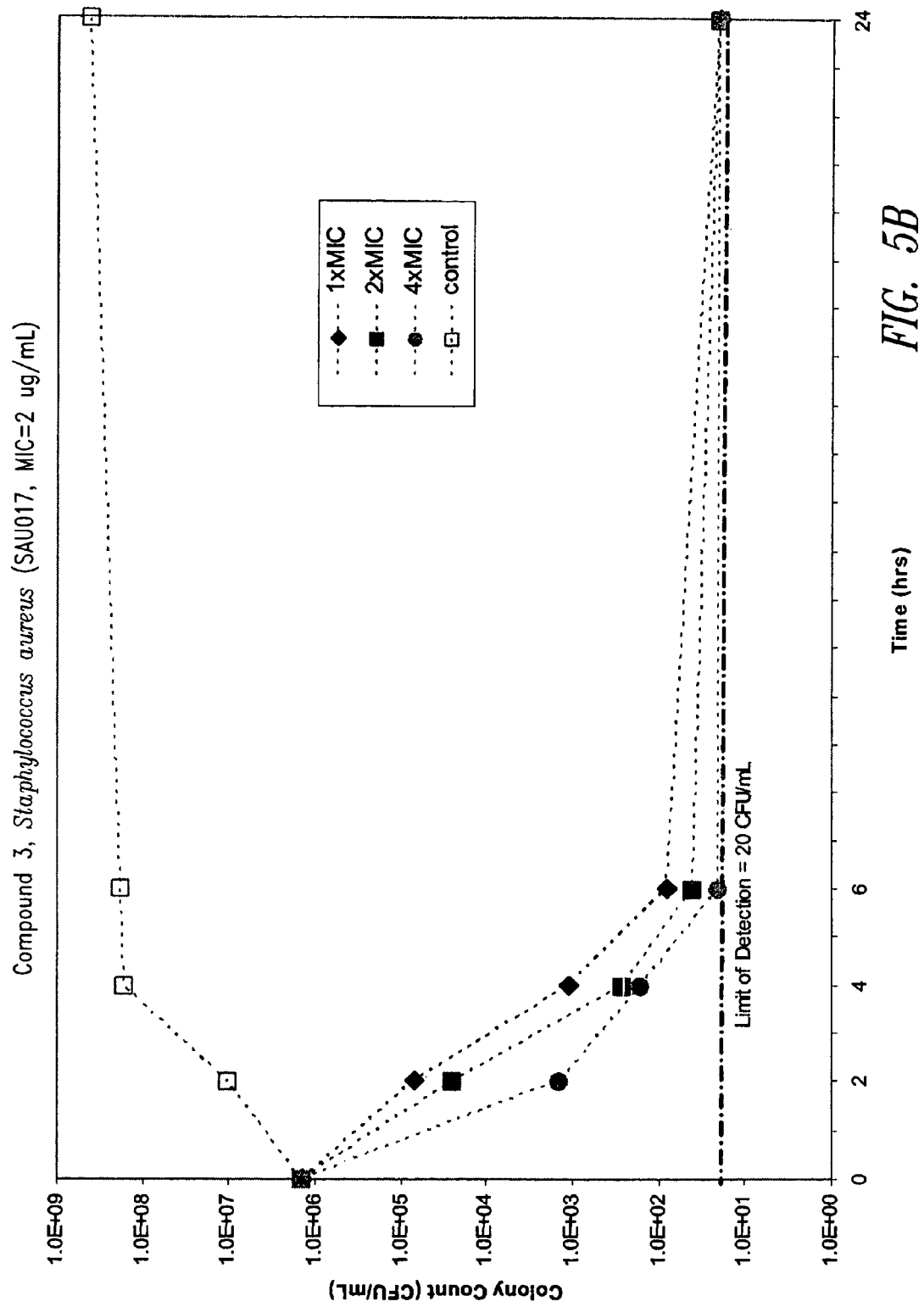
Figure 5C:
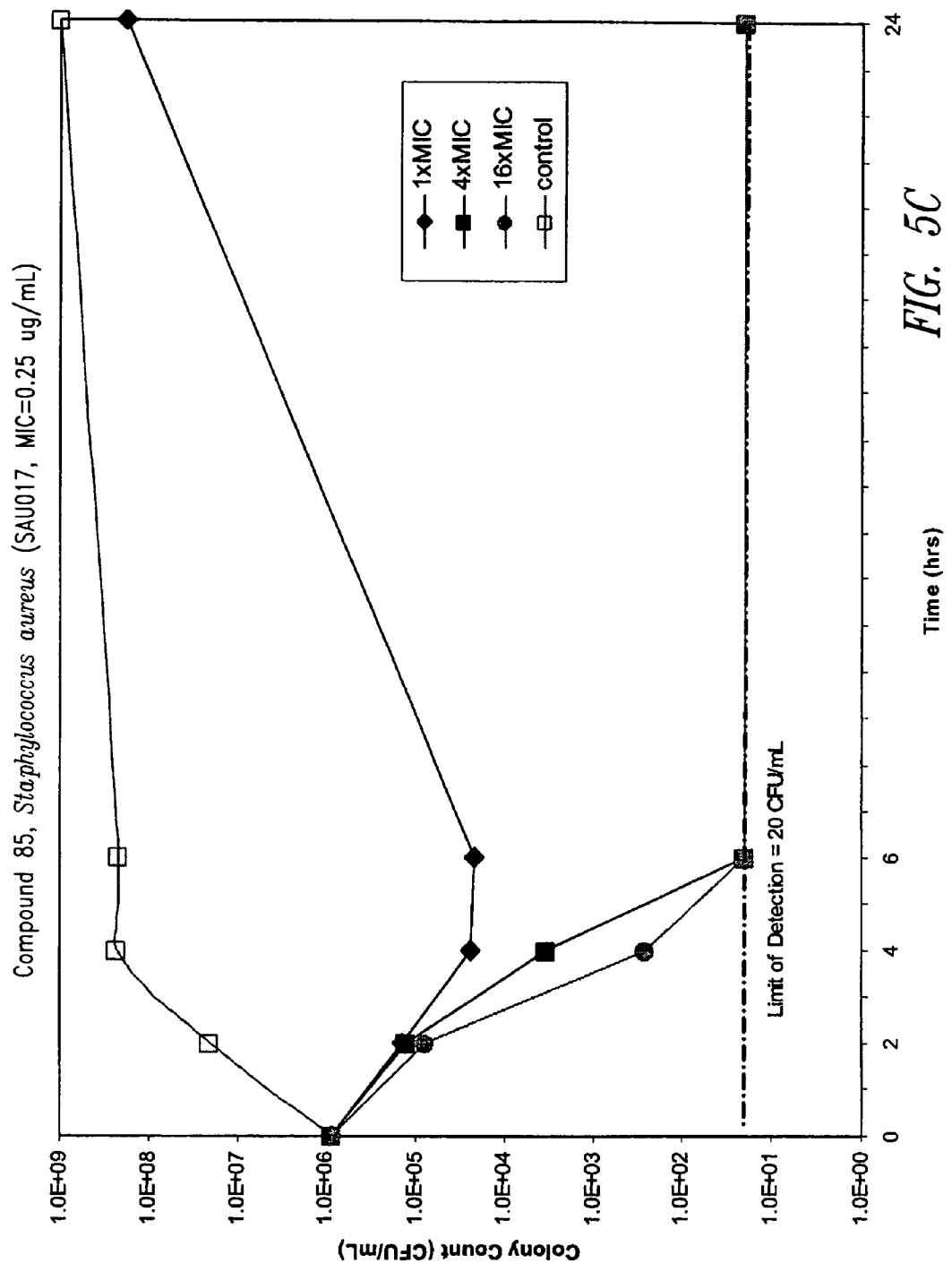
Figure 5D:
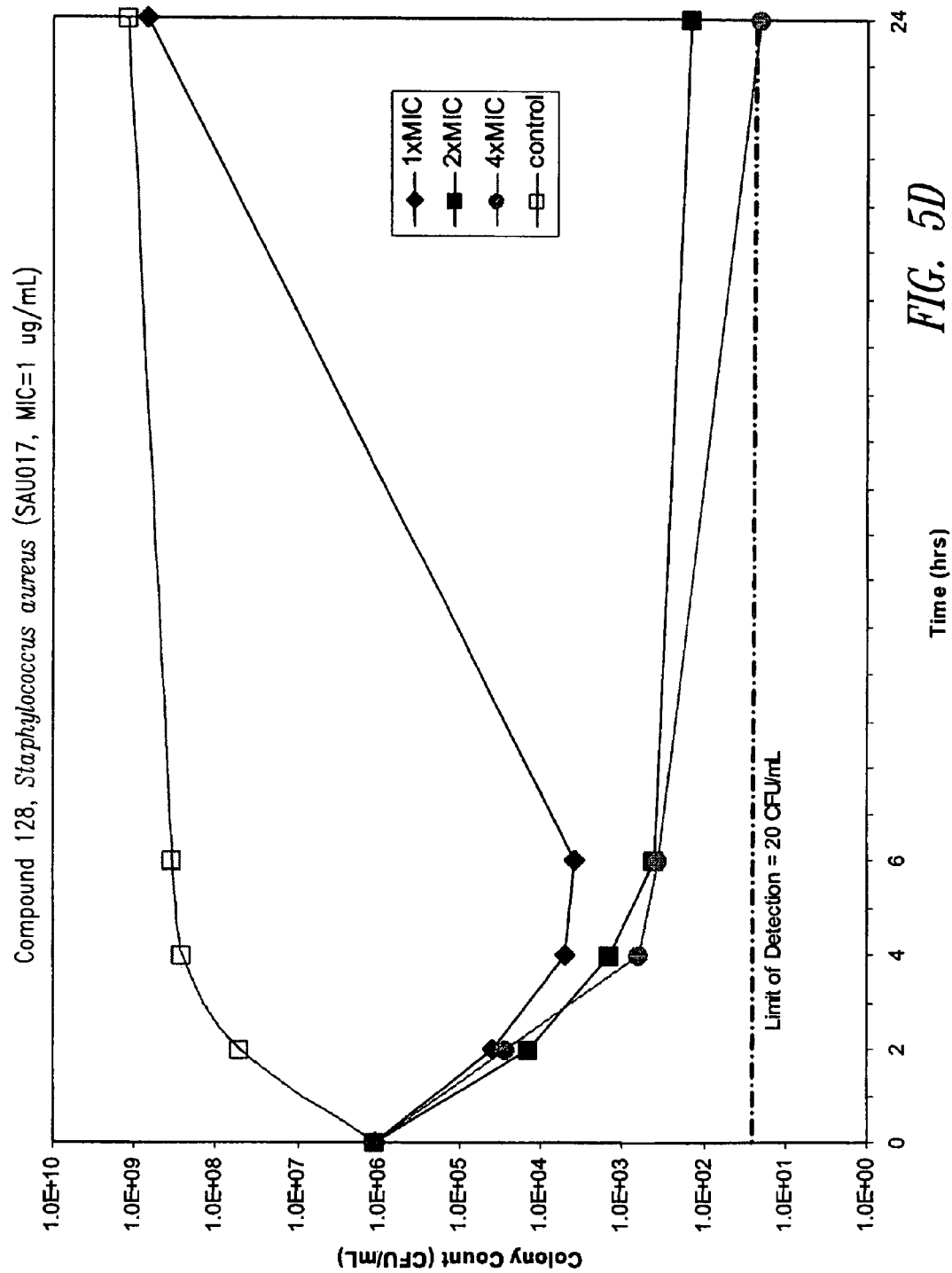
Figure 5E:
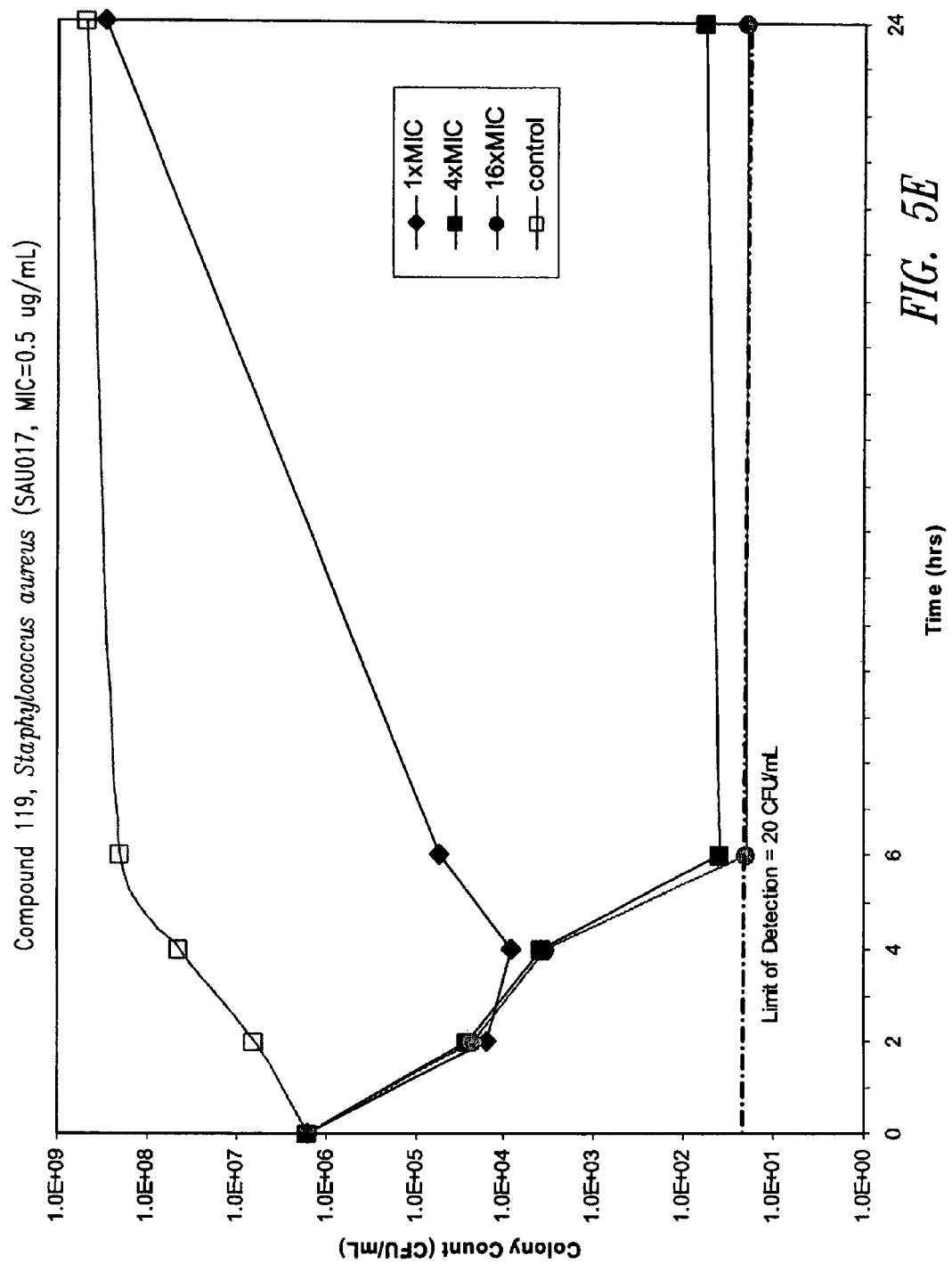
Figure 5F:
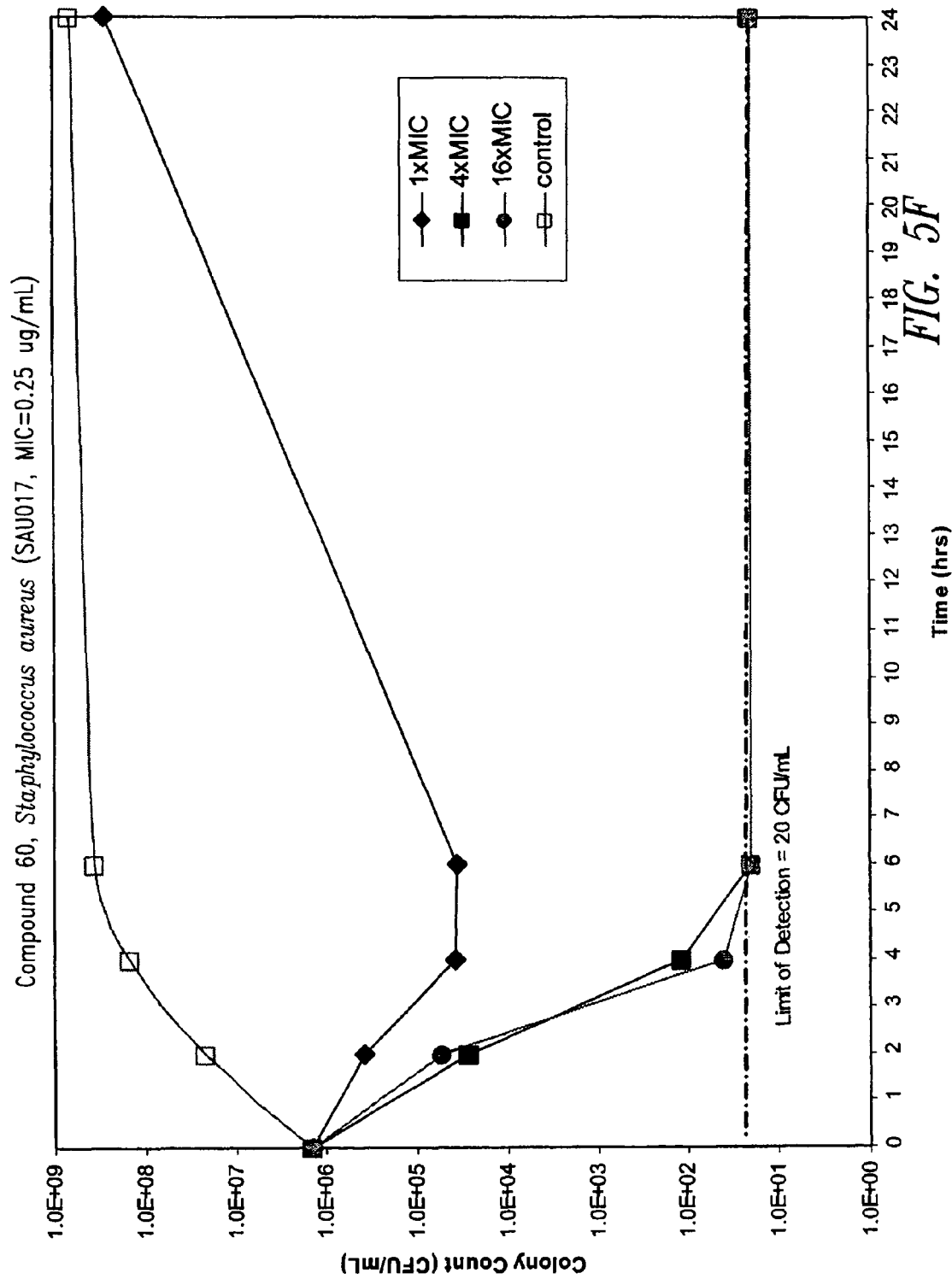
Figure 5G:
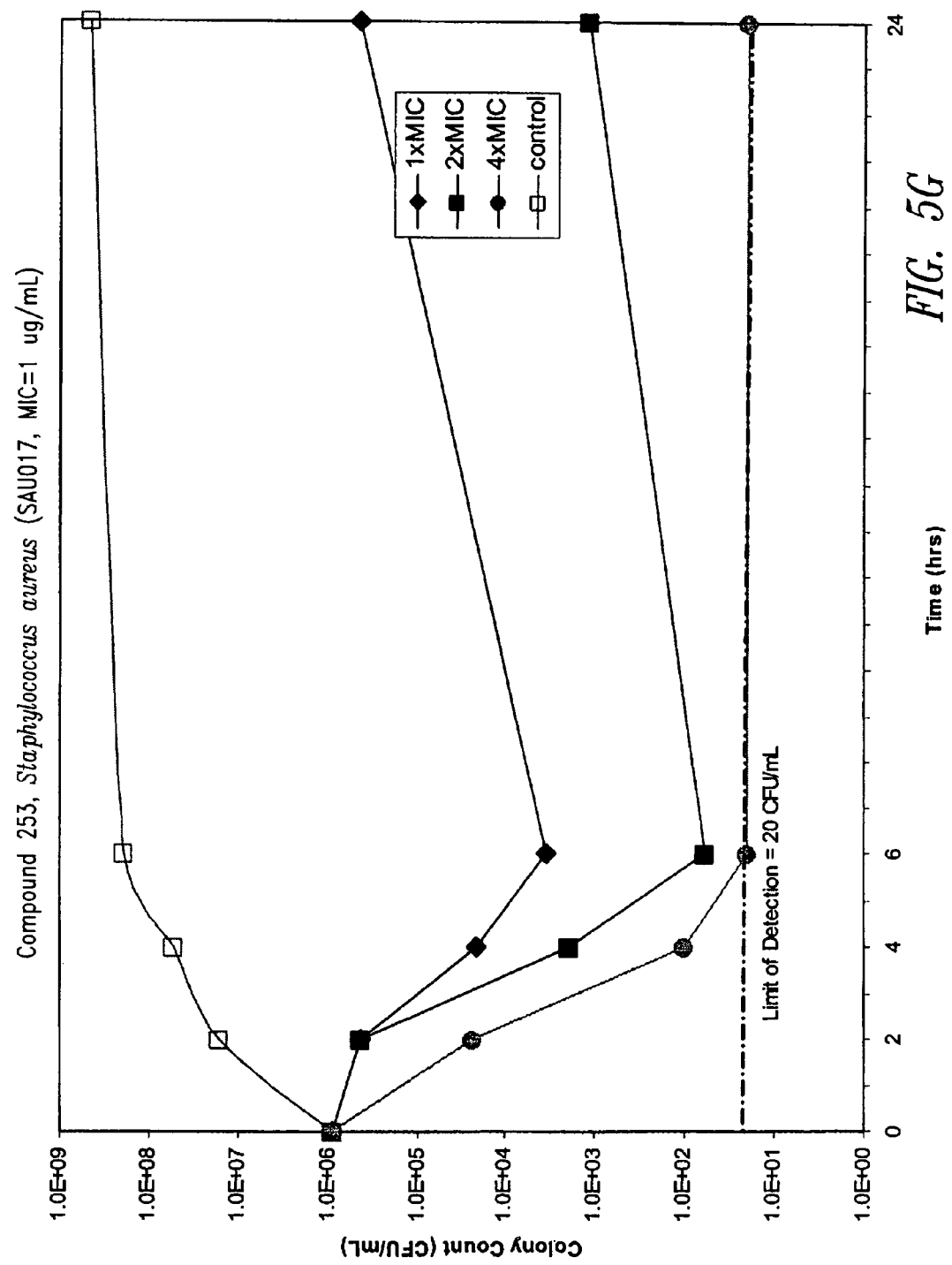
Figure 5H:
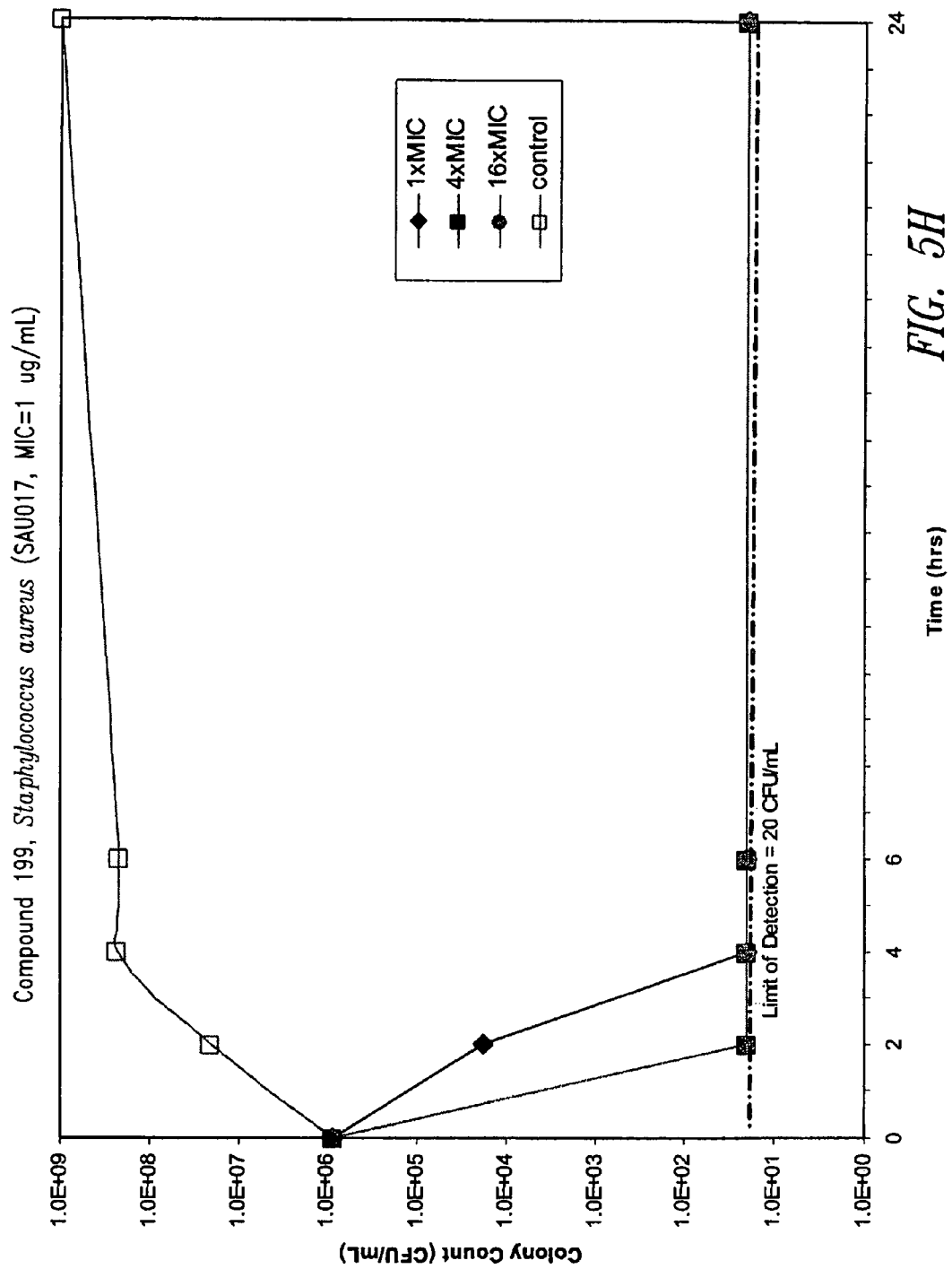
Figure 5I:
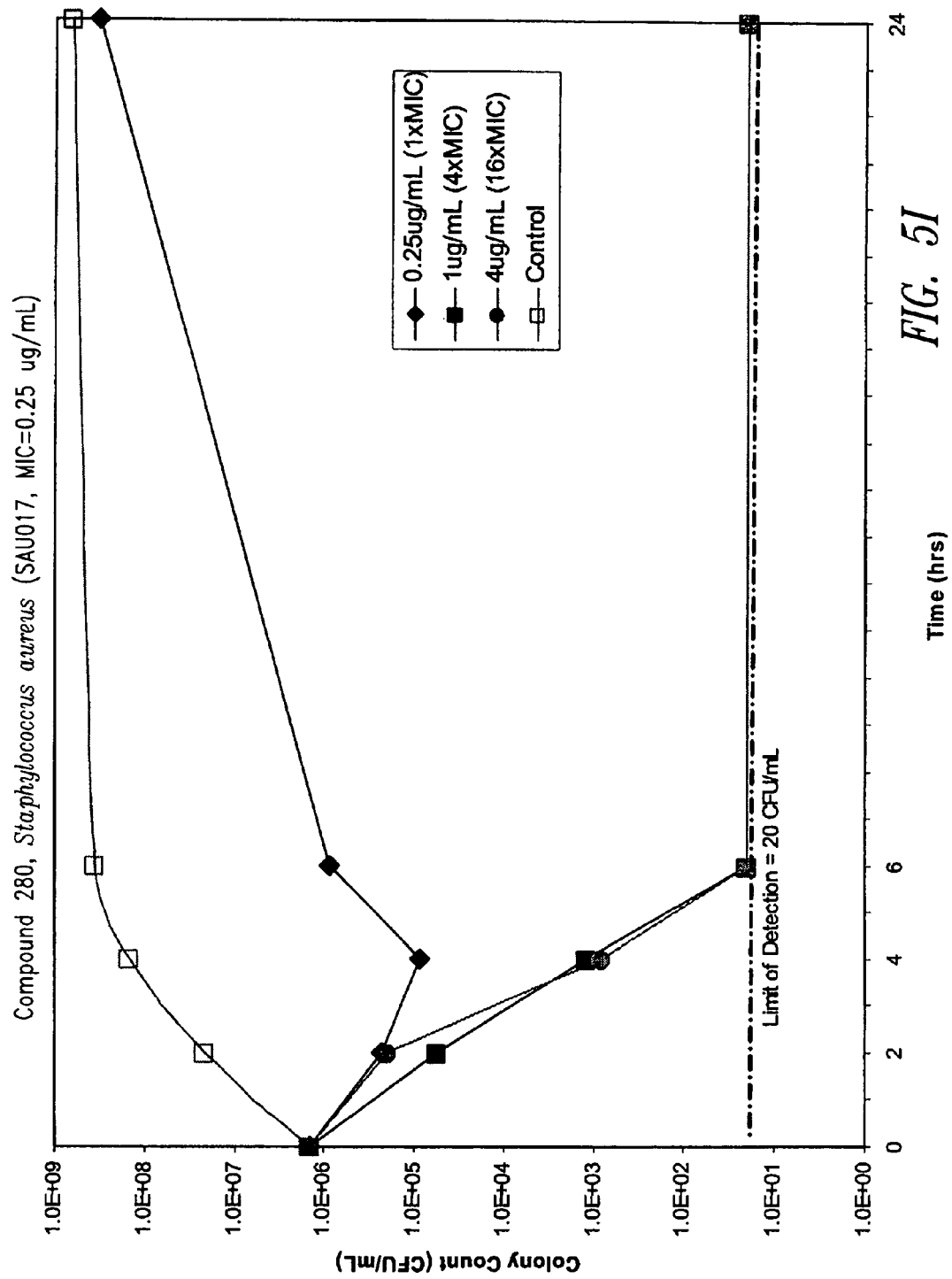
Figure 5J:
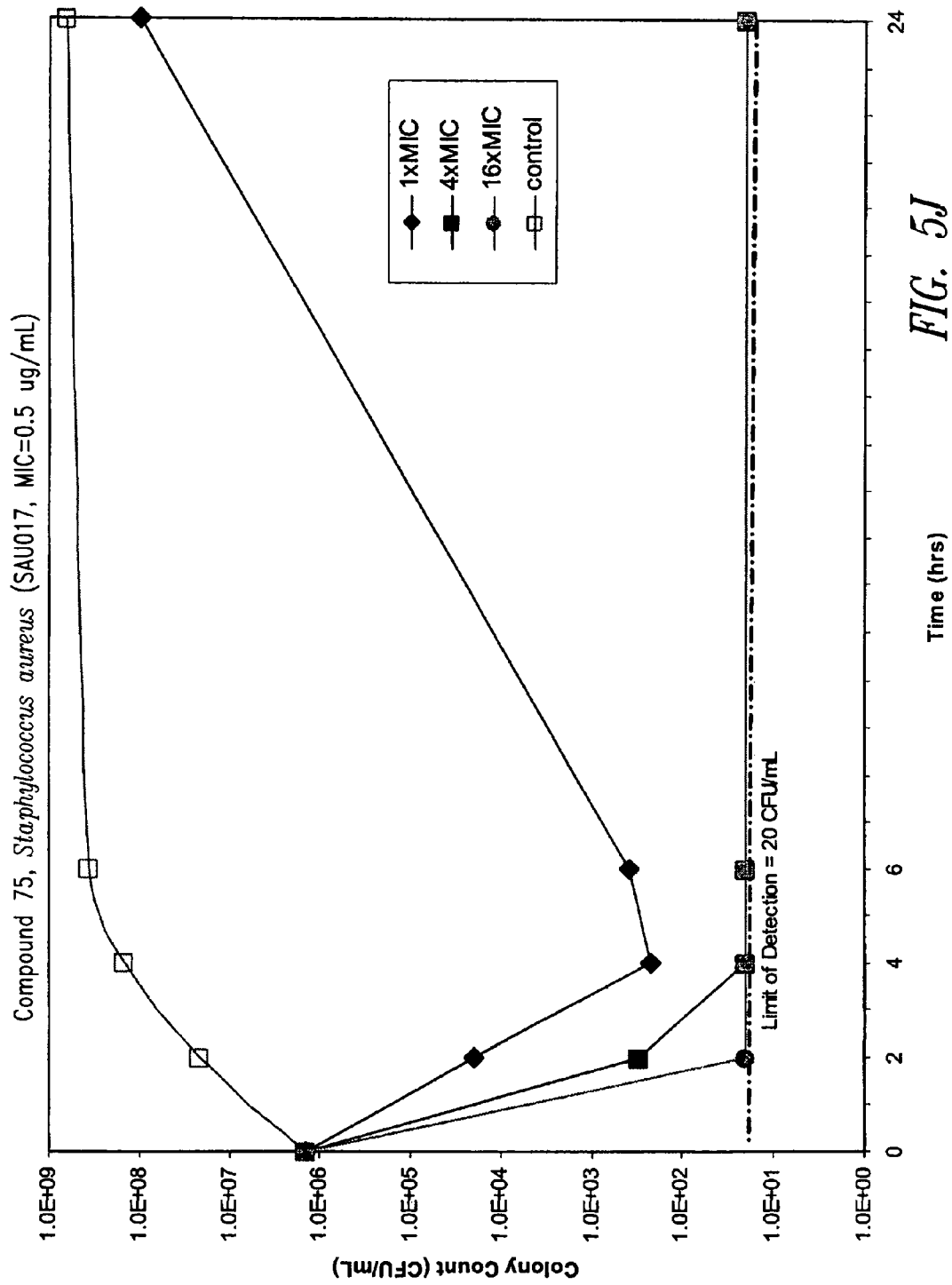
Figure 5K:
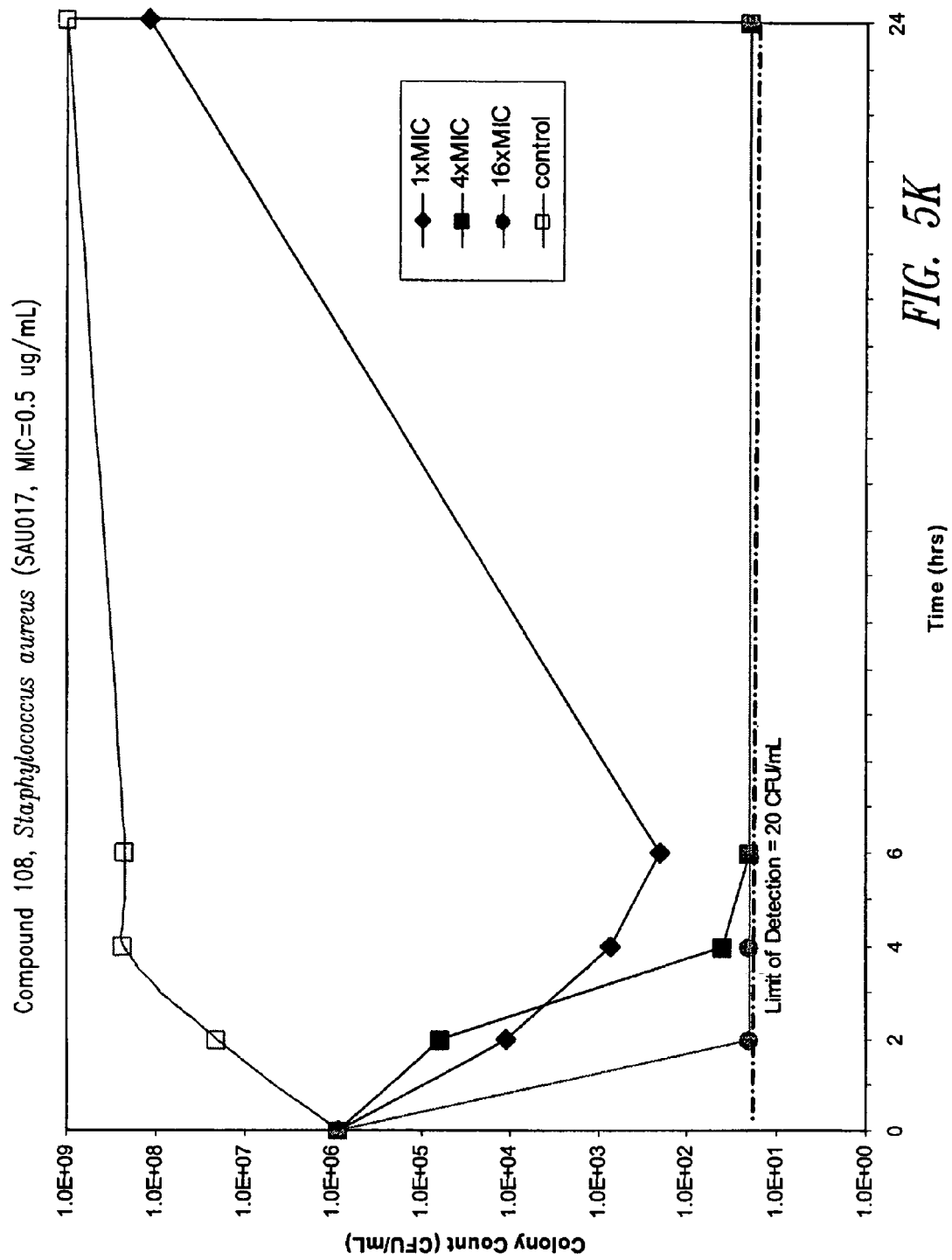

In contrast to vancomycin (see FIGS. 4A and 5A), which is generally bacteriostatic, the lipopeptide derivatives of the instant disclosure were all bactericidal within 24 hours against *Enterococcus faecalis* (FIG. 4) and *Staphylococcus aureus* (FIG. 5). For example, compounds 3, 85, 4, 128, 60, 119, 199, 147, 253, 278, and 280 were rapidly bactericidal, generally killing 99.9% of *Staphylococcus aureus* and/or *Enterococcus faecalis* bacteria within 6 hours (generally at concentrations within two (2) dilutions of the compound MIC). Some compounds (such as 108 and 75) were bactericidal within about 2 to about 4 hours. The lipopeptide antibiotic derivatives of the instant disclosure are highly bactericidal, which is one parameter of potential therapeutic effectiveness.

Example 378

Post-Antibiotic Effect of Lipopeptide Derivatives

Post Antibiotic Effect (PAE) experiments were performed with *Staphylococcus aureus* growing in log phase, which were exposed to varying concentrations (sub (0.5×) to supra (4×) multiples of the MIC) of a lipopeptide derivative for one (1) hour prior to removal of the drug. After removal of the lipopeptide compounds, bacterial titre was determined each hour to monitor bacterial re-growth. The PAE duration is defined as the difference in time required for antimicrobial exposed bacterial cells versus unexposed bacterial cells to achieve an increase of 1 $\log_{10}$ unit in CFU/mL.

TABLE 19

| | Post Antibiotic Effect (hours) | | | |
|---|---|---|---|---|
| Compound* | 0.5 × MIC | 1 × MIC | 2 × MIC | 4 × MIC |
| 4 | 0.6 | 0.7 | 1.9 | 3.0 |
| 147 | 1.6 | 1.6 | 1.9 | 1.0 |
| 278 | 1.5 | 2.6 | 2.2 | 3.2 |
| 280 | 2.5 | 1.5 | 1.9 | 2.4 |

*The MIC used for compounds 4 and 147 was 1 µg/mL, and for compounds 278 and 280 was 2 µg/mL.

Compounds 4, 147, 278 and 280 showed a long antibiotic effect varying from 0.6 hours (exposure at 0.5×MIC for one hour) to 3.2 hours (exposure at 4×MIC for one hour), many of which were dose dependent. The rapidly bactericidal properties and the long PAE shown for lipopeptide derivatives of the instant disclosure are an advantage over many known antibacterial compounds.

Example 379

In Vivo Half-Life of Lipopeptide Derivatives

A pharmacokinetic parameter that can be measured, and which aids in determining efficacy, after a single i.v. administration of an antimicrobial lipopeptide derivative of the instant disclosure is the systemic half-life of the compound. Briefly, test compounds were dissolved in a 5% mannitol solution (pH was then adjusted) to a concentration of 1 mg/mL (w/v). A single intravenous injection in the lateral caudal vein of Swiss CD1 mice (5 to 6 weeks old, female) or Sprague Dawley rats (male) was used to administer the lipopeptide derivative at a final dose of 10 mg/kg. At various time points (ranging from about 4 minutes to about 24 hours for mice, and 48 or 72 hours for rats) mice were sacrificed and blood was harvested. The concentration of lipopeptide derivative in ex vivo plasma was quantified using liquid chromatography (LC) with mass spectrometric detection (MS). As shown in Table 19, lipopeptide derivatives of the instant disclosure showed unusually long half-lives in mice and rats after i.v. administration.

TABLE 20

Half Life of Various Lipopeptide Derivative Compounds In Vivo

| | Cmpd* | | | | | | | | | | | |
|---|---|---|---|---|---|---|---|---|---|---|---|---|
| | 4 | 147 | 278 | 280 | 128 | 253 | 3 | 60 | 85 | 119 | 199 | 108 |
| Mice[†] | 45.1 | 481 | 447 | 345 | 11.9 | 309 | 399 | 248 | 310 | 253 | 371 | 273 |
| Rat[†] | 65.3 | 275 | 425 | 424 | | | | | | | | |

*Cmpd refers to "compound number".
[†]Values are in minutes; a similar acidic lipopeptide, daptomycin, has a half life of 54 minutes (subcutaneous administration at 10 mg/kg) to 108 minutes (i.p administration at 20 mg/kg) (see Safdar et al., Antimicrob. Agents Chemother. 48: 63, 2004; Louie et al., Antimicrob. Agents Chemother. 45: 845, 2001).

Example 380

In Vivo Mouse Model of Protection Against Infection

Antimicrobial lipopeptide derivatives of the instant invention were tested for antimicrobial activity against Gram-positive bacteria in an intraperitoneal (i.p.) murine model (i.e., bacteria were injected i.p. and lipopeptide compounds were administered intravenously (i.v.)). Mice were infected with *Staphylococcus aureus, Streptococcus pneumoniae*, or *Enterococcus faecalis*, which were prepared as follows: *S. aureus* Smith (SAU0017, ATCC 19636) were grown in culture overnight on trypticase soy broth, harvested and then resuspended in fresh media containing 5% mucin (Sigma Chemical Co.); *S. pneumoniae* (SPN 0032, ATCC 10813) were grown overnight on blood agar plates and re-suspended in 0.9% sterile saline; and *E. faecalis* EFS0040 (clinical isolate) were grown overnight in culture on blood heart infusion broth, washed and resuspended in 0.9% saline and mixed with equal volume of sterile fecal rat extract. Swiss CD1 mice were each infected i.p. with bacteria at the following doses: *S. aureus* at $10^6$ CFU/mouse; *S. pneumoniae* at $10^2$ CFU/mouse; or *E. faecalis* at $10^{7.5}$ CFU/mouse. Either immediately after infection (for *E. faecalis*) or two hours post-infection (for *S. aureus* and *S. pneumoniae*), mice were treated i.v. with one of the following compositions: (1) a lipopeptide derivative formulated in a 5% mannitol solution in a dose range of about 0.1 mg/kg to about 10 mg/kg; (2) the 5% mannitol vehicle alone at a dose volume of 10 mL/kg; or (3) a known patent lipopeptide antibiotic, such as amphomycin or aspartocin, or other antibiotic, such as vancomycin, at a similar dose as the lipopeptide derivative compounds. The mice were observed and deaths recorded for seven days post-treatment. The $ED_{50}$ for each compound was calculated using the method of Reed and Meunch (*Am. J. Hyg.* 27: 493, 1938). Surprisingly, several of these lipopeptide compounds showed activity equivalent or superior to parent compounds amphomycin or aspartocin. Furthermore, amphomycin is known in the art to be toxic (see Tisch et al., *Antibiotics Ann.* 55: 1011, 1954, showed amphomycin had an $LD_{50}$ of 177 mg/kg; see also Heinemann et al., *Antibiotics Chemother.* 3: 1239, 1953).

TABLE 21

Lipopeptide Derivative $ED_{50}$ (mg/kg)* in Mice

| Compound | S. aureus (SAU0017) | S. pneumoniae (SPN0032) | E. faecalis (EFS0040) |
|---|---|---|---|
| Vancomycin | 0.9-2.4 | 1.75 | 2 |
| Ampicillin | — | — | 4.2 |
| Amphomycin | 5.4 | 2.0 | — |
| Aspartocin | 5.4 | 0.65 | — |
| 4 | 6.2 | — | — |
| 147 | 6.5 | 0.65 | 0.8 |
| 278 | 7.1 | — | 5.3 |
| 280 | 6.5 | — | 2.1 |
| 128 | 6.2 | — | — |
| 253 | 4.8 | — | — |
| 3 | 4.9 | 1.3 | — |
| 60 | 10 | — | — |
| 85 | 6.5 | — | 5.7 |
| 119 | 7.6 | — | — |
| 199 | 8 | — | 3 |
| 108 | 6.5 | — | — |

*The results shown as a range reflects results from multiple experiments.

Example 381

In Vivo Lung Infection Model

Antimicrobial lipopeptide derivatives of the instant invention were tested for antimicrobial activity against Gram-positive bacteria in an intranasal (i.n.) murine lung infection model (i.e., bacteria were innoculated i.n. and lipopeptide compounds were administered i.v.). *Streptococcus pneumoniae* (SPN032, ATCC 1081) were grown on 5% sheep blood agar plates for 24 h at 37° C., harvested and then resuspended in 0.9% saline. A group of eight Swiss CD1 mice were sedated with 2% isoflurane, and each was infected i.n. dropwise to the nares with 50 µl of the prepared bacterial inoculum (i.e., a dose of about $10^6$ CFU/mouse). At three, 24 and 48 hours post-infection, the groups of mice received i.v. (1) a lipopeptide derivative formulated in a 5% D-mannitol solution at a dose of about 0.3 mg/kg, 1 mg/kg, 3 mg/kg, or 10 mg/kg; (2) the 5% mannitol vehicle alone at a dose volume of 10 mL/kg; or (3) a known antibiotic, such as vancomycin, at a similar dose as the lipopeptide compounds. The mice were observed and deaths recorded for ten days post-treatment. The $ED_{50}$ (mg/kg) for each compound was calculated using the method of Reed and Meunch (*Am. J. Hyg.* 27: 493, 1938). As shown in Table 22, representative compounds 4, 147, 278, and 280 displayed quite effective $ED_{50}$ values in the range of about 1.0 mg/kg to about 2.5 mg/kg after i.v. administration.

TABLE 22

Lung (Pneumonia-Like) Infection with *S. pneumoniae*

| Compound | $ED_{50}$ (mg/kg)* |
|---|---|
| Vancomycin | 3.0-4.3 |
| 4 | 1.3 |
| 147 | 2.3 |
| 278 | 2.2 |
| 280 | 1.8 |

*The results shown as a range reflects results from multiple experiments.

Example 382

In Vivo Lung Infection Model in Neutropenic Mice

Antimicrobial lipopeptide derivatives of the instant invention were tested for antimicrobial activity against Gram-positive bacteria in an intranasal (i.n.), immunocomprimised murine lung infection model (i.e., bacteria were innoculated i.n. and lipopeptide compounds were administered i.v.). *Streptococcus pneumoniae* (SPN0002) were grown on 5% sheep blood agar plates for 24 h at 37° C., harvested and then resuspended in 0.9% saline. A group of three to four Swiss CD1 mice were rendered neutropenic by administration of cyclophosphamide (Sigma Chemical Co.; 150 mg/kg, i.p.) on day −4 and −1 before infection. At time −18 to −24 hours, each mouse was infected i.n. dropwise via the nares with 50 µl of the prepared bacterial inoculum (i.e., a dose of about $5 \times 10^6$ CFU/mouse). At 18 to 24 hours post-infection, the groups of mice received i.v. (1) a lipopeptide derivative formulated in a 5% D-mannitol solution at a dose of about 1 mg/kg, 3 mg/kg, 10 mg/kg, or 30 mg/kg; (2) the 5% mannitol vehicle alone at a dose volume of 10 mL/kg; or (3) a known antibiotic, such as ampicillin, at a similar dose as the lipopeptide compounds. At 18 to 24 hours post-antibiotic treatment, mice were sacrificed and lungs harvested. Lungs were sampled by spreading homogenates on blood agar plates and incubating for 24 h at 37° C., and then counting the number of CFU. The $E_{Kill}$ (killing effect; i.e., $\log_{10}$ CFU/lung reduction as compared to CFU count at intial treatment time) and the $E_{Max}$ (maximum reduction effect; i.e., $\log_{10}$ CFU/lung reduction as compared to CFU count of control at 24 hours) for each compound was calculated.

When administered at 18 to 24 h post-infection, the lipopeptide derivatives showed a dose-dependent antimicrobial effect as measured by a decrease in CFU in the lungs of treated mice as compared to untreated mice. At the highest dose level (30 mg/kg), for example, compound 147 showed a 4.0 $\log_{10}$ CFU/lung reduction (P<0.001), while ampicillin showed a comparable 2.58 $\log_{10}$ CFU/lung reduction. The $E_{Kill}$ for these compounds was a 3.2 and 1.8 $\log_{10}$ CFU/lung reduction, respectively. Hence, this example and Example 381 show that the lipopeptide antibiotic derivatives of the instant disclosure may be therapeutically effective against an acute lung infection, such as pneumonia.

Example 383

In Vivo Localized Tissue Infection Model in Neutropenic Mice

Antimicrobial lipopeptide derivatives of the instant invention were tested for antimicrobial activity against Gram-positive bacteria in an intramuscular (i.m.) murine thigh infection model (i.e., bacteria were injected i.m. and lipopeptide compounds were administered i.v.). *Staphylococcus aureus* (SAU0017) were grown on 5% sheep blood agar plates for 24 h at 37° C., harvested and then resuspended in 0.9% saline. A group of three to four Swiss CD1 mice were rendered neutropenic by administration of cyclophosphamide (Sigma Chemical Co.; 150 mg/kg, i.p.) on day −4 and −1 before infection. On day 0, an overnight broth culture of *S. aureus* Smith (SAU0017, ATCC 19636) in trypticase soy broth was used to inoculate animals by i.m. injection into each thigh ($10^5$ CFU/thigh). At two hours post-infection, the groups of mice received i.v. (1) a lipopeptide derivative formulated in a 5% mannitol solution in a dose range of about 1 mg/kg to about 80 mg/kg; (2) the 5% mannitol vehicle alone at a dose volume of 10 ml/kg; or (3) a known antibiotic, such as vancomycin, at a similar dose-range as the lipopeptide compounds. At 24 hours post-antibiotic treatment, mice were sacrificed and thighs harvested. The thighs were sampled by spreading homogenates on blood agar plates and incubating for 24 h at 37° C., and then counting the number of CFU. The $ED_{50}$ and $E_{Max}$ were determined using a nonlinear regression technique. The dose of antibiotic that achieves a bacteriostatic effect in the thigh over 24 hours was estimated from an additional equation. $E_{kill}$ was calculated as a difference between counts at treatment initiation and 24 hours after treatment (corresponding to a computational max effect).

TABLE 23

Thigh Infection with *S. aureus*

| Compound | $ED_{50}$ (mg/kg) |
|---|---|
| Vancomycin | 0.9-1.6 |
| 3 | 6.1 |
| 4 | 4.9-6.9 |
| 128 | 7.6 |
| 147 | 1.1-1.8 |
| 278 | 6.4 |
| 280 | 5.3 |

*The results shown as a range reflects results from multiple experiments.

As shown in Table 23, representative compounds 3, 4, 128, 147, 278, and 280 displayed $ED_{50}$ values in the range of about 1 mg/kg to about 8 mg/kg. In this same experiment, those same representative compounds displayed a maximum effect (log reduction of bacterial counts in infected tissues at 24 hours post treatment) in the range of about −2.8 logs to about −4.9 logs, with a typical static dose (dose required to produce a bacteriostatic effect in infected tissues at 24 hours) in the range of about 1 mg/kg to about 11 mg/kg. Hence, this example shows that the lipopeptide antibiotic derivatives of the instant disclosure may be therapeutically effective against acute localized infections.

Example 384

In Vivo Combined Lung and Thigh Muscle Infection Model

Antimicrobial lipopeptide derivatives of the instant invention were tested for antimicrobial activity against Gram-positive bacteria in a combination i.m./i.n. murine thigh/lung infection model (i.e., bacteria were administered i.m. and i.n., and lipopeptide compounds were administered i.v.). *Streptococcus pneumoniae* (SPN0032, ATCC 10813) were grown on 5% sheep blood agar plates for 24 h at 37° C., harvested and then resuspended in 0.9% saline. A group of three to four Swiss CD1 mice were sedated with 2% isoflurane, and each was infected i.n. dropwise to the nares with 50 μl of the prepared bacterial inoculum (i.e., a dose of about $10^6$ CFU/mouse). Immediately after i.n. inoculation, the mice were each injected i.m. in each thigh with 0.1 ml of a prepared bacterial inoculum (i.e., a dose of about $10^5$ CFU/mouse). At four hours post-infection, the groups of mice received i.v. (1) a lipopeptide derivative formulated in a 5% mannitol solution at a dose of about 0.16 mg/kg, 0.32 mg/kg, 0.63 mg/kg, 1.25 mg/kg, 2.5 mg/kg, 5 mg/kg, or 10 mg/kg; (2) the 5% mannitol vehicle alone at a dose volume of 10 ml/kg; or (3) a known lipopeptide antibiotic, such as vancomycin, at a similar dose as the test compounds. At 24 hours post-antibiotic treatment, mice were sacrificed, and thighs and lungs harvested. The thighs and lungs were sampled by spreading homogenates on blood agar plates and incubating for 24 h at 37° C., and then counting the number of CFU. The $ED_{50}$ and $E_{Max}$ were determined using a nonlinear regression technique. The dose of antibiotic that achieves a bacteriostatic effect in the thigh over 24 hours was estimated from an additional equation. $E_{kill}$ was calculated as a difference between counts at treatment initiation and at 24 hours after treatment (corresponding to a computational max effect).

In the combined murine model of lung and thigh muscle tissue infection, with *Steptococcus pneumoniae*, representative compounds 147, 278, and 280 displayed $ED_{50}$ values in the range of about 0.25 mg/kg to about 1.5 mg/kg for lung tissue, and $ED_{50}$ values in the range of about 1 mg/kg to about 2 mg/kg for thigh muscle tissue. In this same experiment, for lung tissue, those same representative compounds displayed a maximum effect in a range of about −3.6 logs to about −4.4 logs, with a typical static dose in the range of about 0.4 mg/kg to about 1.5 mg/kg. Also, in this same experiment, for thigh muscle tissue, those same representative compounds displayed a maximum effect in a range of about −5.4 logs to about −6 logs, with a typical static dose in a range of about 1 mg/kg to 2 mg/kg. Hence, this example shows that the lipopeptide antibiotic derivatives of the instant disclosure may be therapeutically effective against acute systemic infections, such as bacteremia.

43. The method according to claim 42 wherein the compound is
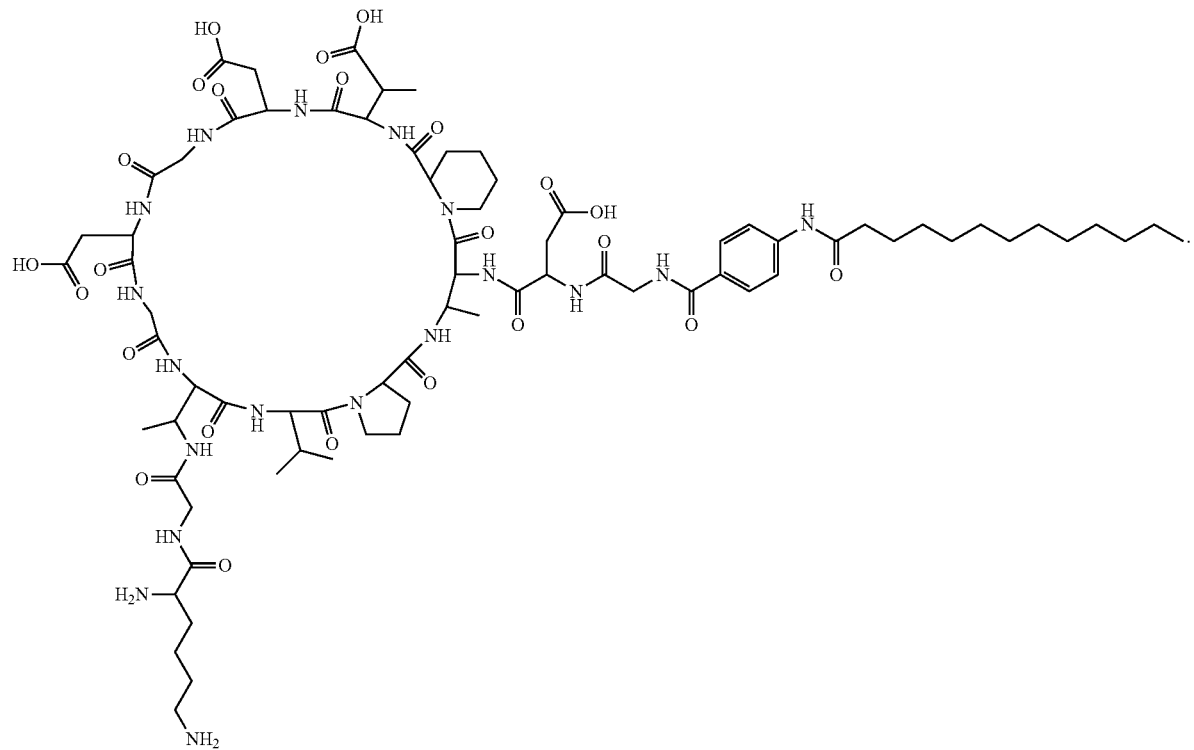
44. The method according to claim 42 wherein the compound is
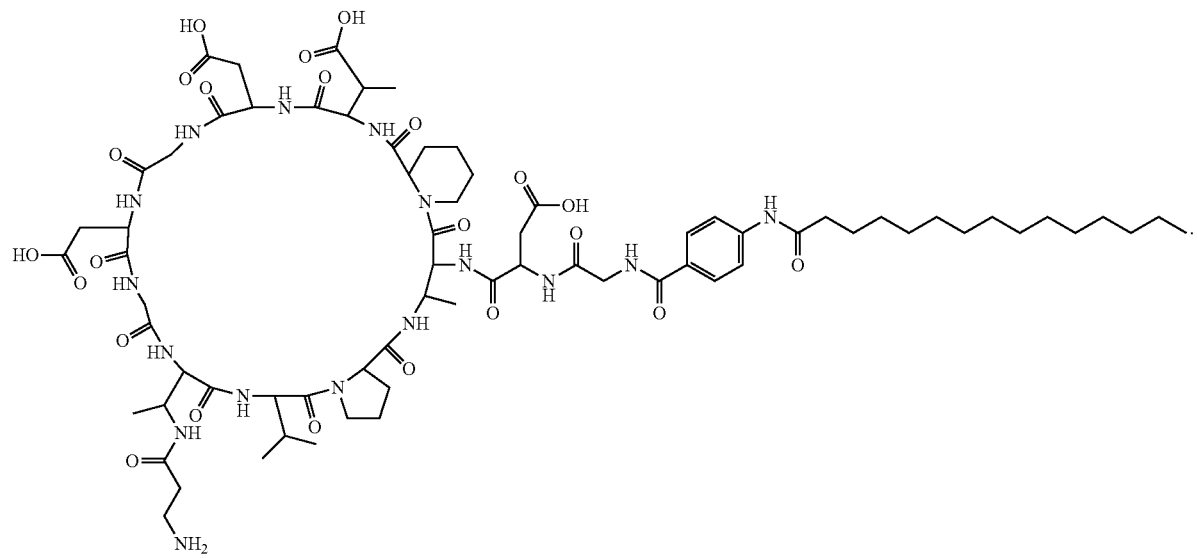

45. The method according to claim 42 wherein the compound is
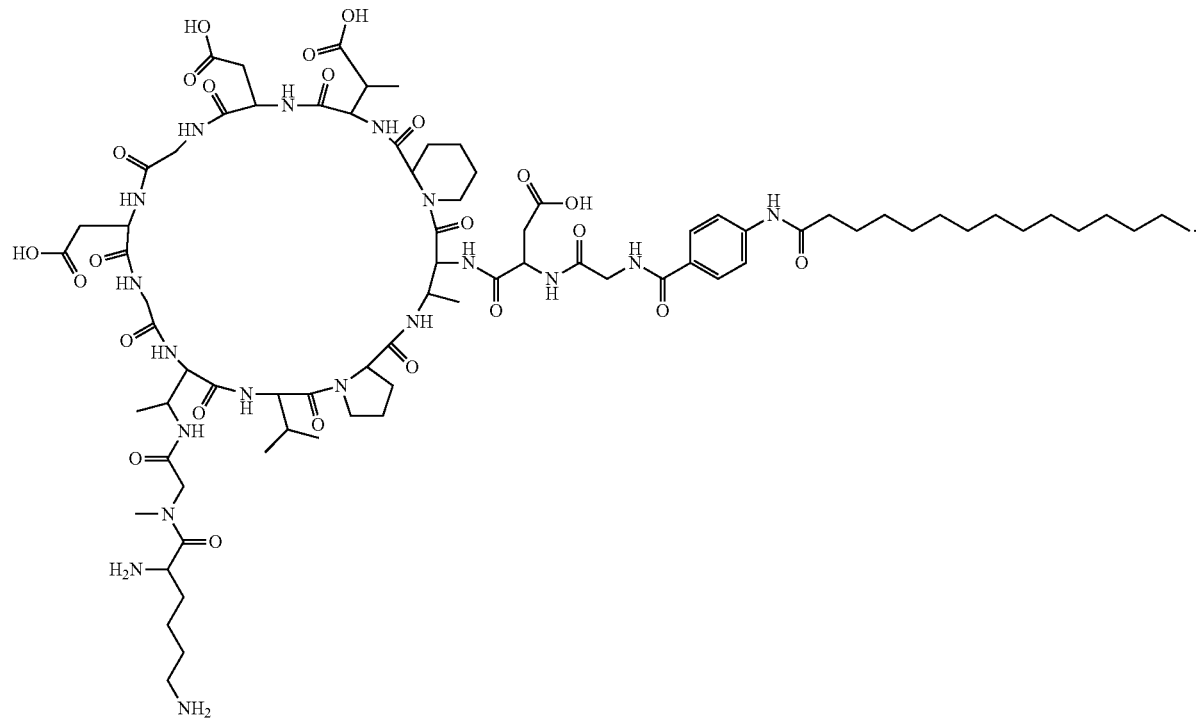
46. The method according to claim 42 wherein the compound is
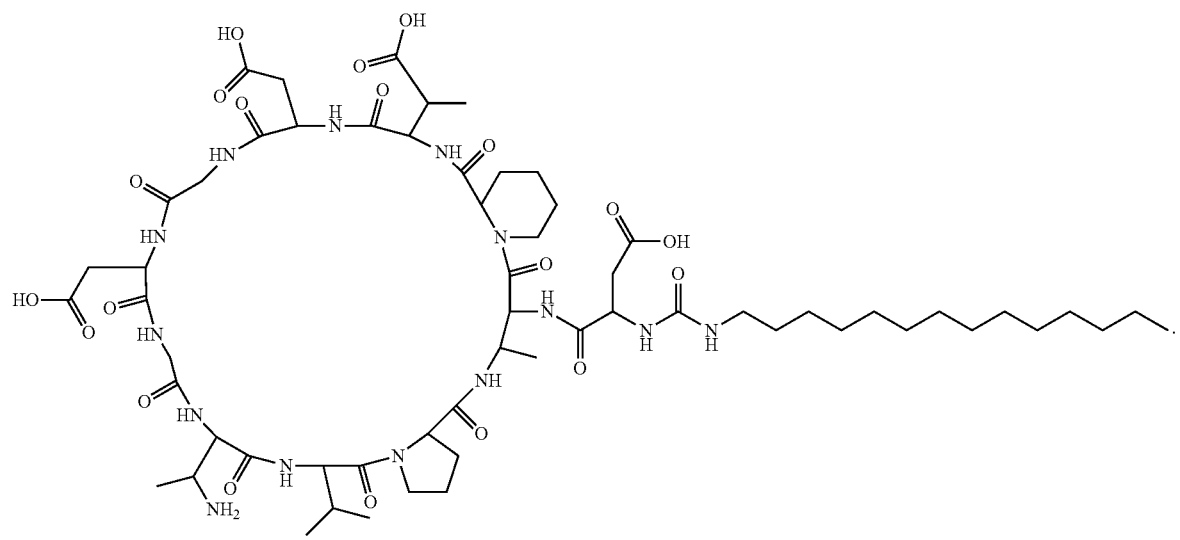

47. The method according to claim 42 wherein the compound is
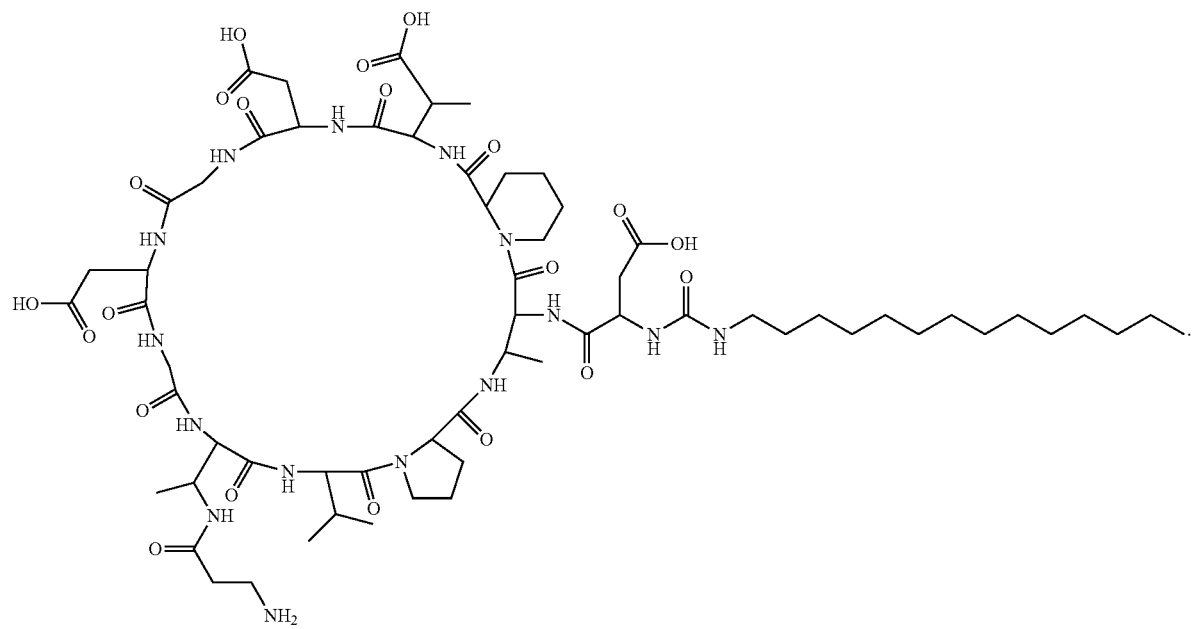
48. A compound and pharmaceutically acceptable salts thereof, wherein the compound is
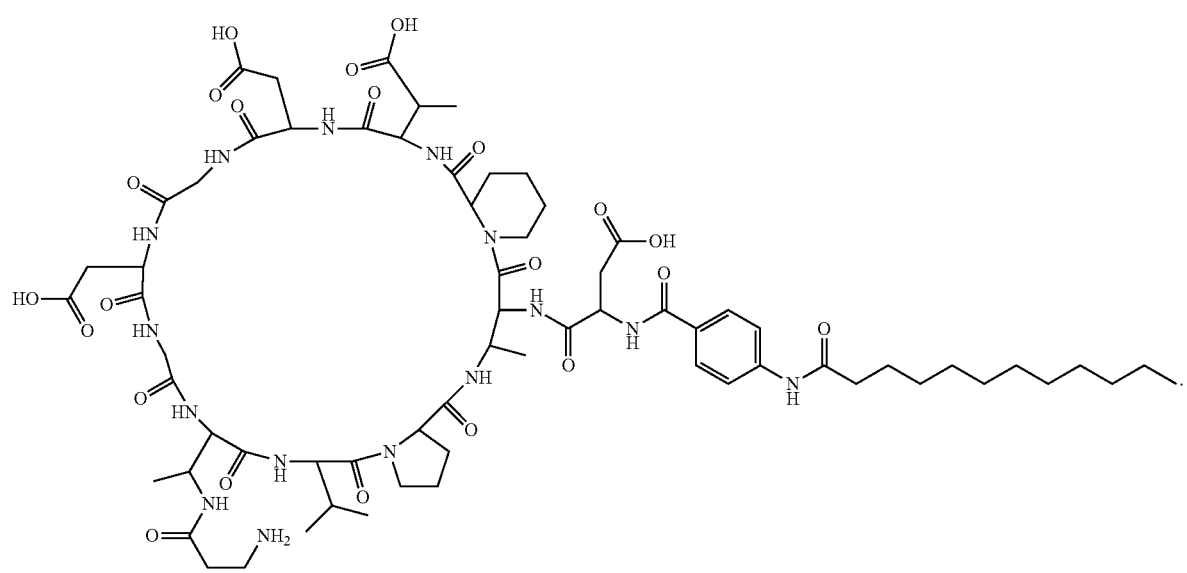

49. The method according to claim 42, wherein the compound is
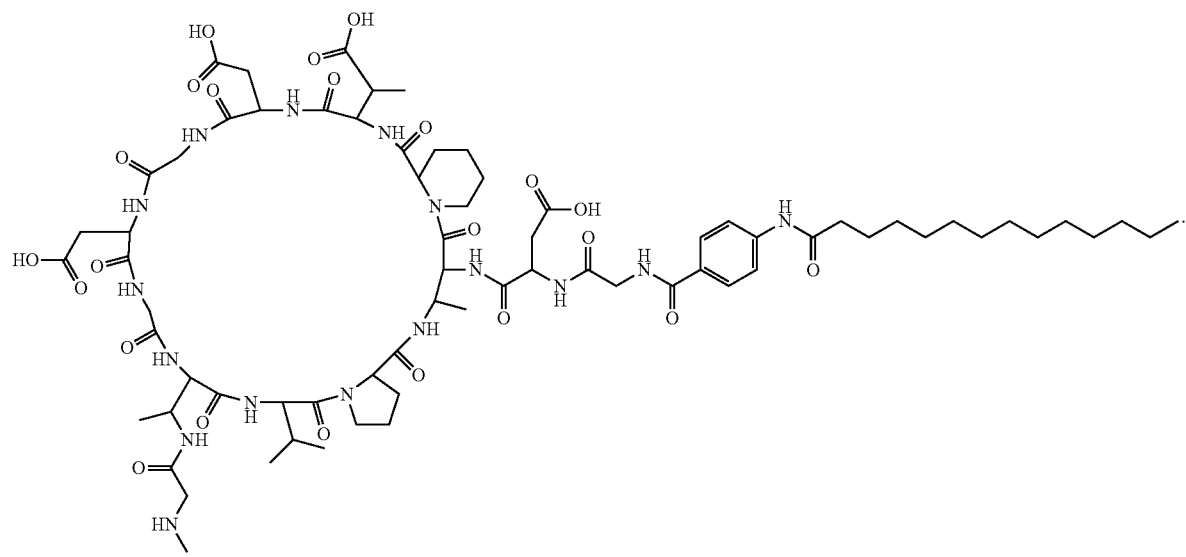

The invention claimed is:

1. A compound and pharmaceutically acceptable salts thereof, according to structural formula (II):

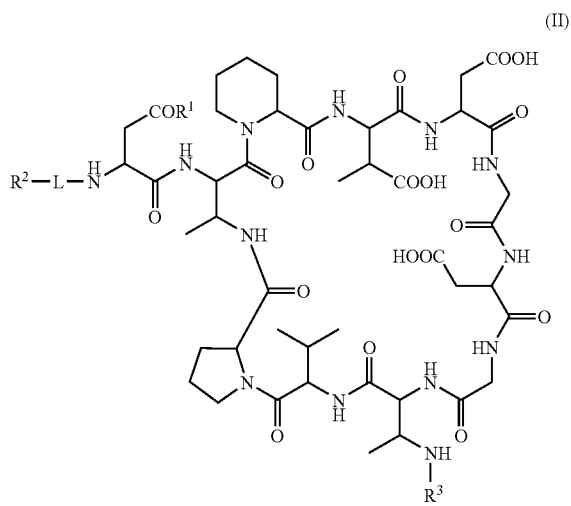

wherein:

$R^1$ is OH or $NH_2$;

L is selected from at least one amino acid, at least one substituted amino acid, and —O-PhC(=O)—;

$R^2$ is selected from —C(=O)$R^5$, —C(=O)O$R^5$, —C(=O)NH$R^4$, —C(=O)N$R^4R^4$, —C(=S)NH$R^4$, —C(=S)N$R^4R^4$, —C(=N$R^4$)NH$R^4$, and —C(=N$R^4$)N$R^4R^4$;

$R^3$ is at least one amino acid selected from Gly, β-alanine, GABA, 5-aminopentanoic acid, 6-aminohexanoic acid, Lys, gDab, Sar, Orn, Dap, hLys, or any combination thereof;

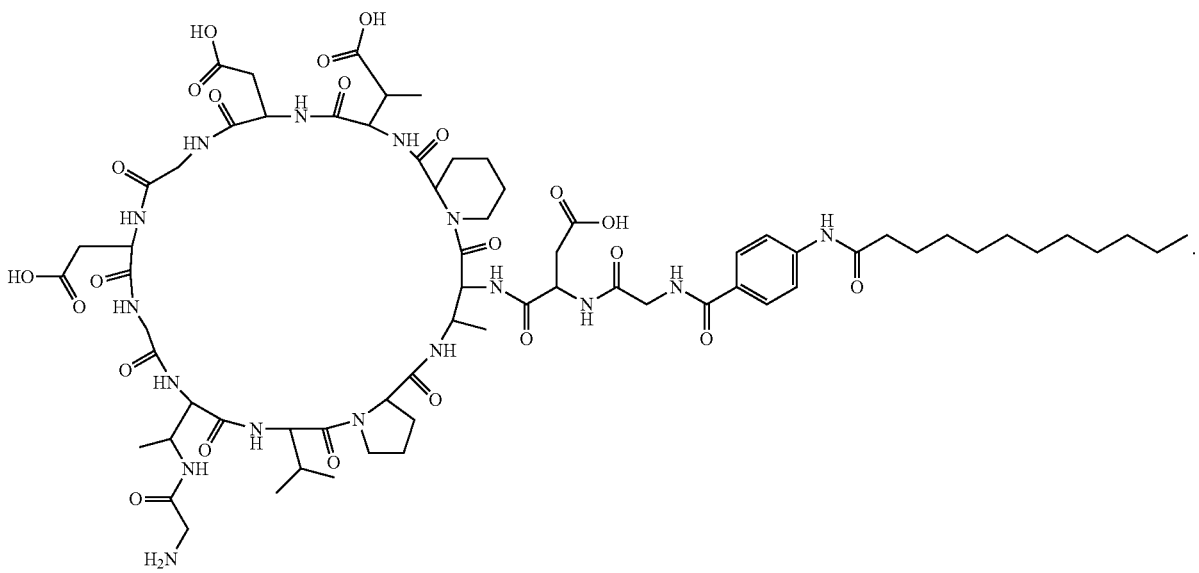

$R^4$ is independently selected from ($C_7$-$C_{10}$) alkyl, ($C_{17}$-$C_{26}$) arylalkyl and 17 to 26 membered heteroarylalkyl, a branched or straight-chained, saturated or singly or multiply unsaturated aliphatic or hydroxy aliphatic moiety having a chain length of from 7 to 25 carbon atoms, a primary or secondary amine, at least one amino acid, and at least one substituted amino acid; and $R^5$ is independently selected from hydrogen, ($C_1$-$C_{10}$) alkyl, ($C_5$-$C_{10}$) aryl, 5 to 10 membered heteroaryl, ($C_6$-$C_{26}$) arylalkyl and 6 to 26 membered heteroarylalkyl, a branched or straight chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof.

2. The compound of claim 1 wherein $R^1$ is OH.

3. The compound of claim 1 wherein $R^1$ is $NH_2$.

4. The compound of claim 1 wherein $R^2$ is —C(=O)O$R^5$ or —C(=O)$R^5$.

5. The compound of claim 1 wherein $R^2$ is —C(=O)$R^5$.

6. The compound of claim 1 wherein $R^2$ is —C(=O)NH$R^4$, —C(=S)NH$R^4$, or —C(=N$R^4$)NH$R^4$.

7. The compound of claim 6 wherein $R^2$ is —C(=O)NH$R^4$.

8. The compound of claim 1 wherein $R^3$ is at least one amino acid selected from glycine, β-alanine, sarcosine, lysine, or any combination thereof.

9. The compound of claim 8 wherein said at least one amino acid is two amino acids selected from glycine-lysine or sarcosine-lysine.

10. The compound of claim 8 wherein said at least one amino acid is glycine.

11. The compound of claim 8 wherein said at least one amino acid is β-alanine.

12. The compound of claim 5 wherein said compound is

13. The compound according to any one of claims 1 to 11 wherein L is at least one amino acid or at least one substituted amino acid selected from p-aminophenylacetyl, (p-aminophenylpropanoyl)$_n$ wherein n is 1 or 2, m-aminophenylacetyl, (m-aminophenylpropanoyl)$_n$ wherein n is 1 or 2, o-aminophenylacetyl, (o-aminophenylpropanoyl)$_n$ wherein n is 1 or 2, GABA, p-aminobenzoic acid (PABA), m-aminobenzoic acid, o-aminobenzoic acid, p-hydrazinobenzoic acid, m-hydrazinobenzoic acid, o-hydrazinobenzoic acid, p-amino-trans-cinnamyl, m-amino-trans-cinnamyl, o-amino-trans-cinnamyl, L-BBTA, or any combination thereof.

14. The compound of claim 4 wherein L is at least one amino acid selected from p-aminophenylacetyl, PABA, m-aminobenzoic acid, o-aminobenzoic acid, p-amino-trans-cinnamyl, m-amino-trans-cinnamyl, o-amino-trans-cinnamyl, or any combination thereof.

15. The compound of claim 14 wherein $R^5$ is a straight chain saturated aliphatic or hydroxy aliphatic moiety having a chain length of from 10 to 15 carbon atoms.

16. The compound of claim 14 or 15 wherein said compound is
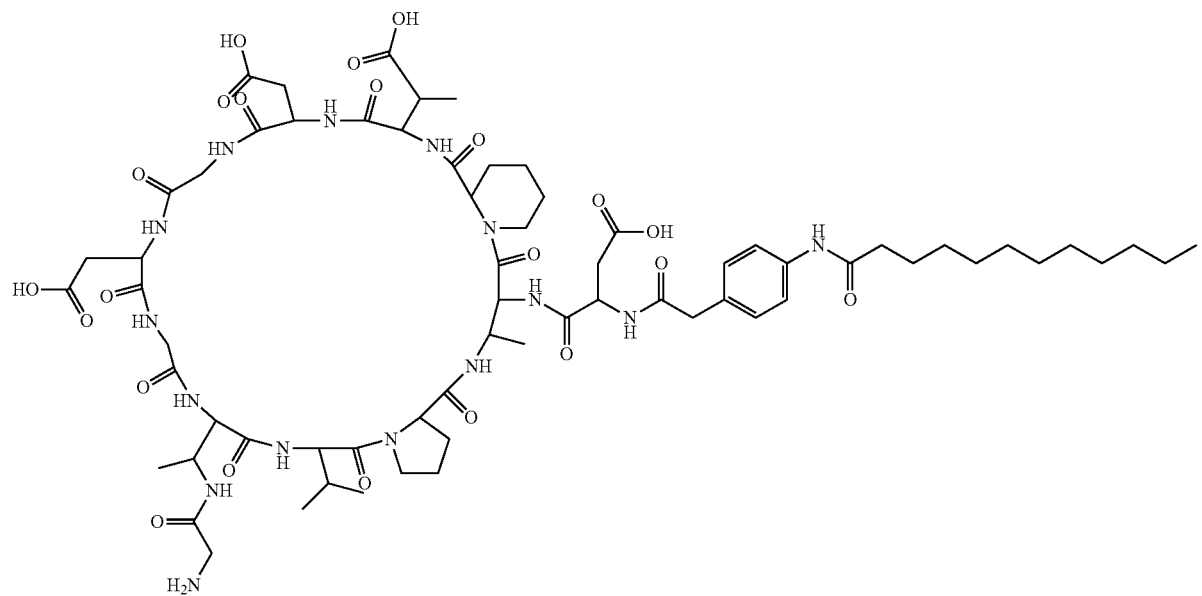
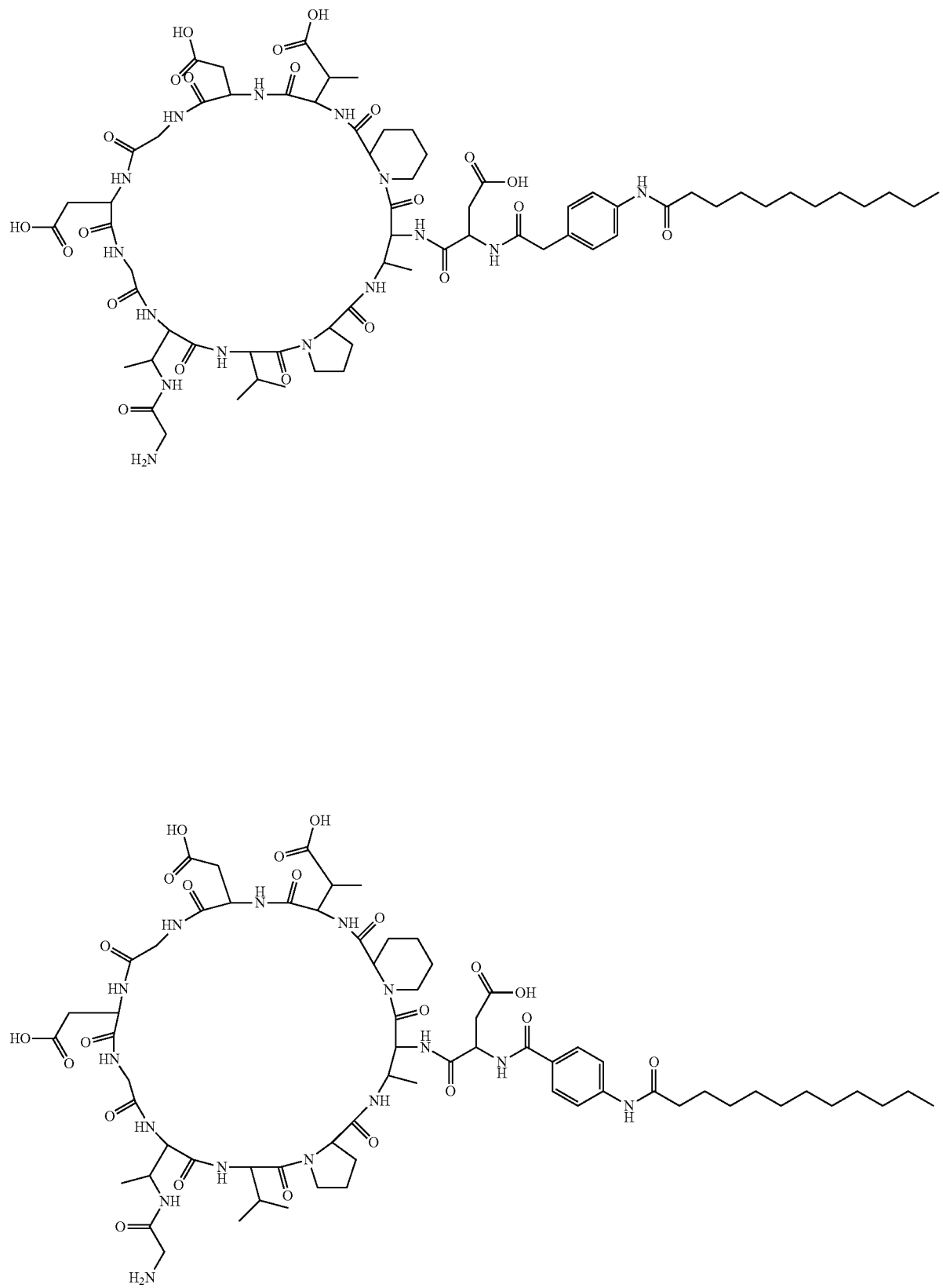

-continued
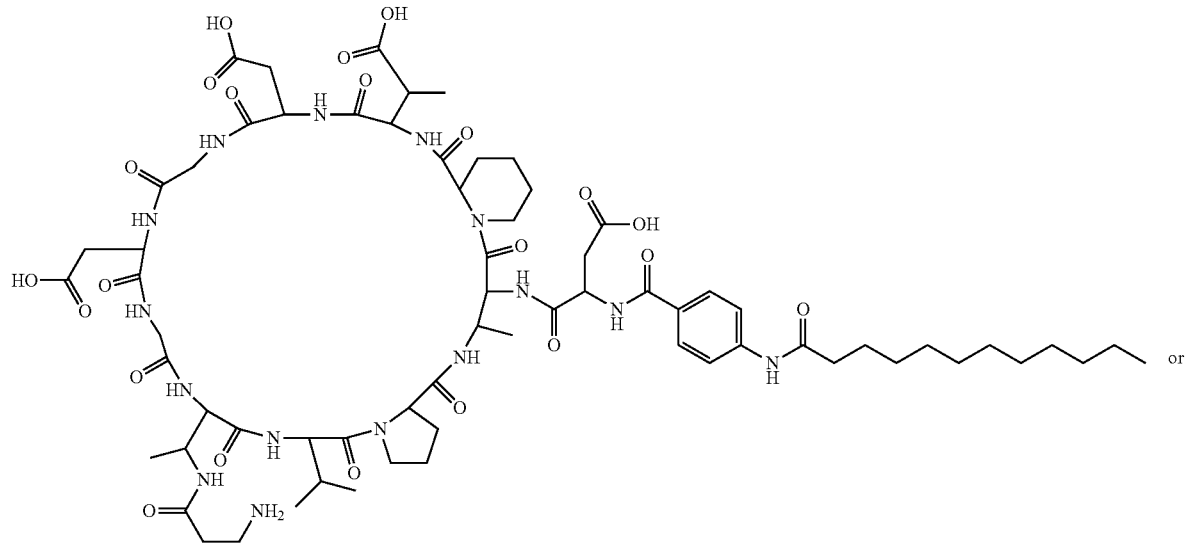 or
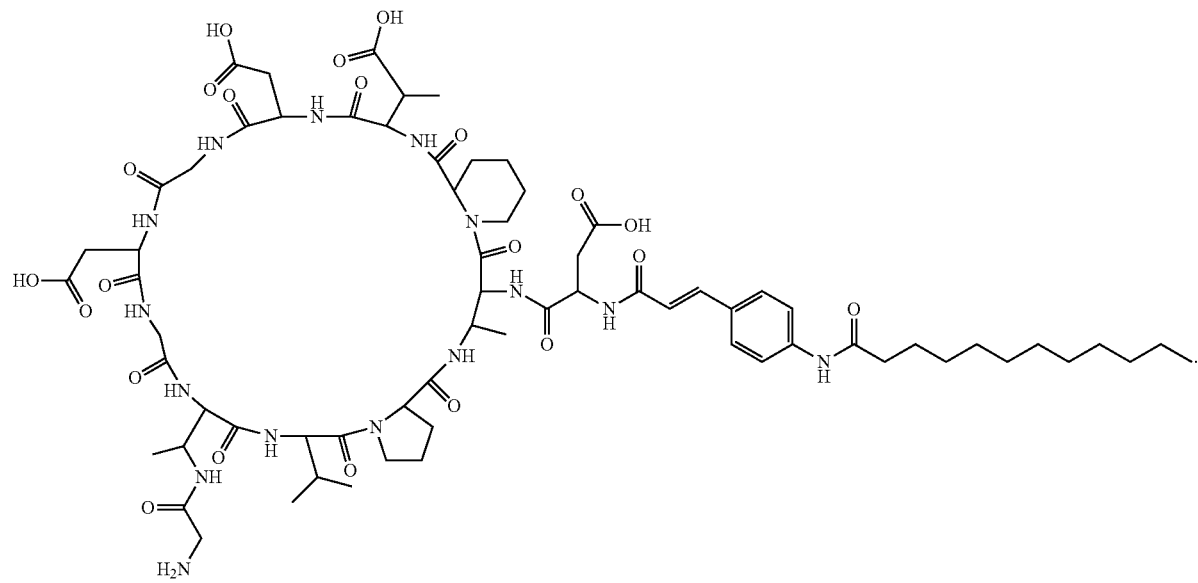

17. A compound and pharmaceutically acceptable salts thereof, according to structural formula (IV):

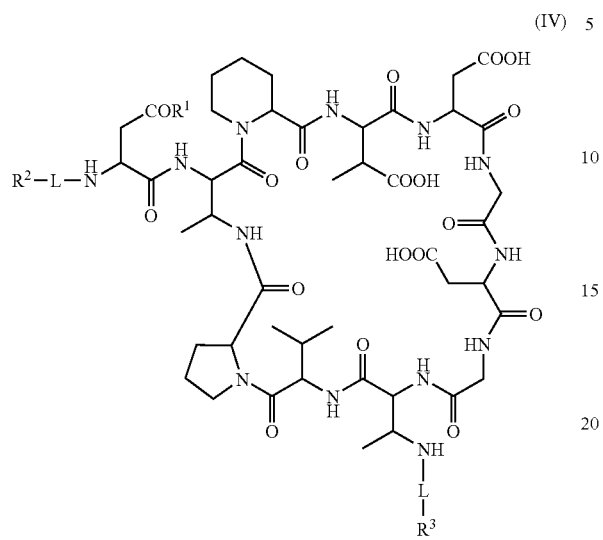

(IV)

wherein:

$R^1$ is OH or $NH_2$;

L is independently selected from at least one amino acid, at least one substituted amino acid, —C(=O)—, —SO$_2$, —C(=S)—, —P(=O)—, —OP(=O)—, —OC(=O)—, —NHC(=O)—, and —O-PhC(=O)—, with the proviso that L at Dab$^9$ is —C(=O)—;

$R^2$ is selected from —OR$^4$, —SR$^4$, NR$^4$R$^4$, —CN, —NO$_2$, —N$_3$, —C(=O)OR$^4$, —C(=O)R$^4$, —C(=O)NR$^4$R$^4$, —C(=S)NR$^4$R$^4$, —C(=NR$^4$)NR$^4$R$^4$, —C(=O)H, —R$^4$C(=O), —SO$_2$R$^4$, —S(=O)R$^4$, —P(=O)(OR$^4$)$_2$, —P(=O)(OR$^4$), —CO$_2$H, —SO$_3$H, —PO$_3$H, halogen, trihalomethyl, (C$_1$-C$_{25}$)alkyl, substituted (C$_1$-C$_{25}$)alkyl, (C$_1$-C$_{25}$)heteroalkyl, substituted (C$_1$-C$_{25}$)heteroalkyl, (C$_5$-C$_{10}$)aryl, substituted (C$_5$-C$_{10}$)aryl, (C$_5$-C$_{15}$)arylaryl, substituted (C$_5$-C$_{15}$)arylaryl, (C$_5$-C$_{15}$)biaryl, substituted (C$_5$-C$_{15}$)biaryl, 5-10 membered heteroaryl, substituted 5 to 10 membered heteroaryl, (C$_6$-C$_{26}$)arylalkyl, substituted (C$_6$-C$_{26}$)arylalkyl, 6 to 26 membered heteroarylalkyl, substituted 6 to 26 membered heteroarylalkyl, at least one amino acid, and at least one substituted amino acid;

$R^3$ is at least one amino acid or substituted amino acid selected from Gly, β-alanine, GABA, 5-aminopentanoic acid, 6-aminohexanoic acid, Lys, gDab, Sar, Orn, Dap, and hLys; and $R^4$ is independently selected from hydrogen, (C$_1$-C$_{10}$)alkyl, (C$_5$-C$_{10}$)aryl, 5 to 10 membered heteroaryl, (C$_6$-C$_{26}$)arylalkyl and 6 to 26 membered heteroarylalkyl, a branched or straight-chained, saturated or singly or multiply unsaturated aliphatic or hydroxy aliphatic moiety having a chain length of from 5 to 25 carbon atoms, a primary or secondary amine, at least one amino acid, at least one substituted amino acid, and any combination thereof.

18. The compound of claim 17 wherein $R^1$ is OH.
19. The compound of claim 17 wherein $R^1$ is $NH_2$.
20. The compound of claim 17 wherein at least one of L and $R^3$ further comprise at least one protecting group.
21. A compound and pharmaceutically acceptable salts thereof, wherein the compound is

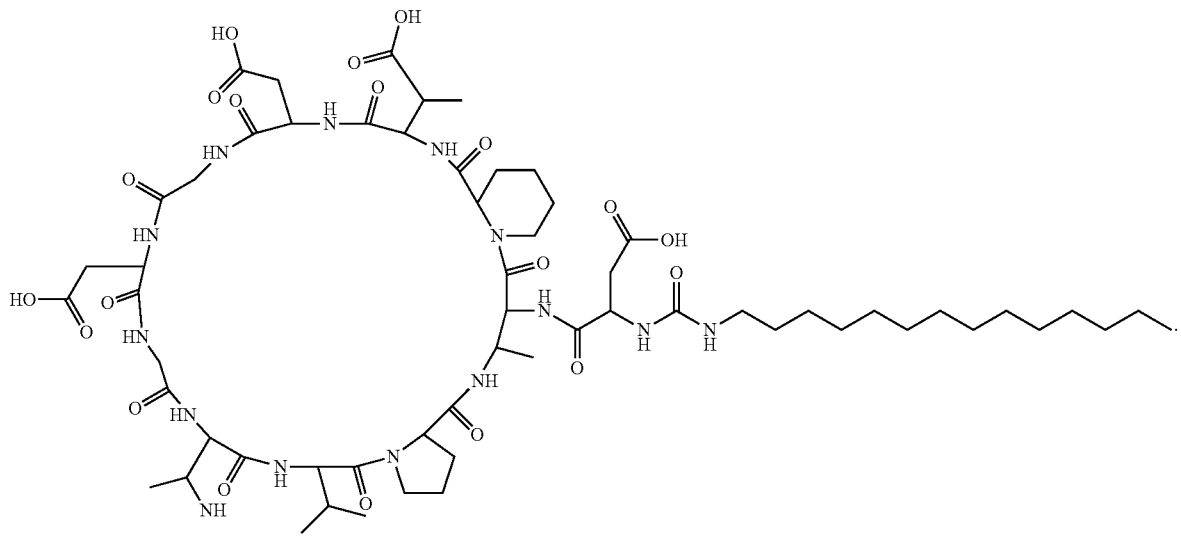

22. A compound and pharmaceutically acceptable salts thereof, wherein the compound is

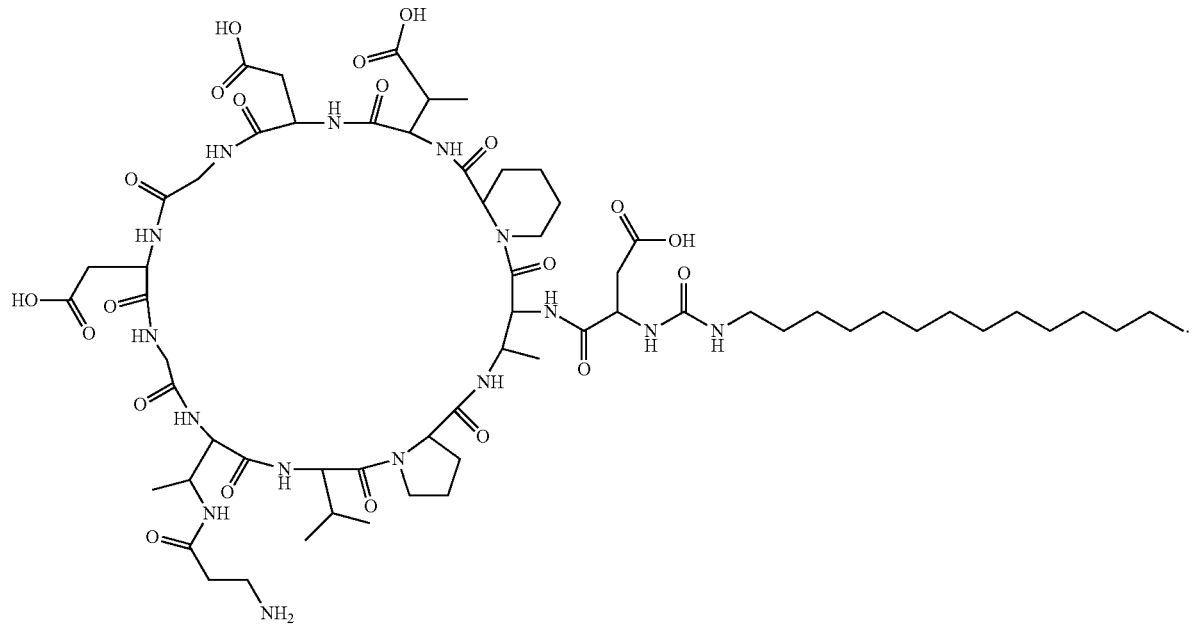

23. A pharmaceutical composition, comprising a compound according to claim 1 or 17 and a pharmaceutically acceptable carrier, excipient, or diluent.

24. A method for treating a bacterial infection, comprising administering to a subject in need thereof a compound according to claim 1 or 17.

25. A method for treating a bacterial infection, comprising administering to a subject in need thereof a pharmaceutical composition according to claim 23.

26. The method of claim 25 wherein the bacterial infection is caused by a Gram-positive microorganism.

27. The method according to claim 26 wherein the Gram-positive microorganism is selected from a *Streptococcus*, a *Staphylococcus*, an *Enterococcus*, a *Bacillus*, a *Corynebacterium*, a diphtheroid, and a *Listeria*.

28. The method according to claim 26 wherein the Gram-positive microorganism is *Streptococcus pyogenes, Streptococcus pneumoniae,* or *Viridans Streptococcus*.

29. The method according to claim 26 wherein the Gram-positive microorganism is *Staphylococcus aureus, Staphylococcus epidermidis,* or coagulase-negative *Staphylococcus*.

30. The method according to claim 26 wherein the Gram-positive microorganism is *Enterococcus faecalis* or *Enterococcus faecium*.

31. The method according to claim 26 wherein the Gram-positive microorganism is drug resistant.

32. The method according to claim 31 wherein the drug resistant microorganism is penicillin-resistant *Streptococcus pneumoniae*, penicillin-intermediate *Streptococcus pneumoniae*, or a multidrug-resistant *Streptococcus*.

33. The method according to claim 31 wherein the drug resistant microorganism is methicillin-resistant *Staphylococcus aureus*, methicillin-resistant *Staphylococcus epidermidis*, vancomycin-intermediate *Staphylococcus aureus*, or a multidrug-resistant *Staphylococcus*.

34. The method according to claim 31 wherein the drug resistant microorganism is vancomycin-resistant *Enterococcus* or multidrug resistant *Enterococcus*.

35. The method according to claim 25 wherein the bacterial infection is selected from a complicated or uncomplicated skin infection; a surgical wound infection; an intra-abdominal infection; a urinary tract infection; pyelonephritis; a nosocomial infection; a nosocomial pneumonia; a community-acquired infection; a community-acquired pneumonia; and infective endocarditis.

36. The method according to claim 35 wherein the complicated or uncomplicated skin infection is impetigo, folliculitis, furunculosis, eethyma, erysipelas, cellulitis, acute paronychia, felon, necrotizing fasciitis, Staphylococcal scalded skin infection, nodular lymphangitis, preseptal cellulitis, or periorbital cellulitis.

37. The method according to claim 35 wherein the nosocomial infection is caused by a *Staphylococcus* or an *Enterococcus*.

38. The method according to claim 37 wherein the *Staphylococcus* is *S. aurueus* or methicillin-resistant *S. aureus*.

39. The method according to claim 37 wherein the *Enterococcus* is vancomycin-resistant *Enterococcus*.

40. The method according to claim 35 wherein the community-acquired pneumonia is caused by *Streptococcus pneumoniae.*

41. The method according to claim 35 wherein the urinary tract infection or pyelonephritis is caused by an *Enterococcus.*

42. A method for treating a bacterial infection, comprising administering to a subject in need thereof a pharmaceutical composition comprising an antibacterial compound, wherein the antibacterial compound is 153 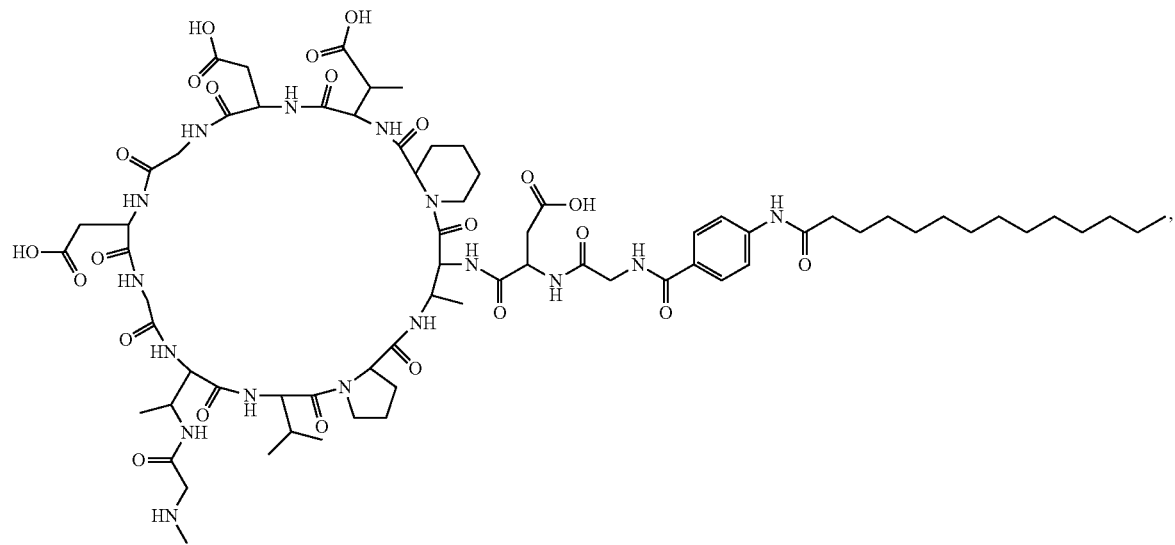
154 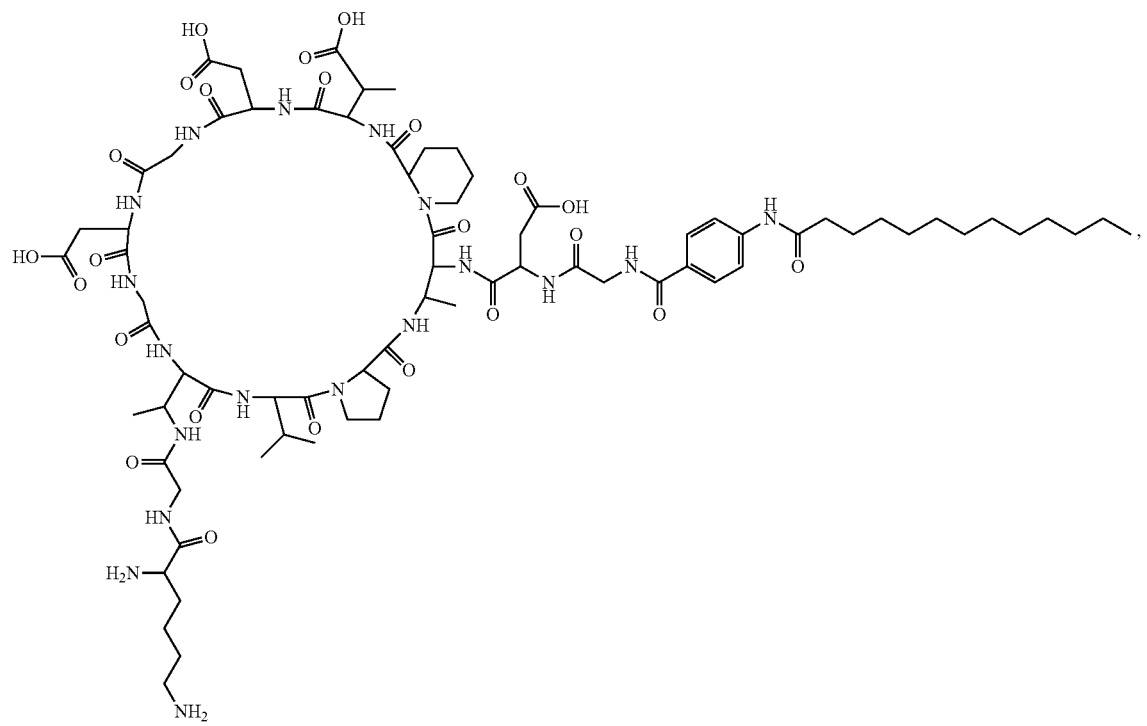

-continued
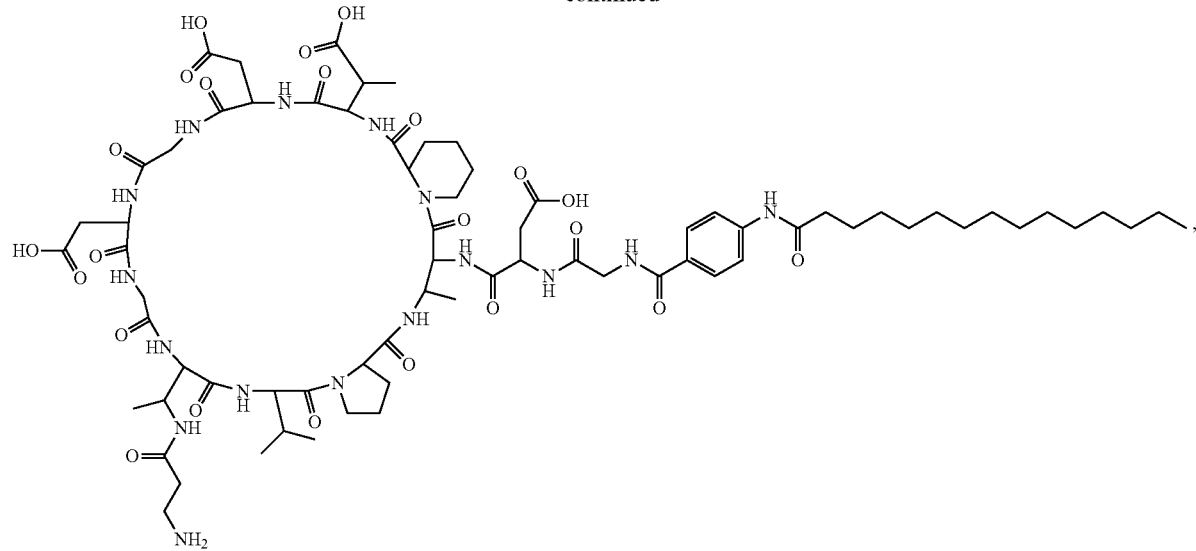
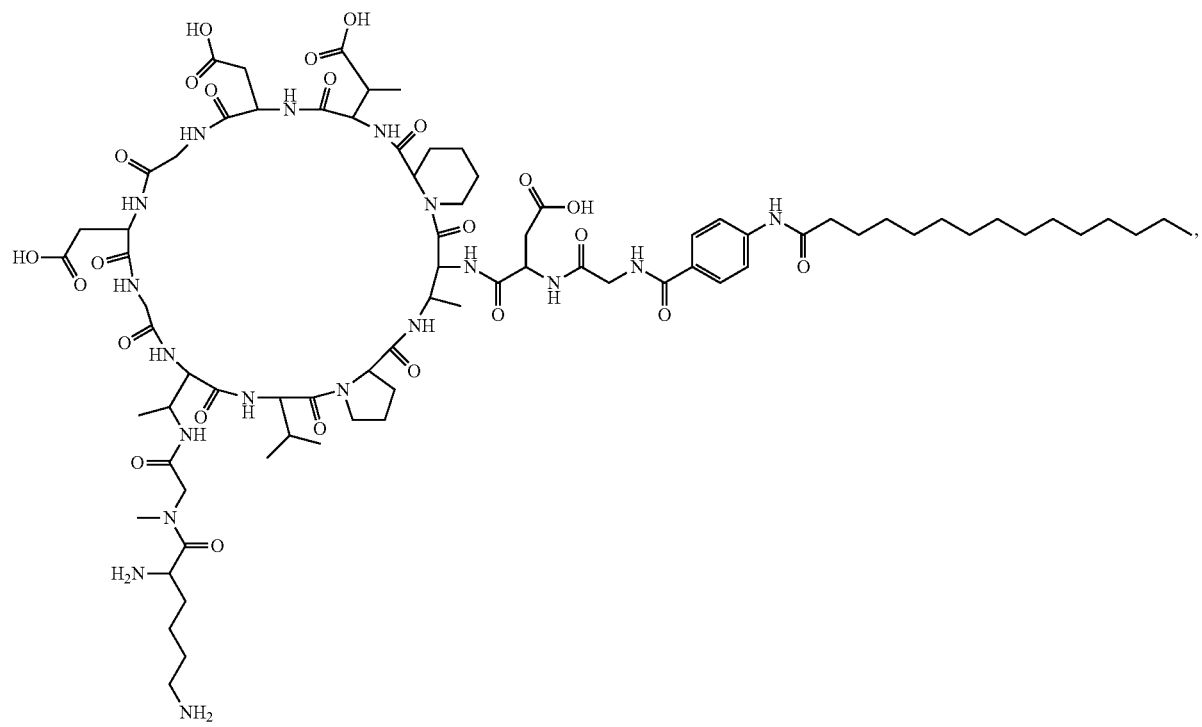

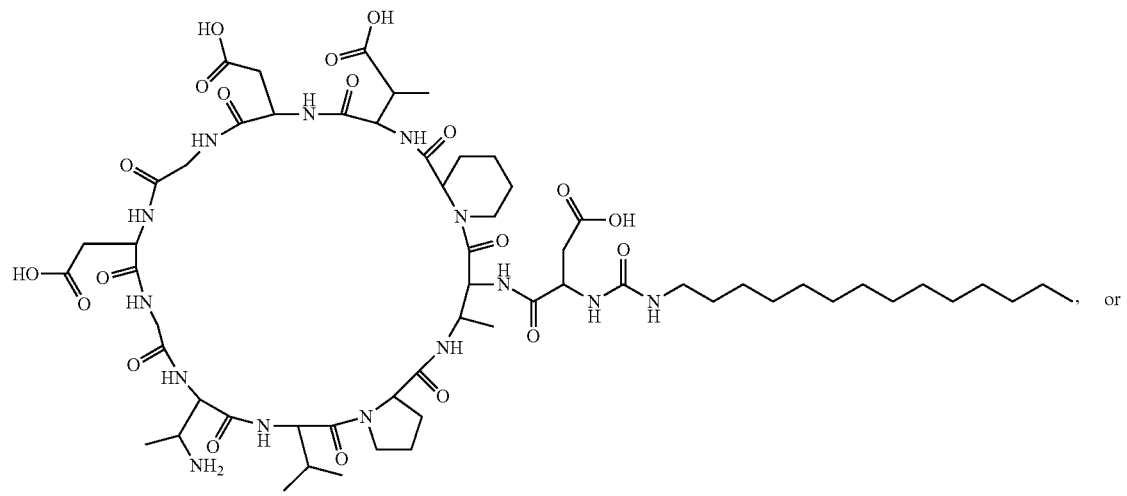, or
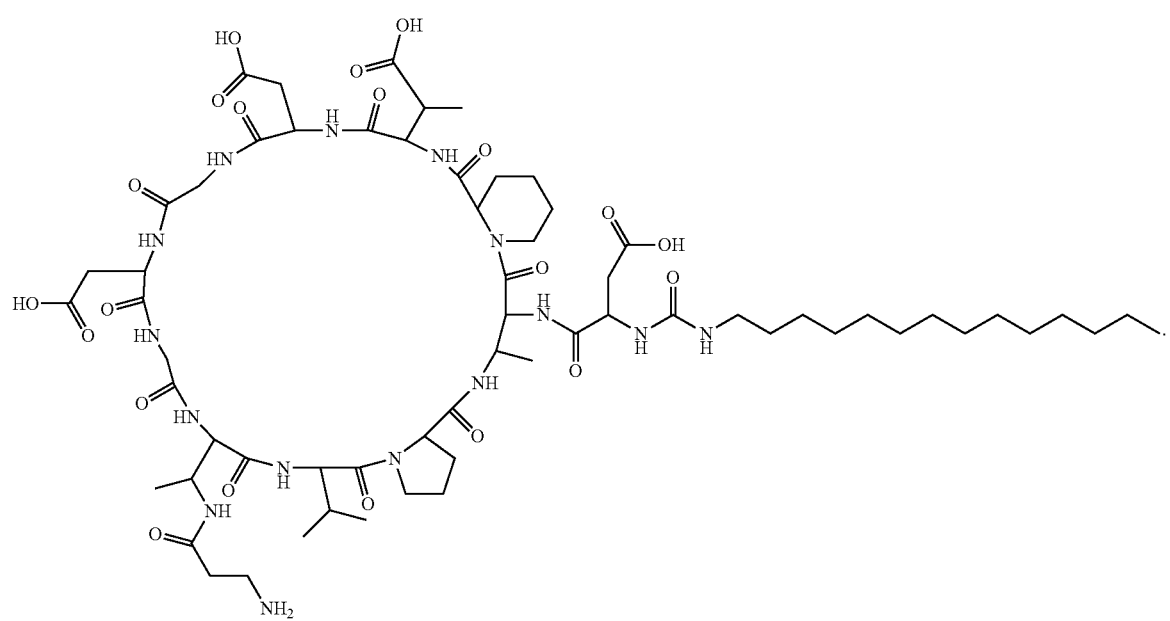.